United States Patent
Brandhuber et al.

(10) Patent No.: US 12,268,666 B2
(45) Date of Patent: Apr. 8, 2025

(54) SPRAY-DRIED DISPERSIONS, FORMULATIONS, AND POLYMORPHS OF (S)-5-AMINO-3-(4-((5-FLUORO-2-METHOXYBENZAMIDO)METHYL) PHENYL)-1-(1,1,1-TRIFLUOROPROPAN-2-YL)-1H-PYRAZOLE-4-CARBOXAMIDE

(71) Applicant: Loxo Oncology, Inc., Indianapolis, IN (US)

(72) Inventors: Barbara J. Brandhuber, Boulder, CO (US); Lauren T. Brent, San Diego, CA (US); Charles Todd Eary, Longmont, CO (US); Andrew Kenna, San Diego, CA (US); Firas Khan, San Diego, CA (US); Vivian F. H. Renshaw, San Diego, CA (US); Stacey Renee Spencer, Lyons, CO (US)

(73) Assignee: Loxo Oncology, Inc., Indianapolis, IN (US)

( * ) Notice: Subject to any disclaimer, the term of this patent is extended or adjusted under 35 U.S.C. 154(b) by 0 days.

(21) Appl. No.: 18/440,563

(22) Filed: Feb. 13, 2024

(65) Prior Publication Data
US 2024/0238253 A1 Jul. 18, 2024

Related U.S. Application Data

(62) Division of application No. 17/260,745, filed as application No. PCT/US2019/043937 on Jul. 29, 2019.

(60) Provisional application No. 62/769,308, filed on Nov. 19, 2018, provisional application No. 62/729,855, filed on Sep. 11, 2018, provisional application No. 62/712,861, filed on Jul. 31, 2018.

(51) Int. Cl.
| | | |
|---|---|---|
| *A61K 31/415* | (2006.01) | |
| *A61K 9/00* | (2006.01) | |
| *A61K 9/20* | (2006.01) | |
| *A61K 31/635* | (2006.01) | |
| *A61P 35/04* | (2006.01) | |
| *C07K 16/28* | (2006.01) | |

(52) U.S. Cl.
CPC .......... *A61K 31/415* (2013.01); *A61K 9/0053* (2013.01); *A61K 9/2009* (2013.01); *A61K 9/2018* (2013.01); *A61K 9/2054* (2013.01); *A61K 9/2059* (2013.01); *A61K 31/635* (2013.01); *A61P 35/04* (2018.01); *C07K 16/2887* (2013.01); *C07B 2200/13* (2013.01)

(58) Field of Classification Search
CPC .................................................. A61K 31/415
See application file for complete search history.

(56) References Cited

U.S. PATENT DOCUMENTS

2016/0038496 A1  2/2016  Shu et al.

FOREIGN PATENT DOCUMENTS

| WO | 2017/103611 | 6/2017 |
|---|---|---|
| WO | 2017/218844 | 12/2017 |
| WO | 2021/113497 A1 | 6/2021 |
| WO | 2022/056100 A1 | 3/2022 |

OTHER PUBLICATIONS

Ashizawa, Kazuhide et al., "Polymorphic Phenomena and Crystallization Science of Pharmaceuticals," Japan, Maruzen Planet Co., Ltd., Sep. 20, 2002, p. 3-16, 273-278.
"Experimental Chemistry (continued) 2 Separation and purification," Japan, Maruzen Co., Ltd., Jan. 25, 1967, p. 159-178, 186-187.
Japanese Patent Office, Notice of Reasons for Rejection, JP Patent Application No. 2023-085024, May 7, 2024.
"New general remarks for Pharmaceutical Sciences (Revised 3rd Edition)," Nankodo Co., Ltd., Apr. 10, 1987, p. 111.
"New Pharmaceutical Science," Nanzando Co., Ltd., Apr. 25, 1984, p. 102-103, 232-233.
Oshima, Hiroshi, "Crystallization of Polymorphs and Pseudopolymorphs and Its Control," Pharm Stage, Jan. 15, 2007, vol. 6, No. 10, p. 48-53.
Takada, Noriyuki, "API form screening and selection in drug discovery stage," Pharm Stage, vol. 6, No. 10, Jan. 15, 2007, p. 20-25.
"The Japanese Pharmacopeia 16th edition", 2011, pp. 64-68, 2070.
Yamano, Mitsuhisa, "Approach to Crystal Polymorphism in Process Research of New Drug," Journal of the Society of Synthetic Organic Chemistry, Japan, Sep. 1, 2007, vol. 65, No. 9, p. 907(69)-913(75).
International Search Report and Written Opinion in International Application No. PCT/US2019/043937, mailed Oct. 17, 2019, 7 pages.
薬剤学 (Pharmaceutics), 2013, vol. 73, No. 4, pp. 214-222.
AU Office Action, Examination Report No. 1, Oct. 27, 2021.
JP Office Action, Notice of Reasons for Rejection , May 10, 2022.
CA Office Action, Mar. 22, 2022.
CN Office Action, The First Office Action, Jul. 20, 2022.

(Continued)

*Primary Examiner* — Golam M Shameem
(74) *Attorney, Agent, or Firm* — Tina M. Tyson

(57) ABSTRACT

A spray-dried dispersions and pharmaceutical composition of (S)-5-amino-3-(4-((5-fluoro-2-methoxybenzamido) methyl)phenyl)-1-(1,1,1-trifluoropropan-2-yl)-1H-pyrazole-4-carboxamide, pharmaceutically acceptable salts thereof, or a combination thereof and the use of the spray-dried dispersion and pharmaceutical composition in the treatment of cancer and autoimmune and inflammatory diseases are disclosed. Also provided are crystalline forms of (S)-5-amino-3-(4-((5-fluoro-2-methoxybenzamido) methyl)phenyl)-1-(1,1,1-trifluoropropan-2-yl)-1H-pyrazole-4-carboxamide also useful in the treatment of cancer and autoimmune and inflammatory diseases.

8 Claims, 21 Drawing Sheets

Specification includes a Sequence Listing.

(56) References Cited

OTHER PUBLICATIONS

KR Office Action, Notice of Preliminary Rejection, Sep. 16, 2022.
JP Office Action, Notice of Reasons for Rejection, Dec. 13, 2022.
(Original) 森部久仁一, ファルマシア, 2016, vol. 52, No. 5, pp. 397-401 Partial translation of relevant section of 森部久仁一, ファルマシア, 2016, vol. 52, No. 5, pp. 397-401.
Machine translation of 森部久仁一, ファルマシア, 2016, vol. 52, No. 5, pp. 397-401.
(Translation of section of 森部久仁一, ファルマシア, 2016, vol. 52, No. 5, pp. 397-401, specifically p. 399, left column, line 7 to p. 400, left column, line 1 and Fig. 3).

SPRAY-DRIED DISPERSIONS, FORMULATIONS, AND POLYMORPHS OF (S)-5-AMINO-3-(4-((5-FLUORO-2-METHOXYBENZAMIDO)METHYL)PHENYL)-1-(1,1,1-TRIFLUOROPROPAN-2-YL)-1H-PYRAZOLE-4-CARBOXAMIDE

REFERENCE TO SEQUENCE LISTING SUBMITTED ELECTRONICALLY

The present application is being filed along with a Sequence Listing in ST.26 XML format. The Sequence Listing is provided as a file titled "X22366A_US" created Feb. 7, 2024 and is 3,000 bytes in size. The Sequence Listing information in the ST.26 XML format is incorporated herein by reference in its entirety.

TECHNICAL FIELD

The present disclosure relates to the compound of Formula I, or a pharmaceutically acceptable salt, amorphous, or polymorph form thereof, a spray-dried dispersion (SDD) thereof, or a pharmaceutical composition thereof. More particularly, it relates to compositions of the compound of Formula I useful in the treatment and prevention of diseases that can be treated with a BTK inhibitor, including BTK-associated diseases and disorders.

BACKGROUND

BTK is a cytoplasmic, non-receptor tyrosine kinase belonging to the Tec family kinases (Herman, S. E. M. et al., *Blood.* 2011, 117 (23): 6287-6296). The structure of BTK has several domains: an N-terminal pleckstrin homology (PH) domain, a proline-rich TEC homology domain, two SRC homology domains (SH3 followed by SH2), and a C-terminal kinase domain (BTK-KD)(Marcotte, D. J. et al., Protein Sci. 2010, 19(3): 429-439).

BTK is expressed in hematopoietic cells, excluding T cells and plasma cells, and is involved in all aspects of B-cell development, including proliferation, maturation, differentiation, apoptosis, and cell migration (Wu J., et al., J Hematol Oncol. 2016; 9: 80). BTK is also expressed in specific myeloid cells including monocytes/macrophages, neutrophils, and mast cells. In these myeloid cells, BTK has been indicated in the immune complex mediated activation of FcγR and FcεR, which may contribute to the pathogenesis of rheumatoid arthritis (Whang 2014). BTK is also required for the maturation of osteoclast cells, so inhibiting BTK could prevent the bone erosion that is associated with rheumatoid arthritis.

PIP3 (phosphatidylinositol-3,4,5-triphosphate) generation and bonding to the PH domain of BTK and phosphorylation of Tyr-551 of BTK by Src family kinases stimulate membrane localization and activation of BTK. Activation of BTK leads to $Ca^{2+}$ mobilization and activation of NF-κB and MAP (mitogen-activated protein) kinase pathways (Honigberg et al. *Proc. Natl. Acad. Sci. U.S.A* 2010 Jul. 20; 107(29): 13075-13080).

Aberrant BTK expression and/or activity have been demonstrated in different cancers and in autoimmune disorders.

Examples of BTK inhibitors are disclosed in WO17/103661.

There is a need to provide improved formulations for BTK inhibitors, particularly for BTK inhibitors that exhibit low solubility. Further, there is a need to provide formulations to increase the plasma concentrations of the BTK inhibitor and/or provide consistent plasma concentrations. The present invention provides various formulations that address one or more of these needs.

SUMMARY

In one form the present invention provides pharmaceutical composition that comprises a compound of Formula I

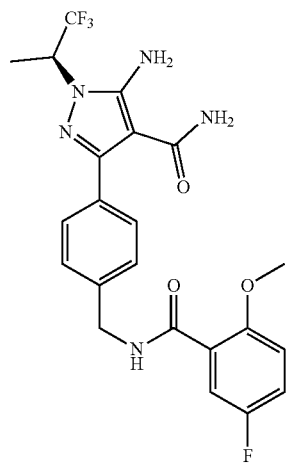

present in an amount between about 5% w/w and about 30% w/w; an HPMCAS polymer present in an amount between about 5% w/w and about 30% w/w; microcrystalline cellulose present in an amount between about 30% w/w and about 60% w/w; mannitol or lactose monohydrate, or a combination thereof, present in a total amount between about 10% w/w and about 60% w/w; sodium starch glycolate or croscarmellose sodium, or a combination thereof, present in a total amount between about 0.5% w/w and about 5% w/w; and magnesium stearate present in an amount between about 0.05% w/w and about 2% w/w; and optionally, silicon dioxide in an amount between about 0.3% w/w and about 0.6% w/w, when present, and wherein the total is not greater than 100%.

In one form, the present invention provides a pharmaceutical composition that comprises a compound of Formula I present in an amount between about 5% w/w and about 30% w/w; an HPMCAS polymer present in an amount between about 5% w/w and about 30% w/w; microcrystalline cellulose present in an amount between about 30% w/w and about 60% w/w; mannitol or lactose monohydrate, or a combination thereof, present in a total amount between about 10% w/w and about 60% w/w; sodium starch glycolate or croscarmellose sodium, or a combination thereof, present in a total amount between about 0.5% w/w and about 5% w/w; and magnesium stearate present in an amount between about 0.05% w/w and about 2% w/w; and optionally, silicon dioxide in an amount between about 0.3% w/w and about 0.6% w/w, when present, and wherein the total is not greater than 100%.

In one form, the present invention provides a pharmaceutical composition that comprises the compound of Formula I present in an amount between about 5% w/w and about 30% w/w; the HPMCAS polymer present in an amount between about 5% w/w and about 30% w/w; microcrystalline cellulose present in an amount between about 30% w/w and about 60% w/w; lactose monohydrate present in an amount between about 10% w/w and about 60% w/w;

croscarmellose sodium, present in a total amount between about 0.5% w/w and about 5% w/w; and magnesium stearate present in an amount between about 0.05% w/w and about 2% w/w; and, silicon dioxide in an amount between about 0.3% w/w and about 0.6% w/w, when present, and wherein the total is not greater than 100%.

In one embodiment, the ratio of the compound of Formula I to the HPMCAS polymer is about 1:4 to about 4:1. In another embodiment ratio of the compound of Formula I to the HPMCAS polymer is about 1:1.

In another form, the present invention provides a pharmaceutical composition that comprises the compound of Formula I present in an amount between about 21% w/w and about 23% w/w; the HPMCAS polymer present in an amount between about 21% w/w and about 23% w/w; microcrystalline cellulose present in an amount between about 38% w/w and about 39% w/w; mannitol present in an amount between about 12% w/w and about 13% w/w; sodium starch glycolate present in an amount between about 4% w/w and about 6% w/w; and magnesium stearate present in an amount between about 0.4% w/w and about 0.6% w/w and wherein the total is not greater than 100% w/w.

In another form, the present invention provides a pharmaceutical composition that comprises the compound of Formula I present in an amount between about 21% w/w and about 23% w/w; the HPMCAS polymer present in an amount between about 21% w/w and about 23% w/w; microcrystalline cellulose present in an amount between about 33% w/w and about 34% w/w; lactose monohydrate present in an amount between about 16% w/w and about 17% w/w; croscarmellose sodium present in an amount between about 2% w/w and about 6% w/w; magnesium stearate present in an amount between about 0.4% w/w and about 0.6% w/w; and silicon dioxide present in an amount between about 0.4% w/w and about 0.6% w/w and wherein the total is not greater than 100%.

In another form, the present invention provides a pharmaceutical composition that comprises the compound of Formula I present in an amount between about 21% w/w and about 23% w/w; the HPMCAS polymer present in an amount between about 21% w/w and about 23% w/w; microcrystalline cellulose present in an amount between about 25% w/w and about 26% w/w; mannitol present in an amount between about 25% w/w and about 26% w/w; sodium starch glycolate present in an amount between about 4% w/w and about 6% w/w; and magnesium stearate present in an amount between about 0.4% w/w and about 0.6% w/w and wherein the total is not greater than 100% w/w.

In yet another form, the present invention provides a pharmaceutical composition that comprises a compound of Formula I present in an amount of about 8% w/w; HPMCAS polymer present in an amount of about 8% w/w; microcrystalline cellulose present in an amount about 40% w/w; mannitol present in an amount of about 40% w/w; sodium starch glycolate present in an amount of about 3.5% w/w; and magnesium stearate present in an amount of about 0.3% w/w.

In one embodiment, the pharmaceutical composition as described above is formulated as a tablet. In another embodiment, the pharmaceutical composition comprises between about 25 mg and about 220 mg of the compound of Formula I. In still yet another embodiment, the pharmaceutical composition comprises the compound of Formula I in amount selected from one of the following: about 25 mg, about 50 mg, and about 100 mg.

In another form, the present invention provides a method for treating a BTK-associated cancer in a subject in need thereof, the method comprising administering to the subject a pharmaceutical composition as described above. In one embodiment, the BTK associated cancer is selected from: mantle cell lymphoma, chronic lymphocytic leukemia, small lymphocytic lymphoma, Waldenstrom's macroglobulinemia, and marginal zone lymphoma.

In another form, the present invention provides a method of treating a cancer in subject in need of treatment. The method comprises administering to the subject a compound of Formula I in a dose between about 20 mg and about 120 mg. The cancer is selected from the following cancers: mantle cell lymphoma, chronic lymphocytic leukemia, small lymphocytic lymphoma, Waldenstrom's macroglobulinemia, and marginal zone lymphoma. In certain embodiments, the dose is selected from one of the following: about 25 mg, about 50 mg, and about 100 mg.

In another form, the present invention provides for the use of a pharmaceutical composition as described above for the treatment of a BTK-associated cancer selected from the following: mantle cell lymphoma, chronic lymphocytic leukemia, small lymphocytic lymphoma, Waldenstrom's macroglobulinemia, and marginal zone lymphoma where the compound of Formula I is administered at a dose between about 20 mg and 120 mg. In certain embodiments, the dose that the compound of Formula I is administered is selected from the following: about 25 mg, about 50 mg and about 100 mg.

In still yet another form, the present invention provides a pharmaceutical composition as described above for use in the treatment of a BTK-associated cancer selected from the following: mantle cell lymphoma, chronic lymphocytic leukemia, small lymphocytic lymphoma, Waldenstrom's macroglobulinemia, and marginal zone lymphoma. In certain embodiments, the compound of Formula I is administered at dose selected from one of the following: about 25 mg, about 50 mg and about 100 mg.

In other forms the present invention provides a compound of Formula I:

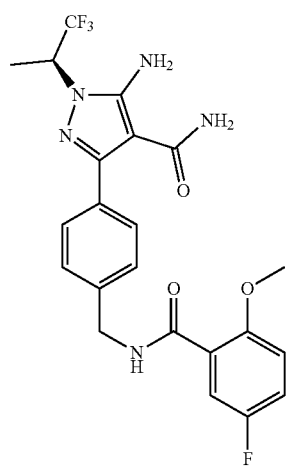

in a spray-dried dispersion thereof, or a pharmaceutical composition thereof, that is useful in the treatment and prevention of diseases, which can be treated with a BTK inhibitor, including BTK-associated diseases and disorders.

Accordingly provided herein is a spray-dried dispersion comprising the compound of Formula I and a hypromellose acetate succinate (HPMCAS) polymer.

In some embodiments, the ratio of the compound of Formula I, or a pharmaceutically acceptable salt, amorphous, or polymorph form thereof, to the HPMCAS polymer is about 1:4 to about 4:1. In some embodiments, the ratio of the compound of Formula I, to the HPMCAS polymer is about 1:1. In some embodiments, the HPMCAS polymer is HPMCAS-MG.

Also provided herein is a process of preparing the spray-dried dispersion, wherein the compound of Formula I, is dissolved in one or more organic solvents prior to being spray-dried. In some embodiments, the compound of Formula I, or a pharmaceutically acceptable salt, amorphous, or polymorph form thereof, is dissolved in dichloromethane:methanol, preferably in a ratio of about 80:20 wt/wt dichloromethane:methanol prior to being spray-dried. In other embodiments the compound of Formula I is dissolved in methanol. In still other embodiments, the Form A of the compound of Formula I is dissolved in the one or more organic solvents.

Also provided herein is a pharmaceutical composition comprising: a first composition comprising a spray-dried dispersion and one or more pharmaceutical excipients, wherein the spray-dried dispersion comprises a HPMCAS polymer and the compound of Formula I, or a pharmaceutically acceptable salt, amorphous, or polymorph form thereof.

In some embodiments, the ratio of the compound of Formula I, or a pharmaceutically acceptable salt, amorphous, or polymorph form thereof, to the HPMCAS polymer in the spray-dried dispersion is about 1:4 to about 4:1. In some embodiments, the ratio of the compound of Formula I, or a pharmaceutically acceptable salt, amorphous, or polymorph form thereof, to the HPMCAS polymer in the spray-dried dispersion is about 1:1. In some embodiments, the HPMCAS polymer is HPMCAS-MG.

In some embodiments, the spray-dried dispersion is present in an amount of about 20% to about 75% w/w of the first composition. In some embodiments, the spray-dried dispersion is present in an amount of about 30% to about 60% w/w of the first composition. In some embodiments, the spray-dried dispersion is present in an amount of about 40% to about 50% w/w of the first composition. In some embodiments, the spray-dried dispersion is present in an amount of about 45% w/w of the first composition.

In some embodiments, the pharmaceutical excipients are selected from the group consisting of: a filler, a lubricant, and combinations thereof.

In some embodiments, the filler is present in an amount of about 25% to about 80% w/w of the first composition. In some embodiments, the filler is present in an amount of about 45% to about 65% w/w of the first composition. In some embodiments, the filler is present in an amount of about 55% w/w of the first composition.

In some embodiments, the filler is selected from the group consisting of: a saccharide, gelatin, a synthetic polymer, or combinations thereof. In some embodiments, the filler is selected from the group consisting of: sucrose, lactose, microcrystalline cellulose, methyl cellulose, ethyl cellulose, hydroxypropyl cellulose, hydroxypropyl methylcellulose, a starch, xylitol, sorbitol, mannitol, a polyvinylpyrrolidone, a polyethylene glycol, a polyvinyl alcohol, a polymethacrylate, a poloxamer, magnesium stearate, calcium stearate, sodium stearate, stearic acid, a hydrogenated vegetable oil, a mineral oil, sodium lauryl sulfate, magnesium lauryl sulfate, glyceryl palmitostearate, sodium stearyl fumarate, colloidal silicon dioxide, sodium benzoate, sodium oleate, sodium acetate, and combinations thereof.

In some embodiments, the filler is a binder, a disintegrant, or a combination thereof.

In some embodiments, the binder is present in an amount of about 30% to about 80% w/w of the first composition. In some embodiments, the binder is present in an amount of about 40% to about 60% w/w of the first composition. In some embodiments, wherein the binder is present in an amount of about 52% w/w of the first composition.

In some embodiments, the binder is selected from the group consisting of: microcrystalline cellulose, cellulose ethers, hydroxypropyl cellulose, hydroxypropyl methylcellulose, sodium carboxy methyl cellulose starches, methyl cellulose, ethyl cellulose, mannitol, xylitol, sorbitol, lactose, sucrose, sorbitol, gelatin, polyvinylpyrrolidone, polyethylene glycol, polyvinyl alcohols, polymethacrylates, and combinations thereof.

In some embodiments, the binder is microcrystalline cellulose, mannitol, or a combination thereof.

In some embodiments, the microcrystalline cellulose is present in an amount of about 5% to about 55% w/w of the first composition. In some embodiments, the microcrystalline cellulose is present in an amount of about 10% to about 40% w/w of the first composition. In some embodiments, the microcrystalline cellulose is present in an amount of about 20% to about 30% w/w of the first composition. In some embodiments, the microcrystalline cellulose is present in an amount of about 30% to about 60% w/w of the first composition. In some embodiments, the microcrystalline cellulose is present in an amount of about 26% w/w of the first composition.

In some embodiments, the mannitol is present in an amount of about 5% to about 55% w/w of the first composition. In some embodiments, the mannitol is present in an amount of about 10% to about 40% w/w of the first composition. In some embodiments, the mannitol is present in an amount of about 20% to about 30% w/w of the first composition. In some embodiments, the mannitol is present in an amount of about 26% w/w of the first composition.

In some embodiments, the disintegrant is present in an amount of about 0.5% to about 5% w/w of the first composition. In some embodiments, the disintegrant is present in an amount of about 1.5% to about 3.5% w/w of the first composition. In some embodiments, the disintegrant is present in an amount of about 2.5% w/w of the first composition.

In some embodiments, the disintegrant is selected from the group consisting of: sodium starch glycolate, alginic acid, sodium alginate, croscarmellose sodium an ion exchange resin, and combinations thereof. In some embodiments, the disintegrant is sodium starch glycolate.

In some embodiments, the lubricant is present in an amount of about 0.05% to about 2.5% w/w of the first composition. In some embodiments, the lubricant is present in an amount of about 0.1% to about 1% w/w of the first composition. In some embodiments, the lubricant is present in an amount of about 0.25% w/w of the first composition.

In some embodiments, the lubricant is selected from the group consisting of: magnesium stearate, calcium stearate, sodium stearate, stearic acid, a hydrogenated vegetable oil, a mineral oil, a polyethylene glycol, sodium lauryl sulfate, magnesium lauryl sulfate, glyceryl palmitostearate, sodium benzoate, sodium stearyl fumarate, colloidal silicon dioxide, sodium benzoate, sodium oleate, sodium acetate, and combinations thereof. In some embodiments, the lubricant is magnesium stearate.

In some embodiments, the spray-dried dispersion is present in an amount of about 20% to about 75% w/w of the first composition, the filler is present in an amount of about 25% to about 80% w/w of the first composition, and the lubricant is present in an amount of about 0.05% to about 2% w/w of the first composition.

In some embodiments, the spray-dried dispersion is present in an amount of about 45% w/w of the first composition, the filler is present in an amount of about 55% w/w of the first composition, and the lubricant is present in an amount of about 0.25% w/w of the first composition.

In some embodiments, the spray-dried dispersion is present in an amount of about 40% to about 50% w/w of the first composition, the microcrystalline cellulose is present in an amount of about 20% to about 30% w/w of the first composition, the mannitol is present in an amount of about 20% to about 30% w/w of the first composition, the sodium starch glycolate is present in an amount of about 0.5% to about 5% w/w of the first composition, and the magnesium stearate is present in an amount of about 0.05% to about 2% w/w of the first composition.

In some embodiments, wherein the spray-dried dispersion and pharmaceutical excipients are blended. In some embodiments, first composition is granulated. In some embodiments, the first composition is granulated by roller compaction.

Also provided herein is a pharmaceutical composition comprising the first composition and one or more pharmaceutical excipients.

In some embodiments, the first composition is present in an amount of about 15% to about 99% w/w of the total composition.

In some embodiments, the one or more pharmaceutical excipients are selected from the group consisting of: a filler, a lubricant, and combinations thereof.

In some embodiments, the lubricant is present in an amount of about 0.05% to about 2% w/w of the total composition. In some embodiments, the lubricant is present in an amount of about 0.1% to about 1.0% w/w of the total composition. In other embodiments, the lubricant is present in an amount of about 0.1% to about 0.8% w/w of the total composition. In other embodiments, the lubricant is present in an amount of about 0.4% to about 0.6% w/w of the total composition. In still other embodiments, the lubricant is present in an amount of about 0.3% w/w of the total composition.

In some embodiments, the lubricant is selected from the group consisting of: magnesium stearate, calcium stearate, sodium stearate, stearic acid, a hydrogenated vegetable oil, a mineral oil, polyethylene glycol, sodium lauryl sulfate, magnesium lauryl sulfate, glyceryl palmitostearate, sodium benzoate, sodium stearyl fumarate, colloidal silicon dioxide, sodium benzoate, sodium oleate, sodium acetate, and combinations thereof. In some embodiments, the lubricant is magnesium stearate.

In some embodiments, the filler is present in an amount of about 1% to about 85% w/w of the total composition.

In some embodiments, the filler is selected from the group consisting of: sucrose, lactose, microcrystalline cellulose, methyl cellulose, ethyl cellulose, hydroxypropyl cellulose, hydroxypropyl methylcellulose, starch, xylitol, sorbitol, mannitol, a polyvinylpyrrolidone, a polyethylene glycol, a polyvinyl alcohol, a polymethacrylate, a poloxamer, magnesium stearate, calcium stearate, sodium stearate, stearic acid, a hydrogenated vegetable oil, a mineral oil, sodium lauryl sulfate, magnesium lauryl sulfate, glyceryl palmitostearate, sodium stearyl fumarate, colloidal silicon dioxide, sodium benzoate, sodium oleate, sodium acetate, and combinations thereof.

In some embodiments, wherein the filler is a binder, a disintegrant, or a combination thereof.

In some embodiments, the disintegrant is present in an amount of about 0.5% to about 5% w/w of the total composition. In some embodiments, the disintegrant is present in an amount of about 4% to about 6% w/w of the total composition. In some embodiments, the disintegrant is present in an amount of about 2.5% w/w of the total composition.

In some embodiments, the disintegrant is selected from the group consisting of: sodium starch glycolate, alginic acid, sodium alginate, croscarmellose sodium anion exchange resin, and combinations thereof. In some embodiments, the disintegrant is sodium starch glycolate.

In some embodiments, first composition is present in an amount of about 90% to about 99% w/w of the total composition. In some embodiments, the first composition is present in an amount of about 97% w/w of the total composition.

In some embodiments, the first composition is present in an amount of about 15% to about 60% w/w of the total composition. In some embodiments, the first composition is present in an amount of about 30% to about 40% w/w of the total composition. In some embodiments, the first composition is present in an amount of about 35% w/w of the total composition.

In some embodiments, the binder is present in an amount of about 40% to about 85% w/w of the total composition. In some embodiments, the binder is present in an amount of about 55% to about 75% w/w of the total composition.

In some embodiments, the binder is selected from the group consisting of: microcrystalline cellulose, a cellulose ether, hydroxypropyl cellulose, hydroxypropyl methylcellulose, sodium carboxy methyl cellulose starch, a cellulose, methyl cellulose, ethyl cellulose, mannitol, xylitol, sorbitol, lactose, sucrose, sorbitol, gelatin, a polyvinylpyrrolidone, a polyethylene glycol, a polyvinyl alcohol, a polymethacrylate, and combinations thereof.

In some embodiments, the binder is microcrystalline cellulose, mannitol, or a combination thereof.

In some embodiments, the microcrystalline cellulose is present in an amount of about 25% to about 35% w/w of the total composition. In some embodiments, the microcrystalline cellulose is present in an amount of about 31% w/w of the total composition.

In some embodiments, mannitol is present in an amount of about 25% to about 35% w/w of the total composition. In some embodiments, the mannitol is present in an amount of about 31% w/w of the total composition.

In some embodiments, the first composition is blended with the pharmaceutical excipients. In some embodiments, the pharmaceutical composition is co-milled.

In some embodiments, the pharmaceutical composition is formulated as a tablet. In some embodiments, the compound of Formula I, or a pharmaceutically acceptable salt, amorphous, or polymorph form thereof, is present in an amount of about 10 mg to about 50 mg. In some embodiments, the compound of Formula I, or a pharmaceutically acceptable salt, amorphous, or polymorph form thereof, is present in an amount of about 25 mg to about 220 mg, more preferably an amount of about 50 mg to about 150 mg, still more preferably in an amount of about 80 mg to about 120 mg, in still yet a more preferably embodiment in amount about of about 100 mg.

Also provided herein is a pharmaceutical composition, wherein the pharmaceutical composition comprises:

(S)-5-amino-3-(4-((5-fluoro-2-methoxybenzamido)
methyl)phenyl)-1-(1,1,1-trifluoropropan-2-yl)-1H-
pyrazole-4-carboxamide;
a HPMCAS polymer; and
one or more pharmaceutical excipients.

In some embodiments, the HPMCAS polymer is HPMCAS-MG.

In some embodiments, the one or more pharmaceutical excipients are selected from the group consisting of: a filler, a lubricant, and a combination thereof.

In some embodiments, the filler is selected from the group consisting of: sucrose, lactose, microcrystalline cellulose, methyl cellulose, ethyl cellulose, hydroxypropyl cellulose, hydroxypropyl methylcellulose, starch, xylitol, sorbitol, mannitol, polyvinylpyrrolidone, a polyethylene glycol, a polyvinyl alcohol, a polymethacrylate, magnesium stearate, calcium stearate, sodium stearate, stearic acid, a hydrogenated vegetable oil, a mineral oil, sodium lauryl sulfate, magnesium lauryl sulfate, glyceryl palmitostearate, sodium stearyl fumarate, colloidal silicon dioxide, sodium benzoate, sodium oleate, sodium acetate, and combinations thereof.

In some embodiments, the lubricant is selected from the group consisting of: magnesium stearate, calcium stearate, sodium stearate, stearic acid, a hydrogenated vegetable oil, a mineral oil, polyethylene glycol, sodium lauryl sulfate, magnesium lauryl sulfate, glyceryl palmitostearate, sodium benzoate, sodium stearyl fumarate, colloidal silicon dioxide, sodium benzoate, sodium oleate, sodium acetate, and combinations thereof.

In some embodiments, the composition comprises:
(S)-5-amino-3-(4-((5-fluoro-2-methoxybenzamido)
methyl)phenyl)-1-(1,1,1-trifluoropropan-2-yl)-1H-
pyrazole-4-carboxamide;
a HPMCAS polymer;
microcrystalline cellulose;
mannitol;
sodium starch glycolate; and
magnesium stearate.

In some embodiments, the composition comprises:
(S)-5-amino-3-(4-((5-fluoro-2-methoxybenzamido)
methyl)phenyl)-1-(1,1,1-trifluoropropan-2-yl)-1H-
pyrazole-4-carboxamide present in an amount of about 5% to about 30% w/w of the composition;
a HPMCAS polymer present in an amount of about 5% to about 30% w/w of the composition;
microcrystalline cellulose present in an amount of about 30% to about 60% w/w of the composition;
mannitol present in an amount of about 30% to about 60% w/w of the composition; sodium starch glycolate present in an amount of about 0.5% to about 5% w/w of the composition; and
magnesium stearate present in an amount of about 0.05% to about 2% w/w of the composition.

In some embodiments, the composition comprises:
(S)-5-amino-3-(4-((5-fluoro-2-methoxybenzamido)
methyl)phenyl)-1-(1,1,1-trifluoropropan-2-yl)-1H-
pyrazole-4-carboxamide present in an amount of about 8% w/w of the composition;
an HPMCAS polymer present in an amount of about 8% w/w of the composition;
microcrystalline cellulose present in an amount of about 40% w/w of the composition;
mannitol present in an amount of about 40% w/w of the composition;
sodium starch glycolate present in an amount of about 3.5% w/w of the composition; and magnesium stearate present in an amount of about 0.3% w/w of the composition.

In some embodiments, the composition comprises:
(S)-5-amino-3-(4-((5-fluoro-2-methoxybenzamido)
methyl)phenyl)-1-(1,1,1-trifluoropropan-2-yl)-1H-
pyrazole-4-carboxamide present in an amount of about 10% to about 30% w/w of the composition;
an HPMCAS polymer present in an amount of about 10% to about 30% w/w of the composition;
microcrystalline cellulose present in an amount of about 20% to about 30% w/w of the composition;
mannitol present in an amount of about 20% to about 30% w/w of the composition; sodium starch glycolate present in an amount of about 2% to about 8% w/w of the composition; and
magnesium stearate present in an amount of about 0.05% to about 2% w/w of the composition.

In some embodiments, herein the composition comprises:
(S)-5-amino-3-(4-((5-fluoro-2-methoxybenzamido)
methyl)phenyl)-1-(1,1,1-trifluoropropan-2-yl)-1H-
pyrazole-4-carboxamide present in an amount of about 22% w/w of the composition;
an HPMCAS polymer present in an amount of about 22% w/w of the composition;
microcrystalline cellulose present in an amount of about 25% w/w the composition;
mannitol present in an amount of about 25% w/w the composition;
sodium starch glycolate present in an amount of about 5% w/w of the composition; and
magnesium stearate present in an amount of about 0.5% w/w of the composition.

In some embodiments, the HPMCAS polymer is HPMCAS-MG.

In some embodiments, the pharmaceutical composition is formulated as a tablet. In some embodiments, the tablet is coated.

Also provided herein is a method for preparing the pharmaceutical composition, comprising:
mixing (S)-5-amino-3-(4-((5-fluoro-2-methoxybenzamido)methyl)phenyl)-1-(1,1,1-trifluoropropan-2-yl)-1H-pyrazole-4-carboxamide, an HPMCAS polymer, and an organic solvent to form a mixture;
spray-drying the mixture to form a spray-dried dispersion; and
granulating the spray-dried dispersion to form a first composition.

In some embodiments, the organic solvent is a mixture of dichloromethane and methanol. In some embodiments, the organic solvent is 80:20 dichloromethane:methanol. In some embodiments, the spray-dried dispersion is blended with one or more pharmaceutical excipients prior to being granulated. In some embodiments, the spray-dried dispersion is dried in an oven prior to being granulated. In some embodiments, the spray-dried dispersion is blended with one or more pharmaceutical excipients prior to being granulated. In some embodiments, the spray-dried dispersion is granulated by roller compaction. In some embodiments, wherein the first composition is blended with one or more pharmaceutical excipients. In some embodiments, the first composition is co-milled. In some embodiments, the first composition is pressed into a tablet. In some embodiments, the tablet is coated. In some embodiments, the coating comprises a polymer, a plasticizer, a pigment, or combinations thereof.

In some embodiments, the ratio of (S)-5-amino-3-(4-((5-fluoro-2-methoxybenzamido)methyl)phenyl)-1-(1,1,1-trifluoropropan-2-yl)-1H-pyrazole-4-carboxamide to the HPMCAS polymer in the spray-dried dispersion is about 1:4 to about 4:1. In some embodiments, the ratio of (S)-5-amino-3-(4-((5-fluoro-2-methoxybenzamido)methyl)phenyl)-1-(1,1,1-trifluoropropan-2-yl)-1H-pyrazole-4-carboxamide to the HPMCAS polymer in the spray-dried dispersion is about 1:1. In some embodiments, the HPMCAS polymer is HPMCAS-MG.

Also provided herein is a crystalline form of the compound of Formula I having the formula

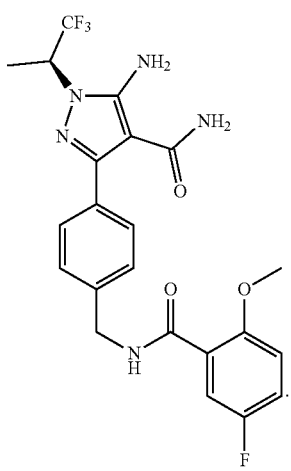

I

Also provided herein is Form A of the compound of Formula I characterized by having an X-ray powder diffraction (XRPD) pattern comprising peaks at °2θ values of 15.8±0.2, 16.2±0.2, and 11.9±0.2.

Also provided herein is Form A of the compound of Formula I characterized by having an X-ray powder diffraction (XRPD) pattern comprising peaks at °2θ values of 15.8±0.2, 16.2±0.2, 11.9±0.2, 19.0±0.2, and 18.3±0.2.

Also provided herein is Form A of the compound of Formula I characterized by having an X-ray powder diffraction (XRPD) pattern comprising peaks at °2θ values of 15.8±0.2, 16.2±0.2, 11.9±0.2, 19.0±0.2, 18.3±0.2, 23.8±0.2, and 20.5±0.2.

Also provided herein is Form A of the compound of Formula I characterized by having an X-ray powder diffraction (XRPD) pattern comprising peaks at °2θ values of 15.8±0.2, 16.2±0.2, 11.9±0.2, 19.0±0.2, 18.3±0.2, 23.8±0.2, 20.5±0.2, 25.7±0.2, 20.1±0.2, and 9.5±0.2.

Also provided herein is Form A of the compound of Formula I characterized by having an X-ray powder diffraction (XRPD) pattern comprising peaks at °2θ values of 15.8±0.2, 16.2±0.2, 11.9±0.2, 19.0±0.2, 18.3±0.2, 23.8±0.2, 20.5±0.2, 25.7±0.2, 20.1±0.2, 9.5±0.2, 25.0±0.2, and 11.1±0.2.

Also provided herein is Form A of the compound of Formula I that has an XRPD pattern substantially as shown in FIG. 4A.

Also provided herein is Form A of the compound of Formula I that has a differential scanning calorimetry (DSC) curve comprising an endotherm with an onset of about 185° C.

Also provided herein is Form A of the compound of Formula I that has a DSC thermogram substantially as shown in FIG. 4C.

Also provided herein is a solid oral pharmaceutical composition comprising a pharmaceutical excipient and a crystalline form the compound of Formula I.

Also provided herein is a solid oral pharmaceutical composition made by mixing a crystalline form of the compound of Formula I and a pharmaceutical excipient.

Also provided herein is a process for making a solid oral pharmaceutical composition comprising mixing a crystalline form of the compound of Formula I and a pharmaceutical excipient.

Also provided herein is a method for treating cancer in a subject in need thereof, the method comprising administering a spray-dried dispersion, a pharmaceutical composition, or a therapeutically effective amount of the compound of Formula I. In some embodiments, the cancer is a BTK-associated cancer.

Also provided herein is a method for treating cancer in a subject in need thereof, the method comprising:
(a) detecting a dysregulation of a BTK gene, a BTK kinase, or expression or activity or level of any of the same; and
(b) administering to the subject the compound of Formula I, or a pharmaceutically acceptable salt, amorphous, or polymorph form thereof, a spray-dried dispersion thereof, or a pharmaceutical composition thereof.

Also provided herein is a method of treating a BTK-associated cancer in a subject, the method comprising administering to a subject identified or diagnosed as having a BTK-associated cancer the compound of Formula I, or a pharmaceutically acceptable salt, amorphous, or polymorph form thereof, a spray-dried dispersion thereof, or a pharmaceutical composition thereof.

Also provided herein is a method of treating a BTK-associated cancer in a subject, the method comprising:
detecting a dysregulation of a BTK gene, a BTK kinase, or expression or activity or level of any of the same; and
administering to a subject determined to have a BTK-associated cancer the compound of Formula I, or a pharmaceutically acceptable salt, amorphous, or polymorph form thereof, a spray-dried dispersion thereof, or a pharmaceutical composition thereof.

Also provided herein is a method of treating a subject, the method comprising administering the compound of Formula I, or a pharmaceutically acceptable salt, amorphous, or polymorph form thereof, a spray-dried dispersion thereof, or a pharmaceutical composition thereof, to a subject having a clinical record that indicates that the subject has a dysregulation of a BTK gene, a BTK kinase, or expression or activity or level of any of the same.

Also provided herein is a method for inhibiting metastasis of a cancer in a subject in need thereof, the method comprising administering to the subject the compound of Formula I, or a pharmaceutically acceptable salt, amorphous, or polymorph form thereof, a spray-dried dispersion thereof, or a pharmaceutical composition thereof.

In some embodiments, the cancer is a BTK-associated cancer

In some embodiments, the compound of Formula I, or a pharmaceutically acceptable salt, amorphous, or polymorph form thereof, a spray-dried dispersion thereof, or a pharmaceutical composition thereof is used in combination with another chemotherapeutic agent.

Also provided here in is a method of selecting a treatment for a subject, the method comprising selecting a treatment comprising administration of the compound of Formula I, or a pharmaceutically acceptable salt, amorphous, or polymorph form thereof, a spray-dried dispersion thereof, or a pharmaceutical composition thereof, for a subject identified or diagnosed as having a BTK-associated cancer.

Also provided herein is a method of selecting a treatment for a subject having a cancer, the method comprising:
- detecting a dysregulation of a BTK gene, a BTK kinase, or expression or activity or level of any of the same in the subject; and
- selecting a treatment for the subject including administration of the compound of Formula I, or a pharmaceutically acceptable salt, amorphous, or polymorph form thereof, a spray-dried dispersion thereof, or a pharmaceutical composition thereof.

Also provided here in is a method of selecting a subject for treatment including administration of the compound of Formula I, or a pharmaceutically acceptable salt, amorphous, or polymorph form thereof, a spray-dried dispersion thereof, or a pharmaceutical composition thereof, the method comprising:
- identifying a subject having a BTK-associated cancer; and
- selecting the subject for treatment including administration of the compound of Formula I, or a pharmaceutically acceptable salt, amorphous, or polymorph form thereof, a spray-dried dispersion thereof, or a pharmaceutical composition thereof.

Also provided herein is a method of selecting a subject having cancer for treatment including administration of the compound of Formula I, or a pharmaceutically acceptable salt, amorphous, or polymorph form thereof, a spray-dried dispersion thereof, or a pharmaceutical composition thereof, the method comprising:
- detecting a dysregulation of a BTK gene, a BTK kinase, or expression or activity or level of any of the same in the subject; and
- selecting the subject for treatment including administration of the compound of Formula I, or a pharmaceutically acceptable salt, amorphous, or polymorph form thereof, a spray-dried dispersion thereof, or a pharmaceutical composition thereof.

In some embodiments, the step of determining if the cancer in the subject is a BTK-associated cancer includes performing an assay to detect dysregulation in a BTK gene, a BTK kinase protein, or expression or activity or level of any of the same in a sample from the subject. In some embodiments, the method further comprises obtaining a sample from the subject. In some embodiments, the sample is a biopsy sample. In some embodiments, the assay is selected from the group consisting of sequencing, immunohistochemistry, immunoblots, enzyme-linked immunosorbent assay, and fluorescence in situ hybridization (FISH). In some embodiments, the FISH is break apart FISH analysis. In some embodiments, the sequencing is pyrosequencing or next generation sequencing.

In some embodiments, the dysregulation in a BTK gene, a BTK kinase protein, or expression or activity or level of any of the same is the result of a dysregulation in BCR signaling pathway gene, a BCR (breakpoint cluster protein) signaling pathway protein, or expression or activity or level of any one of the same.

In some embodiments, the BCR signaling pathway gene or BCR signaling pathway protein is selected from the group consisting of: cyclin-D1, CARD11, CD79B, CD79A, MYD88, and combinations thereof.

In some embodiments, the dysregulation in the BCR signaling pathway gene, a BCR signaling pathway protein, or expression or activity or level of any one of the same is the result of one or more genetic alterations.

In some embodiments, the one or more genetic alterations are selected from the group consisting of: chromosomal translocation t(11;14)(q13;q32), deletions of the chromosomal region 17p13, deletions of the chromosomal region 11q23, deletions of the chromosomal region 13q14, and trisomy of chromosome 12.

In some embodiments, the one or more genetic alterations is one or more point mutations in a gene encoding a BCR signaling pathway protein.

In some embodiments, the one or more point mutations in a gene encoding a BCR signaling pathway protein results in the translation of BCR signaling pathway protein having one or more amino acid substitutions, wherein the BCR signaling pathway protein is selected from the group consisting of: CARD11, CD79B, CD79A, MYD88, and combinations thereof. In some embodiments, the one or more point mutations in a gene encoding a BCR signaling pathway protein results in the translation of BCR signaling pathway protein having one or more amino acid substitutions at one or more of the following amino acid positions: $MYD88^{L265}$. In some embodiments, the amino acid substitution is $MYD88^{L265P}$.

In some embodiments, the dysregulation in a BTK gene, a BTK kinase protein, or expression or activity or level of any of the same is one or more point mutations in the BTK gene. In some embodiments, the one or more point mutations in a BTK gene results in the translation of a BTK protein having one or more amino acid substitutions at one or more of the following amino acid positions: 117, 316, 474, 481, 528, 560, 562, and 601. In some embodiments, the one or more point mutations in a BTK gene results in the translation of a BTK protein having one or more of the following amino acid substitutions: T117P, T316A, T474I, T474M, T474S, C481S, C481F, C481T, C481G, C481R, L528W, P560L, R562W, R562G, and F601L.

Also provided herein is a method for treating cancer in a subject in need thereof, the method comprising:
(a) detecting a dysregulation of a BCR signaling pathway gene, a BCR signaling pathway protein, or expression or activity or level of any of the same; and
(b) administering to the subject the compound of Formula I, or a pharmaceutically acceptable salt, amorphous, or polymorph form thereof, a spray-dried dispersion thereof, or a pharmaceutical composition thereof.

Also provided herein is a method of treating a subject, the method comprising administering the compound of Formula I, or a pharmaceutically acceptable salt, amorphous, or polymorph form thereof, a spray-dried dispersion thereof, or a pharmaceutical composition thereof, to a subject having a clinical record that indicates that the subject has a dysregulation of a BCR signaling pathway gene, a BCR signaling pathway protein, or expression or activity or level of any of the same.

In some embodiments, the BTK-associated cancer is selected from the group consisting of: Hodgkin lymphoma, diffuse large B cell lymphoma (DLBCL) (e.g., activated B cell-like DLBCL (ABC-DLBCL)), follicular lymphoma, mantle cell lymphoma, marginal zone lymphoma (e.g., extranodal marginal zone B cell lymphoma, splenic marginal zone lymphoma), Burkitt lymphoma, Waldenstrom's macroglobulinemia (lymphoplasmacytic lymphoma (LPL)), primary central nervous system lymphoma, small lymphocytic lymphoma, chronic lymphocytic leukemia (CLL), acute lymphocytic leukemia (ALL), B-cell prolymphocytic leukemia, precursor B-lymphoblastic leukemia, hairy cell leukemia, acute myeloid leukemia (AML), chronic myeloid leukemia, multiple myeloma, plasma cell myeloma, plasmacytoma, bone cancer, bone metastasis, breast cancer, gastro-esophageal cancer, pancreatic cancer, ovarian cancer, prostate cancer, lung cancer, colon cancer, uterine cancer, hepatocellular cancer, head and neck cancer, or glioma.

In some embodiments, the BTK-associated cancer is a hematological cancer. In some embodiments, the hematological cancer is selected from the group consisting of: leukemias, lymphomas (non-Hodgkin's lymphoma), Hodgkin's disease, and myeloma.

In some embodiments, the hematological cancer is selected from the group consisting of: acute lymphocytic leukemia (ALL), acute myeloid leukemia (AML), acute promyelocytic leukemia (APL), chronic lymphocytic leukemia (CLL), chronic myeloid leukemia (CML), chronic myelomonocytic leukemia (CMML), chronic neutrophilic leukemia (CNL), acute undifferentiated leukemia (AUL), anaplastic large-cell lymphoma (ALCL), prolymphocytic leukemia (PML), juvenile myelomonocytic leukemia (JMML), adult T-cell ALL, AML with trilineage myelodysplasia (AML/TMDS), mixed lineage leukemia (MLL), myelodysplastic syndromes (MDSs), myeloproliferative disorders (MPD), diffuse large B cell lymphoma (DLBCL) (e.g., activated B cell-like DLBCL (ABC-DLBCL)), follicular lymphoma, mantle cell lymphoma, marginal zone lymphoma (e.g., extranodal marginal zone B cell lymphoma, splenic marginal zone lymphoma), Burkitt lymphoma, Waldenstrom's macroglobulinemia (lymphoplasmacytic lymphoma (LPL)), primary central nervous system lymphoma, small lymphocytic lymphoma, precursor B-lymphoblastic leukemia, hairy cell leukemia, chronic myeloid leukemia, anaplastic large cell lymphoma, MALT lymphoma, plasma cell myeloma, plasmacytoma, and multiple myeloma (MM).

In some embodiments, the BTK-associated cancer is a B-cell malignancy. In some embodiments, the B-cell malignancy is selected from the group consisting of: a Hodgkin lymphoma, diffuse large B cell lymphoma (DLBCL) (e.g., activated B cell-like DLBCL (ABC-DLBCL)), follicular lymphoma, mantle cell lymphoma, marginal zone lymphoma (e.g., extranodal marginal zone B cell lymphoma, splenic marginal zone lymphoma), Burkitt lymphoma, Waldenstrom's macroglobulinemia (lymphoplasmacytic lymphoma (LPL)), primary central nervous system lymphoma, small lymphocytic lymphoma, chronic lymphocytic leukemia, acute lymphoblastic leukemia (ALL), B-cell prolymphocytic leukemia, precursor B-lymphoblastic leukemia, or hairy cell leukemia.

In some embodiments, the BTK-associated cancer is selected from the group consisting of: mantle cell lymphoma, chronic lymphocytic leukemia, small lymphocytic lymphoma, Waldenstrom's macroglobulinemia, and marginal zone lymphoma.

In some embodiments, the BTK-associated cancer has not undergone transformation. Non-limiting examples of transformation in BTK-associated cancers include Richter's transformation, prolymphocytic transformation (e.g., prolymphocytic transformation of CLL), transformed non-Hodgkins lymphoma, and blastoid lymphoma (e.g., blastoid variant mantle cell lymphoma).

In some embodiments, the BTK-associated cancer is not a cancer with known central nervous system involvement by lymphoma.

In some embodiments, the BTK-associated cancer is a solid tumor.

In some embodiments, the solid tumor is selected from the group consisting of: bone cancer, bone metastasis, breast cancer, gastro-esophageal cancer, pancreatic cancer, ovarian cancer, prostate cancer, lung cancer, colon cancer, uterine cancer, hepatocellular cancer, head and neck cancer, and glioma.

In some embodiments, the compound of Formula I, or the pharmaceutically acceptable salt, amorphous, or polymorph form thereof, the spray-dried dispersion thereof, or the pharmaceutical composition thereof is orally administered.

In some embodiments, the method further comprises administering an additional therapy or therapeutic agent to the subject.

In some embodiments, the additional therapy or therapeutic agent is selected from the group consisting of: radiotherapy, cytotoxic chemotherapeutics, kinase-targeted therapeutics, apoptosis modulators, signal transduction inhibitors, immune-targeted therapies, transcriptional regulation inhibitors, and angiogenesis-targeted therapies. In some embodiments, the additional therapeutic agent is selected from one or more kinase-targeted therapeutics. In some embodiments, the kinase-targeted therapeutic targets a kinase from a kinase family selected from: JAK, Src, IRAK, and combinations thereof.

In some embodiments, the additional therapeutic agent is selected from one or more protein inhibitors. In some embodiments, the one or more protein inhibitors inhibit a protein selected from the group consisting of: antiapoptotic proteins, heat shock proteins, nuclear export proteins, kinases, histone deacetylases, E3 ubiquitin ligases, histone-lysine N-methyltransferases, and combinations thereof. In some embodiments, the one or more protein inhibitors inhibit a protein selected from the group consisting of: PI3K, JAK-2, IRAK1, IRAK4, BMX, TAK1, Src family, HDAC6, MDM2, BCL-2, EZH2, EHMT2, PIM, JAK3, mTOR, ROR-1, Syk, PKC, Hsp90, XPO1, and combinations thereof. In some embodiments, two additional therapeutic agents are administered (e.g., an inhibitor of mTOR and an inhibitor of BCL-2).

In some embodiments, the additional therapeutic inhibits a protein selected from the group consisting of: antiapoptotic proteins, heat shock proteins, nuclear export proteins, kinases, histone deacetylases, E3 ubiquitin ligases, histone-lysine N-methyltransferases, and combinations thereof.

In some embodiments, the additional therapeutic inhibits a protein selected from the group consisting of: PI3K, JAK-2, IRAK1, IRAK4, BMX, TAK1, Src family, HDAC6, MDM2, BCL-2, EZH2, EHMT2, PIM, JAK3, mTOR, ROR-1, Syk, PKC, Hsp90, XPO1, and combinations thereof.

In some embodiments, the compound of Formula I, or the pharmaceutically acceptable salt, amorphous, or polymorph form thereof, the spray-dried dispersion thereof, or the pharmaceutical composition thereof and the additional therapeutic agent are administered simultaneously as separate dosages.

In some embodiments, the compound of Formula I, or the pharmaceutically acceptable salt, amorphous, or polymorph form thereof, the spray-dried dispersion thereof, or the pharmaceutical composition thereof and the additional therapeutic agent are administered as separate dosages sequentially in any order.

Also provided herein is a method of treating a subject having a cancer, wherein the method comprises:
(a) administering one or more doses of a first BTK inhibitor to the subject for a period of time;
(b) after (a), determining whether a cancer cell in a sample obtained from the subject has at least one BTK inhibitor resistance mutation that confers increased resistance to a cancer cell or tumor to treatment with the first BTK inhibitor of step (a); and (c) administering a spray-dried dispersion thereof or a pharmaceutical composition of the compound of Formula I, as a monotherapy or in conjunction with another anticancer agent to the subject if the subject has a cancer cell that has at least one BTK inhibitor resistance mutation that confers increased resistance to a cancer cell or tumor to treatment with the first BTK inhibitor of step (a); or (d) administering additional doses of the first BTK inhibitor of step (a) to the subject if the subject has a cancer cell that does not have a BTK inhibitor resistance mutation that confers increased resistance to a cancer cell or tumor to treatment with the first BTK inhibitor of step (a).

In some embodiments, the anticancer agent in step (c) is a second BTK inhibitor, an immunotherapy, or a combination thereof.

In some embodiments, the anticancer agent in step (c) is the first BTK inhibitor administered in step (a).

In some embodiments, the anticancer agent in step (c) is selected from one or more kinase-targeted therapeutics. In some embodiments, the kinase-targeted therapeutic targets a kinase from a kinase family selected from: JAK, Src, IRAK, and combinations thereof.

In some embodiments, the anticancer agent in step (c) is a protein inhibitor that inhibits a protein selected from the group consisting of: antiapoptotic proteins, heat shock proteins, nuclear export proteins, kinases, histone deacetylases, E3 ubiquitin ligases, histone-lysine N-methyltransferases, and combinations thereof.

In some embodiments, the anticancer agent in step (c) is selected from one or more protein inhibitors that inhibit a protein selected from the group consisting of antiapoptotic proteins, heat shock proteins, nuclear export proteins, kinases, histone deacetylases, E3 ubiquitin ligases, histone-lysine N-methyltransferases, and combinations thereof.

In some embodiments, the protein inhibitor inhibits a protein selected from the group consisting of: PI3K, JAK-2, IRAK1, IRAK4, BMX, TAK1, Src family, HDAC6, MDM2, BCL-2, EZH2, EHMT2, PIM, JAK3, mTOR, ROR-1, Syk, PKC, Hsp90, XPO1, and combinations thereof.

In some embodiments, the subject is administered additional doses of the first BTK inhibitor of step (a), and the method further comprises (e) administering another anticancer agent to the subject.

In some embodiments, wherein the anticancer agent of step (e) is a second BTK inhibitor, an immunotherapy, or a combination thereof.

In some embodiments, the anticancer agent of step (e) is the compound of Formula I, or a pharmaceutically acceptable salt, amorphous, or polymorph form thereof, a spray-dried dispersion thereof, or a pharmaceutical composition thereof.

Also provided herein is a method of treating a subject having a cancer, wherein the method comprises:
(a) administering one or more doses of a first BTK inhibitor, to the subject for a period of time;
(b) after (a), determining whether a cancer cell in a sample obtained from the subject has at least one BTK inhibitor resistance mutation that confers increased resistance to a cancer cell or tumor to treatment with the first BTK inhibitor of step (a);
(c) administering a second BTK inhibitor as a monotherapy or in conjunction with another anticancer agent to the subject if the subject has a cancer cell that has at least one BTK inhibitor resistance mutation that confers increased resistance to a cancer cell or tumor to treatment with the first BTK inhibitor of step (a); or
(d) administering additional doses of the first BTK inhibitor of step (a) to the subject if the subject has a cancer cell that does not have a BTK inhibitor resistance mutation that confers increased resistance to a cancer cell or tumor to treatment with the first BTK inhibitor of step (a); wherein the mutation is a substitution at amino acid position 481, e.g., C481S, C481F, C481T, C481G, and C481R.

In some embodiments, the anticancer agent of step (c) is the first BTK inhibitor administered in step (a).

In some embodiments, the subject is administered additional doses of the first BTK inhibitor of step (a), and the method further comprises (e) administering another anticancer agent.

In some embodiments, the anticancer agent of step (e) is a second BTK inhibitor, an immunotherapy, or a combination thereof.

In some embodiments, the anticancer agent of step (e) is a pharmaceutical composition of the compound of Formula I, or a pharmaceutically acceptable salt thereof.

Also provided herein is a method of treating a subject having a cancer, wherein the method comprises:
(a) administering one or more doses of a first BTK inhibitor, to the subject for a period of time;
(b) after (a), determining whether a cancer cell in a sample obtained from the subject has at least one BTK inhibitor resistance mutation that confers increased resistance to a cancer cell or tumor to treatment with the first BTK inhibitor of step (a);
(c) administering a spray-dried dispersion or a pharmaceutical composition according of the compound of Formula I or a pharmaceutically acceptable salt thereof, as a monotherapy or in conjunction with another anticancer agent to the subject if the subject has a cancer cell that has at least one BTK inhibitor resistance mutation that confers increased resistance to a cancer cell or tumor to treatment with the first BTK inhibitor of step (a); or
(d) administering additional doses of the first BTK inhibitor of step (a) to the subject if the subject has a cancer cell that does not have a BTK inhibitor resistance mutation that confers increased resistance to a cancer cell or tumor to treatment with the first BTK inhibitor of step (a); wherein the mutation is a substitution at one or more amino acid positions 244, 257, 334, 495, 664, 665, 707, 708, 742, 845, 848, 993, 1140, or 1141 of PLCγ2.

Also provided herein is a method of treating a subject having a cancer, wherein the method comprises:
(a) determining whether a cancer cell in a sample obtained from a subject having a cancer and previously administered one or more doses of a first BTK inhibitor has one or more BTK inhibitor resistance mutations that confer increased resistance to a cancer cell or tumor to treatment with the first BTK inhibitor that is previously administered to the subject; and
(b) administering a spray-dried dispersion according or a pharmaceutical composition of the compound of Formula I or a pharmaceutically acceptable salt thereof, as a monotherapy or in conjunction with another anticancer agent to the subject if the subject has a cancer cell that has at least one BTK inhibitor resistance mutation that confers increased resistance to a cancer cell or tumor to treatment with the first BTK inhibitor that is previously administered to the subject; or (c) administering additional doses of the first BTK inhibitor to the subject if the subject has cancer cell that does not have a BTK inhibitor resistance mutation that confers increased resistance to a cancer cell or tumor to treatment with the first BTK inhibitor previously administered to the subject.

Also provided herein is a method of treating a subject having a cancer, wherein the method comprises:
(a) determining whether a cancer cell in a sample obtained from a subject having a cancer and previously administered one or more doses of a first BTK inhibitor has one or more BTK inhibitor resistance mutations that confer increased resistance to a cancer cell or tumor to treatment with the first BTK inhibitor previously administered to the subject; and
(b) administering a second BTK inhibitor to the subject as a monotherapy or in conjunction with another anticancer agent to the subject if the subject has a cancer cell that has at least one BTK inhibitor resistance mutation that confers increased resistance to a cancer cell or tumor to treatment with the first BTK inhibitor that is previously administered to the subject; or
(c) administering additional doses of the first BTK inhibitor that is previously administered to the subject if the subject has cancer cell that does not have a BTK inhibitor resistance mutation that confers increased resistance to a cancer cell or tumor to treatment with the first BTK inhibitor that is previously administered to the subject.

Also provided herein is a method of treating a subject having a cancer, wherein the method comprises:
(a) administering one or more doses of a spray-dried dispersion or a pharmaceutical composition of the compound of Formula I, or a pharmaceutically acceptable salt thereof, for a period of time;
(b) after (a), determining whether a cancer cell in a sample obtained from the subject has one or more BTK inhibitor resistance mutations that confer increased resistance to a cancer cell or tumor to treatment with the spray-dried dispersion or the pharmaceutical composition of the compound of Formula I, or a pharmaceutically acceptable salt thereof, of step (a); and
(c) administering a second BTK inhibitor as a monotherapy or in conjunction with another anticancer agent to a subject having a cancer cell that has one or more BTK inhibitor resistance mutations that confer increased resistance to a cancer cell or tumor to treatment with the spray-dried dispersion or the pharmaceutical composition of the compound of Formula I, of step (a); or
(d) administering additional doses of the spray-dried dispersion or the pharmaceutical composition of the compound of Formula I, or a pharmaceutically acceptable salt thereof, of step (a) to a subject having a cancer cell that does not have a BTK inhibitor resistance mutation that confers increased resistance to a cancer cell or tumor to treatment with the spray-dried dispersion or the pharmaceutical composition of the compound of Formula I, or a pharmaceutically acceptable salt thereof, of step (a).

Also provided herein are is a method of treating a subject having a cancer, wherein the method comprises:
(a) determining whether a cancer cell in a sample obtained from a subject having a cancer and previously administered one or more doses of a spray-dried dispersion or a pharmaceutical composition of the compound of Formula I, or a pharmaceutically acceptable salt thereof, has one or more BTK inhibitor resistance mutations that confer increased resistance to a cancer cell or tumor to treatment with the spray-dried dispersion or the pharmaceutical composition of the compound of Formula I, or a pharmaceutically acceptable salt thereof, that is previously administered to the subject;
(b) administering a second BTK inhibitor as a monotherapy or in conjunction with another anticancer agent to a subject having a cancer cell that has one or more BTK inhibitor resistance mutations that confer increased resistance to a cancer cell or tumor to treatment with the spray-dried dispersion or the pharmaceutical composition of the compound of Formula I, or a pharmaceutically acceptable salt thereof, that is previously administered to the subject; or
(c) administering additional doses of the spray-dried dispersion or the pharmaceutical composition of the compound of Formula I, or a pharmaceutically acceptable salt thereof, previously administered to a subject having a cancer cell that does not have a BTK inhibitor resistance mutation that confers increased resistance to a cancer cell or tumor to treatment with the spray-dried dispersion or the pharmaceutical composition of the compound of Formula I, or a pharmaceutically acceptable salt thereof, that is previously administered to the subject.

Also provided herein is a method of treating a BTK-associated cancer in a subject, the method comprising:
(a) administering one or more doses of a spray-dried dispersion or a pharmaceutical composition of the compound of Formula I, or a pharmaceutically acceptable salt thereof, as a monotherapy to a subject identified or diagnosed as having a BTK-associated cancer;
(b) after step (a), determining a level of circulating tumor DNA in a biological sample obtained from the subject;
(c) administering a spray-dried dispersion or a pharmaceutical composition of the compound of Formula I, or a pharmaceutically acceptable salt thereof, and an additional therapeutic agent or treatment to a subject identified as having about the same or an elevated level of circulating tumor DNA as compared to a reference level of circulating tumor DNA.

In some embodiments, the additional therapeutic agent is a second BTK kinase inhibitor. In some embodiments, the additional therapeutic agent or treatment comprises one or more of radiation therapy, a chemotherapeutic agent, a checkpoint inhibitor, surgery, and one or more second kinase inhibitors.

In some embodiments, the reference level of circulating tumor DNA is a level of circulating tumor DNA in a biological sample obtained from the subject prior to step (a).

Also provided herein is a method of treating a BTK-associated cancer in a subject, the method comprising: administering a therapeutically effective amount of a spray-dried dispersion or a pharmaceutical composition of the compound of Formula I, or a pharmaceutically acceptable salt thereof, and an additional therapeutic agent or treatment to a subject (i) identified or diagnosed as having a BTK-associated cancer, (ii) previously administered one or more doses of the spray-dried dispersion or the pharmaceutical composition of the compound of Formula I, or a pharmaceutically acceptable salt thereof, as a monotherapy, and (ii) after administration of the one or more doses of the spray-dried dispersion or a pharmaceutical composition of the compound of Formula I, or the pharmaceutically acceptable salt thereof, as a monotherapy, identified as having about the same or an elevated level of circulating tumor DNA as compared to a reference level of circulating tumor DNA.

In some embodiments, the reference level of circulating tumor DNA is a level of circulating tumor DNA in a biological sample obtained from the subject prior to administration of the one or more doses of the compound of Formula I, or a pharmaceutically acceptable salt, amorphous, or polymorph form thereof, a spray-dried dispersion thereof, or a pharmaceutical composition thereof, as a monotherapy.

In some embodiments, the additional therapeutic agent is a second BTK kinase inhibitor. In some embodiments, the additional therapeutic agent or treatment comprises one or more of radiation therapy, a chemotherapeutic agent, a checkpoint inhibitor, surgery, and one or more second protein inhibitors.

Also provided herein is a method of selecting a treatment for a subject, the method comprising: selecting a therapeutically effective amount of a spray-dried dispersion or a pharmaceutical composition of the compound of Formula I, or a pharmaceutically acceptable salt thereof, for a subject (i) identified or diagnosed as having a BTK-associated cancer, (ii) previously administered one or more doses of a second BTK kinase inhibitor, and (ii) after administration of the one or more doses of the second BTK kinase inhibitor, identified as having about the same or an elevated level of circulating tumor DNA as compared to a reference level of circulating tumor DNA.

Also provided herein is a method of selecting a treatment for a subject, the method comprising: selecting a therapeutically effective amount of a spray-dried dispersion or a pharmaceutical composition of the compound of Formula I, or a pharmaceutically acceptable salt thereof, and an additional therapeutic treatment for a subject (i) identified or diagnosed as having a BTK-associated cancer, (ii) previously administered one or more doses of the spray-dried dispersion or the pharmaceutical composition of the compound of Formula I, or a pharmaceutically acceptable salt thereof, as a monotherapy, and (ii) after administration of the one or more doses of the spray-dried dispersion or the pharmaceutical composition of the compound of Formula I, or a pharmaceutically acceptable salt thereof, identified as having about the same or an elevated level of circulating tumor DNA as compared to a reference level of circulating tumor DNA.

In some embodiments, the reference level of circulating tumor DNA is a level of circulating tumor DNA in a biological sample obtained from the subject prior to administration of the one or more doses of the compound of Formula I, or a pharmaceutically acceptable salt, amorphous, or polymorph form thereof, a spray-dried dispersion thereof, or a pharmaceutical composition thereof, as a monotherapy. In some embodiments, the additional therapeutic treatment is a second BTK kinase inhibitor. In some embodiments, the additional therapeutic treatment comprises one or more of radiation therapy, a chemotherapeutic agent, a checkpoint inhibitor, and one or more second protein inhibitors.

Also provided herein is a method of determining efficacy of a treatment in a subject, the method comprising:
(a) determining a first level of circulating tumor DNA in a biological sample obtained from a subject identified or diagnosed as having a BTK-associated cancer at a first time point;
(b) administering a treatment comprising one or more doses of a spray-dried dispersion or a pharmaceutical composition of the compound of Formula I, or a pharmaceutically acceptable salt thereof, to the subject, after the first time point and before a second time point;
(c) determining a second level of circulating tumor DNA in a biological sample obtained from the subject at the second time point; and
(d) identifying that the treatment is effective in a subject determined to have a decreased second level of circulating tumor DNA as compared to the first level of circulating tumor DNA; or
identifying the treatment is not effective in a subject determined to have about the same or an elevated second level of circulating tumor DNA as compared to the first level of circulating tumor DNA.

Also provided herein is a method of determining whether a subject has developed resistance to a treatment, the method comprising:
(a) determining a first level of circulating tumor DNA in a biological sample obtained from a subject identified or diagnosed as having a BTK-associated cancer at a first time point;
(b) administering a treatment comprising one or more doses of a spray-dried dispersion or a pharmaceutical composition of the compound of Formula I, or a pharmaceutically acceptable salt thereof, to the subject, after the first time point and before a second time point;
(c) determining a second level of circulating tumor DNA in a biological sample obtained from the subject at the second time point; and
(d) determining that a subject having a decreased second level of circulating tumor DNA as compared to the first level of circulating tumor DNA has not developed resistance to the treatment; or
determining that a subject having about the same or an elevated second level of circulating tumor DNA as compared to the first level of circulating tumor DNA has developed resistance to the treatment.

In some of any of the above embodiments, the subject does not have active uncontrolled autoimmune cytopenia. In some embodiments, the subject has not been diagnosed with autoimmune cytopenia. In some embodiments, the subject does not have clinically significant, uncontrolled cardiac, cardiovascular disease or history of myocardial infarction within 6 months of beginning a treatment as described herein. In some embodiments, the subject has not been diagnosed with a cardiac or cardiovascular disease. In some embodiments, the subject has not had a myocardial infarction. In some embodiments, the subject does not have a clinically significant active malabsorption syndrome. In some embodiments, the subject has not been diagnosed with a malabsorption syndrome. In some embodiments, the subject is not being treated with strong cytochrome P450 3A4 (CYP3A4) inhibitors (e.g., ritonavir, indinavir, nelfinavir, saquinavir, clarithromycin, telithromycin, chloramphenicol, ketoconazole, itraconazole, posaconazole, voriconazole, nefazodone, and cobicistat) or inducers (e.g., carbamazepine, dexamethasone, ethosuximide, glucocorticoids, griseofulvin, phenytoin, primidone, progesterone, rifampin, nafcillin, nelfinavir, nevirapine, oxcarbazepine, phenobarbital, phenylbutazone, rofecoxib (mild), st john's wort, sulfadimidine, sulfinpyrazone, and troglitazone) during any of the treatments as described herein. In some embodiments, the subject is not being treated with proton pump inhibitors (e.g., omeprazole, lansoprazole, dexlansoprazole, esomeprazole, pantoprazole, rabeprazole, ilaprazole) within 7 days of starting any of the treatments described herein. In some embodiments, the subject does not have an active second malignancy. In some embodiments, the subject has an active second malignancy, which is in remission, and the life expectancy of the subject is >2 years.

Also provided herein is a method for inhibiting BTK kinase activity in a mammalian cell, the method comprising contacting the mammalian cell with a spray-dried dispersion, a pharmaceutical composition, or a polymorph form, of the compound of Formula I, or a pharmaceutically acceptable salt thereof.

Also provided herein is a method of treating an autoimmune or inflammatory disease in a subject, the method comprising administering to a subject identified or diagnosed as having an autoimmune or inflammatory disease a spray-dried dispersion or a pharmaceutical composition of the compound of Formula I, or a pharmaceutically acceptable salt thereof to the subject.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 2A is a differential scanning calorimetry (DSC) scan of a mixture of polymorphs Form A and Form B of the compound of Formula I. FIG. 2B is a 1H NMR spectrum of the mixture of polymorphs Form A and Form B of the compound of Formula I.

FIG. 3A is a 1H NMR spectrum of Form C of the compound of Formula I. FIG. 3B is a differential scanning calorimetry scan of Form C of the compound of Formula I (hemi-1,4-dioxane solvate).

FIG. 4A is an X-ray powder diffraction scan of Form A of the compound of Formula I. FIG. 4B is a 1H NMR spectrum of Form A of the compound of Formula I. FIG. 4C is a differential scanning calorimetry scan of Form A of the compound of Formula I.

FIGS. 10A and 10B are Western blots showing the compound of Formula I and ibrutinib dose response effects on Y223 autophosphorylation in HEK293 cells stably expressing BTK (tBTK) refers to total BTK) (FIG. 10A) and BTK C481S (FIG. 10B). FIGS. 10C and 10D are dose response curves generated from the Western blot data for Y223 autophosphorylation in HEK293 cells stably expressing BTK (FIG. 10C) and BTK C481S (FIG. 10D). The compound of Formula I inhibited autophosphorylation of BTK Y223 in both wild type and the C481S mutant proteins with IC50 values of 8.6±0.3 nM and 8.8±1.8 nM, respectively. Ibrutinib inhibited BTK wild type with an IC50 of 5.7±0.5 nM, and its activity on the C481S mutant could not be fit to an IC50 curve.

FIG. 13A shows tumor growth with the tumor volumes displayed as mean±SEM for the human B-cell lymphoma cell line xenograft tumor mouse model dosed with the indicated vehicle or inhibitor. FIG. 13B shows the tumor growth after treatment is stopped in the human B-cell lymphoma cell line xenograft tumor mouse model. FIG. 13C shows the normalized body weight values displayed as mean±SEM for the mice during the course of treatment.

FIG. 14A shows tumor growth with the tumor volumes displayed as mean±SEM for the TMD8 human B-cell lymphoma cell line xenograft tumor mouse model dosed with the indicated vehicle or inhibitor. FIG. 14B shows the tumor weights after 14 days of dosing with the compound of Formula I in the TMD8 human B-cell lymphoma cell line xenograft tumor mouse model. FIG. 14C shows the normalized body weight values displayed as mean±SEM for the mice during the course of treatment.

FIG. 15A shows the concentration of the compound of Formula I in plasma for fed or fasted dogs for dogs administered crystalline compound of Formula I in suspension.

FIG. 15B shows the concentration of the compound of Formula I in plasma for fed or fasted dogs for dogs administered the compound of Formula I 50% SDI.

Like reference symbols in the various drawings indicate like elements.

DETAILED DESCRIPTION

Definitions

Figure 1:
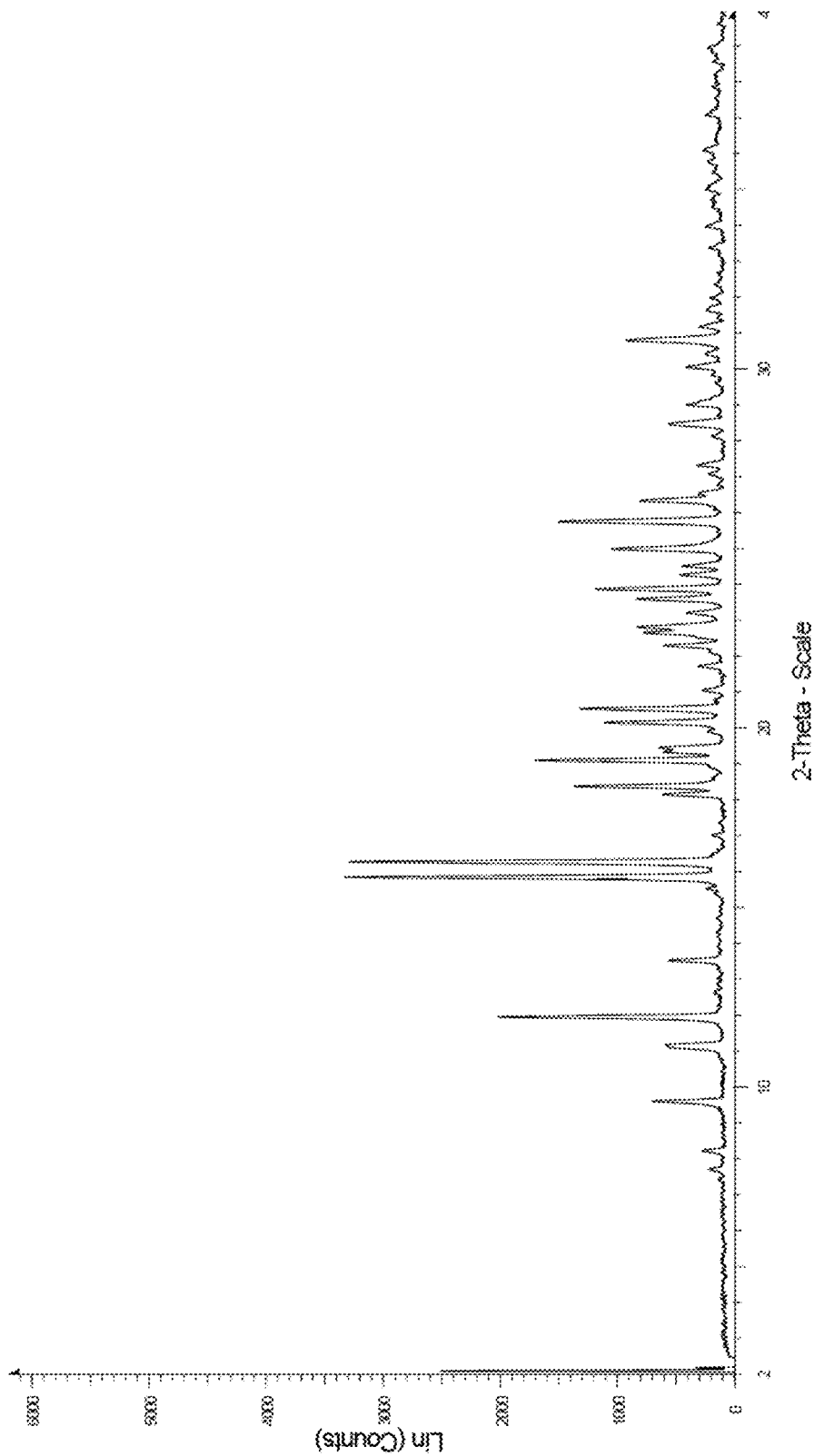
FIG. 1 is an X-ray powder diffraction scan of Form A of the compound of Formula I (free base).

The term "polymorph," as used herein, refers to crystals of the same compound having different physical properties as a result of the order of the molecules in the crystal lattice. Different polymorphs of a single compound have one or more different chemical, physical, mechanical, electrical, thermodynamic, and/or biological properties from each other. Differences in physical properties exhibited by polymorphs can affect pharmaceutical parameters such as storage stability, compressibility, density (important in composition and product manufacturing), dissolution rates (an important factor in determining bio-availability), solubility, melting point, chemical stability, physical stability, powder flowability, water sorption, compaction, and particle morphology. Differences in stability can result from changes in chemical reactivity (e.g., differential oxidation, such that a dosage form discolors more rapidly when comprised of one polymorph than when comprised of another polymorph) or mechanical changes (e.g., crystal changes on storage as a kinetically favored polymorph converts to a thermodynamically more stable polymorph) or both (e.g., one polymorph is more hygroscopic than the other). As a result of solubility/ dissolution differences, some transitions affect potency and/ or toxicity. In addition, the physical properties of the crystal may be important in processing; for example, one polymorph might be more likely to form solvates or might be difficult to filter and wash free of impurities (i.e., particle shape and size distribution might be different between one polymorph relative to the other). "Polymorph", as used herein, does not include amorphous forms of the compound. As used herein, "amorphous" refers to a noncrystalline form of a compound which can be a solid state form of the compound or a solubilized form of the compound. For example, "amorphous" refers to a compound (e.g., a solid form of the compound) without a regularly repeating arrangement of molecules or external face planes.

The term "anhydrous," as used herein, refers to a crystal form of the compound of Formula I that has 1% or less by weight water. For example, 0.5% or less, 0.25% or less, or 0.1% or less by weight water.

The term "solvate" as used herein refers to a crystalline form of the compound of Formula I, such as a polymorph form of the compound, where the crystal lattice comprises one or more solvents of crystallization.

"Purity," when used in reference to a composition including a polymorph of the compound of Formula I, refers to the percentage of one specific polymorph form relative to another polymorph form or an amorphous form of the compound of Formula I in the referenced composition. For example, a composition comprising polymorph Form 1 having a purity of 90% would comprise 90 weight parts Form 1 and 10 weight parts of other polymorph and/or amorphous forms of the compound of Formula I.

As used herein, a compound or composition is "substantially free of" one or more other components if the compound or composition contains no significant amount of such other components. For example, the composition can contain less than 5%, 4%, 3%, 2%, or 1% by weight of other components. Such components can include starting materials, residual solvents, or any other impurities that can result from the preparation of and/or isolation of the compounds and compositions provided herein. In some embodiments, a polymorph form provided herein is substantially free of other polymorph forms. In some embodiments, a particular polymorph of the compound of Formula I is "substantially free" of other polymorphs if the particular polymorph constitutes at least about 95% by weight of the compound of Formula I present. In some embodiments, a particular polymorph of the compound of Formula I is "substantially free" of other polymorphs if the particular polymorph constitutes at least about 97%, about 98%, about 99%, or about 99.5% by weight of the compound of Formula I present. In certain embodiments, a particular polymorph of the compound of Formula I is "substantially free" of water if the amount of water constitutes no more than about 2%, about 1%, or about 0.5% by weight of the polymorph.

As used herein, "substantially pure," when used in reference to a polymorph form of the compound of Formula I, means a sample of a polymorph form of the compound having a purity greater than 90%, including greater than 90%, 91%, 92%, 93%, 94%, 95%, 96%, 97%, 98%, and 99%, and also including equal to about 100% of the compound, based on the weight of the compound. The remaining material comprises other form(s) of the compound, and/or reaction impurities and/or processing impurities arising from its preparation. For example, a polymorph form of the compound of Formula I may be deemed substantially pure in that it has a purity greater than 90% of a polymorph form of the compound of Formula I, as measured by means that are at this time known and generally accepted in the art, where the remaining less than 10% of material comprises other form(s) of the compound of Formula I and/or reaction impurities and/or processing impurities. The presence of reaction impurities and/or processing impurities may be determined by analytical techniques known in the art, such as, for example, chromatography, nuclear magnetic resonance spectroscopy, mass spectrometry, or infrared spectroscopy.

The term "about" preceding a value for DSC, TGA, TG, (glass transition temperature) or DTA (Differential Thermal Analysis), which are reported as degrees Celsius, have an allowable variability of ±5° C.

To provide a more concise description, some of the quantitative expressions herein are recited as a range from about amount X to about amount Y It is understood that when a range is recited, the range is not limited to the recited upper and lower bounds, but rather includes the full range from about amount X through about amount Y, or any range therein.

"Room temperature" or "RT" refers to the ambient temperature of a typical laboratory, which is typically around 25° C.

"Spray-drying" refers to the method of producing a dry powder from a solution or slurry. The solution or slurry is atomized or rapidly dried with a hot gas, e.g., air or nitrogen, that causes the solvent to evaporate quickly and uniformly. A "spray-dried dispersion" refers to the powder obtained from the spray-drying process.

The term "pharmaceutically acceptable carrier" or "pharmaceutically acceptable excipient" includes any and all solvents, co-solvents, complexing agents, dispersion media, coatings, antibacterial and antifungal agents, isotonic and absorption delaying agents, and the like, which are not biologically or otherwise undesirable. The use of such media and agents for pharmaceutically active substances is well-known in the art. Except insofar as any conventional media or agent is incompatible with the active ingredient, its use in the therapeutic compositions provided herein is contemplated. Supplementary active ingredients can also be incorporated into the compositions. In addition, various excipients, such as are commonly used in the art, can be included. These and other such compounds are described in the literature, e.g., in the Merck Index, Merck & Company, Rahway, NJ. Considerations for the inclusion of various components in pharmaceutical compositions are described, e.g., in Gilman et al. (Eds.) (2010); Goodman and Gilman's: The Pharmacological Basis of Therapeutics, 12th Ed., The McGraw-Hill Companies.

As used herein, the terms "subject," "individual," or "patient," used interchangeably, refer to any animal, including mammals such as mice, rats, other rodents, rabbits, dogs, cats, swine, cattle, sheep, horses, primates, and humans. In some embodiments, the subject is a human.

In some embodiments, the subject has experienced and/or exhibited at least one symptom of the disease or disorder to be treated and/or prevented. In some embodiments, the subject has been identified or diagnosed as having a cancer with dysregulation of a BTK gene, a BTK protein, or expression or activity, or level of any of the same (a BTK-associated cancer) (e.g., as determined using a regulatory agency-approved, e.g., FDA-approved, assay or kit). In some embodiments, the subject has a tumor that is positive for dysregulation of a BTK gene, a BTK protein, or expression or activity, or level of any of the same (e.g., as determined using a regulatory agency-approved assay or kit). The subject can be a subject with a tumor(s) that is positive for dysregulation of a BTK gene, a BTK protein, or expression or activity, or level of any of the same (e.g., identified as positive using a regulatory agency-approved, e.g., FDA-approved, assay or kit). The subject can be a subject whose tumors have dysregulation of a BTK gene, a BTK protein, or expression or activity, or a level of the same (e.g., where the tumor is identified as such using a regulatory agency-approved, e.g., FDA-approved, kit or assay). In some embodiments, the subject is suspected of having a BTK-associated cancer. In some embodiments, the subject has been identified or diagnosed as having a hematological cancer. In some embodiments, the subject has been identified or diagnosed as having a B-cell malignancy. In some embodiments, the subject has a clinical record indicating that the subject has a tumor that has dysregulation of a BTK gene, a BTK protein, or expression or activity, or level of any of the same (and optionally the clinical record indicates that the subject should be treated with any of the compositions provided herein). In some embodiments, the subject is a pediatric patient.

The term "pediatric patient" as used herein refers to a patient under the age of 21 years at the time of diagnosis or treatment. The term "pediatric" can be further divided into various subpopulations including: neonates (from birth through the first month of life); infants (1 month up to two years of age); children (two years of age up to 12 years of age); and adolescents (12 years of age through 21 years of age (up to, but not including, the twenty-second birthday)). Berhman R E, Kliegman R, Arvin A M, Nelson W E, *Textbook of Pediatrics,* 15th Ed. Philadelphia: W. B. Saunders Company, 1996; Rudolph A M, et al., *Rudolph's Pediatrics,* 21st Ed. New York: McGraw-Hill, 2002; and Avery M D, First L R, *Pediatric Medicine,* 2nd Ed. Baltimore: Williams & Wilkins; 1994. In some embodiments, a pediatric patient is from birth through the first 28 days of life, from 29 days of age to less than two years of age, from two years of age to less than 12 years of age, or 12 years of age through 21 years of age (up to, but not including, the twenty-second birthday). In some embodiments, a pediatric patient is from birth through the first 28 days of life, from 29 days of age to less than 1 year of age, from one month of age to less than four months of age, from three months of age to less than seven months of age, from six months of age to less than 1 year of age, from 1 year of age to less than 2 years of age, from 2 years of age to less than 3 years of age, from 2 years of age to less than seven years of age, from 3 years of age to less than 5 years of age, from 5 years of age to less than 10 years of age, from 6 years of age to less than 13 years of age, from 10 years of age to less than 15 years of age, or from 15 years of age to less than 22 years of age.

As used herein, the terms "treat" or "treatment" refer to therapeutic or palliative measures. Beneficial or desired clinical results include, but are not limited to, alleviation, in whole or in part, of symptoms associated with a disease or disorder or condition, diminishment of the extent of disease, stabilized (i.e., not worsening) state of disease, delay or slowing of disease progression, amelioration or palliation of the disease state (e.g., one or more symptoms of the disease), and remission (whether partial or total), whether detectable or undetectable. "Treatment" can also mean prolonging survival as compared to expected survival if not receiving treatment.

The term "therapy" refers to the administration of one or more doses of an active compound or pharmaceutical agent to a subject as part of a therapeutic regimen.

In one embodiment, the term "preventing" as used herein means the prevention of the onset, recurrence or spread, in whole or in part, of the disease or condition as described herein (e.g., multiple types of pain including inflammatory pain, neuropathic pain, and pain associated with cancer, surgery, and bone fracture), or a symptom thereof.

The term "progression" refers to cancer that becomes worse or spreads in the body, as defined by the National Cancer Institute (NCI Dictionary of Cancer Terms). For example, progression can include an increase in the number of cancer cells in the subject, an increase in the size of one or more tumors in the subject, an increase in tumor burden, an increase in the rate or extent of metastasis, worsening symptoms, in whole or in part, associated with the cancer, an increase in the extent of disease, and/or an acceleration of disease progression. "Progression" can also mean shortening survival as compared to expected survival if not receiving therapy. In some embodiments, progression can include detecting one or more of an increase in the percentage of blast cells, an increase in the myeloid to erythroid ratio, an increase in dysplasia (e.g., white blood cell dysplasia), an increase in the percentage of bone marrow plasma cells, and an increase in the percentage of bone marrow lymphocytes (see e.g., Sever, et al., Arch Pathol Lab Med. 2016 September; 140(9):932-49, which is incorporated by reference herein in its entirety). In some embodiments, progression can include detecting one or more of an increase in the percentage of leukocytes (e.g., polymorphonuclear leukocytes), a decrease in the number of platelets, and a decrease in hemoglobin in peripheral blood. In some embodiments, the tumor burden can be assessed using RECIST (e.g., RECIST version 1 or version 1.1). See, for example, Eisenhauer et al., Eur. J. Cancer. 2009, 45(2):228-47, which is incorporated by reference in its entirety herein. In some embodiments, the tumor burden can be assessed using PERCIST. See, for example, Wahl, et al. J. nucl. med. 2009, 50:122S-150S, which is incorporated by reference in its entirety herein.

The term "relapse" refers to the return of a disease or the signs and symptoms of a disease after a period of improvement, as defined by the National Cancer Institute (NCI Dictionary of Cancer Terms). For example, relapse can include detecting an increase in the number of cancer cells in the subject, an increase in the size of one or more tumors in the subject, an increase in tumor burden, an increase in the rate or extent of metastasis, worsening symptoms, in whole or in part, associated with the cancer, an increase in the extent of disease, and/or an acceleration of disease progression after a period of improvement. In some embodiments, relapse can include progression of the cancer after a period of improvement. In some embodiments, a period of improvement can include detecting a decrease in the number of cancer cells in a subject, a decrease in the size of one or more tumors in the subject, a decrease in tumor burden, a decrease in the rate or extent of metastasis, improving symptoms, in whole or in part, associated with the cancer, a decrease in the extent of disease, and/or a slowing of disease progression. In some embodiments, relapse can include detecting one or more of an increase in the percentage of blast cells, an increase in the myeloid to erythroid ratio, an increase in dysplasia (e.g., white blood cell dysplasia), an increase in the percentage of bone marrow plasma cells, and an increase in the percentage of bone marrow lymphocytes after a period of improvement. In some embodiments, a period of improvement can include detecting one or more of a decrease in the percentage of blast cells, a decrease in the myeloid to erythroid ratio, a decrease in dysplasia (e.g., white blood cell dysplasia), a decrease in the percentage of bone marrow plasma cells, and a decrease in the percentage of bone marrow. In some embodiments, relapse can include detecting one or more of an increase in the percentage of leukocytes (e.g., polymorphonuclear leukocytes), a decrease in the number of platelets, and a decrease in hemoglobin in peripheral blood after a period of improvement. In some embodiments, a period of improvement can include detecting one or more of a decrease in the percentage of leukocytes (e.g., polymorphonuclear leukocytes), an increase in the number of platelets, and an increase in hemoglobin in peripheral blood.

"Relapse" can also include "recurrence," which the National Cancer institute defines as cancer that has recurred, usually after a period of time during which the cancer could not be detected. The cancer may come back to the same location in the body as the original (primary) tumor or to another location in the body (NCI Dictionary of Cancer Terms). In some embodiments, not detecting a cancer can include not detecting a cancer cells in the subject, not detecting a tumors in the subject, and/or no symptoms, in whole or in part, associated with the cancer.

As used herein, the terms "intolerance" and "intolerant" can refer to the occurrence of a severe, disabling, or life-threatening adverse event that leads to unplanned hospitalization during therapy, therapy discontinuation, and/or therapy dose reduction, functional decline attributed to therapy, and/or a decrease in performance status. In some embodiments, a decrease in performance status can be assessed using the Eastern Cooperative Oncology Group (ECOG) Scale of Performance Status (see, e.g., Oken et al. Am. J. Clin. Oncol. 5:649-655 (1982), which is incorporated by reference in its entirety herein). In some embodiments, a decrease in performance status can be assessed using the Karnofsky Performance Status (see, e.g., Péus et al., BMC Med. Inform. Decis. Mak. 13: 72 (2013), which is incorporated by reference in its entirety herein). In some embodiments, the subject is a pediatric patient and the performance status is assessed by the Lansky Performance Score (see, e.g., Lansky et al., Cancer. 60(7):1651-6 (1987), which is incorporated by reference in its entirety herein).

The term "preventing" as used herein means the prevention of the onset, recurrence or spread, in whole or in part, of the disease or condition as described herein, or a symptom thereof.

The term "administration" or "administering" refers to a method of giving a dosage of a compound or pharmaceutical composition to a vertebrate or invertebrate, including a mammal, a bird, a fish, or an amphibian. The preferred method of administration can vary depending on various factors, e.g., the components of the pharmaceutical composition, the site of the disease, and the severity of the disease.

By "therapeutically effective amount" or "pharmaceutically effective amount" of a compound as provided herein is an amount which is sufficient to achieve the desired effect and can vary according to the nature and severity of the disease condition, and the potency of the compound. A therapeutic effect is the relief, to some extent, of one or more of the symptoms of the disease, and can include curing a disease. "Curing" means that the symptoms of active disease are eliminated. However, certain long-term or permanent effects of the disease can exist even after a cure is obtained (such as, e.g., extensive tissue damage).

The phrase "dysregulation of a gene, a protein, or the expression or activity or level of any of the same" refers to a genetic mutation (e.g., a chromosomal translocation that results in the expression of a fusion protein including a kinase domain and a fusion partner, a mutation in a gene that results in the expression of a protein that includes a deletion of at least one amino acid as compared to a wildtype protein, a mutation in a gene that results in the expression of a protein with one or more point mutations as compared to a wildtype protein, a mutation in a gene that results in the expression of a protein with at least one inserted amino acid as compared to a wildtype protein, a gene duplication that results in an increased level of protein in a cell, or a mutation in a regulatory sequence (e.g., a promoter and/or enhancer) that results in an increased level of protein in a cell), an alternative spliced version of a mRNA that results in a protein having a deletion of at least one amino acid in the protein as compared to the wild-type protein), or increased expression (e.g., increased levels) of a wildtype protein in a mammalian cell due to aberrant cell signaling and/or dysregulated autocrine/paracrine signaling (e.g., as compared to a control non-cancerous cell). As another example, a dysregulation of a gene, a protein, or expression or activity, or level of any of the same, can be a mutation in a gene that encodes a protein that is constitutively active or has increased activity as compared to a protein encoded by a gene that does not include the mutation. For example, a dysregulation of a gene, a protein, or expression or activity, or level of any of the same, can be the result of a gene or chromosome translocation which results in the expression of a fusion protein that contains a first portion of a protein that includes a functional kinase domain, and a second portion of a partner protein (i.e., that is not the primary protein). In some examples, dysregulation of a gene, a protein, or expression or activity or level of any of the same can be a result of a gene translocation of one gene with a different gene.

The phrase "dysregulation of a BTK gene, a BTK kinase, or the expression or activity or level of any of the same" refers to increased expression of a BTK kinase, increased transcription of a BTK gene, or increased activation or phosphorylation of a BTK kinase. As an example, a dysregulation of a BTK gene, a BTK protein, or expression or activity, or level of any of the same can be a genetic mutation (e.g., a BTK gene translocation that results in the expression of a fusion protein, a deletion in a BTK gene that results in the expression of a BTK protein that includes a deletion of at least one amino acid as compared to the wild-type BTK protein, or a mutation in a BTK gene that results in the expression of a BTK protein with one or more point mutations), or a BTK gene amplification that results in overexpression of a BTK protein or an autocrine activity resulting from the overexpression of a BTK gene in a cell, that results in a pathogenic increase in the activity of a kinase domain of a BTK protein (e.g., a constitutively active kinase domain of a BTK protein) in a cell. As another example, a dysregulation of a BTK gene, a BTK protein, or expression or activity, or level of any of the same can be an alternatively-spliced version of a BTK mRNA or a BTK mRNA transcribed starting at an alternative promoter as compared to the wild-type BTK mRNA. In some embodiments, the alternatively-spliced version of a BTK mRNA results in a BTK with a deletion of at least one amino acid in the BTK protein as compared to the wild-type BTK protein. In some embodiments, the BTK mRNA transcribed from an alternative promoter as compared to a wild-type BTK kinase results in a BTK kinase having at least one amino acid added to the N-terminus of the BTK kinase as compared to the wildtype BTK kinase. As another example, a dysregulation of a BTK gene, a BTK protein, or expression or activity, or level of any of the same, can be a mutation in a BTK gene that encodes a BTK protein that is constitutively active or has increased activity as compared to a protein encoded by a BTK gene that does not include the mutation. Additional examples of a dysregulation of a BTK gene, a BTK protein, or expression or activity, or level of any of the same are BTK inhibitor resistance mutations. Non-limiting examples of BTK inhibitor resistance mutations are described in Table 2.

In some embodiments, a dysregulation of a BTK gene, a BTK kinase, or the expression or activity or level of any of the same is a dysregulation of a BCR signaling pathway gene, a BCR signaling pathway protein, or expression or activity or level of any of the same. In some embodiments, a dysregulation of a BCR signaling pathway gene, a BCR signaling pathway protein, or expression or activity or level of any of the same is one or more activating mutations within the BCR complex or downstream signaling components, continuous BCR stimulation by microbial antigens or autoantigens present in the tissue microenvironment, or ligand-independent tonic BCR signaling that result in the pathogenic increase in the expression or activation of a BTK protein. In some embodiments, a dysregulation of a BCR signaling pathway gene, a BCR signaling pathway protein, or expression or activity or level of any of the same is an overexpression or over-activation of one or more BCR signaling pathway proteins. For example, a dysregulation of a BTK gene, a BTK protein, or expression or activity, or level of any of the same can be the result of a genetic mutation in a BCR signaling pathway protein (e.g., a BCR signaling pathway gene translocation that results in the expression of a fusion protein, a deletion in a BCR signaling pathway gene that results in the expression of a BCR signaling pathway protein that includes a deletion of at least one amino acid as compared to the wild-type BCR signaling pathway protein, or a mutation in a BCR signaling pathway gene that results in the expression of a BCR signaling pathway protein with one or more point mutations, or an alternative spliced version of a BCR signaling pathway protein mRNA that results in a BCR signaling pathway protein that results in the deletion of at least one amino acid in the BCR signaling pathway protein as compared to the wild-type BCR signaling pathway protein). Non-limiting examples of BCR signaling pathway mutations are described in Table 4. Additional examples of a dysregulation of a BTK gene, a BTK protein, or expression or activity, or level of any of the same are BTK inhibitor resistance mutations. Non-limiting examples of BTK inhibitor resistance mutations in BCR signaling pathway proteins are described in Table 3.

The term "BTK-associated disease or disorder" as used herein refers to diseases or disorders associated with or having a dysregulation of a BTK gene, a BTK kinase (also called herein BTK kinase protein or BTK kinase), or the expression or activity or level of any (e.g., one or more) of the same (e.g., any of the types of dysregulation of a BTK gene, a BTK kinase, a BTK kinase domain, or the expression or activity or level of any of the same described herein). Non-limiting examples of a BTK-associated disease or disorder include, for example, cancer and autoimmune disorders such as arthritis or lupus.

The term "BTK-associated cancer" as used herein refers to cancers associated with or having a dysregulation of a BTK gene, a BTK kinase (also called herein BTK kinase protein or BTK kinase), or expression or activity, or level of any of the same. Non-limiting examples of a BTK-associated cancer are described herein.

The term "activating mutation" describes a mutation in a gene that results in the expression of a protein that has an increased activity, e.g., as compared to the wildtype protein, e.g., when assayed under identical conditions. For example, an activating mutation can result in the expression of a fusion protein that includes a kinase domain and a fusion partner. In another example, an activating mutation can be a mutation in a gene that results in the expression of a protein that has one or more (e.g., two, three, four, five, six, seven, eight, nine, or ten) amino acid substitutions (e.g., any combination of any of the amino acid substitutions described herein) that has increased protein activity, e.g., as compared to the wildtype protein, e.g., when assayed under identical conditions. In another example, an activating mutation can be a mutation in a gene that results in the expression of a protein that has one or more (e.g., two, three, four, five, six, seven, eight, nine, or ten) amino acids deleted, e.g., as compared to the wildtype protein, e.g., when assayed under identical conditions. In another example, an activating mutation can be a mutation in a gene that results in the expression of a protein that has at least one (e.g., at least 2, at least 3, at least 4, at least 5, at least 6, at least 7, at least 8, at least 9, at least 10, at least 12, at least 14, at least 16, at least 18, or at least 20) amino acid inserted as compared to the wildtype protein, e.g., when assayed under identical conditions.

In some embodiments, "activating mutation" describes a mutation in a BTK kinase gene that results in the expression of a BTK kinase that has an increased kinase activity, e.g., as compared to a wildtype BTK kinase, e.g., when assayed under identical conditions. For example, an activating mutation can result in the expression of a fusion protein that includes a BTK kinase domain and a fusion partner. In another example, an activating mutation can be a mutation in a BTK kinase gene that results in the expression of a BTK kinase that has one or more (e.g., two, three, four, five, six, seven, eight, nine, or ten) amino acid substitutions (e.g., any combination of any of the amino acid substitutions described herein) that has increased kinase activity, e.g., as compared to a wildtype BTK kinase, e.g., when assayed under identical conditions. In another example, an activating mutation can be a mutation in a BTK kinase gene that results in the expression of a BTK kinase that has one or more (e.g., two, three, four, five, six, seven, eight, nine, or ten) amino acids deleted, e.g., as compared to a wildtype BTK kinase, e.g., when assayed under identical conditions. In another example, an activating mutation can be a mutation in a BTK kinase gene that results in the expression of a BTK kinase that has at least one (e.g., at least 2, at least 3, at least 4, at least 5, at least 6, at least 7, at least 8, at least 9, at least 10, at least 12, at least 14, at least 16, at least 18, or at least 20) amino acid inserted as compared to a wildtype BTK kinase, e.g., the exemplary wildtype BTK kinase described herein, e.g., when assayed under identical conditions. Additional examples of activating mutations are known in the art.

In some embodiments, "activating mutation" describes a mutation in a BCR signaling pathway protein gene that results in the expression of a BCR signaling pathway protein that has an increased activity, e.g., as compared to a wildtype BCR signaling pathway protein, e.g., when assayed under identical conditions. For example, an activating mutation can result in the expression of a fusion protein that includes a BCR signaling pathway protein domain and a fusion partner. In another example, an activating mutation can be a mutation in a BCR signaling pathway protein gene that results in the expression of a BTK kinase that has one or more (e.g., two, three, four, five, six, seven, eight, nine, or ten) amino acid substitutions (e.g., any combination of any of the amino acid substitutions described herein) that has increased activity, e.g., as compared to a wildtype BCR signaling pathway protein, e.g., when assayed under identical conditions. In another example, an activating mutation can be a mutation in a BCR signaling pathway protein gene that results in the expression of a BCR signaling pathway protein that has one or more (e.g., two, three, four, five, six, seven, eight, nine, or ten) amino acids deleted, e.g., as compared to a wildtype BCR signaling pathway protein, e.g., when assayed under identical conditions. In another example, an activating mutation can be a mutation in a BCR signaling pathway protein gene that results in the expression of a BCR signaling pathway protein that has at least one (e.g., at least 2, at least 3, at least 4, at least 5, at least 6, at least 7, at least 8, at least 9, at least 10, at least 12, at least 14, at least 16, at least 18, or at least 20) amino acid inserted as compared to a wildtype BCR signaling pathway protein, e.g., when assayed under identical conditions. Additional examples of activating mutations are known in the art.

The term "wildtype" or "wild-type" describes a nucleic acid (e.g., a BTK gene or a BTK mRNA) or protein (e.g., a BTK protein) that is found in a subject that does not have a BTK-associated disease, e.g., a BTK-associated cancer (and optionally also does not have an increased risk of developing a BTK-associated disease and/or is not suspected of having a BTK-associated disease), or is found in a cell or tissue from a subject that does not have a BTK-associated disease, e.g., a BTK-associated cancer (and optionally also does not have an increased risk of developing a BTK-associated disease and/or is not suspected of having a BTK-associated disease).

The term "regulatory agency" refers to a country's agency for the approval of the medical use of pharmaceutical agents with the country. For example, a non-limiting example of a regulatory agency is the U.S. Food and Drug Administration (FDA).

A "BTK kinase inhibitor" as defined herein includes any compound exhibiting BTK inhibition activity. In some embodiments, a BTK kinase inhibitor is selective for a BTK kinase. Exemplary BTK kinase inhibitors can exhibit inhibition activity ($IC_{50}$) against a BTK kinase of less than about 1000 nM, less than about 500 nM, less than about 200 nM, less than about 100 nM, less than about 50 nM, less than about 25 nM, less than about 10 nM, or less than about 1 nM as measured in an assay as described herein. In some embodiments, a BTK kinase inhibitor can exhibit inhibition activity ($IC_{50}$) against a BTK kinase of less than about 25 nM, less than about 10 nM, less than about 5 nM, or less than about 1 nM as measured in an assay as provided herein.

As used herein, a "first BTK kinase inhibitor" or "first BTK inhibitor" is a BTK kinase inhibitor as defined herein, but which does not include the compound of Formula I, or a pharmaceutically acceptable salt, amorphous, or polymorph form thereof, a spray-dried dispersion thereof, or a pharmaceutical composition thereof, as defined herein. As used herein, a "second BTK kinase inhibitor" or a "second BTK inhibitor" is a BTK kinase inhibitor as defined herein, but which does not include a compound the Formula I, or a pharmaceutically acceptable salt, amorphous, or polymorph form thereof as defined herein. When both a first and a second BTK inhibitor are present in a method provided herein, the first and second BTK kinase inhibitor are different.

The term "immunotherapy" refers to an agent that modulates the immune system. In some embodiments, an immunotherapy can increase the expression and/or activity of a regulator of the immune system. In some embodiments, an immunotherapy can decrease the expression and/or activity of a regulator of the immune system. In some embodiments, an immunotherapy can recruit and/or enhance the activity of an immune cell.

The term "pharmaceutical combination", as used herein, refers to a pharmaceutical therapy resulting from the mixing or combining of more than one active ingredient and includes both fixed and non-fixed combinations of the active ingredients.

The term "fixed combination" means that the compound of Formula I, or a pharmaceutically acceptable salt, amorphous, or polymorph form thereof, a spray-dried dispersion thereof, or a pharmaceutical composition thereof, and at least one additional therapeutic agent (e.g., a chemotherapeutic agent), are both administered to a subject simultaneously in the form of a single composition or dosage.

The term "non-fixed combination" means that the compound of Formula I, or a pharmaceutically acceptable salt, amorphous, or polymorph form thereof, a spray-dried dispersion thereof, or a pharmaceutical composition thereof, and at least one additional therapeutic agent (e.g., chemotherapeutic agent) are formulated as separate compositions or dosages such that they may be administered to a subject in need thereof simultaneously, concurrently or sequentially with variable intervening time limits, wherein such administration provides effective levels of the two or more compounds in the body of the subject. These also apply to cocktail therapies, e.g. the administration of three or more active ingredients.

The term "metastasis" is an art known term and means the formation of an additional tumor (e.g., a solid tumor) at a site distant from a primary tumor in a subject or subject, where the additional tumor includes the same or similar cancer cells as the primary tumor.

The phrase "risk of developing a metastasis" means the risk that a subject or subject having a primary tumor will develop an additional tumor (e.g., a solid tumor) at a site distant from a primary tumor in a subject or subject over a set period of time, where the additional tumor includes the same or similar cancer cells as the primary tumor. Methods for reducing the risk of developing a metastasis in a subject or subject having a cancer are described herein.

The phrase "risk of developing additional metastases" means the risk that a subject or subject having a primary tumor and one or more additional tumors at sites distant from the primary tumor (where the one or more additional tumors include the same or similar cancer cells as the primary tumor) will develop one or more further tumors distant from the primary tumor, where the further tumors include the same or similar cancer cells as the primary tumor. Methods for reducing the risk of developing additional metastasis are described herein.

As used herein, the term "contacting" refers to the bringing together of indicated moieties in an in vitro system or an in vivo system. For example, "contacting" a BTK kinase with a compound provided herein includes the administration of a compound provided herein to an individual or subject, such as a human, having a BTK kinase, as well as, for example, introducing a compound provided herein into a sample containing a cellular or purified preparation containing the BTK kinase.

The phrase "effective amount" means an amount of compound that, when administered to a subject in need of such treatment, is sufficient to (i) treat a BTK kinase-associated disease or disorder, (ii) attenuate, ameliorate, or eliminate one or more symptoms of the particular disease, condition, or disorder, or (iii) delay the onset of one or more symptoms of the particular disease, condition, or disorder described herein. The amount of the compound of Formula I, or a pharmaceutically acceptable salt, amorphous, or polymorph form thereof, a spray-dried dispersion thereof, or a pharmaceutical composition thereof, that will correspond to such an amount will vary depending upon factors such as the particular compound, disease condition and its severity, the identity (e.g., weight) of the subject in need of treatment, but can nevertheless be routinely determined by one skilled in the art.

1. Pharmaceutical Compositions of the Compound of Formula I

The present disclosure relates to pharmaceutical compositions including a polymer and the compound of Formula I:

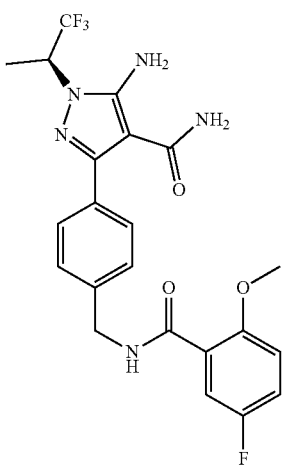 [SMILES: COc1ccc(F)cc1C(=O)NCc1ccc(-c2nn([C@@H](C)C(F)(F)F)c(N)c2C(N)=O)cc1]

a pharmaceutically acceptable salt, amorphous, or polymorph form thereof. More particularly, it relates to a spray-dried dispersion or an oral pharmaceutical composition of the compound of Formula I and a pharmaceutically acceptable salt, amorphous, or polymorph form thereof useful in the treatment and prevention of diseases which can be treated with a BTK kinase inhibitor, including BTK-associated diseases and disorders.

Spray-Dried Dispersions

Provided herein are spray-dried dispersions comprising the compound of Formula I and a hypromellose acetate succinate (HPMCAS) polymer. Non-limiting examples of HPMCAS polymers include HPMCAS-MG, HPMCAS-LF, HPMCAS-LG, HPMCAS-MF, HMPCAS-IF, and HPMCAS-HG. HPMCAS Type L is a polymer with a high ratio of succinoyl substitution to acetyl substitution (S/A ratio), while type H HPMCAS is a polymer with a low S/A ratio, and type M HPMCAS polymer has a medium S/A ratio. HPMCAS types F and G refer to fine and granular particles sizes, respectively. In some embodiments, the ratio of the compound of Formula I to the HPMCAS polymer is about 1:4 to about 4:1. In some embodiments, the ratio of the compound of Formula I to HPMCAS polymer is about 4:1, about 3:1, about 7:3, about 13:7, about 3:2, about 11:9, about 1:1, about 9:11, about 2:3, about 7:13, about 3:7, about 1:3, or about 1:4. In some embodiments, the ratio of the compound of Formula I to HPMCAS polymer is about 1:1. In some embodiments, the HPMCAS polymer is HPMCAS-LF, HPMCAS-LG, HPMCAS-MF, HMPCAS-HF, HPMCAS-HG, or a combination thereof. In some embodiments, the HPMCAS polymer is HPMCAS-MG.

Also provided herein are methods of preparing a spray-dried dispersion of the compound of Formula I. The method comprises adding an HPMCAS polymer to the compound of Formula I and spray-drying the mixture to form a spray-dried dispersion. In some embodiments, the ratio of the compound of Formula I to the HPMCAS polymer is about 1:4 to about 4:1. In some embodiments, the ratio of the compound of Formula I to the HPMCAS polymer is about 4:1, about 3:1, about 7:3, about 13:7, about 3:2, about 11:9, about 1:1, about 9:11, about 2:3, about 7:13, about 3:7, about 1:3, or about 1:4. In some embodiments, the ratio of the compound of Formula I to the HPMCAS polymer is about 1:1. In some embodiments, the ratio of the compound of Formula I to the HPMCAS polymer is about 1:1. In some embodiments, the HPMCAS polymer is HPMCAS-MG.

In some embodiments, the compound of Formula I is dissolved in one or more solvents forming a solution prior to being spray-dried. In some embodiments, the solvent is one or more organic solvents. In some embodiments, the organic solvent is selected from the group consisting of: methanol, acetone, dichloromethane, tetrahydrofuran, and combinations thereof. In some embodiments, the solvent is a mixture of an organic solvent and water. In some embodiments, the solvent is a mixture of tetrahydrofuran and water. For example, the organic solvent can be 95:5 tetrahydrofuran:water. In some embodiments, the organic solvent is a mixture of dichloromethane and methanol. For example, the organic solvent can be 80:20 w/w % volume) dichloromethane:methanol. In other examples the solvent is 100% methanol. In some embodiments, the compound of Formula I Form A is dissolved in the one or more organic solvents.

In some embodiments, the solution of the compound of Formula I is polish-filtered prior to adding the HPMCAS polymer. In some embodiments, the solution of the compound of Formula I and the HPMCAS polymer is polish-filtered prior to being spray-dried. In some embodiments, the HPMCAS polymer is HPMCAS-MG.

In some embodiments, the HPMCAS polymer is dissolved in the organic solvent. In some embodiments, the HPMCAS polymer is HPMCAS-MG.

In some embodiments, the HPMCAS polymer is dissolved in one or more solvents. In some embodiments, the solvent is one or more organic solvents. In some embodiments, the organic solvent is selected from the group consisting of: methanol, acetone, dichloromethane, tetrahydrofuran, and combinations thereof. In some embodiments, the solvent is a mixture of an organic solvent and water. In some embodiments, the solvent is a mixture of tetrahydrofuran and water. For example, the organic solvent can be 95:5 tetrahydrofuran:water. In some embodiments, the organic solvent is a mixture of dichloromethane and methanol. For example, the organic solvent can be 80:20 w/w % dichloromethane:methanol. In other examples the solvent is 100% methanol. The compound of Formula I is then added and dissolved. In some embodiments, the HPMCAS polymer is HPMCAS-MG.

The method further comprises spray-drying the solution of the compound of Formula I and the HPMCAS polymer. In some embodiments, the HPMCAS polymer is HPMCAS-MG.

In some embodiments, the method further comprises drying the spray-dried dispersion. In some embodiments, the spray-dried dispersion is dried. For example, to remove residual solvent. In some embodiments, the spray-dried dispersion is dried in an oven. In some embodiments, the spray-dried dispersion is dried at a temperature between about 30° C. to about 50° C. In some embodiments, the spray-dried dispersion is dried at a temperature from about 35° C. to about 45° C., for example, about 40° C. In some embodiments, the spray-dried dispersion is dried in a vacuum under an $N_2$ purge. In some embodiments, the spray-dried dispersion is dried for a period of about 10 to about 40 hours, about 30 to about 60 hours, about 50 to about 80, about 70 to about 100 hours, about 40 hours, about 50 hours, about 60 hours, about 70 hours, about 80 hours, about 90 hours, or about 100 hours. In some embodiments, the spray dried dispersion is dried until less than about 40,000 ppm of the solvent remains, less than about 20,000 ppm of the solvent remains, less than about 10,000 ppm of the solvent remains, less than about 5,000 ppm of the solvent remains, less than about 2,500 ppm of the solvent remains, less than about 1,000 ppm of the solvent remains, or less than about 600 ppm of the solvent remains. In some embodiments, the solvent is a mixture of dichloromethane and methanol, and the spray-dried dispersion is dried until less than about 2,000 ppm of the dichloromethane and less than about 15,000 ppm of the methanol remains, less than about 1,500 ppm of the dichloromethane and less than about 10,000 ppm of the methanol remains, or less than about 600 ppm of the dichloromethane and less than about 3,000 ppm of the methanol remains. In some embodiments using 100% methanol as the solvent, the spray dried dispersion is dried until less than about 3,000 ppm of the methanol remains.

Pharmaceutical Compositions

Also provided herein are pharmaceutical compositions comprising a spray-dried dispersion of the compound of Formula I and an HPMCAS polymer. In some embodiments, the IPMCAS polymer is IPMCAS-MG.

In some embodiments, the pharmaceutical composition includes a first composition having a spray-dried dispersion and one or more pharmaceutical excipients, wherein the spray-dried dispersion comprises an HPMCAS polymer and the compound of Formula I as described herein. In some embodiments, the IPMCAS polymer is IPMCAS-MG.

In some embodiments, the spray-dried dispersion is present in an amount of about 20% to about 75% w/w of the first composition. In some embodiments, the spray-dried dispersion is present in an amount of about 20% to about 50% w/w, about 50% to about 75% w/w, or about 30% to about 60% w/w of the first composition. For example, about 20% to about 40% w/w, about 30% to about 50% w/w, about 40% to about 60% w/w, or about 50 to about 75% w/w of the first composition. In some embodiments, the spray-dried dispersion is present in an amount of about 30% to about 40% w/w, about 40% to about 50% w/w, about 50% to about 60% w/w of the composition. For example, about 35% w/w, about 40% w/w, about 45% w/w, about 50% w/w, about 55% w/w, or about 60% w/w of the first composition.

In some embodiments, the pharmaceutical excipients of the first composition are selected from the group consisting of: a filler, a lubricant, and combinations thereof.

In some embodiments, the first compositions described herein can include a filler. Fillers can include binders, diluents, disintegrants, glidants, and surfactants added to pharmaceutical compositions. In some embodiments, fillers include saccharides (e.g., sugars, starch, and cellulose), gelatin, and synthetic polymers [e.g., polyvinylpyrrolidone, polyethylene glycol, and poloxamers (e.g., Poloxamer 188, a copolymer of polyoxyethylene and polyoxypropylene)]. Exemplary fillers include, but are not limited to, glucose, sucrose, lactose, (e.g. Foremost Fast Flo 316 Lactose monohydrate) a starch [including modified starches such as sodium starch glycolate (e.g., EXPLOTAB®)], xylitol, dextrin, saccharose, sorbitol, mannitol [e.g., PARTECK® M 200 (mannitol with an average particle size of about 50 μm to about 500 μm) or PARTECK® M 100 (mannitol with an average particle size of less than 212 μm)] or Mannogem EZ Spray Dried mannitol, a cellulose, a polyvinylpyrrolidone, a polyethylene glycol, a polyvinyl alcohol, a polymethacrylate, dibasic calcium phosphate, magnesium stearate, calcium stearate, sodium stearate, stearic acid, hydrogenated vegetable oils, a mineral oil, sodium lauryl sulfate, magnesium lauryl sulfate, glyceryl palmitostearate, sodium stearyl fumarate, colloidal silicon dioxide (e.g., sodium benzoate, sodium oleate, sodium acetate, aliginic acid, alginates (e.g. Syloid 244FP) sodium alginate, calcium silicate, and ion exchange resins. Exemplary cellulose fillers include microcrystalline cellulose [e.g., AVICEL® PH-101 (microcrystalline cellulose with an average particle size of approximately 50 μm) or AVICEL® PH 200 (microcrystalline cellulose with an average particle size of approximately 180 μm)], or AVICEL® PH 102 methyl cellulose, ethyl cellulose, croscarmellose sodium (e.g., AC-Di Sol®), hydroxypropyl cellulose, and hydroxypropyl methyl cellulose. Exemplary polyvinylpyrrolidone fillers include cross-linked polyvinylpyrrolidone such as KOLLIDON® CL (crospovidone with an average particle size of 90 μm to 130 μm) or KOLLIDON® CL-SF (crospovidone with an average particle size of 10 μm to 30 μm). Other fillers known to those of skill in the art are also contemplated as being useful when formulated in the compositions described herein.

In some embodiments, the filler is selected from the group consisting of: glucose, sucrose, lactose, a starch [including modified starches such as sodium starch glycolate (EXPLOTAB®)], xylitol, dextrin, saccharose, sorbitol, mannitol [e.g., PARTECK® M 200 (mannitol with an average particle size of about 50 μm to about 500 μm) or PARTECK® M 100 (mannitol with an average particle size of less than 212 μm)], a cellulose, a polyvinylpyrrolidone, a polyethylene glycol, a polyvinyl alcohol, a polymethacrylate, dibasic calcium phosphate, magnesium stearate, calcium stearate, sodium stearate, stearic acid, hydrogenated vegetable oils, a mineral oil, sodium lauryl sulfate, magnesium lauryl sulfate, glyceryl palmitostearate, sodium stearyl fumarate, colloidal silicon dioxide, sodium benzoate, sodium oleate, sodium acetate, aliginic acid, alginates (e.g., sodium alginate), calcium silicate, ion exchange resins, or combinations thereof. In some embodiments, the cellulose is microcrystalline cellulose [e.g., AVICEL® PH-101 (microcrystalline cellulose with an average particle size of approximately 50 μm) or AVICEL® PH 200 (microcrystalline cellulose with an average particle size of approximately 180 μm)], methyl cellulose, ethyl cellulose, croscarmellose sodium, hydroxypropyl cellulose, hydroxypropyl methylcellulose, or combinations thereof. In some embodiments, the polyvinylpyrrolidone is cross-linked polyvinylpyrrolidone such as KOLLIDON® CL (crospovidone with an average particle size of 90 µm to 130 µm), KOLLIDON® CL-SF (crospovidone with an average particle size of 10 µm to 30 µm), or a combination thereof.

In some embodiments, the filler is present in an amount of about 25% to about 80% w/w of the first composition. For example, about 25% to about 50% w/w, about 50% to about 80% w/w, about 40% to about 70% w/w of the first composition. In some embodiments, the filler is present in an amount of about 30% to about 50% w/w, about 45% to about 65% w/w, about 55% to about 75% w/w of the first composition. For example, about 40% w/w, about 45% w/w, about 50% w/w, about 55% w/w, about 60% w/w, about 65% w/w, or about 70% w/w of the first composition.

In some embodiments, the filler is selected from a binder, a disintegrant, or a combination thereof.

Binders include agents that hold the active pharmaceutical ingredient and inactive ingredients together in a cohesive mix. Exemplary binders include, but are not limited to, glucose, sucrose, lactose, a starch [including modified starches such as sodium starch glycolate (EXPLOTAB®)], xylitol, dextrin, saccharose, sorbitol, mannitol [e.g., PARTECK® M 200 (mannitol with an average particle size of about 50 µm to about 500 µm), PARTECK® M 100 (mannitol with an average particle size of less than 212 µm)], a cellulose, a polyvinylpyrrolidone, a polyethylene glycol, a polyvinyl alcohol, a polymethacrylate, and sodium starch glycolate. Exemplary cellulose fillers include microcrystalline cellulose [e.g., AVICEL® PH-101 (microcrystalline cellulose with an average particle size of approximately 50 µm) or AVICEL® PH 200 (microcrystalline cellulose with an average particle size of approximately 180 µm)], methyl cellulose, ethyl cellulose, croscarmellose sodium, hydroxypropyl cellulose, and hydroxypropyl methylcellulose. Exemplary polyvinylpyrrolidone fillers include cross-linked polyvinylpyrrolidone such as KOLLIDON® CL (crospovidone with an average particle size of 90 µm to 130 µm) or KOLLIDON® CL-SF (crospovidone with an average particle size of 10 µm to 30 µm). Other binders known to those of skill in the art are also contemplated as being useful when formulated in the compositions described herein.

In some embodiments, the binder is present in an amount of about 30% to about 80% w/w of the first composition. For example, about 30% to about 50% w/w, about 50% to about 80% w/w, about 40% to about 70% w/w of the first composition. In some embodiments, the filler is present in an amount of about 30% to about 50% w/w, about 35% to about 55% w/w, about 40% to about 60% w/w, about 45% to about 65% w/w, about 55% to about 75% w/w of the first composition. For example, about 40% w/w, about 45% w/w, about 50% w/w, about 52% w/w, about 55% w/w, about 60% w/w, about 65% w/w, or about 70% w/w of the first composition.

In some embodiments, the binder is selected from the group consisting of microcrystalline cellulose, cellulose ethers, hydroxypropyl cellulose, hydroxypropyl methylcellulose, sodium carboxy methyl cellulose starches, methyl cellulose, ethyl cellulose, mannitol, xylitol, sorbitol, lactose, sucrose, sorbitol, gelatin, polyvinylpyrrolidone, polyethylene glycol, polyvinyl alcohols, polymethacrylates, and combinations thereof.

In some embodiments, the binder is microcrystalline cellulose, mannitol, or a combination thereof. In some embodiments, the microcrystalline cellulose is present in an amount of about 5% to about 80% w/w of the first composition. For example, about 5% to about 40% w/w, about 40% to about 80% w/w, about 20% to about 60% w/w, about 5% to about 30% w/w, about 30% to about 55% w/w, about 10% to about 40% w/w, or about 15% to about 35% w/w of the first composition. In some embodiments, the microcrystalline cellulose is present in an amount of about 10% to about 20% w/w, about 20% to about 30% w/w, about 30% to about 40% w/w, about 40% to about 50% w/w, about 50% to about 60% w/w, or about 60% to about 70% w/w of the first composition. For example, about 15% w/w, about 20% w/w, about 25% w/w, about 26% w/w, about 30% w/w, about 35% w/w, about 40% w/w, about 45% w/w, about 50% w/w, or about 60% w/w of the first composition.

In some embodiments, the mannitol is present in an amount of about 5% to about 80% w/w of the first composition. For example, about 5% to about 40% w/w, about 40% to about 80% w/w, about 20% to about 60% w/w, about 5% to about 30% w/w, about 30% to about 55% w/w, about 10% to about 40% w/w, or about 15% to about 35% w/w of the first composition. In some embodiments, the mannitol is present in an amount of about 10% to about 20% w/w, about 20% to about 30% w/w, about 30% to about 40% w/w, about 40% to about 50% w/w, about 50% to about 60% w/w, or about 60% to about 70% w/w of the first composition. For example, about 15% w/w, about 20% w/w, about 25% w/w, about 26% w/w, about 30% w/w, about 35% w/w, about 40% w/w, about 45% w/w, about 50% w/w, or about 60% w/w of the first composition.

In some embodiments, the binder is a combination of microcrystalline cellulose and mannitol. In some embodiments, the microcrystalline cellulose is present in an amount of about 5% to about 40% w/w, about 40% to about 75% w/w, about 20% to about 60% w/w, about 5% to about 30% w/w, about 30% to about 55% w/w, about 10% to about 40% w/w, or about 15% to about 35% w/w of the first composition and the mannitol is present in an amount of about 5% to about 40% w/w, about 40% to about 75% w/w, about 20% to about 60% w/w, about 5% to about 30% w/w, about 30% to about 55% w/w, about 10% to about 40% w/w, or about 15% to about 35% w/w of the first composition. In some embodiments, the microcrystalline cellulose is present in an amount of about 10% to about 20% w/w, about 20% to about 30% w/w, about 30% to about 40% w/w, about 40% to about 50% w/w, about 50% to about 60% w/w, or about 60% to about 70% w/w of the first composition and the mannitol is present in an amount of about 10% to about 20% w/w, about 20% to about 30% w/w, about 30% to about 40% w/w, about 40% to about 50% w/w, about 50% to about 60% w/w, or about 60% to about 70% w/w of the first composition. For example, the microcrystalline cellulose is present in an amount of about 15% w/w, about 20% w/w, about 25% w/w, about 26% w/w, about 30% w/w, about 35% w/w, about 40% w/w, about 45% w/w, about 50% w/w, or about 60% w/w of the first composition and the mannitol present in an amount of about 15% w/w, about 20% w/w, about 25% w/w, about 26% w/w, about 30% w/w, about 35% w/w, about 40% w/w, about 45% w/w, about 50% w/w, or about 60% w/w of the first composition Disintegrants include any agent that promotes breakup of the formulation in an aqueous environment. For example, to promote more rapid release of the active pharmaceutical ingredient. Exemplary disintegrants include, but are not limited to, starch and modified starches such as sodium starch glycolate, croscarmellose sodium, alginic acid, alginates such as sodium alginate, polyvinylpyrrolidone, calcium silicate, and an ion exchange resin. In one embodiment, the disintegrant is selected from sodium starch glycolate, and croscarmellose sodium. Other disintegrants known to those of skill in the art are also contemplated as being useful when formulated in the compositions described herein.

In some embodiments, the disintegrant is present in an amount of about 0.5% to about 5% w/w of the first composition. For example, about 0.5% to about 2.5% w/w, about 2.5% w/w to about 5% w/w, or about 1.5% to about 3.5% w/w of the first composition. In some embodiments, the disintegrant is present in an amount of about 0.5% to about 2% w/w, about 1% to about 3% w/w, about 2% to about 4% w/w, or about 3% to about 5% w/w of the first composition. For example about 1% w/w, about 1.5% w/w, about 2% w/w, about 2.5% w/w, about 3% w/w, about 3.5% w/w, or about 4% w/w of the first composition.

In some embodiments, the disintegrant is selected from the group consisting of sodium starch glycolate, alginic acid, sodium alginate, croscarmellose sodium, an ion exchange resin, and combinations thereof. In one embodiment, the disintegrant is selected from sodium starch glycolate, and croscarmellose sodium.

In some embodiments, the sodium starch glycolate is present in an amount of about 0.5% to about 5% w/w of the first composition. For example, about 0.5% to about 2.5% w/w, about 2.5% w/w to about 5% w/w, or about 1.5% to about 3.5% w/w of the first composition. In some embodiments, the sodium starch glycolate is present in an amount of about 0.5% to about 2% w/w, about 1% to about 3% w/w, about 2% to about 4% w/w, or about 3% to about 5% w/w of the first composition. For example about 1% w/w, about 1.5% w/w, about 2% w/w, about 2.5% w/w, about 3% w/w, about 3.5% w/w, or about 4% w/w of the first composition.

In some embodiments, the first compositions described herein can include a lubricant. Lubricants are agents added to pharmaceutical formulations to reduce friction during processing. Exemplary lubricants include, but are not limited to, magnesium stearate, calcium stearate, sodium stearate, stearic acid, a hydrogenated vegetable oil, a mineral oil, a polyethylene glycol, sodium lauryl sulfate, magnesium lauryl sulfate, glyceryl palmitostearate, sodium benzoate, sodium stearyl fumarate, colloidal silicon dioxide, sodium benzoate, sodium oleate, and sodium acetate. Other lubricants known to those of skill in the art are also contemplated as being useful when formulated in the compositions described herein.

In some embodiments, the lubricant is present in an amount of about 0.05% to about 2.5% w/w of the first composition. For example, about 0.05% w/w to about 1.25% w/w, about 1.25% to about 2.5% w/w, or about 0.1% to about 1% w/w of the first composition. In some embodiments, the lubricant is present in an amount of about 0.05% to about 0.15% w/w, about 0.15% to about 0.25% w/w, about 0.25% to about 0.35% w/w, about 0.35% to about 0.45% w/w, about 0.45% to about 0.55% w/w of the first composition. In some embodiments, the lubricant is present in an amount of about 0.2% to about 0.3% w/w of the first composition. In some embodiments, the lubricant is present in an amount of about 0.1%, about 0.15%, about 0.2% w/w, about 0.25% w/w, about 0.3% w/w, about 0.35% w/w, about 0.4% w/w, about 0.45% w/w, about 1% w/w, about 1.5% w/w, or about 2% w/w of the first composition.

In some embodiments, the lubricant is magnesium stearate and/or silicon dioxide. In some embodiments, the magnesium stearate is present in an amount of about 0.05% to about 2.5% w/w of the first composition. For example, about 0.05% w/w to about 1.25% w/w, about 1.25% to about 2.5% w/w, or about 0.1% to about 1% w/w of the first composition. In some embodiments, the magnesium stearate is present in an amount of about 0.05% to about 0.15% w/w, about 0.15% to about 0.25% w/w, about 0.25% to about 0.35% w/w, about 0.35% to about 0.45% w/w, about 0.45% to about 0.55% w/w of the first composition. In some embodiments, the magnesium stearate is present in an amount of about 0.2% to about 0.3% w/w of the first composition. In some embodiments, the magnesium stearate is present in an amount of about 0.1%, about 0.15%, about 0.2% w/w, about 0.25% w/w, about 0.3% w/w, about 0.35% w/w, about 0.4% w/w, about 0.45% w/w, about 1% w/w, about 1.5% w/w, or about 2% w/w of the first composition.

In some embodiments, the spray-dried dispersion and pharmaceutical excipients are blended to form the first composition. In some embodiments, the first composition is granulated. In some embodiments, the first composition is granulated by roller compaction.

Pharmaceutical Compositions Comprising the First Composition

Also provided herein are pharmaceutical compositions comprising a first composition as described herein and one or more additional pharmaceutical excipients. In some embodiments, the first composition is present in an amount of about 15% to about 99% w/w of the total composition.

In some embodiments, the additional pharmaceutical excipients are selected from the group consisting of: a filler, a lubricant, a glident, and a combination thereof.

In some embodiments, the lubricant is present in an amount of about 0.05% to about 2% w/w of the total composition. For example, about 0.05% to about 1% w/w, about 1% to about 2% w/w, or about 0.5% to about 1.5% w/w of the total composition. In some embodiments, the lubricant is present in an amount of about 0.05% to about 0.5% w/w, about 0.1% to about 0.8% w/w, or about 0.5% to about 1% w/w of the total composition. For example, about 0.1% w/w, about 0.2% w/w, about 0.30% w/w, about 0.4% w/w, or about 0.5% w/w of the total composition.

In some embodiments, the lubricant is selected from the group consisting of: magnesium stearate, calcium stearate, sodium stearate, stearic acid, a hydrogenated vegetable oil, a mineral oil, polyethylene glycol, sodium lauryl sulfate, magnesium lauryl sulfate, glyceryl palmitostearate, sodium benzoate, sodium stearyl fumarate, colloidal silicon dioxide, sodium benzoate, sodium oleate, sodium acetate, and combinations thereof.

In some embodiments, the lubricant is magnesium stearate and/or silicon dioxide. In some embodiments, the magnesium stearate is present in an amount of about 0.05% to about 2% w/w of the total composition. For example, about 0.05% to about 1% w/w, about 1% to about 2% w/w, or about 0.5% to about 1.5% w/w of the total composition. In some embodiments, the magnesium stearate is present in an amount of about 0.05% to about 0.5% w/w, about 0.1% to about 0.8% w/w, or about 0.5% to about 1% w/w of the total composition. For example, about 0.1% w/w, about 0.2% w/w, about 0.3% w/w, about 0.4% w/w, or about 0.5% w/w of the total composition.

In some embodiments, the filler is present in an amount of about 1% to about 85% w/w of the total composition. In some embodiments, the filler is selected from the group consisting of: glucose, sucrose, lactose, a starch [including modified starches such as sodium starch glycolate (EXPLOTAB®)], xylitol, dextrin, saccharose, sorbitol, mannitol [e.g., PARTECK® M 200 (mannitol with an average particle size of about 50 µm to about 500 µm), PARTECK® M 100

(mannitol with an average particle size of less than 212 µm)], a cellulose, a polyvinylpyrrolidone, a polyethylene glycol, a polyvinyl alcohol, a polymethacrylate, dibasic calcium phosphate, magnesium stearate, calcium stearate, sodium stearate, stearic acid, hydrogenated vegetable oils, a mineral oil, sodium lauryl sulfate, magnesium lauryl sulfate, glyceryl palmitostearate, sodium stearyl fumarate, colloidal silicon dioxide, sodium benzoate, sodium oleate, sodium acetate, aliginic acid, alginates (e.g., sodium alginate), calcium silicate, ion exchange resins, and combinations thereof. In some embodiments, the cellulose is microcrystalline cellulose [e.g., AVICEL® PH-101 (microcrystalline cellulose with an average particle size of approximately 50 µm) or AVICEL® PH 200 (microcrystalline cellulose with an average particle size of approximately 180 µm)], methyl cellulose, ethyl cellulose, croscarmellose sodium, hydroxypropyl cellulose, hydroxypropyl methylcellulose, or combinations thereof. In some embodiments, the polyvinylpyrrolidone is cross-linked polyvinylpyrrolidone such as KOLLIDON® CL (crospovidone with an average particle size of 90 µm to 130 µm) or KOLLIDON® CL-SF (crospovidone with an average particle size of 10 µm to 30 µm). In some embodiments, the filler is a binder, a disintegrant, or a combination thereof.

In some embodiments, the filler comprises a disintegrant. In some embodiments, the disintegrant is present in an amount of about 0.5% to about 5% w/w of the total composition. For example, about 0.5% to about 2.5% w/w, about 2.5% to about 5% w/w, or about 1% to about 4% w/w of the total composition. In some embodiments, the disintegrant is present in an amount of about 1% to about 2% w/w, about 1.5% to about 2.5% w/w, about 2% to about 3% w/w, about 2.5% to about 3.5% w/w, or about 3% to about 4% w/w of the total composition. For example, about 1.5% w/w, about 2% w/w, about 2.5% w/w, about 3% w/w, or about 3.5% w/w of the total composition.

In some embodiments, the disintegrant is selected from the group consisting of sodium starch glycolate, alginic acid, sodium alginate, an ion exchange resin, and combinations thereof.

In some embodiments, the disintegrant is sodium starch glycolate or croscarmellose sodium. In some embodiments, the sodium starch glycolate is present in an amount of about 0.5% to about 5% w/w of the total composition. For example, about 0.5% to about 2.5% w/w, about 2.5% to about 5% w/w, or about 1% to about 4% w/w of the total composition. In some embodiments, the sodium starch glycolate is present in an amount of about 1% to about 2% w/w, about 1.5% to about 2.5% w/w, about 2% to about 3% w/w, about 2.5% to about 3.5% w/w, or about 3% to about 4% w/w of the total composition. For example, about 1.5% w/w, about 2% w/w, about 2.5% w/w, about 3% w/w, or about 3.5% w/w of the total composition.

In some embodiments the composition comprises a glidant which is magnesium stearate. The glidant is present in an about 0.1% to about 1% wt/wt of the weight of the total composition. In another embodiment, the glidant is present in an amount of about 0.25% and 0.75% wt/wt, more preferably in an amount of about 0.5% wt/wt of the total composition.

In some embodiments, the first composition is present in an amount of about 90% to about 99% w/w of the total composition. In some embodiments, the pharmaceutical composition comprises the first composition, a disintegrant, and a lubricant. In some embodiments, the first composition is present in an amount of about 90% to about 99% w/w of the total composition, the disintegrant is present in an amount of about 0.5% to about 5% w/w of the total composition, and the lubricant is present in an amount of about 0.05% to about 2% w/w of the total composition. In some embodiments, the first composition is present in an amount of about 97% w/w of the total composition, the disintegrant is present in an amount of about 2.5% w/w of the total composition, and the lubricant is present in an amount of about 0.25% w/w of the total composition.

In some embodiments, the disintegrant is sodium starch glycolate and the lubricant is magnesium stearate. In some embodiments, the sodium starch glycolate is present in an amount of about 0.5% to about 5% w/w of the total composition and the magnesium stearate is present in an amount of about 0.05% to about 2% w/w of the total composition. For example, the sodium starch glycolate is present in an amount of about 0.5% to about 2.5% w/w, about 2.5% to about 5% w/w, or about 1% to about 4% w/w of the total composition, and the magnesium stearate is present in an amount of about 0.05% to about 1% w/w, about 1% to about 2% w/w, or about 0.5% to about 1.5% w/w of the total composition. In some embodiments, the sodium starch glycolate is present in an amount of about 1% to about 2% w/w, about 1.5% to about 2.5% w/w, about 2% to about 3% w/w, about 2.5% to about 3.5% w/w, or about 3% to about 4% w/w of the total composition, and the magnesium stearate is present in an amount of about 0.05% to about 0.5% w/w, about 0.1% to about 0.8% w/w, or about 0.5% to about 1% w/w of the total composition. For example, the sodium starch glycolate is present in an amount of about 1.5% w/w, about 2% w/w, about 2.5% w/w, about 3% w/w, or about 3.5% w/w of the total composition, and the magnesium stearate is present in an amount of about 0.1% w/w, about 0.2% w/w, about 0.3% w/w, about 0.4% w/w, or about 0.5% w/w of the total composition.

In other embodiments, the first composition is present in an amount of about 15% to about 60% w/w of the total composition. For example, about 15% to about 35% w/w, about 35% to about 60% w/w, or about 25% to about 45% w/w of the total composition. In some embodiments, the first composition is present in an amount of about 20% to about 30% w/w, about 25% to about 35% w/w, about 30% to about 40% w/w, about 35% to about 45% w/w, or about 40% to about 50% w/w of the total composition. For example, about 20% w/w, about 25% w/w, about 30% w/w, about 35% w/w, about 40% w/w, about 45% w/w, or about 50% w/w of the total composition.

In some embodiments, the binder is present in an amount of about 40% to about 85% w/w of the total composition. For example, about 40% w/w to about 60% w/w, about 60% to about 85% w/w, or about 55% to about 75% w/w of the total composition. In some embodiments, the binder is present in an amount of about 40% to about 50% w/w, about 45% to about 55% w/w, about 50% to about 60% w/w, about 55% to about 65% w/w, about 60% to about 70% w/w, about 65% to about 75% w/w, or about 70% to about 80% w/w of the total composition. In some embodiments, the binder is present in an amount of about 45% w/w, about 50% w/w, about 55% w/w, about 60% w/w, about 62% w/w, about 65% w/w, about 70% w/w, about 75% w/w, or about 80% w/w of the total composition.

In some embodiments, the binder is selected from the group consisting of: microcrystalline cellulose, cellulose ethers, hydroxypropyl cellulose, hydroxypropyl methylcellulose, sodium carboxy methyl cellulose starches, methyl cellulose, ethyl cellulose, mannitol, xylitol, sorbitol, lactose, sucrose, sorbitol, gelatin, polyvinylpyrrolidone, polyethylene glycol, polyvinyl alcohols, polymethacrylates, and combinations thereof.

In some embodiments, the binder is microcrystalline cellulose, mannitol, or combinations thereof. In some embodiments, the microcrystalline cellulose is present in an amount of about 10% to about 85% w/w of the total composition. For example, about 10% to about 45% w/w, about 45% to about 85%, or about 20% to about 60% w/w of the total composition. In some embodiments, the microcrystalline cellulose is present in an amount of about 10% to about 20%, about 15% to about 25%, about 20% to about 30%, about 25% to about 35% w/w, about 30% to about 40% w/w, about 35% to about 45% w/w, or about 40% to about 50% w/w of the total composition. For example, about 20% w/w, about 25% w/w, about 30% w/w, about 31% w/w, about 35% w/w, about 40% w/w, or about 45% w/w of the total composition.

In some embodiments, the mannitol is present in an amount of about 10% to about 85% w/w of the total composition. For example, about 10% to about 45% w/w, about 45% to about 85%, or about 20% to about 60% w/w of the total composition. In some embodiments, the mannitol is present in an amount of about 10% to about 20%, about 15% to about 25%, about 20% to about 30%, about 25% to about 35% w/w, about 30% to about 40% w/w, about 35% to about 45% w/w, or about 40% to about 50% w/w of the total composition. For example, about 20% w/w, about 25% w/w, about 30% w/w, about 31% w/w, about 35% w/w, about 40% w/w, or about 45% w/w of the total composition.

In some embodiments, the microcrystalline cellulose and mannitol are present in an amount of about 10% to about 85% w/w of the total composition. For example, the microcrystalline cellulose is present in an amount of about 10% to about 45% w/w, about 45% to about 85%, or about 20% to about 60% w/w of the total composition and the mannitol is present in amount of about 10% to about 45% w/w, about 45% to about 85%, or about 20% to about 60% w/w of the total composition. In some embodiments, the microcrystalline cellulose is present in an amount of about 10% to about 20%, about 15% to about 25%, about 20% to about 30%, about 25% to about 35% w/w, about 30% to about 40% w/w, about 35% to about 45% w/w, or about 40% to about 50% w/w of the total composition and the mannitol is present in an amount of about 10% to about 20%, about 15% to about 25%, about 20% to about 30%, about 25% to about 35% w/w, about 30% to about 40% w/w, about 35% to about 45% w/w, or about 40% to about 50% w/w of the total composition. For example, the microcrystalline cellulose is present in an amount of about 20% w/w, about 25% w/w, about 30% w/w, about 31% w/w, about 35% w/w, about 40% w/w, or about 45% w/w of the total composition and the mannitol is present in an amount of about 20% w/w, about 25% w/w, about 30% w/w, about 31% w/w, about 35% w/w, about 40% w/w, or about 45% w/w of the total composition.

In some embodiments, the first composition is blended with the one or more pharmaceutical excipients. In some embodiments, the pharmaceutical composition is co-milled.

In some embodiments, the pharmaceutical compositions as described herein are formulated as a tablet. In some embodiments, the compound of Formula I is present in an amount of about 10 mg to about 50 mg in the pharmaceutical composition formulated as a tablet. For example, about 10 mg to about 30 mg, about 30 mg to about 50 mg, or about 15 mg to about 35 mg. In some embodiments, the compound of Formula I is present in an amount of about 10 mg to about 20 mg, about 15 mg to about 25 mg, about 30 mg to about 40 mg, about 35 mg to about 45 mg, or about 40 mg to about 50 mg in the pharmaceutical composition formulated as a tablet. For example, about 10 mg, about 15 mg, about 20 mg, about 25 mg, about 30 mg, about 35 mg, about 40 mg, about 45 mg, or about 50 mg.

In some embodiments, the compound of Formula I is present in an amount of about 25 mg to about 220 mg in the pharmaceutical composition formulated as a tablet. For example, about 25 mg to about 120 mg, about 120 mg to about 220 mg, or about 70 mg to about 170 mg. In some embodiments, the compound of Formula I is present in an amount of about 25 mg to about 75 mg, about 50 mg to about 100 mg, about 75 mg to about 125 mg, about 100 mg to about 150 mg, about 125 mg to about 175 mg, about 150 mg to about 200 mg, or about 175 mg to about 220 mg in the pharmaceutical composition formulated as a tablet. In some embodiments, the compound of Formula I is present in an amount of about 50 mg to about 60 mg, about 60 mg to about 70 mg, about 70 mg to about 80 mg, about 80 mg to about 90 mg, about 85 mg to about 95 mg, about 90 mg to about 100 mg, 80 mg to about 120 mg, about 95 mg to about 105 mg, about 100 mg to about 110 mg, about 105 mg to about 115 mg, about 120 mg to about 130 mg, about 130 mg to about 140 mg, about 140 mg to about 150 mg, about 150 mg to about 160 mg, about 160 mg to about 170 mg, or about 170 mg to about 180 mg. For example, about 50 mg, about 55 mg, about 60 mg, about 65 mg, about 70 mg, about 75 mg, about 80 mg, about 85 mg, about 90 mg, about 95 mg, about 100 mg, about 105 mg, about 110 mg, about 115 mg, about 120 mg, about 125 mg, about 130 mg, about 135 mg, about 140 mg, about 145 mg, about 150 mg, about 155 mg, about 160 mg, about 170 mg, about 175 mg, or about 180 mg.

In some embodiments, the tablet is coated.

Also provided herein are pharmaceutical compositions comprising the compound of Formula I, an HPMCAS polymer, and one or more pharmaceutical excipients. In some embodiments, the HPMCAS polymer is HPMCAS-MG.

In some embodiments, the one or more pharmaceutical excipients are selected from the group consisting of: a filler, a lubricant, and a combination thereof.

In some embodiments, the filler is selected from the group consisting of: glucose, sucrose, lactose, a starch [including modified starches such as sodium starch glycolate (EXPLOTAB®)], xylitol, dextrin, saccharose, sorbitol, mannitol [e.g., PARTECK® M 200 (mannitol with an average particle size of about 50 μm to about 500 μm), PARTECK® M 100 (mannitol with an average particle size of less than 212 μm)], a cellulose, a polyvinylpyrrolidone, a polyethylene glycol, a polyvinyl alcohol, a polymethacrylate, dibasic calcium phosphate, magnesium stearate, calcium stearate, sodium stearate, stearic acid, hydrogenated vegetable oils, a mineral oil, sodium lauryl sulfate, magnesium lauryl sulfate, glyceryl palmitostearate, sodium stearyl fumarate, colloidal silicon dioxide, sodium benzoate, sodium oleate, sodium acetate, aliginic acid, alginates (e.g., sodium alginate), calcium silicate, ion exchange resins, or combinations thereof. In some embodiments, the cellulose is microcrystalline cellulose [e.g., AVICEL® PH-101 (microcrystalline cellulose with an average particle size of approximately 50 μm) or AVICEL® PH 200 (microcrystalline cellulose with an average particle size of approximately 180 μm)], methyl cellulose, ethyl cellulose, croscarmellose sodium, hydroxypropyl cellulose, hydroxypropyl methylcellulose, or combinations thereof. In some embodiments, the polyvinylpyrrolidone is cross-linked polyvinylpyrrolidone such as KOLLIDON® CL (crospovidone with an average particle size of 90 µm to 130 µm) or KOLLIDON® CL-SF (crospovidone with an average particle size of 10 µm to 30 µm).

In some embodiments, the filler is selected from a binder, a disintegrant, or a combination thereof. In some embodiments, the binder is selected from the group consisting of microcrystalline cellulose, cellulose ethers, hydroxypropyl cellulose, hydroxypropyl methylcellulose, sodium carboxy methyl cellulose starches, methyl cellulose, ethyl cellulose, mannitol, xylitol, sorbitol, lactose, sucrose, sorbitol, gelatin, polyvinylpyrrolidone, polyethylene glycol, polyvinyl alcohols, polymethacrylates, and combinations thereof. In some embodiments, the disintegrant is selected from the group consisting of sodium starch glycolate, alginic acid, sodium alginate, an ion exchange resin, and combinations thereof.

In some embodiments, the lubricant is selected from the group consisting of: magnesium stearate, calcium stearate, sodium stearate, stearic acid, a hydrogenated vegetable oil, a mineral oil, polyethylene glycol, sodium lauryl sulfate, magnesium lauryl sulfate, glyceryl palmitostearate, sodium benzoate, sodium stearyl fumarate, colloidal silicon dioxide, sodium benzoate, sodium oleate, sodium acetate, and combinations thereof.

In some embodiments, the pharmaceutical composition comprises the compound of Formula I, an HPMCAS polymer, a binder, a disintegrant, and a lubricant.

In some embodiments, the pharmaceutical composition comprises the compound of Formula I present in an amount of about 5% to about 30% w/w of the total composition, the HPMCAS polymer present in an amount of about 5% to about 30% w/w of the total composition, a binder present in an amount of about 10% to about 90% w/w of the total composition, a disintegrant present in an amount of about 0.5% to about 5% w/w of the total composition, and a lubricant present in an amount of about 0.05% to about 2% w/w of the total composition. In some embodiments, the compound of Formula I is present in an amount of about 5% to about 15% w/w of the total composition, the HPMCAS polymer is present in an amount of about 5% to about 15% w/w of the total composition, the binder is present in an amount of about 70% to about 85% w/w of the total composition, the disintegrant is present in an amount of about 2.5% to about 4.5% w/w of the total composition, and the lubricant is present in an amount of about 0.1% to about 1% w/w of the total composition. For example, the compound of Formula I is present in an amount of about 8% w/w of the total composition, the HPMCAS polymer is present in an amount of about 8% w/w of the total composition, the binder is present in an amount of about 80% w/w of the total composition, the disintegrant is present in an amount of about 3.5% w/w of the total composition, and the lubricant is present in an amount of about 0.3% w/w of the total composition. In some embodiments, the HPMCAS polymer is HPMCAS-MG.

In some embodiments, the binder is a combination of mannitol and microcrystalline cellulose. In some embodiments, the compound of Formula I is present in an amount of about 5% to about 30% w/w of the total composition, the HPMCAS polymer is present in an amount of about 5% to about 30% w/w of the total composition, the mannitol and microcrystalline cellulose are present in an amount of about 10% to about 90% w/w of the total composition, the disintegrant is present in an amount of about 0.5% to about 5% w/w of the total composition, and the lubricant is present in an amount of about 0.05% to about 2% w/w of the total composition. In some embodiments, the compound of Formula I is present in an amount of about 5% to about 15% w/w of the total composition, the HPMCAS polymer is present in an amount of about 5% to about 15% w/w of the total composition, the microcrystalline cellulose and mannitol are present in an amount of about 70% to about 85% w/w of the total composition, the disintegrant is present in an amount of about 2.5% to about 4.5% w/w of the total composition, and the lubricant is present in an amount of about 0.1% to about 1% w/w of the total composition. For example, the compound of Formula I is present in an amount of about 8% w/w of the total composition, the HPMCAS polymer is present in an amount of about 8% w/w of the total composition, the mannitol and microcrystalline cellulose are present in an amount of about 80% w/w of the total composition, the disintegrant is present in an amount of about 3.5% w/w of the total composition, and the lubricant is present in an amount of about 0.3% w/w of the total composition. In some embodiments, the mannitol and microcrystalline cellulose are present at about a 4:1, about a 3:2, about a 1:1, about a 2:3, or about a 1:4 ratio. In some embodiments, the HPMCAS polymer is HPMCAS-MG.

In some embodiments, the disintegrant is sodium starch glycolate. In some embodiments, the compound of Formula I is present in an amount of about 5% to about 30% w/w of the total composition, the HPMCAS polymer is present in an amount of about 5% to about 30% w/w of the total composition, the binder is present in an amount of about 10% to about 90% w/w of the total composition, the sodium starch glycolate is present in an amount of about 0.5% to about 5% w/w of the total composition, and the lubricant is present in an amount of about 0.05% to about 2% w/w of the total composition. In some embodiments, the compound of Formula I is present in an amount of about 5% to about 15% w/w of the total composition, the HPMCAS polymer is present in an amount of about 5% to about 15% w/w of the total composition, the binder is present in an amount of about 70% to about 85% w/w of the total composition, the sodium starch glycolate is present in an amount of about 2.5% to about 4.5% w/w of the total composition, and the lubricant is present in an amount of about 0.1% to about 1% w/w of the total composition. For example, the compound of Formula I is present in an amount of about 8% w/w of the total composition, the HPMCAS polymer is present in an amount of about 8% w/w of the total composition, the binder is present in an amount of about 80% w/w of the total composition, the sodium starch glycolate is present in an amount of about 3.5% w/w of the total composition, and the lubricant is present in an amount of about 0.3% w/w of the total composition. In some embodiments, the HPMCAS polymer is HPMCAS-MG.

In some embodiments, the lubricant is magnesium stearate. In some embodiments, the compound of Formula I is present in an amount of about 5% to about 30% w/w of the total composition, the HPMCAS polymer is present in an amount of about 5% to about 30% w/w of the total composition, the binder is present in an amount of about 10% to about 90% w/w of the total composition, the disintegrant is present in an amount of about 0.5% to about 5% w/w of the total composition, and the magnesium stearate is present in an amount of about 0.05% to about 2% w/w of the total composition. In some embodiments, the compound of Formula I is present in an amount of about 5% to about 15% w/w of the total composition, the HPMCAS polymer is present in an amount of about 5% to about 15% w/w of the total composition, the binder is present in an amount of about 70% to about 85% w/w of the total composition, the disintegrant is present in an amount of about 2.5% to about 4.5% w/w of the total composition, and the magnesium stearate is present in an amount of about 0.1% to about 1% w/w of the total composition. For example, the compound of Formula I is present in an amount of about 8% w/w of the total composition, the HPMCAS polymer is present in an amount of about 8% w/w of the total composition, the binder is present in an amount of about 80% w/w of the total composition, the disintegrant is present in an amount of about 3.5% w/w of the total composition, and the magnesium stearate is present in an amount of about 0.3% w/w of the total composition. In some embodiments, the HPMCAS polymer is HPMCAS-MG.

In some embodiments, the binder is a combination of microcrystalline cellulose and mannitol, the disintegrant is sodium starch glycolate, and the lubricant is magnesium stearate. In some embodiments, the pharmaceutical composition comprises the compound of Formula I present in an amount of about 5% to about 30% w/w of the total composition, the HPMCAS polymer present in an amount of about 5% to about 30% w/w of the total composition, microcrystalline cellulose present in an amount of about 30% to about 60% w/w of the total composition, mannitol present in an amount of about 30% to about 60% w/w of the total composition, sodium starch glycolate present in an amount of about 0.5% to about 5% w/w of the total composition, and magnesium stearate present in an amount of about 0.05% to about 2% w/w of the total composition. For example, the compound of Formula I is present in an amount of about 8% w/w of the total composition, the HPMCAS polymer is present in an amount of about 8% w/w of the total composition, the microcrystalline cellulose is present in an amount of about 40% w/w of the total composition, the mannitol is present in an amount of about 40% w/w of the total composition, the sodium starch glycolate is present in an amount of about 3.5% w/w of the total composition, and the magnesium stearate is present in an amount of about 0.3% w/w of the total composition. In some embodiments, the HPMCAS polymer is HPMCAS-MG.

In other embodiments, the pharmaceutical composition comprises the compound of Formula I present in an amount of about 10% to about 30% w/w of the total composition, an HPMCAS polymer present in an amount of about 10% to about 30% w/w of the total composition, a binder present in an amount of about 35% to about 70% w/w of the total composition, a disintegrant present in an amount of about 2% to about 8% w/w of the total composition, and a lubricant present in an amount of about 0.05% to about 2% w/w of the total composition. In some embodiments, the compound of Formula I is present in an amount of about 15% to about 25% w/w of the total composition, the HPMCAS polymer is present in an amount of about 15% to about 25% w/w of the total composition, the binder is present in an amount of about 40% to about 60% w/w of the total composition, the disintegrant is present in an amount of about 4% to about 6% w/w of the total composition, and the lubricant is present in an amount of about 0.1% to about 1% w/w of the total composition. For example, the compound of Formula I is present in an amount of about 22% w/w of the total composition, the HPMCAS polymer is present in an amount of about 22% w/w of the total composition, the binder is present in an amount of about 50% w/w of the total composition, the disintegrant is present in an amount of about 5% w/w of the total composition, and the lubricant is present in an amount of about 0.5% w/w of the total composition. In some embodiments, the HPMCAS polymer is HPMCAS-MG.

In some embodiments, the binder is a combination of mannitol and microcrystalline cellulose. In some embodiments, the compound of Formula I is present in an amount of about 10% to about 30% w/w of the total composition, the HPMCAS polymer is present in an amount of about 10% to about 30% w/w of the total composition, the mannitol and microcrystalline cellulose are present in an amount of about 35% to about 70% w/w of the total composition, the disintegrant is present in an amount of about 2% to about 8% w/w of the total composition, and the lubricant is present in an amount of about 0.05% to about 2% w/w of the total composition. In some embodiments, the pharmaceutical composition comprises the compound of Formula I present in an amount of about 15% to about 25% w/w of the total composition, the HPMCAS polymer present in an amount of about 15% to about 25% w/w of the total composition, mannitol and microcrystalline cellulose present in an amount of about 40% to about 60% w/w of the total composition, a disintegrant present in an amount of about 4% to about 6% w/w of the total composition, and a lubricant present in an amount of about 0.1% to about 1% w/w of the total composition. For example, the compound of Formula I is present in an amount of about 22% w/w of the total composition, the HPMCAS polymer is present in an amount of about 22% w/w of the total composition, the microcrystalline cellulose and mannitol are present in an amount of about 50% w/w of the total composition, the disintegrant is present in an amount of about 5% w/w of the total composition, and the lubricant is present in an amount of about 0.5% w/w of the total composition. In some embodiments, the mannitol and microcrystalline cellulose are present at about a 4:1, about a 3:2, about a 1:1, about a 2:3, or about a 1:4 ratio. In some embodiments, the HPMCAS polymer is HPMCAS-MG.

In some embodiments, the disintegrant is sodium starch glycolate. In some embodiments, the compound of Formula I is present in an amount of about 10% to about 30% w/w of the total composition, the HPMCAS polymer is present in an amount of about 10% to about 30% w/w of the total composition, the binder is present in an amount of about 35% to about 70% w/w of the total composition, the sodium starch glycolate is present in an amount of about 2% to about 8% w/w of the total composition, and the lubricant is present in an amount of about 0.05% to about 2% w/w of the total composition. In some embodiments, the compound of Formula I is present in an amount of about 15% to about 25% w/w of the total composition, the HPMCAS polymer is present in an amount of about 15% to about 25% w/w of the total composition, the binder is present in an amount of about 40% to about 60% w/w of the total composition, the sodium starch glycolate is present in an amount of about 4% to about 6% w/w of the total composition, and the lubricant is present in an amount of about 0.1% to about 1% w/w of the total composition. For example, the compound of Formula I is present in an amount of about 22% w/w of the total composition, the HPMCAS polymer is present in an amount of about 22% w/w of the total composition, the binder is present in an amount of about 50% w/w of the total composition, the sodium starch glycolate is present in an amount of about 5% w/w of the total composition, and the lubricant is present in an amount of about 0.5% w/w of the total composition. In some embodiments, the HPMCAS polymer is HPMCAS-MG.

In some embodiments, the lubricant is magnesium stearate. In some embodiments, the compound of Formula I is present in an amount of about 10% to about 30% w/w of the total composition, the HPMCAS polymer is present in an amount of about 10% to about 30% w/w of the total composition, the binder is present in an amount of about 35% to about 70% w/w of the total composition, the disintegrant is present in an amount of about 2% to about 8% w/w of the total composition, and the magnesium stearate is present in an amount of about 0.05% to about 2% w/w of the total composition. In some embodiments, the compound of Formula I is present in an amount of about 15% to about 25% w/w of the total composition, the HPMCAS polymer is present in an amount of about 15% to about 25% w/w of the total composition, the binder is present in an amount of about 40% to about 60% w/w of the total composition, the disintegrant is present in an amount of about 4% to about 6% w/w of the total composition, and the magnesium stearate is present in an amount of about 0.1% to about 1% w/w of the total composition. For example, the compound of Formula I is present in an amount of about 22% w/w of the total composition, the HPMCAS polymer is present in an amount of about 22% w/w of the total composition, the binder is present in an amount of about 50% w/w of the total composition, the disintegrant is present in an amount of about 5% w/w of the total composition, and the magnesium stearate is present in an amount of about 0.5% w/w of the total composition. In some embodiments, the HPMCAS polymer is HPMCAS-MG.

In some embodiments, the pharmaceutical composition comprises the compound of Formula I present in an amount of about 10% to about 30% w/w of the total composition, the HPMCAS polymer present in an amount of about 10% to about 30% w/w of the total composition, microcrystalline cellulose present in an amount of about 20% to about 30% w/w of the total composition, mannitol present in an amount of about 20% to about 30% w/w of the total composition, sodium starch glycolate present in an amount of about 2% to about 8% w/w of the total composition, and magnesium stearate present in an amount of about 0.05% to about 2% w/w of the total composition. In some embodiments, the HPMCAS polymer is HPMCAS-MG.

In some embodiments, the pharmaceutical composition comprises the compound of Formula I present in an amount of about 22% w/w of the total composition, the HPMCAS polymer present in an amount of about 22% w/w of the total composition, microcrystalline cellulose present in an amount of about 25% w/w of the total composition, mannitol present in an amount of about 25% w/w of the total composition, sodium starch glycolate present in an amount of about 5% w/w of the total composition, and magnesium stearate present in an amount of about 0.5% w/w of the total composition. In some embodiments, the HPMCAS polymer is HPMCAS-MG.

In some embodiments, the pharmaceutical composition as described herein is formulated as a tablet. In some embodiments, the tablet is coated.

Also provided herein are methods for preparing the pharmaceutical compositions as described herein comprising:
  mixing the compound of Formula I, an HPMCAS polymer, and a solvent to form a solution;
  spray-drying the solution to form a spray-dried dispersion; and
  granulating the spray-dried dispersion to form a first composition.

In some embodiments, the HPMCAS polymer is HPMCAS-MG.

In some embodiments, the solvent is an organic solvent. In some embodiments, the organic solvent is selected from the group consisting of: methanol, acetone, dichloromethane, tetrahydrofuran, and combinations thereof. In some embodiments, the solvent is a mixture of an organic solvent and water. In some embodiments, the solvent is a mixture of tetrahydrofuran and water. In some embodiments, the mixture is 95:5 tetrahydrofuran:water. In some embodiments, the organic solvent is a mixture of dichloromethane and methanol. In some embodiments, the organic solvent is 80:20 dichloromethane:methanol.

In some embodiments, the spray-dried dispersion is blended with one or more pharmaceutical excipients prior to being granulated. In some embodiments, the spray-dried dispersion is dried in an oven prior to being granulated. In some embodiments, the spray-dried dispersion is blended with one or more pharmaceutical excipients prior to being granulated. In some embodiments, the spray-dried dispersion is granulated by roller compaction.

In some embodiments, the first composition is blended with one or more pharmaceutical excipients. In some embodiments, the first composition is co-milled. In some embodiments, the first composition is pressed into a tablet. In some embodiments, the tablet is coated. In some embodiments, the coating comprises a polymer, a plasticizer, a pigment, or combinations thereof.

In some embodiments, the ratio of the compound of Formula I to the HPMCAS polymer is about 1:4 to about 4:1 in the spray-dried dispersion. In some embodiments, the ratio of the compound of Formula I to the HPMCAS polymer is about 4:1, about 3:1, about 7:3, about 13:7, about 3:2, about 11:9, about 1:1, about 9:11, about 2:3, about 7:13, about 3:7, about 1:3, or about 1:4. In some embodiments, the ratio of the compound of Formula I to the HPMCAS polymer is about 1:1 in the spray-dried dispersion. In some embodiments, the ratio of the compound of Formula I to the HPMCAS polymer is about 1:1 in the spray-dried dispersion. In some embodiments, the HPMCAS polymer is HPMCAS-MG.

The daily dosage of the compound of Formula I, or a pharmaceutically acceptable salt, amorphous, or polymorph form thereof, a spray-dried dispersion thereof, or a pharmaceutical composition thereof as described herein may be varied over a wide range from 1.0 to 10,000 mg per adult human per day, or higher, or any range therein. For oral administration, the compositions are preferably provided in the form of tablets containing, 0.01, 0.05, 0.1, 0.5, 1.0, 2.5, 5.0, 10.0, 15.0, 20.0, 25.0, 30.0, 40.0, 50.0, 60.0, 70.0, 75.0, 80.0, 90.0, 100, 125, 150, 175, 200, 225, 250, 275, 300, 325, 350, 375, 400, 425, 450, 475, and 500 milligrams of the active ingredient for the symptomatic adjustment of the dosage to the subject to be treated. An effective amount of the drug is ordinarily supplied at a dosage level of from about 0.1 mg/kg to about 1000 mg/kg of body weight per day, or any range therein. The range can be from about 0.5 to about 500 mg/kg of body weight per day, or any range therein. The range can be from about 1.0 to about 250 mg/kg of body weight per day, or any range therein. The range can be from about 0.1 to about 100 mg/kg of body weight per day, or any range therein. In an example, the range may be from about 0.1 to about 50.0 mg/kg of body weight per day, or any amount or range therein. In another example, the range may be from about 0.1 to about 15.0 mg/kg of body weight per day, or any range therein. In yet another example, the range may be from about 0.5 to about 7.5 mg/kg of body weight per day, or any amount to range therein. A pharmaceutical composition as provided herein may be administered on a regimen of 1 to 4 times per day or in a single daily dose Optimal dosages to be administered may be readily determined by those skilled in the art, and will vary with the mode of administration, the strength of the preparation, the mode of administration, and the advancement of the disease condition. In addition, factors associated with the particular subject being treated, including subject age, weight, diet and time of administration, will result in the need to adjust dosages.

One skilled in the art will recognize that, both in vivo and in vitro trials using suitable, known and generally accepted cell and/or animal models are predictive of the ability of a test compound to treat or prevent a given disorder.

One skilled in the art will further recognize that human clinical trials including first-in-human, dose ranging and efficacy trials, in healthy subjects and/or those suffering from a given disorder, may be completed according to methods well known in the clinical and medical arts. For example, determining proper dosages for pediatric patients can be determined using known methods, including weight, age, and models such as Simcyp® Pediatric Simulation modeling (CERTARA, Princeton, N.J.) which can be used to establish a pharmacokinetic approach for dosing that takes into account patient age, ontogeny of the clearance pathways that the compound of formula I, a pharmaceutically acceptable salt thereof, or a combination thereof, and body surface area (BSA).

2. Polymorphs

The present disclosure also relates to crystalline forms of (S)-5-amino-3-(4-((5-fluoro-2-methoxybenzamido)methyl)phenyl)-1-(1,1,1-trifluoropropan-2-yl)-1H-pyrazole-4-carboxamide having the Formula I.

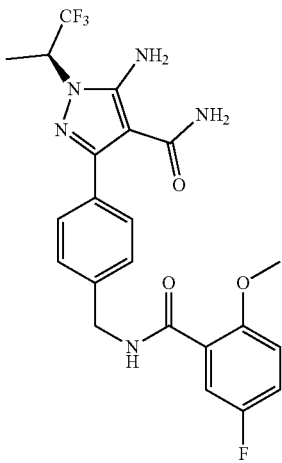 [SMILES: COc1ccc(F)cc1C(=O)NCc1ccc(-c2nn([C@@H](C)C(F)(F)F)c(N)c2C(N)=O)cc1]

and pharmaceutically acceptable salts thereof, pharmaceutical compositions comprising the crystalline forms of the compound of Formula I, processes for making the crystalline forms of the compound of Formula I, and the use of the crystalline forms of the compound of Formula I in the treatment and prevention of diseases which can be treated with a BTK kinase inhibitor, including BTK-associated diseases and disorders.

Provided herein are polymorphs of the compound of Formula I. The forms include, e.g., free bases, solvates, hydrates, salts, and non-solvated forms of the compound of Formula I, including, for example, polymorph Form A. In some embodiments, the polymorph form of the compound of Formula I is a pharmaceutically acceptable salt.

Form A

One such polymorph is a polymorph of the compound of Formula I known as Form A. In some embodiments, Form A has an XRPD pattern, obtained with CuKα1-radiation, with at least peaks at °2θ values of 11.9±0.2, 15.8±0.2, and 16.2±0.2. In some embodiments, Form A has an XRPD pattern with at least peaks at °2θ values of 11.9±0.2, 15.8±0.2, 16.2±0.2, 18.3±0.2, and 19.0±0.2. In some embodiments, Form A has an XRPD pattern with at least peaks at °2θ values of 11.9±0.2, 15.8±0.2, 16.2±0.2, 18.3±0.2, 19.0±0.2, 20.5±0.2, and 23.8±0.2. In some embodiments, Form A has an XRPD pattern with at least peaks at °2θ values of 9.5±0.2, 11.9±0.2, 15.8±0.2, 16.2±0.2, 18.3±0.2, 19.0±0.2, 20.1±0.2, 20.5±0.2, 23.8±0.2, and 25.7±0.2. For example, in some embodiments, Form A has an XRPD pattern with at least peaks at °2θ values of 9.5±0.2, 11.1±0.2, 11.9±0.2, 15.8±0.2, 16.2±0.2, 18.3±0.2, 19.0±0.2, 20.1±0.2, 20.5±0.2, 23.8±0.2, 25.0±0.2, and 25.7±0.2.

In some embodiments, provided herein is a composition comprising polymorph Form A. In some embodiments, the composition can be substantially pure. For example, the composition has a purity of at least about 90%. In some embodiments, the composition has a purity of at least about 95%. In some embodiments, the composition has a purity of at least about 98%. For example, the composition can have a purity of at least 98.5%, 98.6%, 98.7%, 98.8%, 98.9%, 99%, 99.1%, 99.2%, 99.3%, 99.4%, 99.5%, 99.6%, 99.7%, 99.8%, or 99.9%. In some embodiments, the composition is substantially free of other forms of the compound of Formula I. In some embodiments, the composition contains less than about 15% by weight of other forms of the compound of Formula I. For example, the composition can contain less than 14%l, 3%, 12%, 11%, 10%, 9%, 8%, 7%, 6%, 5%, 4%, 3%, 2%, 1% by weight of one or more other forms of the compound of Formula I. For example, the composition can contain less than about 15% of amorphous form.

In some embodiments, provided herein is polymorph Form A that exhibits an endotherm that is observed between about 185-195° C., e.g., about 189.9° C., as measured by DSC related to absorbed water.

In some embodiments, polymorph Form A of the compound of Formula I exhibits a weight loss of about 0.14% from the onset of heating to about 150° C., as measured by TGA.

Also provided herein are methods of preparing polymorph Form A. In some embodiments, polymorph Form A of the compound of Formula I is prepared by dissolving the compound of Formula I in a polar protic solvent to form a solution of the compound of Formula I. In some embodiments, the polar protic solvent is methanol. In some embodiments, the method further comprises heating the solution of the compound of Formula I to about 55° C. In some embodiments, water is added to the solution of the compound of Formula I over the course of about 2 hours at a rate of about 5 mL/min. In some embodiments, the compound of Formula I crashes out of the solution to afford a suspension comprising a solid of the compound of Formula I suspended in the solvent. In some embodiments, the method further comprises cooling the suspension to about 15° C. at a rate of about 10° C./hr. In some embodiments, the method further comprises stirring the cooled suspension at room temperature for about 10-20 hours, e.g., about 15 hours. In some embodiments, the method comprises isolating the solid of the compound of Formula I from the suspension through filtration. In some embodiments, the solid of the compound of Formula I is dried. In some embodiments, the solid of the compound of Formula I is dried under vacuum. In some embodiments, the solid is dried at about 55° C.

In some embodiments, the polymorph Form A of the compound of Formula I is prepared by adding the compound of Formula I to a polar protic solvent to form a mixture. In some embodiments, the mixture is heated until a solution is formed. In some embodiments, the polar protic solvent is isopropanol, ethanol, water, or combinations thereof. In some embodiments, the polar protic solvent is isopropanol. In some embodiments, the solution is cooled slowly to room temperature. In some embodiments, the solution is polish filtered prior to being cooled. In some embodiments, the solution is added to a reactor containing water. In some embodiments, the solution is polish filtered prior to being added to the reactor. In some embodiments, the compound of Formula I crashes out of the solution to afford a suspension comprising a solid of the compound of Formula I suspended in the solvent. In some embodiments, the method comprises isolating the solid of the compound of Formula I from the suspension through filtration. In some embodiments, the solid of the compound of Formula I is dried. In some embodiments, the solid of the compound of Formula I is dried under vacuum. In some embodiments, the solid is dried at about 55° C.

In some embodiments, the compound of Formula I is crystallized using a polar protic and a nonpolar solvent, e.g., ethanol or ethyl acetate and heptane. In some embodiments, the polymorph Form A of the compound of Formula I is prepared by adding the compound of Formula I to a polar protic solvent to form a mixture. In some embodiments, the mixture is heated until a solution is formed. In some embodiments, the mixture is heated to about 70° C. In some embodiments, the polar protic solvent is ethanol. In some embodiments, the solution is cooled and charged with Form A seeds of the compound of Formula I to form a charged solution. In some embodiments, the solution is cooled to about 59° C. In some embodiments, the solution is polish filtered prior to being cooled. In some embodiments, the charged solution is cooled to about 55° C. and heptane is added to the charged solution. In some embodiments, the heptane is added dropwise. In some embodiments, the heptane is added dropwise over about 4 hours. In some embodiments, the compound of Formula I crashes out of the charged solution to afford a suspension comprising a solid of the compound of Formula I suspended in the solvent. In some embodiments, the suspension is cooled to about 15° C. In some embodiments, the suspension is cooled to about 15° C. over about 1 hour. In some embodiments, the method comprises isolating the solid of the compound of Formula I from the suspension through filtration. In some embodiments, the solid of the compound of Formula I is dried. In some embodiments, the solid of the compound of Formula I is dried under vacuum. In some embodiments, the solid is dried at about 55° C.

In some embodiments, the compound of Formula I is crystallized using a polar protic and a nonpolar solvent, e.g., ethanol or ethyl acetate and heptane. In some embodiments, the polymorph Form A of the compound of Formula I is prepared by adding the compound of Formula I to a polar protic solvent to form a mixture. In some embodiments, the mixture is heated until a solution is formed. In some embodiments, the mixture is heated to about 75° C. In some embodiments, the polar protic solvent is ethyl acetate. In some embodiments, the solution is cooled and charged with Form A seeds of the compound of Formula I to form a charged solution. In some embodiments, the solution is cooled to about 45° C. prior to being charged. In some embodiments, the solution is polish filtered prior to being cooled. In some embodiments, heptane is added slowly to the charged solution. In some embodiments, the compound of Formula I crashes out of the solution to afford a suspension comprising a solid of the compound of Formula I suspended in the solvent. In some embodiments, the suspension is incubated to form an incubated suspension. In some embodiments, the suspension is incubated at 45° C. In some embodiments, the suspension is incubated overnight. In some embodiments, the incubated suspension is cooled. In some embodiments, the incubated suspension is cooled to about 24° C. In some embodiments, the method comprises isolating the solid of the compound of Formula I from the incubated suspension through filtration. In some embodiments, the solid of the compound of Formula I is dried. In some embodiments, the solid of the compound of Formula I is dried under vacuum. In some embodiments, the solid is dried at about 55° C.

Forms B and C

In addition to Form A, other forms of the compound of Formula I have been observed. Form B is observed as a mixture with Form A. The DSC of the mixture of Forms A and B exhibits a small exotherm having an onset of approximately 120° C. and an onset of a melt at approximately 145° C., likely the melt of Form B. Following the melt at approximately 145° C., is an exothermic event, which is ascribed to the conversion of the melt to Form A. An endothermic event of onset temperature 180° C. is ascribed to the melt of Form A. However, a pure sample of Form B is required to determine the DSC curve for Form B.

In some embodiments, Form B of the compound of Formula I is prepared as a mixture with Form A by 1) dissolving the compound of Formula I in methanol to form a solution of the compound of Formula I, and 2) stirring the solution. In some embodiments, the solution is stirred at a temperature between about 20° C. to about 30° C. In some embodiments, the solution is stirred at a temperature of about 25° C. In some embodiments, the compound of Formula I crashes out of the solution to afford a suspension comprising a solid of the compound of Formula I suspended in the solvent. In some embodiments, the method comprises isolating the solid of the compound of Formula I through filtration. In some embodiments, the solid of the compound of Formula I is dried. In some embodiments, the solid of the compound of Formula I is dried under vacuum. In some embodiments, the solid is dried at about 55° C.

Form C is a hemi-1,4-dioxane solvate formed from crystallization of the compound of Formula I in 1,4-dixoane. The DSC curve of Form C exhibits an endotherm between 40-110° C., associated with loss of 1,4-dioxane. The endothermic event is followed by a small exothermic event which is subsequently followed by a melt endotherm, ascribed to melting of Form A. The desolvation may occur to either afford an isomorphous desolvate or a different physical form prior to conversion to polymorphic Form A.

In some embodiments, Form C of the compound of Formula I is prepared by 1) dissolving the compound of Formula I in 1,4-dioxane to form a solution of the compound of Formula I, and 2) stirring the solution. In some embodiments, the solution is stirred at a temperature between about 20° C. to about 30° C. In some embodiments, the solution is stirred at a temperature of about 25° C. In some embodiments, the compound of Formula I crashes out of the solution to afford a suspension comprising a solid of the compound of Formula I suspended in the solvent. In some embodiments, the method comprises isolating the solid of the compound of Formula I through filtration. In some embodiments, the solid of the compound of Formula I is dried. In some embodiments, the solid of the compound of Formula I is dried under vacuum. In some embodiments, the solid is dried at about 55° C.

It will be understood that the 2-theta values of the XRPD patterns for the crystalline forms of the compound of Formula I, and pharmaceutically acceptable salts thereof, can vary slightly from one instrument to another and also depending on variations in sample preparation and batch to batch variation, and so the values quoted are not to be construed as absolute. It will be understood that the peak positions in an XRPD pattern are reported in terms of angular positions (two theta) with an allowable variability of ±0.2° 2θ. The variability of ±0.2° 2θ is intended to be used when comparing two powder XRPD patterns. In practice, if a diffraction pattern peak from one pattern is assigned a range of angular positions (two theta) which is the measured peak position±0.2° and if those ranges of peak positions overlap, then the two peaks are considered to have the same angular position. For example, if a peak from one pattern is determined to have a position of 11.0° 2θ, for comparison purposes the allowable variability allows the peak to be assigned a position in the range of 10.8°-11.2° 2θ. It will also be understood that the relative intensities of peaks can vary depending on orientation effects so that the intensities shown in the XRPD traces included herein are illustrative and not intended to be used for absolute comparison. It is to be further understood that for comparison purposes some variability in peak intensities from those shown in XRPD traces is allowed. Accordingly, it is to be understood that the phrase "substantially the same XRPD pattern as shown in FIG. 1" means that for comparison purposes, at least 90% of the peaks shown in FIG. 1 are present.

Compounds provided herein can also contain unnatural proportions of atomic isotopes at one or more of the atoms that constitute such compounds. That is, an atom, in particular when mentioned in relation to the compound of Formula I comprises all isotopes and isotopic mixtures of that atom, such as naturally occurring isotopes with natural abundance. For example, when hydrogen is mentioned, it is understood to refer to $^1H$, $^2H$, $^3H$ or mixtures thereof; when carbon is mentioned, it is understood to refer to $^{12}C$, $^{13}C$, $^{14}C$ or mixtures thereof; when nitrogen is mentioned, it is understood to refer to $^{14}N$, $^{15}N$ or mixtures thereof; and when oxygen is mentioned, it is understood to refer to $^{16}O$, $^{17}O$, $^{18}O$ or mixtures thereof. All isotopic variations of the compounds provided herein are intended to be encompassed within the scope of the present invention.

For illustrative purposes, Scheme 1 shows a general method for preparing the compounds provided herein as well as key intermediates. For a more detailed description of the individual reaction steps, see, e.g., International Patent Publication No. WO 2017/103611, which is incorporated by reference in its entirety herein. Those skilled in the art will appreciate that other synthetic routes can be used to synthesize the compounds. Although specific starting materials and reagents are depicted in the Scheme and discussed below, other starting materials and reagents can be easily substituted to provide a variety of derivatives and/or reaction conditions.

Scheme 1

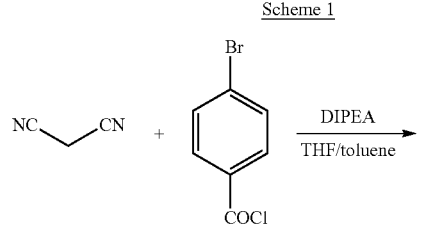

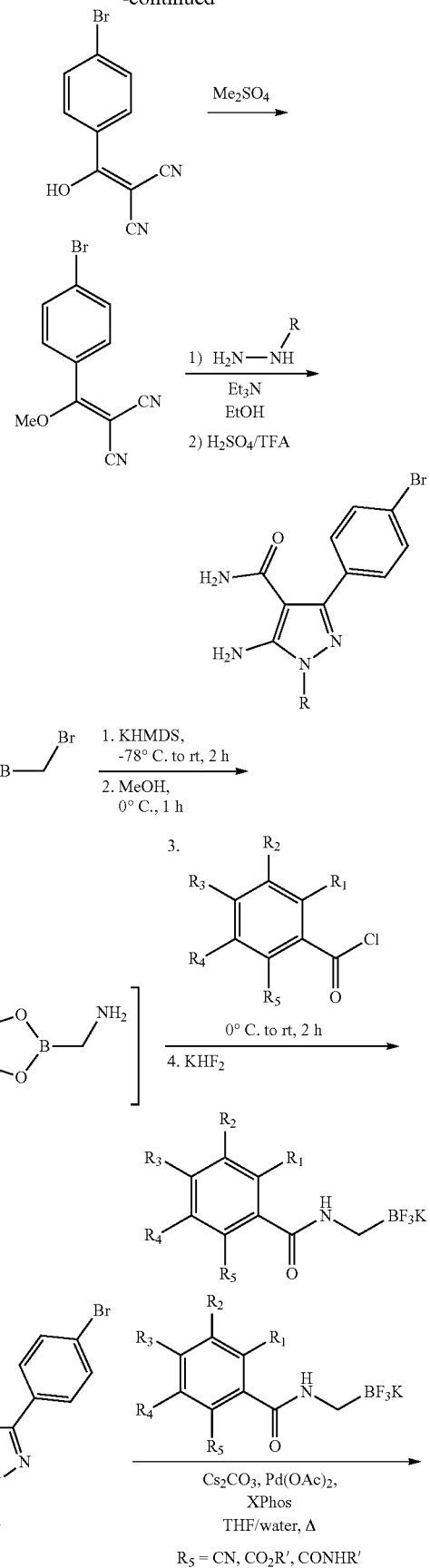

-continued

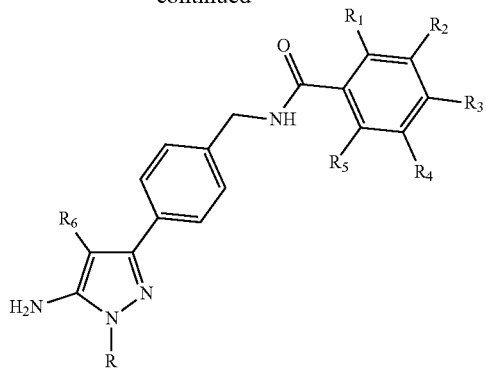

Scheme 1 shows a general scheme for the synthesis of the compound of Formula I.

3. Methods of Treatment

The ability of the compound of Formula I, including polymorph forms and pharmaceutically acceptable salts thereof, to act as a BTK inhibitor can be demonstrated by the assays described in International Patent Application Publication WO 2017/103611 as well as Example 1.

In some embodiments, the compound of Formula I provided herein exhibits potent and selective BTK inhibition. For example, the compound of Formula I exhibits nanomolar potency against wild type BTK and a BTK kinase encoded by a BTK gene including a BTK kinase inhibitor resistance mutation, including, for example, C481S. In some embodiments, inhibition of C481S is similar to that observed for wild-type BTK.

In some embodiments, the compound of Formula I, or a pharmaceutically acceptable salt, amorphous, or polymorph form thereof, selectively targets a BTK kinase. For example, the compound of Formula I, or a pharmaceutically acceptable salt, amorphous, or polymorph form thereof, can selectively target a BTK kinase over another kinase or non-kinase target. In some embodiments, the compound of Formula I, or a pharmaceutically acceptable salt, amorphous, or polymorph form thereof, selectively targets a BTK kinase over one or more of BRK, CSK, ERBB4, FYN, MEK1, MEK2, TEC, TXK, YES1, BMX, BLK, EGFR, ITK, SRC, JAK1, JAK2, and JAK3. In some embodiments, the compound of Formula I, or a pharmaceutically acceptable salt, amorphous, or polymorph form thereof, selectively targets a BTK kinase over a TEC kinase.

In some embodiments, the compound of Formula I, or a pharmaceutically acceptable salt, amorphous, or polymorph form thereof, exhibits at least a 30-fold selectivity for a BTK kinase over another kinase. For example, the compound of Formula I, or a pharmaceutically acceptable salt, amorphous, or polymorph form thereof, exhibits at least a 40-fold selectivity; at least a 50-fold selectivity; at least a 60-fold selectivity; at least a 70-fold selectivity; at least a 80-fold selectivity; at least a 90-fold selectivity; at least 100-fold selectivity; at least 200-fold selectivity; at least 300-fold selectivity; at least 400-fold selectivity; at least 500-fold selectivity; at least 600-fold selectivity; at least 700-fold selectivity; at least 800-fold selectivity; at least 900-fold selectivity; or at least 1000-fold selectivity for a BTK kinase over another kinase. In some embodiments, the compound of Formula I, or a pharmaceutically acceptable salt, amorphous, or polymorph form thereof, exhibits at least a 100-fold selectivity for a BTK kinase over another kinase. In some embodiments, selectivity for a BTK kinase over another kinase is measured in a cellular assay (e.g., a cellular assay as provided herein). In some embodiments, the compound of Formula I, or a pharmaceutically acceptable salt, amorphous, or polymorph form thereof, exhibits lower off-target toxicity due to its selectivity for a BTK kinase over another kinase.

The compound of Formula I or a pharmaceutically acceptable salt, amorphous, or polymorph form thereof, a spray-dried dispersion thereof, or a pharmaceutical composition thereof, is useful for treating diseases and disorders which can be treated with a BTK kinase inhibitor, such as BTK-associated diseases and disorders, e.g., proliferative disorders such as cancers, including hematological cancers and solid tumors, and inflammatory and autoimmune disorders such as rheumatoid arthritis or lupus.

Provided herein is a method of treating cancer (e.g., a BTK-associated cancer) in a subject in need of such treatment, the method comprising administering to the subject a therapeutically effective amount of the compound of Formula I, or a pharmaceutically acceptable salt, amorphous, or polymorph form thereof, a spray-dried dispersion thereof, or a pharmaceutical composition thereof. For example, provided herein are methods for treating a BTK-associated cancer in a subject in need of such treatment, the method comprising a) detecting a dysregulation of a BTK gene, a BTK kinase, or the expression or activity or level of any of the same in a sample from the subject; and b) administering a therapeutically effective amount of the compound of Formula I, or a pharmaceutically acceptable salt, amorphous, or polymorph form thereof, a spray-dried dispersion thereof, or a pharmaceutical composition thereof.

In some embodiments, the dysregulation of a BTK gene, a BTK kinase, or the expression or activity or level of any of the same includes increased expression of a BTK kinase, increased transcription of a BTK gene, or increased activation or phosphorylation of a BTK kinase. In some embodiments, a dysregulation of a BTK gene, a BTK protein, or expression or activity, or level of any of the same can be a genetic mutation (e.g., a BTK gene translocation that results in the expression of a fusion protein, a deletion in a BTK gene that results in the expression of a BTK protein that includes a deletion of at least one amino acid as compared to the wild-type BTK protein, or a mutation in a BTK gene that results in the expression of a BTK protein with one or more point mutations, or an alternative spliced version of a BTK mRNA that results in a BTK protein that results in the deletion of at least one amino acid in the BTK protein as compared to the wild-type BTK protein), or a BTK gene amplification that results in overexpression of a BTK protein or an autocrine activity resulting from the overexpression of a BTK gene in a cell, that results in a pathogenic increase in the activity of a kinase domain of a BTK protein (e.g., a constitutively active kinase domain of a BTK protein) in a cell. In some embodiments, a dysregulation of a BTK gene, a BTK protein, or expression or activity, or level of any of the same, can be a mutation in a BTK gene that encodes a BTK protein that is constitutively active or has increased activity as compared to a protein encoded by a BTK gene that does not include the mutation. Non-limiting examples of BTK mutations (and fusions) are described in Table 1. Additional examples of a dysregulation of a BTK gene, a BTK protein, or expression or activity, or level of any of the same are BTK inhibitor resistance mutations. Non-limiting examples of BTK resistance mutations are described in Tables 2 and 3.

In some embodiments, a dysregulation of a BTK gene, a BTK kinase, or the expression or activity or level of any of the same is the result of activating mutations within the BCR complex or downstream signaling components, continuous BCR stimulation by microbial antigens or autoantigens present in the tissue microenvironment, or ligand-independent tonic BCR signaling that result in the pathogenic increase in the expression or activation of a BTK protein. For example, a dysregulation of a BTK gene, a BTK protein, or expression or activity, or level of any of the same can be the result of a genetic mutation in a BCR signaling pathway protein (e.g., a BCR signaling pathway gene translocation that results in the expression of a fusion protein, a deletion in a BCR signaling pathway gene that results in the expression of a BCR signaling pathway protein that includes a deletion of at least one amino acid as compared to the wild-type BCR signaling pathway protein, or a mutation in a BCR signaling pathway gene that results in the expression of a BCR signaling pathway protein with one or more point mutations, or an alternative spliced version of a BCR signaling pathway protein mRNA that results in a BCR signaling pathway protein that results in the deletion of at least one amino acid in the BCR signaling pathway protein as compared to the wild-type BCR signaling pathway protein). Non-limiting examples of BCR signaling pathway mutations are described in Table 4.

In some embodiments, the compound of Formula I is a polymorph form. In some embodiments, the compound of Formula I is polymorph Form A.

In some embodiments, the spray-dried dispersion comprises the compound of Formula I and an HPMCAS polymer. In some embodiments, the pharmaceutical composition comprises the spray-dried dispersion of the compound of Formula I and an HPMCAS polymer. In some embodiments, the HPMCAS polymer is HPMCAS-MG.

The compound of Formula I, or a pharmaceutically acceptable salt, amorphous, or polymorph form thereof, a spray-dried dispersion thereof, or a pharmaceutical composition thereof, is also useful for treating a BTK-associated cancer.

In some embodiments of any of the methods or uses described herein, the cancer (e.g., BTK-associated cancer) is a hematological cancer. In some embodiments of any of the methods or uses described herein, the cancer (e.g., BTK-associated cancer) is a solid tumor. In some embodiments of any of the methods or uses described herein, the cancer (e.g., BTK-associated cancer) is a B-cell malignancy. In some embodiments of any of the methods or uses described herein, the cancer (e.g., BTK-associated cancer) is a Hodgkin lymphoma, diffuse large B cell lymphoma (DLBCL) (e.g., activated B cell-like DLBCL (ABC-DLBCL)), follicular lymphoma, mantle cell lymphoma, marginal zone lymphoma (e.g., extranodal marginal zone B cell lymphoma, splenic marginal zone lymphoma), Burkitt lymphoma, Waldenstrom's macroglobulinemia (lymphoplasmacytic lymphoma (LPL)), primary central nervous system lymphoma, small lymphocytic lymphoma, chronic lymphocytic leukemia (CLL), acute lymphocytic leukemia (ALL), B-cell prolymphocytic leukemia, precursor B-lymphoblastic leukemia, hairy cell leukemia, acute myeloid leukemia (AML), chronic myeloid leukemia, multiple myeloma, plasma cell myeloma, plasmacytoma, bone cancer, bone metastasis, breast cancer, gastro-esophageal cancer, pancreatic cancer, ovarian cancer, prostate cancer, lung cancer, colon cancer, uterine cancer, hepatocellular cancer, head and neck cancer, or glioma.

In some embodiments, a hematological cancer (e.g., hematological cancers that are BTK-associated cancers) is selected from the group consisting of leukemias, lymphomas (non-Hodgkin's lymphoma), Hodgkin's disease (also called Hodgkin's lymphoma), and myeloma, for instance, acute lymphocytic leukemia (ALL), acute myeloid leukemia (AML), acute promyelocytic leukemia (APL), chronic lymphocytic leukemia (CLL), chronic myeloid leukemia (CML), chronic myelomonocytic leukemia (CMML), chronic neutrophilic leukemia (CNL), acute undifferentiated leukemia (AUL), anaplastic large-cell lymphoma (ALCL), prolymphocytic leukemia (PML), juvenile myelomonocytic leukemia (JMML), adult T-cell ALL, AML with trilineage myelodysplasia (AML/TMDS), mixed lineage leukemia (MLL), myelodysplastic syndromes (MDSs), myeloproliferative disorders (MPD), diffuse large B cell lymphoma (DLBCL) (e.g., activated B cell-like DLBCL (ABC-DLBCL)), follicular lymphoma, mantle cell lymphoma, marginal zone lymphoma (e.g., extranodal marginal zone B cell lymphoma, splenic marginal zone lymphoma), Burkitt lymphoma, Waldenstrom's macroglobulinemia (lymphoplasmacytic lymphoma (LPL)), primary central nervous system lymphoma, small lymphocytic lymphoma, precursor B-lymphoblastic leukemia, hairy cell leukemia, chronic myeloid leukemia, anaplastic large cell lymphoma, MALT lymphoma, plasma cell myeloma, plasmacytoma, and multiple myeloma (MM). Additional examples of hematological cancers include myeloproliferative disorders (MPD) such as polycythemia vera (PV), essential thrombocytopenia (ET) and idiopathic primary myelofibrosis (IMF/IPF/PMF). In one embodiment, the hematological cancer (e.g., the hematological cancer that is a BTK-associated cancer) is mantle cell lymphoma, chronic lymphocytic leukemia, small lymphocytic lymphoma, Waldenstrom's macroglobulinemia, or marginal zone lymphoma.

In some embodiments, the BTK-associated cancer has not undergone transformation. Non-limiting examples of transformation in BTK-associated cancers include Richter's transformation, prolymphocytic transformation (e.g., prolymphocytic transformation of CLL), transformed non-Hodgkins lymphoma, and blastoid lymphoma (e.g., blastoid variant mantle cell lymphoma).

In some embodiments, the BTK-associated cancer is not a cancer with known central nervous system involvement by lymphoma.

In some embodiments, the cancer (e.g., the BTK-associated cancer) is a solid tumor. Examples of solid tumors (e.g., solid tumors that are BTK-associated cancers) include, for example, bone cancer, bone metastasis, breast cancer, gastro-esophageal cancer, pancreatic cancer, ovarian cancer, prostate cancer, lung cancer, colon cancer, uterine cancer, hepatocellular cancer, head and neck cancer, and glioma. See, for example, Campbell, et al., *Journal of Clinical Medicine*, 2018, 7(4): 62 and Zucha et al., *Oncotarget*. 6(15):13255-68, 2015, each of which is incorporated by reference in its entirety herein.

In some embodiments, a B-cell malignancy is a B-cell non-Hodgkin lymphoma, Hodgkin lymphoma, or B-cell leukemia. In some embodiments, the B-cell malignancy is a Hodgkin lymphoma, diffuse large B cell lymphoma (DLBCL) (e.g., activated B cell-like DLBCL (ABC-DLBCL)), follicular lymphoma, mantle cell lymphoma, marginal zone lymphoma (e.g., extranodal marginal zone B cell lymphoma, splenic marginal zone lymphoma), Burkitt lymphoma, Waldenstrom's macroglobulinemia(lymphoplasmacytic lymphoma (LPL)), primary central nervous system lymphoma, small lymphocytic lymphoma, chronic lymphocytic leukemia, acute lymphoblastic leukemia (ALL), B-cell prolymphocytic leukemia, precursor B-lymphoblastic leukemia, or hairy cell leukemia.

In some embodiments, the subject does not have active uncontrolled autoimmune cytopenia. In some embodiments, the subject has not been diagnosed with autoimmune cytopenia. In some embodiments, the subject does not have clinically significant, uncontrolled cardiac, cardiovascular disease or history of myocardial infarction within 6 months of beginning a treatment as described herein. In some embodiments, the subject has not been diagnosed with a cardiac or cardiovascular disease. In some embodiments, the subject has not had a myocardial infarction. In some embodiments, the subject does not have a clinically significant active malabsorption syndrome. In some embodiments, the subject has not been diagnosed with a malabsorption syndrome. In some embodiments, the subject is not being treated with strong cytochrome P450 3A4 (CYP3A4) inhibitors or inducers during any of the treatments as described herein. In some embodiments, the subject is not being treated with proton pump inhibitors within 7 days of starting any of the treatments described herein. In some embodiments, the subject does not have an active second malignancy. In some embodiments, the subject has an active second malignancy, which is in remission, and the life expectancy of the subject is >2 years.

In some embodiments, the subject is a human. In some embodiments of any of the methods or uses described herein, the subject is BTK-inhibitor naive. In other embodiments of any of the methods or uses described herein, the subject is not BTK-inhibitor naive.

Accordingly, also provided herein is a method for treating a subject diagnosed with or identified as having a BTK-associated cancer, e.g., any of the exemplary BTK-associated cancers disclosed herein, comprising administering to the subject a therapeutically effective amount of the compound of Formula I, or a pharmaceutically acceptable salt, amorphous, or polymorph form thereof, a spray-dried dispersion thereof, or a pharmaceutical composition thereof, as defined herein.

Dysregulation of a BTK kinase, a BTK gene, or the expression or activity or level of any (e.g., one or more) of the same can contribute to tumorigenesis. For example, a dysregulation of a BTK kinase, a BTK gene, or expression or activity or level of any of the same can be an overexpression, activation, amplification, mutation, or translocation of a BTK kinase, a BTK gene, or a BTK kinase domain. In some embodiments, dysregulation of a BTK kinase can be increased expression (e.g., increased levels) or increased activation (e.g., increased phosphorylation) of a wildtype BTK kinase in a mammalian cell due to aberrant cell signaling and/or dysregulated autocrine/paracrine signaling (e.g., as compared to a control non-cancerous cell). In some embodiments, the increased expression of a BTK kinase can be due to increased transcription of a BTK gene. In some embodiments, dysregulation of a BTK kinase can be increased expression (e.g., increased levels) of a wildtype BTK kinase in a mammalian cell (e.g., as compared to a control non-cancerous cell), e.g., due to aberrant cell signaling and/or dysregulated autocrine/paracrine signaling. In some embodiments, the dysregulation of a BTK kinase can be over-activation (e.g., as compared to a control non-cancerous cell). In some embodiments, the over-activation can be due to increased phosphorylation of BTK. In some embodiments, a mutation in a BTK gene can involve mutations in the BTK ligand-binding site, extracellular domains, kinase domain, and in regions involved in protein:protein interactions and downstream signaling. In some embodiments, a mutation (e.g., an activating mutation) in a BTK gene can result in the expression of a BTK kinase having one or more (e.g., two, three, four, five, six, seven, eight, nine, or ten) amino acid substitutions (e.g., one or more amino acid substitutions in the kinase domain. In some embodiments, a mutation can be a gene amplification of a BTK gene. In some embodiments, a mutation (e.g., an activating mutation) in a BTK gene can result in the expression of a BTK kinase or BTK receptor that lacks at least one amino acid (e.g., at least 2, at least 3, at least 4, at least 5, at least 6, at least 7, at least 8, at least 9, at least 10, at least 12, at least 14, at least 16, at least 18, at least 20, at least 25, at least 30, at least 35, at least 40, at least 45, or at least 50 amino acids) as compared to a wildtype BTK protein. In some embodiments, a mutation (e.g., an activating mutation) in a BTK gene can result in the expression of a BTK kinase that has at least one amino acid (e.g., at least 2, at least 3, at least 4, at least 5, at least 6, at least 7, at least 8, at least 9, at least 10, at least 12, at least 14, at least 16, at least 18, at least 20, at least 25, at least 30, at least 35, at least 40, at least 45, or at least 50 amino acids) inserted as compared to a wildtype BTK protein. Translocation can include a gene translocation resulting in the expression of a fusion protein that includes a BTK kinase domain and a fusion partner. For example, a fusion protein can have increased kinase activity as compared to a wildtype BTK protein. Other dysregulations can include BTK mRNA splice variants. In some embodiments, the wildtype BTK protein is the exemplary wildtype BTK protein described herein.

In some embodiments, the dysregulation of a BTK gene, a BTK kinase, or expression or activity or level of any of the same, includes overexpression of wild-type BTK kinase. In some embodiments, the dysregulation of a BTK gene, a BTK kinase protein, or expression or activity or level of any of the same, includes overexpression, activation, amplification, or mutation in a chromosomal segment comprising the BTK gene or a portion thereof, including, for example, the kinase domain portion, or a portion capable of exhibiting kinase activity.

In some embodiments, the dysregulation of a BTK gene, a BTK kinase, or expression or activity or level of any of the same, includes one or more deletions (e.g., deletion of an amino acid at position 4), insertions, or point mutation(s) in a BTK kinase. In some embodiments, the dysregulation of a BTK gene, a BTK kinase, or expression or activity or level of any of the same, includes a deletion of one or more residues from the BTK kinase, resulting in constitutive activity of the BTK kinase domain.

In some embodiments, the dysregulation of a BTK gene, a BTK kinase, or expression or activity or level of any of the same, includes at least one point mutation in a BTK gene that results in the production of a BTK kinase that has one or more amino acid substitutions, insertions, or deletions as compared to the wild-type BTK kinase (see, for example, the point mutations listed in Table 1).

TABLE 1

BTK Kinase Protein Amino Acid Substitutions/Insertions/Deletions[A]
Exemplary BTK Substitutions/Insertions/Deletions Amino acid position 117 (e.g., T117P)
E301 in frame deletion
Amino acid position 316 (e.g., T316A)
Amino acid position 474 (e.g., T474I, T474M, T474S)
Amino acid position 481 (e.g., C481S, C481F, C481Y, C481R, C481T, C481G, C481W)
Amino acid position 527 (e.g., C527fs)
Amino acid position 528 (e.g., L528W)
Amino acid position 544 (e.g., R544M, R544W, R544S)

TABLE 1-continued

BTK Kinase Protein Amino Acid Substitutions/Insertions/Deletions[4]
Exemplary BTK Substitutions/Insertions/Deletions Amino acid position 560 (e.g., P560L)
Amino acid position 562 (e.g., R562W, R562G)
Amino acid position 601 (e.g., F601L)
Y627 nonsense mutation

[4]The BTK kinase mutations shown may be activating mutations and/or confer increased resistance of the BTK kinase to a BTK kinase inhibitor and/or a multi-kinase inhibitor (MKI), e.g., as compared to a wildtype BTK kinase.
[1] Krysiak et al., Blood. 129(4): 473-483, 2017.
[2] Johnson et al., A.C.S. Chem. Biol. 11(10): 2897-2907, 2016.
[3] Maddocks et al., JAMA Oncol. 1(1): 80-7, 2015.
[4] Chang et al., J. Clin. Oncol. 31(15): 7014-7014. 2013.
[5] Xu et al., Blood. 129(18): 2519-2525, 2017.
[6] Xu et al., Blood. Abstract Number: 756. Meeting Info: 58th Annual Meeting of the American Society of Hematology, ASH 2016. San Diego, CA, United States, 2016.
[7] Scherer et al., Abstract Number: 1752. Meeting Info: 58th Annual Meeting of the American Society of Hematology, ASH 2016. San Diego, CA, United States, 2016.
[8] Sharma et al, Oncotarget. 7(42): 68833-68841, 2016.

In some embodiments, the dysregulation of a BTK gene, a BTK kinase protein, or expression or activity or level of any of the same, includes one or more chromosome translocations or inversions resulting in a BTK gene fusion. In some embodiments, the dysregulation of a BTK gene, a BTK kinase protein, or expression or activity or level of any of the same, is a result of genetic translocations in which the expressed protein is a fusion protein containing residues from a non-BTK partner protein, and includes a minimum of a functional BTK kinase domain.

Non-limiting examples of BTK fusion proteins are shown in Table 1a.

TABLE 1a

Exemplary BTK Fusion Partners and Cancers.

| Fusion Partner | Non-limiting Exemplary BTK-Associated Cancer(s) |
|---|---|
| TSC22D2 | Breast invasive ductal carcinoma |
| ARMCX4 | Hepatocellular carcinoma |
| LOC442459 | Lung adenocarcinoma |
| BTK-intragenic fusion | Bladder urothelial carcinoma |

In some embodiments, the dysregulation of a BTK gene, a BTK kinase, or expression or activity or level of any of the same, includes an alternatively-spliced variant of a BTK mRNA. In some embodiments, the alternatively-spliced BTK mRNA results in a BTK kinase having at least one residue deleted (as compared to the wild-type BTK kinase) resulting in a constitutive activity of a BTK kinase domain. An example of a BTK kinase that is an alternatively-spliced variant of a wildtype BTK kinase is p65BTK, which contains a different first exon than a wildtype BTK kinase, and translation of p65BTK likely starts at a putative start codon in exon 4 instead of exon 2 as in a wildtype BTK kinase (Grassilli et al., Oncogene. 35(33):4368-78, 2016, which is incorporated by reference in its entirety herein). In some embodiments, p65BTK is expressed in colon cancer.

In some embodiments, the dysregulation of a BTK gene, a BTK kinase, or expression or activity or level of any of the same, includes a BTK mRNA transcribed from an alternative promoter as compared to a wild-type BTK kinase that results in a BTK kinase having at least one amino acid (e.g., at least 2, at least 3, at least 4, at least 5, at least 6, at least 7, at least 8, at least 9, at least 10, at least 12, at least 14, at least 16, at least 18, at least 20, at least 25, at least 30, at least 35, at least 40, at least 45, at least 50 amino acids, or at least 100 amino acids) added to the N-terminus of the BTK kinase as compared to the wildtype BTK kinase. An example of a BTK kinase translated from an alternative promoter includes BTK-C, which has a different first exon due to alternative-splicing compared to a wildtype BTK kinase and a different start codon that leads to a BTK kinase with an N-terminal extension of 34 amino acids compared to a wildtype BTK kinase (Eifert et al., Genes Chromosomes Cancer. 52(10): 961-75, 2013 and Kokabee et al. Cancer Biol. Ther. 16(11): 1604-15, 2015, each of which is incorporated by reference in its entirety herein). In some embodiments, BTK-C is expressed in prostate or breast cancer.

In some embodiments, the dysregulation of a BTK gene, a BTK kinase, or expression or activity or level of any of the same, includes at least one point mutation in a BTK gene that results in the production of a BTK kinase that has one or more amino acid substitutions or insertions or deletions in a BTK gene that results in the production of a BTK kinase that has one or more amino acids inserted or removed, as compared to the wild-type BTK kinase. In some cases, the resulting BTK kinase is more resistant to inhibition of its phosphotransferase activity by one or more first BTK kinase inhibitor(s), as compared to a wildtype BTK kinase or a BTK kinase not including the same mutation. Such mutations, optionally, do not decrease the sensitivity of the cancer cell or tumor having the BTK kinase to treatment with the compound of Formula I, or a pharmaceutically acceptable salt, amorphous, or polymorph form thereof (e.g., as compared to a cancer cell or a tumor that does not include the particular BTK inhibitor resistance mutation). In such embodiments, a BTK inhibitor resistance mutation can result in a BTK kinase that has one or more of an increased $V_{max}$, a decreased $K_m$ for ATP, and an increased $K_D$ for a first BTK kinase inhibitor, when in the presence of a first BTK kinase inhibitor, as compared to a wildtype BTK kinase or a BTK kinase not having the same mutation in the presence of the same first BTK kinase inhibitor. In other embodiments, the dysregulation of a BTK gene, a BTK kinase, or expression or activity or level of any of the same, includes at least one point mutation in a BTK gene that results in the production of a BTK kinase that has one or more amino acid substitutions as compared to the wild-type BTK kinase, and which has increased resistance to the compound of Formula I, or a pharmaceutically acceptable salt, amorphous, or polymorph form thereof, as compared to a wildtype BTK kinase or a BTK kinase not including the same mutation. In such embodiments, a BTK inhibitor resistance mutation can result in a BTK kinase that has one or more of an increased $V_{max}$, a decreased $K_m$, and a decreased $K_D$ in the presence of the compound of Formula I, or a pharmaceutically acceptable salt, amorphous, or polymorph form thereof, as compared to a wildtype BTK kinase or a BTK kinase not having the same mutation in the presence of the compound of Formula I, or a pharmaceutically acceptable salt, amorphous, or polymorph form thereof.

Examples of BTK inhibitor resistance mutations can, e.g., include point mutations, insertions, or deletions in and near the ATP binding site in the tertiary structure of BTK kinase, including but not limited to a gatekeeper residue (e.g., amino acid position 474 in a wildtype BTK kinase), P-loop residues, residues in or near the DFG motif, and ATP cleft solvent front amino acid residues. Additional examples of these types of mutations include changes in residues that may affect enzyme activity and/or drug binding including but are not limited to residues in the activation loop, residues near or interacting with the activation loop, residues contributing to active or inactive enzyme conformations, changes including mutations, deletions, and insertions in the loop proceeding the C-helix and in the C-helix. In some embodiments, the wildtype BTK protein is the exemplary wildtype BTK kinase described herein. Specific residues or residue regions that may be changed (and are BTK inhibitor resistance mutations) include but are not limited to those listed in Table 2, with numbering based on the human wildtype BTK protein sequence (e.g., SEQ ID NO: 1). As can be appreciated by those skilled in the art, an amino acid position in a reference protein sequence that corresponds to a specific amino acid position in SEQ ID NO: 1 can be determined by aligning the reference protein sequence with SEQ ID NO: 1 (e.g., using a software program, such as ClustalW2). Changes to these residues may include single or multiple amino acid changes, insertions within or flanking the sequences, and deletions within or flanking the sequences. See also J. Kooistra, G. K. Kanev, O. P. J. Van Linden, R. Leurs, I. J. P. De Esch, and C. De Graaf, "KLIFS: A structural kinase-ligand interaction database," *Nucleic Acids Res.*, vol. 44, no. D1, pp. D365-D371, 2016, which is incorporated by reference in its entirety herein.

```
Exemplary Sequence of Mature Human BTK Protein
                                    (SEQ ID NO: 1)
MAAVILESIF LKRSQQKKKT SPLNFKKRLF LLTVHKLSYY

EYDFERGRRG SKKGSIDVEK ITCVETVVPE KNPPPERQIP

RRGEESSEME QISIIERFPY PFQVVYDEGP LYVFSPTEEL

RKRWIHQLKN VIRYNSDLVQ KYHPCFWIDG QYLCCSQTAK

NAMGCQILEN RNGSLKPGSS HRKTKKPLPP TPEEDQILKK

PLPPEPAAAP VSTSELKKVV ALYDYMPMNA NDLQLRKGDE

YFILEESNLP WWRARDKNGQ EGYIPSNYVT EAEDSIEMYE

WYSKHMTRSQ AEQLLKQEGK EGGFIVRDSS KAGKYTVSVF

AKSTGDPQGV IRHYVVCSTP QSQYYLAEKH LFSTIPELIN

YHQHNSAGLI SRLKYPVSQQ NKNAPSTAGL GYGSWEIDPK

DLTFLKELGT GQFGVVKYGK WRGQYDVAIK MIKEGSMSED

EFIEEAKVMM NLSHEKLVQL YGVCTKQRPI FIITEYMANG

CLLNYLREMR HRFQTQQLLE MCKDVCEAME YLESKQFLHR

DLAARNCLVN DQGVVKVSDF GLSRYVLDDE YTSSVGSKFP

VRWSPPEVLM YSKFSSKSDI WAFGVLMWEI YSLGKMPYER

FTNSETAEHI AQGLRLYRPH LASEKVYTIM YSCWHEKADE

RPTFKILLSN ILDVMDEES
```

In some embodiments, the compound of Formula I, or a pharmaceutically acceptable salt, amorphous, or polymorph form thereof, a spray-dried dispersion thereof, or a pharmaceutical composition thereof, are useful in treating subjects that develop cancers with BTK inhibitor resistance mutations (e.g., that result in an increased resistance to a first BTK inhibitor, e.g., a substitution at amino acid position 481, e.g., C481S, C481T, C481R, C481G, and/or one or more BTK inhibitor resistance mutations listed in Tables 2 and 3) by either dosing in combination or as a subsequent or additional (e.g., follow-up) therapy to existing drug treatments (e.g., other BTK kinase inhibitors; e.g., first and/or second BTK kinase inhibitors). Exemplary first and second BTK kinase inhibitors are described herein. In some embodiments, a first or second BTK kinase inhibitor can be selected from the group consisting of: ibrutinib, PRN1008, PRN473, ABBV-105, AC0058, acalabrutinib, zanubrutinib, spebrutinib, poseltinib, evobrutinib, M7583, tirabrutinib, CG'806, ARQ 531, BIIB068, vecabrutinib, AS871, CB1763, CB988, GDC-0853, RN486, dasatinib, GNE-504, GNE-309, BCB-311, BTK Max, CT-1530, CGI-1746, CGI-560, LFM A13, TP-0158, dtrmwxhs-12, CNX-774, and LOU064. In some embodiments, the first or second BTK kinase inhibitor is a covalent inhibitor. Exemplary covalent inhibitors of a BTK kinase include, but are not limited to, ibrutinib, PRN1008, PRN473, ABBV-105, AC0058, acalabrutinib, zanubrutinib, spebrutinib, poseltinib, evobrutinib, M7583, and tirabrutinib. In some embodiments, the first or second BTK kinase inhibitor is a non-covalent inhibitor. Exemplary non-covalent inhibitors of a BTK kinase include, but are not limited to, CG'806, ARQ 531, BIIB068, vecabrutinib, AS871, CB1763, CB988, GDC-0853, RN486, and dasatinib.

In some embodiments, the compound of Formula I, or a pharmaceutically acceptable salt, amorphous, or polymorph form thereof, a spray-dried dispersion thereof, or a pharmaceutical composition thereof, is useful for treating a cancer that has been identified as having one or more BTK inhibitor resistance mutations (that result in an increased resistance to a first or second BTK inhibitor, e.g., a substitution at amino acid position 481, e.g., C481S, C481T, C481R, and C481R, or e.g., a substitution at amino acid position 474, e.g., T474I, T474M, and T474S). Non-limiting examples of BTK inhibitor resistance mutations are listed in Table 2.

TABLE 2

Exemplary BTK Resistance Mutations

| Exemplary BTK Resistance Mutations | Exemplary BTK-Associated Cancer(s) |
| --- | --- |
| Amino acid position 117 (e.g., T117P) | Follicular Lymphoma[1] |
| E301 in frame deletion | Follicular Lymphoma[1] |
| Amino acid position 316 (e.g., T316A) | Chronic Lymphocytic Leukemia (CLL)[8] |
| Amino acid position 474 (e.g., T474I, T474M, T474S) | Ibrutinib-Resistant B-Cell Malignancy[1], CLL[3] |
| Amino acid position 481 (e.g., C481S, C481F, C481Y, C481R, C481T, C481G, C481W) | Chronic Lymphocytic Leukemia (CLL)[4], Waldenström Macroglobulinemia[5], Mantle Cell Lymphoma[6], Non-Hodgkin Lymphoma (Follicular Lymphoma)[7] |
| Amino acid position 527 (e.g., C527fs) | Follicular Lymphoma[1] |
| Amino acid position 528 (e.g., L528W) | Follicular Lymphoma[1] |

TABLE 2-continued

Exemplary BTK Resistance Mutations

| Exemplary BTK Resistance Mutations | Exemplary BTK-Associated Cancer(s) |
|---|---|
| Amino acid position 560 (e.g., P560L) | Follicular lymphoma[1] |
| Amino acid position 562 (e.g., R562W, R562G) | Follicular lymphoma[1] |
| Amino acid position 601 (e.g., F601L) | Follicular lymphoma[1] |
| Y627 nonsense mutation | Follicular lymphoma[1] |

[1]Krysiak et al., Blood. 129(4): 473-483, 2017.
[2] Johnson et al., A.C.S. Chem. Biol. 11(10): 2897-2907, 2016.
[3]Maddocks et al., JAMA Oncol. 1(1): 80-7, 2015.
[4]Chang et al., J. Clin. Oncol. 31(15): 7014-7014, 2013.
[5]Xu et al. Blood. 129(18): 2519-2525, 2017.
[6]Xu et al. Blood. Abstract Number: 756. Meeting Info: 58th Annual Meeting of the American Society of Hematology, ASH 2016. San Diego, CA, United States, 2016.
[7]Scherer et al., Abstract Number: 1752. Meeting Info: 58th Annual Meeting of the American Society of Hematology, ASH 2016. San Diego, CA, United States, 2016.
[8]Sharma et al, Oncotarget. 7(42): 68833-68841, 2016.

In other embodiments, the compound of Formula I, or a pharmaceutically acceptable salt, amorphous, or polymorph form thereof, a spray-dried dispersion thereof, or a pharmaceutical composition thereof, is useful for treating a cancer that has been identified as having one or more BTK inhibitor resistance mutations (that result in an increased resistance to a first or second BTK inhibitor, e.g., a substitution in PLCγ2 at amino acid position 707, e.g., S707Y, S707P, and S707F, or e.g., a substitution in CARD11 at amino acid position 251, e.g., L251P). Non-limiting examples of BTK inhibitor resistance mutations are listed in Table 3.

TABLE 3

Exemplary BTK Resistance Mutations

| Exemplary Resistance Mutations | Exemplary BTK-Associated Cancer(s) |
|---|---|
| PLCγ2 Mutations | |
| Amino acid position 244 (e.g., H244R[4]) | CLL[4] |
| Amino acid position 257 (e.g., H257L[4]) | |
| Amino acid position 334 (e.g., D334H[1]) | CLL[1] |
| Amino acid position 495 (e.g., Y495H) | CLL[3] |
| Amino acid position 664 (e.g., P664S[1], P644L[1]) | CLL[1] |
| Amino acid position 665 (e.g., R665W[1]) | Waldenstrom macroglobulinemia[2] |
| Amino acid position 707 (e.g., S707Y[1], S707P[1], S707F[1], S707_A708del, Ser707TyrdelAlaTyr (6NT deletion)) | CLL[1] |
| Amino acid position 708 (e.g., A708P5) | CLL[5] |
| Amino acid position 742 (e.g., R742P[1, 6]) | CLL[1] |
| Amino acid position 845 (e.g., L845F[1, 6], L845fs[1]) | CLL[1] |
| Amino acid position 848 (e.g., L848R[1]) | CLL[1] |
| Amino acid position 993 (e.g., D993G, D993H[1]) | CLL[1] |
| Amino acid position 1139 (e.g., E1139del[1]) | CLL[1] |
| Amino acid position 1140 (e.g., D1140G[1, 6]) | CLL[1] |
| Amino acid position 1141 (e.g., M1141K[1], M1141R[4]) | CLL[1] |
| TNFAIP3 Mutations | |
| Amino acid position 143 (e.g., Q143*[7]) | TMD8 cell line (activated B-cell-like diffuse large B-cell lymphoma model)[7] |

[1]Landau et al., Nat. Commun. 8: 2185, 2017.
[2]Xu et al., Blood. 129: 2519-2525, 2017.
[3]Woyach et al. N. Engl. J. Med. 370(24): 2286-94, 2014.
[4]U.S. Pat. Application Publication No. 2017/0360795A1.
[5]Jones et al., Abstract Number: 3150. Meeting Info: American Association for Cancer Research Annual Meeting 2017, Washington, DC, United States, 2017.
[6]U.S. Pat. No. 9,885,086.
[7]Yahiaoui et al., PLoS One. 12(2): e0171221, 2017.

In some embodiments, a dysregulation of a BTK gene, a BTK kinase, or the expression or activity or level of any of the same is the result of activating mutations within the BCR complex or downstream signaling components, continuous BCR stimulation by microbial antigens or autoantigens present in the tissue microenvironment, or ligand-independent tonic BCR signaling that result in the pathogenic increase in the expression or activation of a BTK protein. In some embodiments, a dysregulation of a BTK gene, a BTK kinase, or the expression or activity or level of any of the same is a dysregulation of a BCR signaling pathway gene, a BCR signaling pathway protein, or the expression or activity or level of any of the same. In some embodiments, a dysregulation of a BCR signaling pathway gene, a BCR signaling pathway protein, or the expression or activity or level of any of the same is one or more activating mutations within the BCR complex or downstream signaling components, continuous BCR stimulation by microbial antigens or autoantigens present in the tissue microenvironment, or ligand-independent tonic BCR signaling that result in the pathogenic increase in the expression or activation of a BTK protein. For example, a dysregulation of a BTK gene, a BTK protein, or expression or activity, or level of any of the same can be the result of a genetic mutation in a BCR signaling pathway protein (e.g., a BCR signaling pathway gene translocation that results in the expression of a fusion protein, a deletion in a BCR signaling pathway gene that results in the expression of a BCR signaling pathway protein that includes a deletion of at least one amino acid as compared to the wild-type BCR signaling pathway protein, or a mutation in a BCR signaling pathway gene that results in the expression of a BCR signaling pathway protein with one or more point mutations, or an alternative spliced version of a BCR signaling pathway protein mRNA that results in a BCR signaling pathway protein that results in the deletion of at least one amino acid in the BCR signaling pathway protein as compared to the wild-type BCR signaling pathway protein).

In some embodiments, the dysregulation of a BTK gene, a BTK kinase, or expression or activity or level of any of the same, includes at least one point mutation in a BCR signaling pathway gene that results in the production of a BCR signaling pathway protein that has one or more amino acid substitutions or insertions or deletions in a BCR signaling pathway gene that results in the production of a BCR signaling pathway protein that has one or more amino acids inserted or removed, as compared to the wild-type BCR signaling pathway protein. In some embodiments, a mutation (e.g., an activating mutation) in a BCR signaling pathway gene can result in the expression of a BCR signaling pathway protein having one or more (e.g., two, three, four, five, six, seven, eight, nine, or ten) amino acid substitutions (e.g., one or more amino acid substitutions in the kinase domain. In some embodiments, a mutation can be a gene amplification of a BCR signaling pathway gene. In some embodiments, a mutation (e.g., an activating mutation) in a BCR signaling pathway gene can result in the expression of a BCR signaling pathway protein or BCR signaling pathway receptor that lacks at least one amino acid (e.g., at least 2, at least 3, at least 4, at least 5, at least 6, at least 7, at least 8, at least 9, at least 10, at least 12, at least 14, at least 16, at least 18, at least 20, at least 25, at least 30, at least 35, at least 40, at least 45, or at least 50 amino acids) as compared to a wildtype BCR signaling pathway protein. In some embodiments, a mutation (e.g., an activating mutation) in a BCR signaling pathway gene can result in the expression of a BCR signaling pathway protein that has at least one amino acid (e.g., at least 2, at least 3, at least 4, at least 5, at least 6, at least 7, at least 8, at least 9, at least 10, at least 12, at least 14, at least 16, at least 18, at least 20, at least 25, at least 30, at least 35, at least 40, at least 45, or at least 50 amino acids) inserted as compared to a wildtype BCR signaling pathway protein. Other dysregulations can include BCR signaling pathway mRNA splice variants. Non-limiting examples of BCR signaling pathway mutations are described in Table 4.

same, includes at least one point mutation in a BCR signaling pathway gene that results in the production of a BCR signaling pathway protein that has one or more amino acid substitutions as compared to the wild-type BCR signaling pathway protein, and which has increased resistance to the compound of Formula I, or a pharmaceutically acceptable salt, amorphous, or polymorph form thereof, a spray-dried dispersion thereof, or a pharmaceutical composition thereof, as compared to a wildtype BCR signaling pathway protein or a BCR signaling pathway protein not including the same mutation.

Accordingly, provided herein are methods for treating a subject diagnosed with (or identified as having) a cancer that include administering to the subject a therapeutically effective amount of the compound of Formula I, or a pharmaceutically acceptable salt, amorphous, or polymorph form thereof, a spray-dried dispersion thereof, or a pharmaceutical composition thereof. Also provided herein are methods for treating a subject identified or diagnosed as having a BTK-associated cancer that include administering to the subject a therapeutically effective amount of the compound of Formula I, or a pharmaceutically acceptable salt, amorphous, or polymorph form thereof, a spray-dried dispersion thereof, or a pharmaceutical composition thereof. In some embodiments, the subject that has been identified or diagnosed as having a BTK-associated cancer through the use of a regulatory agency-approved, e.g., FDA-approved test or assay for identifying dysregulation of a BTK gene, a BTK kinase, or expression or activity or level of any of the same, in a subject or a biopsy sample from the subject or by performing any of the non-limiting examples of assays described herein. In some embodiments, the test or assay is provided as a kit. In some embodiments, the cancer is a BTK-associated cancer. For example, the BTK-associated

TABLE 4

Exemplary BCR Signaling Pathway Mutations

| Disease | Associated Mutation(s) |
|---|---|
| Mantle Cell Lymphoma | t(11; 14)(q13; q32), which results in the aberrant expression of the cell cycle protein, cyclin-D1[1] Mantle Cell Lymphoma (MCL) exhibits mutations or deletion of RB1, ATM, p53, deletion of INK4a/ARF, as well as copy number gains of MYC, CDK4 and BCL2 |
| ABC DLBCL | Mutant CARD11 isoforms (that activate NF-kB)[2] Somatic mutations in CD79B (e.g., Y197N)[2] Somatic mutations in CD79A[2] |
| Waldenstrom's Macroglobulinemia | MYD88$^{L265P}$; enhances Bruton's tyrosine kinase (BTK) phosphorylation[3] |
| Chronic lymphocytic leukemia | Deletions of the chromosomal regions 17p13 (containing the TP53 tumor suppressor gene); 11q23 (containing DNA damage checkpoint protein ATM); or 13q14 (miR-15a, miR-16-1); and trisomy of chromosome 12[4] SYK Mutations FGD3-SYK fusion MDM2-SYK fusion P85-Y91 deletion Amino acid position 17 (e.g., F17L, F17Y) Amino acid position 42 (e.g., R42H, R42C) Amino acid position 45 (e.g., R45H, R45C) Amino acid position 52 (e.g., A52T) |

[1]Cinar et al., Leukemia Research 37 (2013) 1271-1277.
[2]Davis et al., Nature. 2010 Jan. 7; 463(7277): 88-92.
[3]Chin et al., Int J Mol Sci. 2017 October; 18(10): 2038.
[4]Singh et al., Mol Cancer. 2018; 17: 57.
[5] Sun et al., Blood, Vol. 128, No. 22, pp. 1058, Meeting Info. 58th Annual Meeting and Exposition of the American-Society-of-Hematology. San Diego, CA, USA. 2016.

In other embodiments, the dysregulation of a BTK gene, a BTK kinase, or expression or activity or level of any of the cancer can be a cancer that includes one or more BTK inhibitor resistance mutations.

Also provided are methods for treating cancer in a subject in need thereof, the method comprising: (a) detecting a BTK-associated cancer in the subject; and (b) administering to the subject a therapeutically effective amount of the compound of Formula I, or a pharmaceutically acceptable salt, amorphous, or polymorph form thereof, a spray-dried dispersion thereof, or a pharmaceutical composition thereof. Some embodiments of these methods further include administering to the subject another anticancer agent (e.g., a second BTK inhibitor or an immunotherapy). In some embodiments, the subject is previously treated with a first BTK inhibitor or previously treated with another anticancer treatment, e.g., at least partial resection of the tumor or radiation therapy. In some embodiments, the subject is determined to have a BTK-associated cancer through the use of a regulatory agency-approved, e.g., FDA-approved test or assay for identifying dysregulation of a BTK gene, a BTK kinase, or expression or activity or level of any of the same, in a subject or a biopsy sample from the subject or by performing any of the non-limiting examples of assays described herein. In some embodiments, the test or assay is provided as a kit. In some embodiments, the cancer is a BTK-associated cancer. For example, the BTK-associated cancer can be a cancer that includes one or more BTK inhibitor resistance mutations. In some embodiments, the dysregulation of the BTK gene, the BTK kinase, or expression or activity or level of any of the same is the result of one or more mutations in one or more BCR signaling pathway proteins. In some embodiments, the BCR signaling pathway protein is selected from the group consisting of: cyclin-D1, CARD11, CD79B, CD79A, MYD88, and combinations thereof.

Also provided are methods of treating a subject that include performing an assay on a sample obtained from the subject to determine whether the subject has a dysregulation of a BTK gene, a BTK kinase, or expression or activity or level of any of the same, and administering (e.g., specifically or selectively administering) a therapeutically effective amount of the compound of Formula I, or a pharmaceutically acceptable salt, amorphous, or polymorph form thereof, a spray-dried dispersion thereof, or a pharmaceutical composition thereof, to the subject determined to have a dysregulation of a BTK gene, a BTK kinase, or expression or activity or level of any of the same. Some embodiments of these methods further include administering to the subject another anticancer agent (e.g., a second BTK inhibitor or immunotherapy). In some embodiments of these methods, the subject is previously treated with a first BTK inhibitor or previously treated with another anticancer treatment, e.g., at least partial resection of a tumor or radiation therapy. In some embodiments, the subject is a subject suspected of having a BTK-associated cancer, a subject presenting with one or more symptoms of a BTK-associated cancer, or a subject having an elevated risk of developing a BTK-associated cancer. In some embodiments, the assay utilizes next generation sequencing, pyrosequencing, immunohistochemistry, immunoblot, or break apart FISH analysis. In some embodiments, the assay is a regulatory agency-approved assay, e.g., FDA-approved kit. In some embodiments, the assay is a liquid biopsy. Additional, non-limiting assays that may be used in these methods are described herein. Additional assays are also known in the art. In some embodiments, the dysregulation of a BTK gene, a BTK kinase, or expression or activity or level of any of the same includes one or more BTK inhibitor resistance mutations.

Also provided is the compound of Formula I, or a pharmaceutically acceptable salt, amorphous, or polymorph form thereof, a spray-dried dispersion thereof, or a pharmaceutical composition thereof, for use in treating a BTK-associated cancer in a subject identified or diagnosed as having a BTK-associated cancer through a step of performing an assay (e.g., an in vitro assay) on a sample obtained from the subject to determine whether the subject has a dysregulation of a BTK gene, a BTK kinase, or expression or activity or level of any of the same, where the presence of a dysregulation of a BTK gene, a BTK kinase, or expression or activity or level of any of the same, identifies that the subject has a BTK-associated cancer. Also provided is the use of the compound of Formula I, or a pharmaceutically acceptable salt, amorphous, or polymorph form thereof or a spray-dried dispersion thereof for the manufacture of a medicament for treating a BTK-associated cancer in a subject identified or diagnosed as having a BTK-associated cancer through a step of performing an assay on a sample obtained from the subject to determine whether the subject has a dysregulation of a BTK gene, a BTK kinase, or expression or activity or level of any of the same where the presence of dysregulation of a BTK gene, a BTK kinase, or expression or activity or level of any of the same, identifies that the subject has a BTK-associated cancer. Some embodiments of any of the methods or uses described herein further include recording in the subject's clinical record (e.g., a computer readable medium) that the subject is determined to have a dysregulation of a BTK gene, a BTK kinase, or expression or activity or level of any of the same, through the performance of the assay, should be administered the compound of Formula I, or a pharmaceutically acceptable salt, amorphous, or polymorph form thereof, a spray-dried dispersion thereof, or a pharmaceutical composition thereof. In some embodiments, the assay utilizes next generation sequencing, pyrosequencing, immunohistochemistry, immunoblot, or break apart FISH analysis. In some embodiments, the assay is a regulatory agency-approved assay, e.g., FDA-approved kit. In some embodiments, the assay is a liquid biopsy. In some embodiments, the dysregulation of a BTK gene, a BTK kinase, or expression or activity or level of any of the same includes one or more BTK inhibitor resistance mutations. In some embodiments, the dysregulation of the BTK gene, the BTK kinase, or expression or activity or level of any of the same is the result of one or more mutations in one or more BCR signaling pathway proteins. In some embodiments, the BCR signaling pathway protein is selected from the group consisting of: cyclin-D1, CARD11, CD79B, CD79A, MYD88, and combinations thereof.

Also provided is the compound of Formula I, or a pharmaceutically acceptable salt, amorphous, or polymorph form thereof, a spray-dried dispersion thereof, or a pharmaceutical composition thereof, for use in the treatment of a cancer in a subject in need thereof or a subject identified or diagnosed as having a BTK-associated cancer. Also provided is the use of the compound of Formula I, or a pharmaceutically acceptable salt, amorphous, or polymorph form thereof or a spray-dried dispersion thereof for the manufacture of a medicament for treating a cancer in a subject identified or diagnosed as having a BTK-associated cancer. In some embodiments, the cancer is a BTK-associated cancer, for example, a BTK-associated cancer having one or more BTK inhibitor resistance mutations. In some embodiments, a subject is identified or diagnosed as having a BTK-associated cancer through the use of a regulatory agency-approved, e.g., FDA-approved, kit for identifying dysregulation of a BTK gene, a BTK kinase, or expression or activity or level of any of the same, in a subject or a biopsy sample from the sample. As provided herein, a BTK-associated cancer includes those described herein and known in the art.

In some embodiments of any of the methods or uses described herein, the subject has been identified or diagnosed as having a cancer with a dysregulation of a BTK gene, a BTK kinase, or expression or activity or level of any of the same. In some embodiments of any of the methods or uses described herein, the subject has a tumor that is positive for a dysregulation of a BTK gene, a BTK kinase, or expression or activity or level of any of the same. In some embodiments of any of the methods or uses described herein, the subject can be a subject with a tumor(s) that is positive for a dysregulation of a BTK gene, a BTK kinase, or expression or activity or level of any of the same. In some embodiments of any of the methods or uses described herein, the subject can be a subject whose tumors have a dysregulation of a BTK gene, a BTK kinase, or expression or activity or level of any of the same. In some embodiments of any of the methods or uses described herein, the subject is suspected of having a BTK-associated cancer (e.g., a cancer having one or more BTK inhibitor resistance mutations). In some embodiments of any of the methods or uses described herein, the subject is BTK-inhibitor naive. In other embodiments of any of the methods or uses described herein, the subject is not BTK-inhibitor naive. In some embodiments, provided herein are methods for treating a BTK-associated cancer in a subject in need of such treatment, the method comprising a) detecting a dysregulation of a BTK gene, a BTK kinase, or the expression or activity or level of any of the same in a sample from the subject; and b) administering a therapeutically effective amount of the compound of Formula I, or a pharmaceutically acceptable salt, amorphous, or polymorph form thereof, a spray-dried dispersion thereof, or a pharmaceutical composition thereof. In some embodiments, the dysregulation of a BTK gene, a BTK kinase, or the expression or activity or level of any of the same includes one or more fusion proteins. Non-limiting examples of BTK gene fusion proteins are described in Table 1a. In some embodiments, the dysregulation of a BTK gene, a BTK kinase, or the expression or activity or level of any of the same includes one or more BTK kinase protein point mutations/insertions/deletions. Non-limiting examples of BTK kinase protein point mutations/insertions/deletions are described in Table 1. In some embodiments, the BTK kinase protein point mutations/insertions/deletions are selected from the group consisting of T117P, T316A, T474I, T474M, T474S, C481S, C481S, C481T, C481G, C481R, L528W, P560L, R562W, R562G, and F601L. In some embodiments, the dysregulation of a BTK gene, a BTK kinase, or the expression or activity or level of any of the same includes one or more BTK inhibitor resistance mutations. Non-limiting examples of BTK inhibitor resistance mutations are described in Tables 2 and 3. In some embodiments, the BTK resistance mutation is a mutation at amino acid 481 of BTK. In some embodiments, the BTK inhibitor resistance mutation is C481S. In some embodiments, the BTK inhibitor resistance mutation is C481F. In some embodiments, the BTK inhibitor resistance mutation is T474I. In some embodiments, the BTK inhibitor resistance mutation is a mutation in PLCγ2 (e.g., at amino acid position 244, 257, 334, 495, 664, 665, 707, 708, 742, 845, 848, 993, 1140, or 1141). In some embodiments, the dysregulation of the BTK gene, the BTK kinase, or expression or activity or level of any of the same is the result of one or more mutations in one or more BCR signaling pathway proteins. In some embodiments, the BCR signaling pathway protein is selected from the group consisting of: cyclin-D1, CARD11, CD79B, CD79A, MYD88, and combinations thereof. In some embodiments, the cancer with a dysregulation of a BTK gene, a BTK kinase, or expression or activity or level of any of the same is determined using a regulatory agency-approved, e.g., FDA-approved, assay or kit. In some embodiments, the tumor that is positive for a dysregulation of a BTK gene, a BTK kinase, or expression or activity or level of any of the same is a tumor positive for one or more BTK inhibitor resistance mutations. In some embodiments, the tumor with a dysregulation of a BTK gene, a BTK kinase, or expression or activity or level of any of the same is determined using a regulatory agency-approved, e.g., FDA-approved, assay or kit.

In some embodiments of any of the methods or uses described herein, the subject has a clinical record indicating that the subject has a tumor that has a dysregulation of a BTK gene, a BTK kinase, or expression or activity or level of any of the same (e.g., a tumor having one or more BTK inhibitor resistance mutations). In some embodiments, the clinical record indicates that the subject should be treated with the compound of Formula I, or a pharmaceutically acceptable salt, amorphous, or polymorph form thereof, a spray-dried dispersion thereof, or a pharmaceutical composition thereof, as provided herein. In some embodiments, the cancer with a dysregulation of a BTK gene, a BTK kinase, or expression or activity or level of any of the same is a cancer having one or more BTK inhibitor resistance mutations. In some embodiments, the cancer with a dysregulation of a BTK gene, a BTK kinase, or expression or activity or level of any of the same is determined using a regulatory agency-approved, e.g., FDA-approved, assay or kit. In some embodiments, the tumor that is positive for a dysregulation of a BTK gene, a BTK kinase, or expression or activity or level of any of the same is a tumor positive for one or more BTK inhibitor resistance mutations. In some embodiments, the tumor with a dysregulation of a BTK gene, a BTK kinase, or expression or activity or level of any of the same is determined using a regulatory agency-approved, e.g., FDA-approved, assay or kit.

Also provided are methods of treating a subject that include administering a therapeutically effective amount of the compound of Formula I, or a pharmaceutically acceptable salt, amorphous, or polymorph form thereof, a spray-dried dispersion thereof, or a pharmaceutical composition thereof, to a subject having a clinical record that indicates that the subject has a dysregulation of a BTK gene, a BTK kinase, or expression or activity or level of any of the same. Also provided is the use of the compound of Formula I, or a pharmaceutically acceptable salt, amorphous, or polymorph form thereof or a spray-dried dispersion thereof for the manufacture of a medicament for treating a BTK-associated cancer in a subject having a clinical record that indicates that the subject has a dysregulation of a BTK gene, a BTK kinase, or expression or activity or level of any of the same. Some embodiments of these methods and uses can further include: a step of performing an assay (e.g., an in vitro assay) on a sample obtained from the subject to determine whether the subject has a dysregulation of a BTK gene, a BTK kinase, or expression or activity or level of any of the same, and recording the information in a subject's clinical file (e.g., a computer readable medium) that the subject has been identified to have a dysregulation of a BTK gene, a BTK kinase, or expression or activity or level of any of the same. In some embodiments, the assay is an in vitro assay. For example, an assay that utilizes next generation sequencing, immunohistochemistry, immunoblot, or break apart FISH analysis. In some embodiments, the assay is a regulatory agency-approved, e.g., FDA-approved, kit. In some embodiments, the assay is a liquid biopsy. In some embodiments, the dysregulation of a BTK gene, BTK kinase, or expression or activity or level of any of the same includes one or more BTK inhibitor resistance mutations. In some embodiments, the dysregulation of the BTK gene, the BTK kinase, or expression or activity or level of any of the same is the result of one or more mutations in one or more BCR signaling pathway proteins. In some embodiments, the BCR signaling pathway protein is selected from the group consisting of: cyclin-D1, CARD11, CD79B, CD79A, MYD88, and combinations thereof. Also provided herein is a method of treating a subject. In some embodiments, the method includes performing an assay on a sample obtained from the subject to determine whether the subject has a dysregulation of a BTK gene, a BTK protein, or expression or level of any of the same. In some such embodiments, the method also includes administering to a subject determined to have a dysregulation of a BTK gene, a BTK protein, or expression or activity, or level of any of the same a therapeutically effective amount of the compound of Formula I, or a pharmaceutically acceptable salt, amorphous, or polymorph form thereof, a spray-dried dispersion thereof, or a pharmaceutical composition thereof. In some embodiments, the method includes determining that a subject has a dysregulation of a BTK gene, a BTK protein, or expression or level of any of the same via an assay performed on a sample obtained from the subject. In such embodiments, the method also includes administering to a subject a therapeutically effective amount of the compound of Formula I, or a pharmaceutically acceptable salt, amorphous, or polymorph form thereof, a spray-dried dispersion thereof, or a pharmaceutical composition thereof. In some embodiments, the dysregulation in a BTK gene, a BTK kinase protein, or expression or activity of the same is a gene or chromosome translocation that results in the expression of a BTK fusion protein (e.g., any of the BTK fusion proteins described herein). In some embodiments, the dysregulation in a BTK gene, a BTK kinase protein, or expression or activity or level of any of the same is one or more point mutation in the BTK gene (e.g., any of the one or more of the BTK point mutations described herein). The one or more point mutations in a BTK gene can result, e.g., in the translation of a BTK protein having one or more of the following amino acid substitutions: T117P, T316A, T474I, T474M, T474S, C481S, C481F, C481T, C481G, C481R, L528W, P560L, R562W, R562G, and F601L. In some embodiments, the dysregulation in a BTK gene, a BTK kinase protein, or expression or activity or level of any of the same is one or more BTK inhibitor resistance mutations (e.g., any combination of the one or more BTK inhibitor resistance mutations described herein). In some embodiments, the dysregulation of the BTK gene, the BTK kinase, or expression or activity or level of any of the same is the result of one or more mutations in one or more BCR signaling pathway proteins. In some embodiments, the BCR signaling pathway protein is selected from the group consisting of: cyclin-D1, CARD11, CD79B, CD79A, MYD88, and combinations thereof. Some embodiments of these methods further include administering to the subject another anticancer agent (e.g., a second BTK inhibitor or immunotherapy).

Also provided are methods (e.g., in vitro methods) of selecting a treatment for a subject identified or diagnosed as having a BTK-associated cancer. Some embodiments can further include administering the selected treatment to the subject identified or diagnosed as having a BTK-associated cancer. For example, the selected treatment can include administration of a therapeutically effective amount of compound of Formula I, or a pharmaceutically acceptable salt, amorphous, or polymorph form thereof, a spray-dried dispersion thereof, or a pharmaceutical composition thereof. Some embodiments can further include a step of performing an assay on a sample obtained from the subject to determine whether the subject has a dysregulation of a BTK gene, a BTK kinase, or expression or activity or level of any of the same, and identifying and diagnosing a subject determined to have a dysregulation of a BTK gene, a BTK kinase, or expression or activity or level of any of the same, as having a BTK-associated cancer. In some embodiments, the dysregulation of the BTK gene, the BTK kinase, or expression or activity or level of any of the same is the result of one or more mutations in one or more BCR signaling pathway proteins. In some embodiments, the BCR signaling pathway protein is selected from the group consisting of: cyclin-D1, CARD11, CD79B, CD79A, MYD88, and combinations thereof. In some embodiments, the cancer is a BTK-associated cancer having one or more BTK inhibitor resistance mutations. In some embodiments, the subject has been identified or diagnosed as having a BTK-associated cancer through the use of a regulatory agency-approved, e.g., FDA-approved, kit for identifying dysregulation of a BTK gene, a BTK kinase, or expression or activity or level of any of the same, in a subject or a biopsy sample from the subject. In some embodiments, the BTK-associated cancers is a cancer described herein or known in the art. In some embodiments, the assay is an in vitro assay. For example, an assay that utilizes the next generation sequencing, immunohistochemistry, immunoblot or break apart FISH analysis. In some embodiments, the assay is a regulatory agency-approved, e.g., FDA-approved, kit. In some embodiments, the assay is a liquid biopsy.

Also provided herein are methods of selecting a treatment for a subject, wherein the methods include a step of performing an assay on a sample obtained from the subject to determine whether the subject has a dysregulation of a BTK gene, a BTK kinase, or expression or activity or level of any of the same (e.g., one or more BTK inhibitor resistance mutations), and identifying or diagnosing a subject determined to have a dysregulation of a BTK gene, a BTK kinase, or expression or activity or level of any of the same, as having a BTK-associated cancer. Some embodiments further include administering the selected treatment to the subject identified or diagnosed as having a BTK-associated cancer. For example, the selected treatment can include administration of a therapeutically effective amount of the compound of Formula I, or a pharmaceutically acceptable salt, amorphous, or polymorph form thereof, a spray-dried dispersion thereof, or a pharmaceutical composition thereof, to the subject identified or diagnosed as having a BTK-associated cancer. In some embodiments, the assay is an in vitro assay. For example, an assay that utilizes the next generation sequencing, immunohistochemistry, immunoblot, or break apart FISH analysis. In some embodiments, the assay is a regulatory agency-approved, e.g., FDA-approved, kit. In some embodiments, the assay is a liquid biopsy.

Also provided are methods of selecting a subject for treatment, wherein the methods include selecting, identifying, or diagnosing a subject having a BTK-associated cancer, and selecting the subject for treatment including administration of a therapeutically-effective amount of the compound of Formula I, or a pharmaceutically acceptable salt, amorphous, or polymorph form thereof, a spray-dried dispersion thereof, or a pharmaceutical composition thereof.

In some embodiments, identifying or diagnosing a subject as having a BTK-associated cancer can include a step of performing an assay on a sample obtained from the subject to determine whether the subject has a dysregulation of a BTK gene, a BTK kinase, or expression or activity or level of any of the same, and identifying or diagnosing a subject determined to have a dysregulation of a BTK gene, a BTK kinase, or expression or activity or level of any of the same, as having a BTK-associated cancer. In some embodiments, the method of selecting a subject for treatment can be used as a part of a clinical study that includes administration of various treatments of a BTK-associated cancer. In some embodiments, a BTK-associated cancer is a cancer having one or more BTK inhibitor resistance mutations. In some embodiments, the assay is an in vitro assay. For example, an assay that utilizes the next generation sequencing, immuno-histochemistry, or break apart FISH analysis. In some embodiments, the assay is a regulatory agency-approved, e.g., FDA-approved, kit. In some embodiments, the assay is a liquid biopsy. In some embodiments, the dysregulation of the BTK gene, the BTK kinase, or expression or activity or level of any of the same includes one or more BTK inhibitor resistance mutations. In some embodiments, the dysregulation of the BTK gene, the BTK kinase, or expression or activity or level of any of the same is the result of one or more mutations in one or more BCR signaling pathway proteins. In some embodiments, the BCR signaling pathway protein is selected from the group consisting of: cyclin-D1, CARD11, CD79B, CD79A, MYD88, and combinations thereof.

Also, provided herein are methods of treating cancer (e.g., a BTK-associated cancer) in a subject in need of such treatment, the method comprising a) detecting a dysregulation of a BCR signaling pathway gene, a BCR signaling pathway protein, or expression or activity or level of any one of the same in a sample from the subject; and b) administering a therapeutically effective amount of the compound of Formula I, or a pharmaceutically acceptable salt, amorphous, or polymorph form thereof, a spray-dried dispersion thereof, or a pharmaceutical composition thereof. Some embodiments of these methods and can further include: a step of performing an assay (e.g., an in vitro assay) on a sample obtained from the subject to determine whether the subject has a dysregulation of a dysregulation in BCR signaling pathway gene, a BCR signaling pathway protein, or expression or activity or level of any one of the same, and recording the information in a subject's clinical file (e.g., a computer readable medium) that the subject has been identified to have a dysregulation of a BCR signaling pathway gene, a BCR signaling pathway protein, or expression or activity or level of any one of the same. In some embodiments, the assay is an in vitro assay. For example, an assay that utilizes next generation sequencing, immunohistochemistry, immunoblot, or break apart FISH analysis. In some embodiments, the assay is a regulatory agency-approved, e.g., FDA-approved, kit. In some embodiments, the BCR signaling pathway protein is selected from the group consisting of: cyclin-D1, CARD11, CD79B, CD79A, MYD88, and combinations thereof.

Also provided are methods of treating a subject that include administering a therapeutically effective amount of the compound of Formula I, or a pharmaceutically acceptable salt, amorphous, or polymorph form thereof, a spray-dried dispersion thereof, or a pharmaceutical composition thereof, to a subject having a clinical record that indicates that the subject has a dysregulation in BCR signaling pathway gene, a BCR signaling pathway protein, or expression or activity or level of any one of the same. Some embodiments of these methods and can further include: a step of performing an assay (e.g., an in vitro assay) on a sample obtained from the subject to determine whether the subject has a dysregulation of a dysregulation in BCR signaling pathway gene, a BCR signaling pathway protein, or expression or activity or level of any one of the same, and recording the information in a subject's clinical file (e.g., a computer readable medium) that the subject has been identified to have a dysregulation of a BCR signaling pathway gene, a BCR signaling pathway protein, or expression or activity or level of any one of the same. In some embodiments, the assay is an in vitro assay. For example, an assay that utilizes next generation sequencing, immunohistochemistry, immunoblot, or break apart FISH analysis. In some embodiments, the assay is a regulatory agency-approved, e.g., FDA-approved, kit. In some embodiments, the BCR signaling pathway protein is selected from the group consisting of: cyclin-D1, CARD11, CD79B, CD79A, MYD88, and combinations thereof.

In some embodiments of any of the methods or uses described herein, an assay used to determine whether the subject has a dysregulation of a BTK gene, or a BTK kinase, or expression or activity or level of any of the same, using a sample from a subject can include, for example, next generation sequencing, immunohistochemistry, fluorescence microscopy, break apart FISH analysis, Southern blotting, Western blotting, FACS (fluorescence-activated cell sorting) analysis, Northern blotting, and PCR-based amplification (e.g., RT-PCR (reverse transcriptase-polymerase chain reaction) and quantitative real-time RT-PCR). As is well-known in the art, the assays are typically performed, e.g., with at least one labelled nucleic acid probe or at least one labelled antibody or antigen-binding fragment thereof. Assays can utilize other detection methods known in the art for detecting dysregulation of a BTK gene, a BTK kinase, or expression or activity or levels of any of the same (see, e.g., the references cited herein). In some embodiments, the dysregulation of the BTK gene, the BTK kinase, or expression or activity or level of any of the same includes one or more BTK inhibitor resistance mutations. In some embodiments, the sample is a biological sample or a biopsy sample (e.g., a paraffin-embedded biopsy sample) from the subject. In some embodiments, the subject is a subject suspected of having a BTK-associated cancer, a subject having one or more symptoms of a BTK-associated cancer, and/or a subject that has an increased risk of developing a BTK-associated cancer).

In some embodiments, the dysregulation of a BTK gene, a BTK kinase, or the expression or activity or level of any of the same can be identified using a liquid biopsy (variously referred to as a fluid biopsy or fluid phase biopsy). See, e.g., Karachialiou et al., "Real-time liquid biopsies become a reality in cancer treatment", *Ann. Transl. Med.*, 3(3):36, 2016. Liquid biopsy methods can be used to detect total tumor burden and/or the dysregulation of a BTK gene, a BTK kinase, or the expression or activity or level of any of the same. Liquid biopsies can be performed on biological samples obtained relatively easily from a subject (e.g., via a simple blood draw). In some embodiments, liquid biopsies can be used to detect the presence of dysregulation of a BTK gene, a BTK kinase, or the expression or activity or level of any of the same at an earlier stage than traditional methods. In some embodiments, the biological sample to be used in a liquid biopsy can include, blood, plasma, urine, cerebrospinal fluid, saliva, sputum, broncho-alveolar lavage, bile, lymphatic fluid, cyst fluid, stool, ascites, and combinations thereof. In some embodiments, a liquid biopsy can be used to detect circulating tumor cells (CTCs). In some embodiments, a liquid biopsy can be used to detect cell-free DNA. In some embodiments, cell-free DNA detected using a liquid biopsy is circulating tumor DNA (ctDNA) that is derived from tumor cells. Analysis of ctDNA (e.g., using sensitive detection techniques such as, without limitation, next-generation sequencing (NGS), traditional PCR, digital PCR, or microarray analysis) can be used to identify dysregulation of a BTK gene, a BTK kinase, or the expression or activity or level of any of the same.

In some embodiments, ctDNA derived from a single gene can be detected using a liquid biopsy. In some embodiments, ctDNA derived from a plurality of genes (e.g., 2, 3, 4, 5, 6, 7, 8, 9, 10, 15, 20, 25, 30, 35, 40, 45, 50, 55, 60, 65, 70, 75, 80, 85, 90, 95, 100 or more, or any number of genes in between these numbers) can be detected using a liquid biopsy. In some embodiments, ctDNA derived from a plurality of genes can be detected using any of a variety of commercially-available testing panels (e.g., commercially-available testing panels designed to detect dysregulation of a BTK gene, a BTK kinase, or the expression or activity or level of any of the same). Liquid biopsies can be used to detect dysregulation of a BTK gene, a BTK kinase, or the expression or activity or level of any of the same including, without limitation, point mutations or single nucleotide variants (SNVs), copy number variants (CNVs), genetic fusions (e.g., translocations or rearrangements), insertions, deletions, or any combination thereof. In some embodiments, a liquid biopsy can be used to detect a germline mutation. In some embodiments, a liquid biopsy can be used to detect a somatic mutation. In some embodiments, a liquid biopsy can be used to detect a primary genetic mutation (e.g., a primary mutation or a primary fusion that is associated with initial development of a disease, e.g., cancer). In some embodiments, a liquid biopsy can be used to detect a genetic mutation that develops after development of the primary genetic mutation (e.g., a resistance mutation that arises in response to a treatment administered to a subject). In some embodiments, a dysregulation of a BTK gene, a BTK kinase, or the expression or activity or level of any of the same identified using a liquid biopsy is also present in a cancer cell that is present in the subject (e.g., in a tumor). In some embodiments, any of the types of dysregulation of a BTK gene, a BTK kinase, or the expression or activity or level of any of the same described herein can be detected using a liquid biopsy. In some embodiments, a genetic mutation identified via a liquid biopsy can be used to identify the subject as a candidate for a particular treatment. For example, detection of dysregulation of a BTK gene, a BTK kinase, or the expression or activity or level of any of the same in the subject can indicate that the subject will be responsive to a treatment that includes administration of the compound of Formula I, or a pharmaceutically acceptable salt, amorphous, or polymorph form thereof, a spray-dried dispersion thereof, or a pharmaceutical composition thereof.

Liquid biopsies can be performed at multiple times during a course of diagnosis, a course of monitoring, and/or a course of treatment to determine one or more clinically relevant parameters including, without limitation, progression of the disease, efficacy of a treatment, or development of resistance mutations after administering a treatment to the subject. For example, a first liquid biopsy can be performed at a first time point and a second liquid biopsy can be performed at a second time point during a course of diagnosis, a course of monitoring, and/or a course of treatment. In some embodiments, the first time point can be a time point prior to diagnosing a subject with a disease (e.g., when the subject is healthy), and the second time point can be a time point after subject has developed the disease (e.g., the second time point can be used to diagnose the subject with the disease). In some embodiments, the first time point can be a time point prior to diagnosing a subject with a disease (e.g., when the subject is healthy), after which the subject is monitored, and the second time point can be a time point after monitoring the subject. In some embodiments, the first time point can be a time point after diagnosing a subject with a disease, after which a treatment is administered to the subject, and the second time point can be a time point after the treatment is administered; in such cases, the second time point can be used to assess the efficacy of the treatment (e.g., if the genetic mutation(s) detected at the first time point are reduced in abundance or are undetectable) or to determine the presence of resistance mutation that has arisen as a result of the treatment. In some embodiments, a treatment to be administered to a subject can include the compound of Formula I, or a pharmaceutically acceptable salt, amorphous, or polymorph form thereof, a spray-dried dispersion thereof, or a pharmaceutical composition thereof.

In some embodiments, the efficacy of the compound of Formula I, or a pharmaceutically acceptable salt, amorphous, or polymorph form thereof, a spray-dried dispersion thereof, or a pharmaceutical composition thereof, can be determined by assessing the allele frequency of a dysregulation of a BTK gene in cfDNA obtained from a subject at different time points, e.g., cfDNA obtained from the subject at a first time point and cfDNA obtained from the subject at a second time point, where at least one dose of the compound of Formula I, or a pharmaceutically acceptable salt, amorphous, or polymorph form thereof, a spray-dried dispersion thereof, or a pharmaceutical composition thereof, is administered to the subject between the first and second time points. Some embodiments of these methods can further include administering to the subject the at least one dose of the compound of Formula I, or a pharmaceutically acceptable salt, amorphous, or polymorph form thereof, a spray-dried dispersion thereof, or a pharmaceutical composition thereof, between the first and second time points. For example, a reduction (e.g., a 1% to about a 99% reduction, a 1% to about a 95% reduction, a 1% to about a 90% reduction, a 1% to about a 85% reduction, a 1% to about a 80% reduction, a 1% to about a 75% reduction, a 1% reduction to about a 70% reduction, a 1% reduction to about a 65% reduction, a 1% reduction to about a 60% reduction, a 1% reduction to about a 55% reduction, a 1% reduction to about a 50% reduction, a 1% reduction to about a 45% reduction, a 1% reduction to about a 40% reduction, a 1% reduction to about a 35% reduction, a 1% reduction to about a 30% reduction, a 1% reduction to about a 25% reduction, a 1% reduction to about a 20% reduction, a 1% reduction to about a 15% reduction, a 1% reduction to about a 10% reduction, a 1% to about a 5% reduction, about a 5% to about a 99% reduction, about a 10% to about a 99% reduction, about a 15% to about a 99% reduction, about a 20% to about a 99% reduction, about a 25% to about a 99% reduction, about a 30% to about a 99% reduction, about a 35% to about a 99% reduction, about a 40% to about a 99% reduction, about a 45% to about a 99% reduction, about a 50% to about a 99% reduction, about a 55% to about a 99% reduction, about a 60% to about a 99% reduction, about a 65% to about a 99% reduction, about a 70% to about a 99% reduction, about a 75% to about a 95% reduction, about a 80% to about a 99% reduction, about a 90% reduction to about a 99% reduction, about a 95% to about a 99% reduction, about a 5% to about a 10% reduction, about a 5% to about a 25% reduction, about a 10% to about a 30% reduction, about a 20% to about a 40% reduction, about a 25% to about a 50% reduction, about a 35% to about a 55% reduction, about a 40% to about a 60% reduction, about a 50% reduction to about a 75% reduction, about a 60% reduction to about 80% reduction, or about a 65% to about a 85% reduction) in the allele frequency (AF) of the dysregulation of a BTK gene in the cfDNA obtained from the subject at the second time point as compared to the allele frequency (AF) of the dysregulation of a BTK gene in the cfDNA obtained from the subject at the first time point indicates that the compound of Formula I, or a pharmaceutically acceptable salt, amorphous, or polymorph form thereof, a spray-dried dispersion thereof, or a pharmaceutical composition thereof, is effective in the subject. Alternatively, an increase in the allele frequency (AF) of the dysregulation of a BTK gene in the cfDNA obtained from the subject at the second time point as compared to the allele frequency (AF) of the dysregulation of a BTK gene in the cfDNA obtained from the subject at the first time point indicates that the compound of Formula I, or a pharmaceutically acceptable salt, amorphous, or polymorph form thereof, a spray-dried dispersion thereof, or a pharmaceutical composition thereof, is not effective in the subject (e.g., the subject has developed a resistance mutation to the compound of Formula I, or a pharmaceutically acceptable salt, amorphous, or polymorph form thereof, a spray-dried dispersion thereof, or a pharmaceutical composition thereof). Some embodiments of these methods can further include, administering additional doses of the compound of Formula I, or a pharmaceutically acceptable salt, amorphous, or polymorph form thereof, a spray-dried dispersion thereof, or a pharmaceutical composition thereof, to a subject in which the compound of Formula I, or a pharmaceutically acceptable salt, amorphous, or polymorph form thereof, a spray-dried dispersion thereof, or a pharmaceutical composition thereof, is determined to be effective. Some embodiments of these methods can further include, administering a different treatment (e.g., a treatment that does not include the administration of Formula I, or a pharmaceutically acceptable salt, amorphous, or polymorph form thereof, as a monotherapy) to a subject in which the compound of Formula I, or a pharmaceutically acceptable salt, amorphous, or polymorph form thereof, a spray-dried dispersion thereof, or a pharmaceutical composition thereof, is determined not to be effective.

In some examples of these methods, the time difference between the first and second time points can be about 1 day to about 1 year, about 1 day to about 11 months, about 1 day to about 10 months, about 1 day to about 9 months, about 1 day to about 8 months, about 1 day to about 7 months, about 1 day to about 6 months, about 1 day to about 5 months, about 1 day to about 4 months, about 1 day to about 3 months, about 1 day to about 10 weeks, about 1 day to about 2 months, about 1 day to about 6 weeks, about 1 day to about 1 month, about 1 day to about 25 days, about 1 day to about 20 days, about 1 day to about 15 days, about 1 day to about 10 days, about 1 day to about 5 days, about 2 days to about 1 year, about 5 days to about 1 year, about 10 days to about 1 year, about 15 days to about 1 year, about 20 days to about 1 year, about 25 days to about 1 year, about 1 month to about 1 year, about 6 weeks to about 1 year, about 2 months to about 1 year, about 3 months to about 1 year, about 4 months to about 1 year, about 5 months to about 1 year, about 6 months to about 1 year, about 7 months to about 1 year, about 8 months to about 1 year, about 9 months to about 1 year, about 10 months to about 1 year, about 11 months to about 1 year, about 1 day to about 7 days, about 1 day to about 14 days, about 5 days to about 10 days, about 5 day to about 20 days, about 10 days to about 20 days, about 15 days to about 1 month, about 15 days to about 2 months, about 1 week to about 1 month, about 2 weeks to about 1 month, about 1 month to about 3 months, about 3 months to about 6 months, about 4 months to about 6 months, about 5 months to about 8 months, or about 7 months to about 9 months. In some embodiments of these methods, the subject can be previously identified as having a cancer having a dysregulated BTK gene (e.g., any of the examples of a dysregulated BTK gene described herein). In some embodiments of these methods, a subject can have been previously diagnosed as having any of the types of cancer described herein. In some embodiments of these methods, the subject can have one or more metastases (e.g., one or more bone metastases).

In some of the above embodiments, the cfDNA comprises ctDNA such as BTK-associated ctDNA. For example, the cfDNA is ctDNA such as BTK-associated ctDNA. In some embodiments, at least some portion of cfDNA is determined to be BTK-associated ctDNA, for example, a sequenced and/or quantified amount of the total cfDNA is determined to have a BTK fusion and/or a BTK resistance mutation.

In the field of medical oncology it is normal practice to use a combination of different forms of treatment to treat each subject with cancer. In medical oncology the other component(s) of such conjoint treatment or therapy in addition to compositions provided herein may be, for example, surgery, radiotherapy, and chemotherapeutic agents, such as other kinase inhibitors, signal transduction inhibitors and/or monoclonal antibodies. For example, a surgery may be open surgery or minimally invasive surgery. Compounds of Formula I, or a pharmaceutically acceptable salt, amorphous, or polymorph form thereof therefore may also be useful as adjuvants to cancer treatment, that is, they can be used in combination with one or more additional therapies or therapeutic agents, for example a chemotherapeutic agent that works by the same or by a different mechanism of action. In some embodiments, the compound of Formula I, or a pharmaceutically acceptable salt, amorphous, or polymorph form thereof, a spray-dried dispersion thereof, or a pharmaceutical composition thereof, can be used prior to administration of an additional therapeutic agent or additional therapy. For example, a subject in need thereof can be administered one or more doses of the compound of Formula I, or a pharmaceutically acceptable salt, amorphous, or polymorph form thereof, a spray-dispersion thereof, or a pharmaceutical composition thereof, for a period of time and then under go at least partial resection of the tumor. In some embodiments, the treatment with one or more doses of the compound of Formula I, or a pharmaceutically acceptable salt, amorphous, or polymorph form thereof, a spray-dispersion thereof, or a pharmaceutical composition thereof, reduces the size of the tumor (e.g., the tumor burden) prior to the at least partial resection of the tumor.

In some embodiments of any the methods described herein, the compound of Formula I, or a pharmaceutically acceptable salt, amorphous, or polymorph form thereof, a spray-dispersion thereof, or a pharmaceutical composition thereof, is administered in combination with a therapeutically effective amount of at least one additional therapeutic agent selected from one or more additional therapies or therapeutic (e.g., chemotherapeutic) agents.

Non-limiting examples of additional therapeutic agents include: other BTK-targeted therapeutic agents (i.e. a first or second BTK kinase inhibitor), other kinase-targeted therapeutic agents (e.g., JAK, Src, or IRAK family kinase-targeted therapeutic agents such as JAK1, JAK2, JAK3, TYK2, IRAK1, IRAK4, Src, Yes, Fyn, Fgr, Lck, Hck, Blk, Lyn, or Frk inhibitors), signal transduction pathway inhibitors, checkpoint inhibitors, modulators of the apoptosis pathway (e.g. obataclax); other protein inhibitors (e.g., antiapoptotic protein inhibitors, heat shock protein inhibitors, nuclear export protein inhibitors, histone deacetylase inhibitors, E3 ubiquitin ligase inhibitors, or histone-lysine N-methyltransferase inhibitors); cytotoxic chemotherapeutics, angiogenesis-targeted therapies, immune-targeted agents, including immunotherapy, and radiotherapy.

In some embodiments, the other BTK-targeted therapeutic is a multikinase inhibitor exhibiting BTK inhibition activity. In some embodiments, the other BTK-targeted therapeutic inhibitor is selective for a BTK kinase. Exemplary BTK kinase inhibitors can exhibit inhibition activity ($IC_{50}$) against a BTK kinase of less than about 1000 nM, less than about 500 nM, less than about 200 nM, less than about 100 nM, less than about 50 nM, less than about 25 nM, less than about 10 nM, or less than about 1 nM as measured in an assay as described herein. In some embodiments, a BTK kinase inhibitor can exhibit inhibition activity ($IC_{50}$) against a BTK kinase of less than about 25 nM, less than about 10 nM, less than about 5 nM, or less than about 1 nM as measured in an assay as provided herein.

Non-limiting examples of BTK-targeted therapeutic agents (e.g., a first BTK inhibitor or a second BTK inhibitor) include ibrutinib (PCI-32675, Imbruvica®) (1-[(3R)-3-[4-amino-3-(4-phenoxyphenyl)pyrazolo[3,4-d]pyrimidin-1-yl]piperidin-1-yl]prop-2-en-1-one); AC0058 (AC0058TA); N-(3-((2-((3-fluoro-4-(4-methylpiperazin-1-yl)phenyl)amino)-7H-pyrrolo[2,3-d]pyrimidin-4-yl)oxy)phenyl)acrylamide; acalabrutinib (ACP-196, Calquence®, rINN) (4-[8-amino-3-[(2S)-1-but-2-ynoylpyrrolidin-2-yl]imidazo[1,5-a]pyrazin-1-yl]-N-pyridin-2-ylbenzamide); zanubrutinib (BGB-3111) ((7R)-2-(4-phenoxyphenyl)-7-(1-prop-2-enoylpiperidin-4-yl)-1,5,6,7-tetrahydropyrazolo[1,5-a]pyrimidine-3-carboxamide); spebrutinib (AVL-292, 1202757-89-8, Cc-292) (N-[3-[[5-fluoro-2-[4-(2-methoxyethoxy)anilino]pyrimidin-4-yl]amino]phenyl]prop-2-enamide); poseltinib (HM71224, LY3337641) (N-[3-[2-[4-(4-methylpiperazin-1-yl)anilino]furo[3,2-d]pyrimidin-4-yl]oxyphenyl]prop-2-enamide); evobrutinib (MSC 2364447, M-2951) (1-[4-[[[6-amino-5-(4-phenoxyphenyl)pyrimidin-4-yl]amino]methyl]piperidin-1-yl]prop-2-en-1-one); tirabrutinib (ONO-4059, GS-4059, ONO/GS-4059, ONO-WG-307) (1-[4-[[[6-amino-5-(4-phenoxyphenyl)pyrimidin-4-yl]amino]methyl]piperidin-1-yl]prop-2-en-1-one); vecabrutinib (SNS-062) ((3R,4S)-1-(6-amino-5-fluoropyrimidin-4-yl)-3-[(3R)-3-[3-chloro-5-(trifluoromethyl)anilino]-2-oxopiperidin-1-yl]piperidine-4-carboxamide); dasatinib (Sprycel®; BMS-354825) (N-(2-chloro-6-methylphenyl)-2-[[6-[4-(2-hydroxyethyl)piperazin-1-yl]-2-methylpyrimidin-4-yl]amino]-1,3-thiazole-5-carboxamide); PRN1008, PRN473, ABBV-105, CG'806, ARQ 531, BIIB068, AS871, CB1763, CB988, GDC-0853, RN486, GNE-504, GNE-309, BTK Max, CT-1530, CGI-1746, CGI-560, LFM A13, TP-0158, dtrmwxhs-12, CNX-774, and LOU064. A BTK inhibitor can be a covalent inhibitor (e.g., compounds that bind to C481 of BTK) or a non-covalent inhibitor. Exemplary covalent inhibitors of a BTK kinase include, but are not limited to, ibrutinib, PRN1008, PRN473, ABBV-105, AC0058, acalabrutinib, zanubrutinib, spebrutinib, poseltinib, evobrutinib, M7583, and tirabrutinib. Exemplary non-covalent inhibitors of a BTK kinase include, but are not limited to, CG'806, ARQ 531, BIIB068, vecabrutinib, AS871, CB1763, CB988, GDC-0853, RN486, and dasatinib.

Additional examples of other BTK kinase inhibitors include those described in, for example, U.S. Pat. Nos. 9,150,517; 9,149,464, 10,023,534; 10,005,784; 9,994,576; 9,951,056; 9,944,622; 9,926,299; 9,920,031; and 9,908,872; U.S. Publication Nos. 2018/0194762; 2018/0194739; 2018/0186780; 2018/0179210; 2018/0162861; 2018/0141962; 2018/0134719; 2018/0127411; 2018/0118766; 2018/0093973; 2018/0085372; 2018/0079758; 2018/0057500; 2018/0055846; 2018/0051024; 2018/0051036; 2018/0037583; 2018/0030037; and 2018/0030027; and International Publication Nos. WO 2014/075035; 2018/130213; 2018/113085; 2017/134685; 2018/103060; 2018/095398; 2018/092047; 2018/088780; 2018/035080; 2018/035072; 2018/032104; and 2018/022911, all of which are hereby incorporated by reference.

In some embodiments, the additional therapeutic agent is an inhibitor of a protein upstream of BTK in the BCR signaling pathway, e.g., Syk, Lyn, BCR, PI3K, CD19, or BCAP.

In some embodiments, the additional therapeutic agent is an inhibitor of a protein downstream of BTK in the BCR signaling pathway, e.g., PLCγ2, SOS, Ras, c-Raf, MEK1, MEK2, Erk1, Erk2, PKC, MALT1, IKK, NF-κB, or $IP_3R$.

Non-limiting examples of JAK family (e.g., JAK1, JAK2, JAK3, and TYK2) targeted therapeutic agents include tofacitinib, ruxolitinib, oclacitinib, baricitinib (OLUMIANT®; LY-3009104, INCB-28050), filgotinib (G-146034, GLPG-0634), gandotinib (LY-2784544), lestaurtinib (CEP-701), momelotinib (GS-0387, CYT-387), pacritinib (SB1518), PF-04965842, upadacitinib (ABT-494), peficitinib (ASP015K, JNJ-54781532), and fedratinib (SAR302503). Additional JAK family targeted therapeutics include those described in U.S. Pat. Nos. 8,604,043, 7,834,022, 8,486,902, 8,530,485, 7,598,257, 8,541,425, 8,410,265, 9,987,276, and 9,949,971, and U.S. Patent Application Publication Nos. 2018/0051036 A1, 2010/0298355 A1, 2008/0312258 A1, 2011/0082159 A1, 2011/0086810 A1, 2013/0345157 A1, 2014/0018374 A1, 2014/0005210 A1, 2011/0223210 A1, 2011/0224157 A1, 2007/0135461 A1, 2010/0022522 A1, 2013/0253193 A1, 2013/0253191 A1, 2013/0253190 A1, 2010/0190981 A1, 2013/0338134 A1, 2008/0312259 A1, 2014/0094477 A1, and 2014/0094476 A1, the disclosures of which are incorporated by reference herein.

Non-limiting examples of Src, family (Src, Yes, Fyn, Fgr, Lck, Hck, Blk, Lyn, or Frk) targeted therapeutics include dasatinib (SPRYCEL®), INNO-406, LCB03-0110, KX2-391, bosutinib, saracatinib, PP1, PP2, and quercetin. Additional Src family targeted therapeutics include those described in P.C.T. Publication Nos. WO 2018/049127, WO 2018/035072, and WO 2007/026720.

Non limiting examples of IRAK (IRAK1, IRAK2, IRAK3, or IRAK4) family inhibitors include ND-2158 and ND-2110. Additional IRAK family targeted therapeutics include those described in U.S. Pat. Nos. 9,982,000, 9,969,749, 9,969,710, 9,890,145, 9,862,715, 9,815,836, 9,790,234, 9,732,095, and 9,617,282, and U.S. Patent Application Publication Nos. 2017/0035881, and P.C.T. Publication Nos. WO 2016/174183 and WO 2017/205769, all of which are incorporated by reference herein.

In some embodiments, the kinase inhibitor inhibits a kinase selected from the group consisting of: PI3K, JAK1, JAK2, JAK3, TYK2, IRAK1, IRAK2, IRAK3, IRAK4, BMX, TAK1, Src, Yes, Fyn, Fgr, Lck, Hck, Blk, Lyn, Frk, PIM, mTOR, ROR-1, Syk, PKC, and combinations thereof.

Non-limiting examples of receptor tyrosine kinase (e.g., Trk) targeted therapeutic agents, include afatinib, cabozantinib, cetuximab, crizotinib, dabrafenib, entrectinib, erlotinib, gefitinib, imatinib, lapatinib, lestaurtinib, nilotinib, pazopanib, panitumumab, pertuzumab, sunitinib, trastuzumab, 1-((3S,4R)-4-(3-fluorophenyl)-1-(2-methoxyethyl)pyrrolidin-3-yl)-3-(4-methyl-3-(2-methylpyrimidin-5-yl)-1-phenyl-1H-pyrazol-5-yl)urea, AG 879, AR-772, AR-786, AR-256, AR-618, AZ-23, AZ623, DS-6051, Gö 6976, GNF-5837, GTx-186, GW 441756, LOXO-101, MGCD516, PLX7486, RXDX101, VM-902A, TPX-0005, and TSR-011. Additional Trk targeted therapeutic agents include those described in U.S. Pat. Nos. 8,450,322; 8,513,263; 8,933,084; 8,791,123; 8,946,226; 8,450,322; 8,299,057; and 8,912,194; U.S. Publication No. 2016/0137654; 2015/0166564; 2015/0051222; 2015/0283132; and 2015/0306086; International Publication No. WO 2010/033941; WO 2010/048314; WO 2016/077841; WO 2011/146336; WO 2011/006074; WO 2010/033941; WO 2012/158413; WO 2014078454; WO 2014078417; WO 2014078408; WO 2014078378; WO 2014078372; WO 2014078331; WO 2014078328; WO 2014078325; WO 2014078323; WO 2014078322; WO 2015175788; WO 2009/013126; WO 2013/174876; WO 2015/124697; WO 2010/058006; WO 2015/017533; WO 2015/112806; WO 2013/183578; and WO 2013/074518, all of which are hereby incorporated by reference in their entireties.

Further examples of Trk inhibitors can be found in U.S. Pat. No. 8,637,516, International Publication No. WO 2012/034091, U.S. Pat. No. 9,102,671, International Publication No. WO 2012/116217, U.S. Publication No. 2010/0297115, International Publication No. WO 2009/053442, U.S. Pat. No. 8,642,035, International Publication No. WO 2009092049, U.S. Pat. No. 8,691,221, International Publication No. WO2006131952, all of which are incorporated by reference in their entireties herein. Exemplary Trk inhibitors include GNF-4256, described in *Cancer Chemother. Pharmacol.* 75(1):131-141, 2015; and GNF-5837 (N-[3-[[2,3-dihydro-2-oxo-3-(1H-pyrrol-2-ylmethylene)-1H-indol-6-yl]amino]-4-methylphenyl]-N'-[2-fluoro-5-(trifluoromethyl)phenyl]-urea), described in *ACS Med. Chem. Lett.* 3(2):140-145, 2012, each of which is incorporated by reference in its entirety herein.

Additional examples of Trk inhibitors include those disclosed in U.S. Publication No. 2010/0152219, U.S. Pat. No. 8,114,989, and International Publication No. WO 2006/123113, all of which are incorporated by reference in their entireties herein. Exemplary Trk inhibitors include AZ623, described in Cancer 117(6):1321-1391, 2011; AZD6918, described in *Cancer Biol. Ther.* 16(3):477-483, 2015; AZ64, described in *Cancer Chemother. Pharmacol.* 70:477-486, 2012; AZ-23 ((S)-5-Chloro-N2-(1-(5-fluoropyridin-2-yl)ethyl)-N4-(5-isopropoxy-1H-pyrazol-3-yl)pyrimidine-2,4-diamine), described in *Mol. Cancer Ther.* 8:1818-1827, 2009; and AZD7451; each of which is incorporated by reference in its entirety.

A Trk inhibitor can include those described in U.S. Pat. Nos. 7,615,383; 7,384,632; 6,153,189; 6,027,927; 6,025,166; 5,910,574; 5,877,016; and 5,844,092, each of which is incorporated by reference in its entirety.

Further examples of Trk inhibitors include CEP-751, described in Int. J. Cancer 72:672-679, 1997; CT327, described in *Acta Derm. Venereol.* 95:542-548, 2015; compounds described in International Publication No. WO 2012/034095; compounds described in U.S. Pat. No. 8,673,347 and International Publication No. WO 2007/022999; compounds described in U.S. Pat. No. 8,338,417; compounds described in International Publication No. WO 2016/027754; compounds described in U.S. Pat. No. 9,242,977; compounds described in U.S. Publication No. 2016/0000783; sunitinib (N-(2-diethylaminoethyl)-5-[(Z)-(5-fluoro-2-oxo-1H-indol-3-ylidene)methyl]-2,4-dimethyl-1H-pyrrole-3-carboxamide), as described in *PLoS One* 9:e95628, 2014; compounds described in International Publication No. WO 2011/133637; compounds described in U.S. Pat. No. 8,637,256; compounds described in *Expert. Opin. Ther. Pat.* 24(7):731-744, 2014; compounds described in *Expert Opin. Ther. Pat.* 19(3):305-319, 2009; (R)-2-phenylpyrrolidine substituted imidazopyridazines, e.g., GNF-8625, (R)-1-(6-(6-(2-(3-fluorophenyl)pyrrolidin-1-yl)imidazo[1,2-b]pyridazin-3-yl)-[2,4'-bipyridin]-2'-yl)piperidin-4-ol as described in ACS Med. Chem. Lett. 6(5):562-567, 2015; GTx-186 and others, as described in *PLoS One* 8(12):e83380, 2013; K252a ((9S-(9α,10β,12α))-2,3,9,10,11,12-hexahydro-10-hydroxy-10-(methoxycarbonyl)-9-methyl-9,12-epoxy-1H-diindolo[1,2,3-fg:3',2',1'-kl]pyrrolo[3,4-i][1,6]benzodiazocin-1-one), as described in *Mol. Cell Biochem.* 339(1-2):201-213, 2010; 4-aminopyrazolylpyrimidines, e.g., AZ-23 (((S)-5-chloro-N2-(1-(5-fluoropyridin-2-yl)ethyl)-N4-(5-isopropoxy-1H-pyrazol-3-yl)pyrimidine-2,4-diamine)), as described in *J. Med. Chem.* 51(15): 4672-4684, 2008; PHA-739358 (danusertib), as described in *Mol. Cancer Ther.* 6:3158, 2007; Gö 6976 (5,6,7,13-tetrahydro-13-methyl-5-oxo-12H-indolo[2,3-a]pyrrolo[3,4-c]carbazole-12-propanenitrile), as described in *J. Neurochem.* 72:919-924, 1999; GW441756 ((3Z)-3-[(1-methylindol-3-yl)methylidene]-1H-pyrrolo[3,2-b]pyridin-2-one), as described in *IJAE* 115:117, 2010; milciclib (PHA-848125AC), described in J. Carcinog. 12:22, 2013; AG-879 ((2E)-3-[3,5-Bis(1,1-dimethylethyl)-4-hydroxyphenyl]-2-cyano-2-propenethioamide); altiratinib (N-(4-((2-(cyclopropanecarboxamido)pyridin-4-yl)oxy)-2,5-difluorophenyl)-N-(4-fluorophenyl)cyclopropane-1,1-dicarboxamide); cabozantinib (N-(4-((6,7-Dimethoxyquinolin-4-yl)oxy)phenyl)-N'-(4-fluorophenyl)cyclopropane-1,1-dicarboxamide); lestaurtinib ((5S,6S,8R)-6-Hydroxy-6-(hydroxymethyl)-5-methyl-7,8,14,15-tetrahydro-5H-16-oxa-4b,8a,14-triaza-5,8-methanodibenzo[b,h]cycloocta[jkl]cyclopenta[e]-as-indacen-13(6H)-one); dovatinib (4-amino-5-fluoro-3-[6-(4-methylpiperazin-1-yl)-1H-benzimidazol-2-yl]quinolin-2 (1H)-one mono 2-hydroxypropanoate hydrate); sitravatinib (N-(3-fluoro-4-((2-(5-(((2-methoxyethyl)amino)methyl)pyridin-2-yl)thieno[3,2-b]pyridin-7-yl)oxy)phenyl)-N-(4-fluorophenyl)cyclopropane-1,1-dicarboxamide); ONO-5390556; regorafenib (4-[4-({[4-Chloro-3-(trifluoromethyl)phenyl]carbamoyl}amino)-3-fluorophenoxy]-N-methylpyridine-2-carboxamide hydrate); and VSR-902A; all of the references above are incorporated by reference in their entireties herein.

The ability of a Trk inhibitor to act as a TrkA, TrkB, and/or Trk C inhibitor may be tested using the assays described in Examples A and B in U.S. Pat. No. 8,513,263, which is incorporated herein by reference.

In some embodiments, the receptor tyrosine kinase inhibitor is an epidermal growth factor receptor tyrosine kinase family inhibitor (EGFR). For example, EGFR family inhibitors can include osimertinib (AZD9291, merelectinib, TAGRISSO™), erlotinib (TARCEVA®), gefitinib (IRESSA®), cetuximab (ERBITUX®), necitumumab (PORTRAZZA™, IMC-11F8), neratinib (HKI-272, NERLYNX®), lapatinib (TYKERB®), panitumumab (ABX-EGF, VECTIBIX®), vandetanib (CAPRELSA®), rociletinib (CO-1686), olmutinib (OLITA™, HM61713, BI-1482694), naquotinib (ASP8273), nazartinib (EGF816, NVS-816), PF-06747775, icotinib (BPI-2009H), afatinib (BIBW 2992, GILOTRIF®), dacomitinib (PF-00299804, PF-804, PF-299, PF-299804), avitinib (AC0010), AC0010MA EAI045, matuzumab (EMD-7200), nimotuzumab (h-R3, BIOMAb EGFR®), zalutumab, MDX447, depatuxizumab (humanized mAb 806, ABT-806), depatuxizumab mafodotin (ABT-414), ABT-806, mAb 806, canertinib (CI-1033), shikonin, shikonin derivatives (e.g., deoxyshikonin, isobutyryl-shikonin, acetylshikonin, ββ-dimethylacrylshikonin and acetylalkannin), poziotinib (NOV120101, HM781-36B), AV-412, ibrutinib, WZ4002, brigatinib (AP26113, ALUNBRIG®), pelitinib (EKB-569), tarloxotinib (TH-4000, PR610), BPI-15086, Hemay022, ZN-e4, tesevatinib (KD019, XL647), YH25448, epitinib (HMPL-813), CK-101, MM-151, AZD3759, ZD6474, PF-06459988, varlintinib (ASLAN001, ARRY-334543), AP32788, HLX07, D-0316, AEE788, HS-10296, avitinib, GW572016, pyrotinib (SHR1258), SCT200, CPGJ602, Sym004, MAb-425, Modotuximab (TAB-H49), futuximab (992 DS), zalutumumab, KL-140, RO5083945, IMGN289, JNJ-61186372, LY3164530, Sym013, AMG 595, AZD8931, AST1306, CP724714, CUDC101, TAK285, trastuzumab (HERCEPTIN®), pertuzumab (PERJETA®), trastuzumab-dkst (OGIVRI®), DXL-702, E-75, PX-104.1, ZW25, irbinitinib (ARRY-380, ONT-380), TAS0728, perlitinib (EKB-569), PKI-166, D-69491, HKI-357, AC-480 (BMS-599626), RB-200h, emodin, IDM-1, ado-trastuzumab emtansine (KADCYLA®), Zemab, DS-8201a, T-DM1. In some embodiments, the EGFR family inhibitor is osimertinib. In some embodiments, the dysregulation of a BTK gene, a BTK kinase, or expression or activity or level of any of the same includes expression of BTK-C. In some embodiments, BTK-C is expressed in prostate or breast cancer.

In some embodiments, signal transduction pathway inhibitors include Ras-Raf-MEK-ERK pathway inhibitors (e.g., binimetinib, selumetinib, encorafinib, sorafenib, trametinib, and vemurafenib), PI3K-Akt-mTOR-S6K pathway inhibitors (e.g. everolimus, rapamycin, perifosine, temsirolimus), and other kinase inhibitors, such as baricitinib, brigatinib, capmatinib, danusertib, ibrutinib, milciclib, quercetin, regorafenib, ruxolitinib, semaxanib, AP32788, BLU285, BLU554, INCB39110, INCB40093, INCB50465, INCB52793, INCB54828, MGCD265, NMS-088, NMS-1286937, PF 477736 ((R)-amino-N-[5,6-dihydro-2-(1-methyl-1H-pyrazol-4-yl)-6-oxo-1Hpyrrolo[4,3,2-ef][2,3] benzodiazepin-8-yl]-cyclohexaneacetamide), PLX3397, PLX7486, PLX8394, PLX9486, PRN1008, PRN1371, RXDX103, RXDX106, RXDX108, and TG101209 (N-tert-butyl-3-(5-methyl-2-(4-(4-methylpiperazin-1-yl)phenylamino)pyrimidin-4-ylamino)benzenesulfonamide). In some embodiments, the Ras-Raf-MEK-ERK pathway inhibitor is one or more of a BRAF inhibitor, a MEK inhibitor, and an ERK inhibitor. In some embodiments, the BRAF inhibitor is one or more of vemurafenib (ZELBORAF®), dabrafenib (TAFINLAR®), and encorafenib (BRAFTOVI™), BMS-908662 (XL281), sorafenib, LGX818, PLX3603, RAF265, RO5185426, GSK2118436, ARQ 736, GDC-0879, PLX-4720, AZ304, PLX-8394, HM95573, RO5126766, and LXH254. In some embodiments, the MEK inhibitor is one or more of trametinib (MEKINIST®, GSK1120212), cobimetinib (COTELLIC®), binimetinib (MEKTOVI®, MEK162), selumetinib (AZD6244), PD0325901, MSC1936369B, SHR7390, TAK-733, R05126766, CS3006, WX-554, PD98059, CI1040 (PD184352), and hypothemycin. In some embodiments, the ERK inhibitor is one or more of FRI-20 (ON-01060), VTX-11e, 25-OH-D3-3-BE (B3CD, bromoacetoxycalcidiol), FR-180204, AEZ-131 (AEZS-131), AEZS-136, AZ-13767370, BL-EI-001, LY-3214996, LTT-462, KO-947, KO-947, MK-8353 (SCH900353), SCH772984, ulixertinib (BVD-523), CC-90003, GDC-0994 (RG-7482), ASN007, FR148083, 5-7-Oxozeaenol, 5-iodotubercidin, GDC0994, and ONC201. In some embodiments, the PI3K-Akt-mTOR-S6K pathway inhibitor is an AKT inhibitor. Non-limiting examples of AKT inhibitors include miltefosine (IMPADIVO®), wortmannin, NL-71-101, H-89, GSK690693, CCT128930, AZD5363, ipatasertib (GDC-0068, RG7440), A-674563, A-443654, AT7867, AT13148, uprosertib, afuresertib, DC120, 2-[4-(2-aminoprop-2-yl)phenyl]-3-phenylquinoxaline, MK-2206, edelfosine, miltefosine, perifosine, erucylphophocholine, erufosine, SR13668, OSU-A9, PH-316, PHT-427, PIT-1, DM-PIT-1, triciribine (Triciribine Phosphate Monohydrate), API-1, N-(4-(5-(3-acetamidophenyl)-2-(2-aminopyridin-3-yl)-3H-imidazo[4,5-b] pyridin-3-yl)benzyl)-3-fluorobenzamide, ARQ092, BAY 1125976, 3-oxo-tirucallic acid, lactoquinomycin, boc-Phe-vinyl ketone, Perifosine (D-21266), TCN, TCN-P, GSK2141795, and ONC201. In some embodiments, the PI3K-Akt-mTOR-S6K pathway inhibitor is one or more of a PI3K inhibitor, an AKT inhibitor, and an mTOR inhibitor. In some embodiments, the PI3K-Akt-mTOR-S6K pathway inhibitor is a PI3K inhibitor. Non-limiting examples of PI3K inhibitors include buparlisib (BKM120), alpelisib (BYL719), WX-037, copanlisib (ALIQOPA™, BAY80-6946), dactolisib (NVP-BEZ235, BEZ-235), taselisib (GDC-0032, RG7604), sonolisib (PX-866), CUDC-907, PQR309, ZSTK474, SF1126, AZD8835, GDC-0077, ASN003, pictilisib (GDC-0941), pilaralisib (XL147, SAR245408), gedatolisib (PF-05212384, PKI-587), serabelisib (TAK-117, MLN1117, INK 1117), BGT-226 (NVP-BGT226), PF-04691502, apitolisib (GDC-0980), omipalisib (GSK2126458, GSK458), voxtalisib (XL756, SAR245409), AMG 511, CH5132799, GSK1059615, GDC-0084 (RG7666), VS-5584 (SB2343), PKI-402, wortmannin, LY294002, PI-103, rigosertib, XL-765, LY2023414, SAR260301, KIN-193 (AZD-6428), GS-9820, AMG319, and GSK2636771. In some embodiments, the dysregulation of a BTK gene, a BTK kinase, or expression or activity or level of any of the same includes expression of BTK-C. In some embodiments, BTK-C is expressed in prostate or breast cancer. In some embodiments, the PI3K-Akt-mTOR-S6K pathway inhibitor is an AKT inhibitor. Non-limiting examples, of AKT inhibitors include miltefosine (WIPADIVO®), wortmannin, NL-71-101, H-89, GSK690693, CCT128930, AZD5363, ipatasertib (GDC-0068, RG7440), A-674563, A-443654, AT7867, AT13148, uprosertib, afuresertib, DC120, 2-[4-(2-aminoprop-2-yl)phenyl]-3-phenylquinoxaline, MK-2206, edelfosine, miltefosine, perifosine, erucylphophocholine, erufosine, SR13668, OSU-A9, PH-316, PHT-427, PIT-1, DM-PIT-1, triciribine (Triciribine Phosphate Monohydrate), API-1, N-(4-(5-(3-acetamidophenyl)-2-(2-aminopyridin-3-yl)-3H-imidazo[4,5-b] pyridin-3-yl)benzyl)-3-fluorobenzamide, ARQ092, BAY 1125976, 3-oxo-tirucallic acid, lactoquinomycin, boc-Phe-vinyl ketone, Perifosine (D-21266), TCN, TCN-P, GSK2141795, and ONC201. In some embodiments, the PI3K-Akt-mTOR-S6K pathway inhibitor is an mTOR inhibitor. Non-limiting examples of mTOR inhibitors include MLN0128, AZD-2014, CC-223, AZD2014, CC-115, everolimus (RAD001), temsirolimus (CCI-779), ridaforolimus (AP-23573), and sirolimus (rapamycin).

Non-limiting examples of checkpoint inhibitors include ipilimumab, tremelimumab, nivolumab, pidilizumab, MPDL3208A, MEDI4736, MSB0010718C, BMS-936559, BMS-956559, BMS-935559 (MDX-1105), AMP-224, and pembrolizumab.

In some embodiments, protein inhibitors include agents that inhibit antiapoptotic proteins (e.g., the Bcl family such as BCL-2, BCL-$X_L$, BCL-W, BCL-B, and MCL1), heat shock proteins (e.g., Hsp10, Hsp27, HspB6, HspB1, Hsp40, Hsp60, Hsp71, Hsp70, Hsp72, Grp78 (BiP), Hsx70, Hsp90, Grp94, Hsp104, HspI10), nuclear export proteins (e.g., XPO1), histone deacetylases (HDAC1, HDAC2, HDAC3, HDAC8, HDAC4, HDAC5, HDAC7, HDAC6, HDAC10, SIRT1, SIRT2, SIRT3, SIRT4, SIRT5, SIRT6, SIRT7, and HDAC11), E3 ubiquitin ligases (e.g., E3A, MDM2, Anaphase-promoting complex (APC), UBR5 (EDD1), SOCS/BC-box/eloBC/CUL5/RING, LNXp80, CBX4, CBLL1, HACE1, HECTD1, HECTD2, HECTD3, HECTD4, HECW1, HECW2, HERC1, HERC2, HERC3, HERC4, HERC5, HERC6, HUWE1, ITCH, NEDD4, NEDD4L, PPIL2, PRPF19, PIAS1, PIAS2, PIAS3, PIAS4, RANBP2, RNF4, RBX1, SMURF1, SMURF2, STUB1, TOPORS, TRIP12, UBE3A, UBE3B, UBE3C, UBE3D, UBE4A, UBE4B, UBOX5, UBR5, WWP1, WWP2, and Parkin), and histone-lysine N-methyltransferases (e.g., ASH1L, DOT1L, EHMT1, EHMT2, EZH1, EZH2, EHMT2, MLL, MLL2, MLL3, MLL4, MLL5, NSD1, PRDM2, SET, SETBP1, SETD1A, SETD1B, SETD2, SETD3, SETD4, SETD5, SETD6, SETD7, SETD8, SETD9, SETDB1, SETDB2, SETMAR, SMYD1, SMYD2, SMYD3, SMYD4, SMYD5, SUV39H1, SUV39H2, SUV420H1, and SUV420H2).

In some embodiments, the protein inhibitor is an agent that inhibits Bcl-2. Non-limiting examples of Bcl-2 inhibitors include venetoclax (ABT-199, RG7601, GDC-0199), navitoclax (ABT-263), ABT-737, TW-37, sabutoclax, and obatoclax. Further examples of Bcl-2 inhibitors include compounds described in International Publication No. WO 2018/195450.

In some embodiments, the protein inhibitor is an agent that inhibits EHMT2. Non-limiting examples of EHMT2 inhibitors include BIX-01294 (BIX), UNC0638, A-366, UNC0642, DCG066, UNC0321, BRD 4770, UNC 0224, UNC 0646, UNC0631, BIX-01338, and EZM8266.

In some embodiments, the protein inhibitor inhibits a protein selected from the group consisting of: PI3K, JAK-2, IRAK1, IRAK4, BMX, TAK1, Src family, HDAC6, MDM2, BCL-2, EZH2, EHMT2, PIM, JAK3, mTOR, ROR-1, Syk, PKC, HSP90, XPO1, and combinations thereof.

In some embodiments, cytotoxic chemotherapeutics are selected from arsenic trioxide, bleomycin, cabazitaxel, capecitabine, carboplatin, cisplatin, cyclophosphamide, cytarabine, dacarbazine, daunorubicin, docetaxel, doxorubicin, etoposide, fluorouracil, gemcitabine, irinotecan, lomustine, methotrexate, mitomycin C, oxaliplatin, paclitaxel, pemetrexed, temozolomide, and vincristine.

Non-limiting examples of angiogenesis-targeted therapies include aflibercept and bevacizumab.

In some embodiments, the immunotherapy is a cellular immunotherapy (e.g., adoptive T-cell therapy, dendritic cell therapy, natural killer cell therapy). In some embodiments, the cellular immunotherapy is sipuleucel-T (APC8015; PROVENGE™; Plosker (2011) Drugs 71(1): 101-108). In some embodiments, the cellular immunotherapy includes cells that express a chimeric antigen receptor (CAR). In some embodiments, the cellular immunotherapy is a CAR-T cell therapy. In some embodiments, the CAR-T cell therapy is tisagenlecleucel (KYMRIAH™)

In some embodiments, the immunotherapy is an antibody therapy (e.g., a monoclonal antibody, a conjugated antibody). In some embodiments, the antibody therapy is bevacizumab (MVASTI™, AVASTIN®), trastuzumab (HERCEPTIN®), avelumab (BAVENCIO®), rituximab (MABTHERA™, RITUXAN®), edrecolomab (Panorex), daratumuab (DARZALEX®), olaratumab (LARTRUVO™), ofatumumab (ARZERRA®), alemtuzumab (CAMPATH®), cetuximab (ERBITUX®), oregovomab, pembrolizumab (KEYTRUDA®), dinutiximab (UNITUXIN®), obinutuzumab (GAZYVA®), tremelimumab (CP-675,206), ramucirumab (CYRAMZA®), ublituximab (TG-1101), panitumumab (VECTIBIX®), elotuzumab (EMPLICITI™), avelumab (BAVENCIO®), necitumumab (PORTRAZZA™), cirmtuzumab (UC-961), ibritumomab (ZEVALIN®), isatuximab (SAR650984), nimotuzumab, fresolimumab (GC1008), lirilumab (INN), mogamulizumab (POTELIGEO®), ficlatuzumab (AV-299), denosumab (XGEVA®), ganitumab, urelumab, pidilizumab, or amatuximab.

In some embodiments, the immunotherapy is an antibody-drug conjugate. In some embodiments, the antibody-drug conjugate is gemtuzumab ozogamicin (MYLOTARG™), inotuzumab ozogamicin (BESPONSA®), brentuximab vedotin (ADCETRIS®), ado-trastuzumab emtansine (TDM-1; KADCYLA®), mirvetuximab soravtansine (IMGN853), or anetumab ravtansine.

In some embodiments, the immunotherapy includes blinatumomab (AMG103; BLINCYTO®) or midostaurin (Rydapt).

In some embodiments, the immunotherapy includes a toxin. In some embodiments, the immunotherapy is denileukin diftitox (ONTAK®).

In some embodiments, the immunotherapy is a cytokine therapy. In some embodiments, the cytokine therapy is an interleukin 2 (IL-2) therapy, an interferon alpha (IFNα) therapy, a granulocyte colony stimulating factor (G-CSF) therapy, an interleukin 12 (IL-12) therapy, an interleukin 15 (IL-15) therapy, an interleukin 7 (IL-7) therapy or an erythropoietin-alpha (EPO) therapy. In some embodiments, the IL-2 therapy is aldesleukin (PROLEUKIN®). In some embodiments, the IFNα therapy is Introna® (ROFERON-A®). In some embodiments, the G-CSF therapy is filgrastim (NEUPOGEN®).

In some embodiments, the immunotherapy is an immune checkpoint inhibitor. In some embodiments, the immunotherapy includes one or more immune checkpoint inhibitors. In some embodiments, the immune checkpoint inhibitor is a CTLA-4 inhibitor, a PD-1 inhibitor or a PD-L1 inhibitor. In some embodiments, the CTLA-4 inhibitor is ipilimumab (YERVOY®) or tremelimumab (CP-675,206). In some embodiments, the PD-1 inhibitor is pembrolizumab (KEYTRUDA®) or nivolumab (OPDIVO®). In some embodiments, the PD-L1 inhibitor is atezolizumab (TECENTRIQ®), avelumab (BAVENCIO®) or durvalumab (IMFINZI™).

In some embodiments, the immunotherapy is mRNA-based immunotherapy. In some embodiments, the mRNA-based immunotherapy is CV9104 (see, e.g., Rausch et al. (2014) Human Vaccin Immunother 10(11): 3146-52; and Kubler et al. (2015) J. Immunother Cancer 3:26).

In some embodiments, the immunotherapy is bacillus Calmette-Guerin (BCG) therapy.

In some embodiments, the immunotherapy is an oncolytic virus therapy. In some embodiments, the oncolytic virus therapy is talimogene alherparepvec (T-VEC; IMLYGIC®).

In some embodiments, the immunotherapy is a cancer vaccine. In some embodiments, the cancer vaccine is a human papillomavirus (HPV) vaccine. In some embodiments, the HPV vaccine is GARDASIL®, GARDASIL9® or CERVARIX®. In some embodiments, the cancer vaccine is a hepatitis B virus (HBV) vaccine. In some embodiments, the HBV vaccine is ENGERIX-B®, RECOMBIVAX HB® or GI-13020 (TARMOGEN®). In some embodiments, the cancer vaccine is TWINRIX® or PEDIARIX®. In some embodiments, the cancer vaccine is BIOVAXID®, ONCOPHAGE®, GVAX, ADXS11-001, ALVAC-CEA, PROSTVAC®, RINDOPEPIMUT®, CimaVax-EGF, lapuleucel-T (APC8024; NEUVENGE™), GRNVAC1, GRNVAC2, GRN-1201, hepcortespenlisimut-L (Hepko-V5), DCVAX®, SCIB1, BMT CTN 1401, PrCa VBIR, PANVAC, PROSTATAK®, DPX-Survivac, or viagenpumatucel-L (HS-110).

In some embodiments, the immunotherapy is a peptide vaccine. In some embodiments, the peptide vaccine is nelipepimut-S (E75) (NEUVAX™), IMA901, or SurVaxM (SVN53-67). In some embodiments, the cancer vaccine is an immunogenic personal neoantigen vaccine (see, e.g., Ott et al. (2017) Nature 547: 217-221; Sahin et al. (2017) Nature 547: 222-226). In some embodiments, the cancer vaccine is RGSH4K, or NEO-PV-01. In some embodiments, the cancer vaccine is a DNA-based vaccine. In some embodiments, the DNA-based vaccine is a mammaglobin-A DNA vaccine (see, e.g., Kim et al. (2016) OncoImmunology 5(2): e1069940).

In some embodiments, immune-targeted agents are selected from aldesleukin, interferon alfa-2b, ipilimumab, lambrolizumab, nivolumab, prednisone, and sipuleucel-T.

Non-limiting examples of radiotherapy include radioiodide therapy, external-beam radiation, and radium 223 therapy.

Additional kinase inhibitors include those described in, for example, U.S. Pat. Nos. 7,514,446; 7,863,289; 8,026,247; 8,501,756; 8,552,002; 8,815,901; 8,912,204; 9,260,437; 9,273,051; U.S. Publication No. US 2015/0018336; International Publication No. WO 2007/002325; WO 2007/002433; WO 2008/080001; WO 2008/079906; WO 2008/079903; WO 2008/079909; WO 2008/080015; WO 2009/007748; WO 2009/012283; WO 2009/143018; WO 2009/143024; WO 2009/014637; 2009/152083; WO 2010/111527; WO 2012/109075; WO 2014/194127; WO 2015/112806; WO 2007/110344; WO 2009/071480; WO 2009/118411; WO 2010/031816; WO 2010/145998; WO 2011/092120; WO 2012/101032; WO 2012/139930; WO 2012/143248; WO 2012/152763; WO 2013/014039; WO 2013/102059; WO 2013/050448; WO 2013/050446; WO 2014/019908; WO 2014/072220; WO 2014/184069; and WO 2016/075224 all of which are hereby incorporated by reference in their entireties.

Further examples of kinase inhibitors include those described in, for example, WO 2016/081450; WO 2016/022569; WO 2016/011141; WO 2016/011144; WO 2016/011147; WO 2015/191667; WO 2012/101029; WO 2012/113774; WO 2015/191666; WO 2015/161277; WO 2015/161274; WO 2015/108992; WO 2015/061572; WO 2015/058129; WO 2015/057873; WO 2015/017528; WO/2015/017533; WO 2014/160521; and WO 2014/011900, each of which is hereby incorporated by reference in its entirety.

Further examples of kinase inhibitors include luminespib (AUY-922, NVP-AUY922) (5-(2,4-dihydroxy-5-isopropylphenyl)-N-ethyl-4-(4-(morpholinomethyl)phenyl)isoxazole-3-carboxamide) and doramapimod (BIRB-796) (1-[5-tert-butyl-2-(4-methylphenyl)pyrazol-3-yl]-3-[4-(2-morpholin-4-ylethoxy)naphthalen-1-yl]urea).

Accordingly, also provided herein is a method of treating cancer, comprising administering to a subject in need thereof a pharmaceutical combination for treating cancer which comprises (a) the compound of Formula I, or a pharmaceutically acceptable salt, amorphous, or polymorph form thereof, a spray-dried dispersion thereof, or a pharmaceutical composition thereof, (b) an additional therapeutic agent, and (c) optionally at least one pharmaceutically acceptable carrier for simultaneous, separate or sequential use for the treatment of cancer, wherein the amounts of the compound of Formula I, or a pharmaceutically acceptable salt, amorphous, or polymorph form thereof, a spray-dried dispersion thereof, or a pharmaceutical composition thereof, and the additional therapeutic agent are together effective in treating the cancer.

In some embodiments, the additional therapeutic agent(s) includes any one of the above listed therapies or therapeutic agents which are standards of care in cancers wherein the cancer has a dysregulation of a BTK gene, a BTK protein, or expression or activity, or level of any of the same.

These additional therapeutic agents may be administered with one or more doses of the compound of Formula I, or a pharmaceutically acceptable salt, amorphous, or polymorph form thereof, a spray-dried dispersion thereof, or pharmaceutical composition thereof, as part of the same or separate dosage forms, via the same or different routes of administration, and/or on the same or different administration schedules according to standard pharmaceutical practice known to one skilled in the art.

Also provided herein is (i) a pharmaceutical combination for treating a cancer in a subject in need thereof, which comprises (a) the compound of Formula I, or a pharmaceutically acceptable salt, amorphous, or polymorph form thereof, a spray-dried dispersion thereof, or a pharmaceutical composition thereof, (b) at least one additional therapeutic agent (e.g., any of the exemplary additional therapeutic agents described herein or known in the art), and (c) optionally at least one pharmaceutically acceptable carrier for simultaneous, separate or sequential use for the treatment of cancer, wherein the amounts of the compound of Formula I, or a pharmaceutically acceptable salt, amorphous, or polymorph form thereof, a spray-dried dispersion thereof, or a pharmaceutical composition thereof, and of the additional therapeutic agent are together effective in treating the cancer; (ii) a pharmaceutical composition comprising such a combination; (iii) the use of such a combination for the preparation of a medicament for the treatment of cancer; and (iv) a commercial package or product comprising such a combination as a combined preparation for simultaneous, separate or sequential use; and to a method of treatment of cancer in a subject in need thereof. In one embodiment the subject is a human. In some embodiments, the cancer is a BTK-associated cancer. For example, a BTK-associated cancer having one or more BTK inhibitor resistance mutations.

Accordingly, also provided herein is a method of treating a cancer, comprising administering to a subject in need thereof a pharmaceutical combination for treating cancer which comprises (a) the compound of Formula I, or a pharmaceutically acceptable salt, amorphous, or polymorph form thereof, a spray-dried dispersion thereof, or a pharmaceutical composition thereof, (b) an additional therapeutic agent, and (c) optionally at least one pharmaceutically acceptable carrier for simultaneous, separate or sequential use for the treatment of cancer, wherein the amounts of the compound of Formula I, or a pharmaceutically acceptable salt, amorphous, or polymorph form thereof, a spray-dried dispersion thereof, or a pharmaceutical combination thereof and the additional therapeutic agent are together effective in treating the cancer. In one embodiment, the compound of Formula I, or a pharmaceutically acceptable salt, amorphous, or polymorph form thereof, a spray-dried dispersion thereof, or a pharmaceutical combination thereof and the additional therapeutic agent are administered simultaneously as separate dosages. In one embodiment, the compound of Formula I, or a pharmaceutically acceptable salt, amorphous, or polymorph form thereof, and the additional therapeutic agent are administered as separate dosages sequentially in any order, in jointly therapeutically effective amounts, e.g. in daily or intermittently dosages. In one embodiment, the compound of Formula I, or a pharmaceutically acceptable salt, amorphous, or polymorph form thereof, a spray-dried dispersion thereof, or a pharmaceutical combination thereof and the additional therapeutic agent are administered simultaneously as a combined dosage. In some embodiments, the cancer is a BTK-associated cancer. For example, a BTK-associated cancer having one or more BTK inhibitor resistance mutations. In some embodiments, the additional therapeutic agent is ibrutinib. In some embodiments, the additional therapeutic agent is acalabrutinib. In some embodiments, the subject has been administered one or more doses of the compound of Formula I, or a pharmaceutically acceptable salt, amorphous, or polymorph form thereof, a spray-dried dispersion thereof, or a pharmaceutical composition thereof, prior to administration of the pharmaceutical composition.

Also provided herein is a method of treating a disease or disorder mediated by BTK in a subject in need of such treatment, the method comprising administering to the subject a therapeutically effective amount of the compound of Formula I, or a pharmaceutically acceptable salt, amorphous, or polymorph form thereof, a spray-dried dispersion thereof, or a pharmaceutical composition thereof. In some embodiments, the disease or disorder mediated by BTK is a dysregulation of BTK gene, a BTK kinase, or expression or activity or level of any of the same. For example, the dysregulation of a BTK gene, a BTK kinase, or expression or activity or level of any of the same includes one or more BTK inhibitor resistance mutations. A disease or disorder mediated by BTK can include any disease, disorder or condition that is directly or indirectly linked to expression or activity of BTK, including overexpression and/or abnormal activity levels. In one embodiment, the disease is cancer (e.g., a BTK-associated cancer). In one embodiment, the cancer is any of the cancers or BTK-associated cancers described herein. In some embodiments, the additional therapeutic agent is ibrutinib. In some embodiments, the additional therapeutic agent is acalabrutinib. In some embodiments, the subject has been administered one or more doses of the compound of Formula I, or a pharmaceutically acceptable salt, amorphous, or polymorph form thereof, a spray-dried dispersion thereof, or a pharmaceutical composition thereof, prior to administration of the pharmaceutical composition. In some embodiments, the cancer is a hematological cancer (e.g., a BTK-associated hematological cancer).

Accordingly, also provided herein are methods for inhibiting, preventing, aiding in the prevention, or decreasing the symptoms of metastasis of a cancer in a subject in need thereof, the method comprising administering to the subject a therapeutically effective amount of the compound of Formula I, or a pharmaceutically acceptable salt, amorphous, or polymorph form thereof, a spray-dried dispersion thereof, or a pharmaceutical composition thereof. Such methods can be used in the treatment of one or more of the cancers described herein. In some embodiments, the cancer is a BTK-associated cancer. In some embodiments, the compound of Formula I, or a pharmaceutically acceptable salt, amorphous, or polymorph form thereof, a spray-dried dispersion thereof, or a pharmaceutical composition thereof, is used in combination with an additional therapy or another therapeutic agent, including a chemotherapeutic agent, such as a kinase inhibitor. For example, a first or second BTK kinase inhibitor. In some embodiments, the additional therapeutic agent is ibrutinib. In some embodiments, the additional therapeutic agent is acalabrutinib. In some embodiments, the subject has been administered one or more doses of the compound of Formula I, or a pharmaceutically acceptable salt, amorphous, or polymorph form thereof, a spray-dried dispersion thereof, or a pharmaceutical composition thereof, prior to administration of the pharmaceutical composition. In some embodiments, the cancer is a lung cancer (e.g., a BTK-associated lung cancer).

Also provided are methods of decreasing the risk of developing a metastasis or an additional metastasis in a subject having a BTK-associated cancer that include: selecting, identifying, or diagnosing a subject as having a BTK-associated cancer, and administering a therapeutically effective amount of the compound of Formula I, or a pharmaceutically acceptable salt, amorphous, or polymorph form thereof, a spray-dried dispersion thereof, or a pharmaceutical composition thereof, to the subject selected, identified, or diagnosed as having a BTK-associated cancer. Also provided are methods of decreasing the risk of developing a metastasis or an additional metastasis in a subject having a BTK-associated cancer that includes administering a therapeutically effective amount of a Formula I, or a pharmaceutically acceptable salt, amorphous, or polymorph form thereof, a spray-dried dispersion thereof, or a pharmaceutical composition thereof, to a subject having a BTK-associated cancer. The decrease in the risk of developing a metastasis or an additional metastasis in a subject having a BTK-associated cancer can be compared to the risk of developing a metastasis or an additional metastasis in the subject prior to treatment, or as compared to a subject or a population of subjects having a similar or the same BTK-associated cancer that has received no treatment or a different treatment. In some embodiments, the BTK-associated cancer is a BTK-associated cancer having one or more BTK inhibitor resistance mutations. In some embodiments, the additional therapeutic agent is ibrutinib. In some embodiments, the additional therapeutic agent is acalabrutinib. In some embodiments, the subject has been administered one or more doses of the compound of Formula I, or a pharmaceutically acceptable salt, amorphous, or polymorph form thereof, a spray-dried dispersion thereof, or a pharmaceutical composition thereof, prior to administration of the pharmaceutical composition. In some embodiments, the cancer is a lung cancer (e.g., a BTK-associated lung cancer).

In some embodiments, the presence of one or more BTK inhibitor resistance mutations in a tumor causes the tumor to be more resistant to treatment with a first BTK inhibitor. Methods useful when a BTK inhibitor resistance mutation causes the tumor to be more resistant to treatment with a first BTK inhibitor are described below. For example, provided herein are methods of treating a subject having a cancer that include: identifying a subject having a cancer cell that has one or more BTK inhibitor resistance mutations; and administering to the identified subject the compound of Formula I, or a pharmaceutically acceptable salt, amorphous, or polymorph form thereof, a spray-dried dispersion thereof, or a pharmaceutical composition thereof. In some embodiments, the compound of Formula I, or a pharmaceutically acceptable salt, amorphous, or polymorph form thereof, a spray-dried dispersion thereof, or a pharmaceutical composition thereof, is administered in combination with the first BTK inhibitor. Also provided are methods of treating a subject identified as having a cancer cell that has one or more BTK inhibitor resistance mutations that include administering to the subject the compound of Formula I, or a pharmaceutically acceptable salt, amorphous, or polymorph form thereof, a spray-dried dispersion thereof, or a pharmaceutical composition thereof. In some embodiments, the compound of Formula I, or a pharmaceutically acceptable salt, amorphous, or polymorph form thereof, a spray-dried dispersion thereof, or a pharmaceutical composition thereof, is administered in combination with the first BTK inhibitor. In some embodiments, the one or more BTK inhibitor resistance mutations confer increased resistance to a cancer cell or tumor to treatment with the first BTK inhibitor. In some embodiments, the one or more BTK inhibitor resistance mutations include one or more BTK inhibitor resistance mutations listed in Table 2 and 3. For example, the one or more BTK inhibitor resistance mutations can include a substitution at amino acid position 481, e.g., C481S, C481F, C481T, C481G, and C481R, or a substitution at amino acid position 474, e.g., T474I, T474M, and T474S. As another example, the one or more BTK inhibitor resistance mutations can include a substitution in PLCγ2 (e.g., at amino acid position 244, 257, 334, 495, 664, 665, 707, 708, 742, 845, 848, 993, 1140, or 1141). In some embodiments, the compound of Formula I, or a pharmaceutically acceptable salt, amorphous, or polymorph form thereof, a spray-dried dispersion thereof, or a pharmaceutical composition thereof, is administered in combination with an additional therapeutic agent that inhibits a protein upstream of BTK in the BCR signaling pathway. In some embodiments, the compound of Formula I, or a pharmaceutically acceptable salt, amorphous, or polymorph form thereof, a spray-dried dispersion thereof, or a pharmaceutical composition thereof, is administered in combination with an additional therapeutic agent that inhibits a protein downstream of BTK in the BCR signaling pathway. In some embodiments, the compound of Formula I, or a pharmaceutically acceptable salt, amorphous, or polymorph form thereof, a spray-dried dispersion thereof, or a pharmaceutical composition thereof, is administered in combination with an additional therapeutic agent that inhibits a protein downstream of BTK in the BCR signaling pathway such as a PLCγ2 inhibitor wherein the one or more resistance mutations include a substitution in PLCγ2 (e.g., at amino acid position 244, 257, 334, 495, 664, 665, 707, 708, 742, 845, 848, 993, 1140, or 1141).

For example, provided herein are methods for treating a BTK-associated cancer in a subject in need of such treatment, the method comprising (a) detecting a dysregulation of a BTK gene, a BTK kinase, or the expression or activity or level of any of the same in a sample from the subject; and (b) administering to the subject a therapeutically effective amount of a first BTK inhibitor. In some embodiments, the first BTK inhibitor is selected from the group consisting of: ibrutinib, PRN1008, PRN473, ABBV-105, AC0058, acalabrutinib, zanubrutinib, spebrutinib, poseltinib, evobrutinib, tirabrutinib, CG'806, ARQ 531, BIIB068, vecabrutinib, AS871, CB1763, CB988, GDC-0853, RN486, GNE-504, GNE-309, BTK Max, dasatinib, CT-1530, CGI-1746, CGI-560, LFM A13, TP-0158, dtrmwxhs-12, CNX-774, and LOU064. In some embodiments, the first BTK inhibitor is a covalent inhibitor, e.g., ibrutinib, PRN1008, PRN473, ABBV-105, AC0058, acalabrutinib, zanubrutinib, spebrutinib, poseltinib, evobrutinib, M7583, or tirabrutinib. In some embodiments, the first BTK inhibitor is a non-covalent inhibitor, e.g., CG'806, ARQ 531, BIIB068, vecabrutinib, AS871, CB1763, CB988, GDC-0853, RN486, or dasatinib. In some embodiments, the methods further comprise (after (b)) (c) determining whether a cancer cell in a sample obtained from the subject has at least one BTK inhibitor resistance mutation; and (d) administering the compound of Formula I, or a pharmaceutically acceptable salt, amorphous, or polymorph form thereof, a spray-dried dispersion thereof, or a pharmaceutical composition thereof, as a monotherapy or in conjunction with another anticancer agent to the subject if the subject has a cancer cell that has at least one BTK inhibitor resistance mutation; or (e) administering additional doses of the first BTK inhibitor of step (b) to the subject if the subject has a cancer cell that does not have a BTK inhibitor resistance mutation.

In some embodiments, provided herein are methods for treating a BTK-associated cancer in a subject in need of such treatment, the method comprising (a) detecting a dysregulation of a BTK gene, a BTK kinase, or the expression or activity or level of any of the same in a sample from the subject; and (b) administering to the subject a therapeutically effective amount of a first BTK inhibitor, wherein the first BTK inhibitor is selected from the group consisting of ibrutinib, PRN1008, PRN473, ABBV-105, AC0058, acalabrutinib, zanubrutinib, spebrutinib, poseltinib, evobrutinib, tirabrutinib, CG'806, ARQ 531, BIIB068, vecabrutinib, AS871, CB1763, CB988, GDC-0853, RN486, GNE-504, GNE-309, BTK Max, dasatinib, CT-1530, CGI-1746, CGI-560, LFM A13, TP-0158, dtrmwxhs-12, CNX-774, and LOU064. In some embodiments, the first BTK inhibitor is a covalent inhibitor, e.g., ibrutinib, PRN1008, PRN473, ABBV-105, AC0058, acalabrutinib, zanubrutinib, spebrutinib, poseltinib, evobrutinib, M7583, or tirabrutinib. In some embodiments, the first BTK inhibitor is a non-covalent inhibitor, e.g., CG'806, ARQ 531, BIIB068, vecabrutinib, AS871, CB1763, CB988, GDC-0853, RN486, or dasatinib. In some embodiments, the methods further comprise (after (b)) (c) determining whether a cancer cell in a sample obtained from the subject has at least one BTK inhibitor resistance mutation; and (d) administering the compound of Formula I, or a pharmaceutically acceptable salt, amorphous, or polymorph form thereof, a spray-dried dispersion thereof, or a pharmaceutical composition thereof, as a monotherapy or in conjunction with another anticancer agent to the subject if the subject has a cancer cell that has at least one BTK inhibitor resistance mutation; or (e) administering additional doses of the first BTK inhibitor of step (b) to the subject if the subject has a cancer cell that does not have a BTK inhibitor resistance mutation.

In some embodiments, the compound of Formula I is a polymorph form. In some embodiments, the compound is polymorph Form A of the compound of Formula I. In some embodiments, the spray dried dispersion comprises the compound of Formula I and an HPMCAS polymer at a ratio of about 1:4 to about 4:1 of the compound of Formula I to the HPMCAS polymer. In some embodiments, the spray dried dispersion comprises the compound of Formula I and HPMCAS polymer at a ratio of about 1:1 of the compound of Formula I to the HPMCAS polymer. In some embodiments, the HPMCAS polymer is HPMCAS-MG.

In some embodiments, provided herein are methods for treating a BTK-associated cancer in a subject in need of such treatment, the method comprising (a) detecting one or more point mutations/insertions/deletions of Tables 1 and 4 in a sample from the subject; and (b) administering to the subject a therapeutically effective amount of a first BTK inhibitor. In some embodiments, the first BTK inhibitor is selected from the group consisting of: ibrutinib, PRN1008, PRN473, ABBV-105, AC0058, acalabrutinib, zanubrutinib, spebrutinib, poseltinib, evobrutinib, tirabrutinib, CG'806, ARQ 531, BIIB068, vecabrutinib, AS871, CB1763, CB988, GDC-0853, RN486, GNE-504, GNE-309, BTK Max, dasatinib, CT-1530, CGI-1746, CGI-560, LFM A13, TP-0158, dtrmwxhs-12, CNX-774, and LOU064. In some embodiments, the first BTK inhibitor is a covalent inhibitor, e.g., ibrutinib, PRN1008, PRN473, ABBV-105, AC0058, acalabrutinib, zanubrutinib, spebrutinib, poseltinib, evobrutinib, M7583, or tirabrutinib. In some embodiments, the first BTK inhibitor is a non-covalent inhibitor, e.g., CG'806, ARQ 531, BIIB068, vecabrutinib, AS871, CB1763, CB988, GDC-0853, RN486, or dasatinib. In some embodiments, the methods further comprise (after (b)) (c) determining whether a cancer cell in a sample obtained from the subject has at least one BTK inhibitor resistance mutation of Tables 1 or 4; and (d) administering the compound of Formula I, or a pharmaceutically acceptable salt, amorphous, or polymorph form thereof, a spray-dried dispersion thereof, or a pharmaceutical composition thereof, as a monotherapy or in conjunction with another anticancer agent to the subject if the subject has a cancer cell that has at least one BTK inhibitor resistance mutation; or (e) administering additional doses of the first BTK inhibitor of step (b) to the subject if the subject has a cancer cell that does not have a BTK inhibitor resistance mutation.

In some embodiments, the compound of Formula I is a polymorph form. In some embodiments, the compound is polymorph Form A of the compound of Formula I. In some embodiments, the spray dried dispersion is as described herein.

In some embodiments, provided herein are methods for treating a BTK-associated cancer in a subject in need of such treatment, the method comprising (a) one or more BCR signaling pathway protein mutations of Table 4 in a sample from the subject; and (b) administering to the subject a therapeutically effective amount of a first BTK inhibitor, wherein the first BTK inhibitor is selected from the group consisting of ibrutinib, PRN1008, PRN473, ABBV-105, AC0058, acalabrutinib, zanubrutinib, spebrutinib, poseltinib, evobrutinib, tirabrutinib, CG'806, ARQ 531, BIIB068, vecabrutinib, AS871, CB1763, CB988, GDC-0853, RN486, GNE-504, GNE-309, BTK Max, dasatinib, CT-1530, CGI-1746, CGI-560, LFM A13, TP-0158, dtrmwxhs-12, CNX-774, and LOU064. In some embodiments, the first BTK inhibitor is a covalent inhibitor, e.g., ibrutinib, PRN1008, PRN473, ABBV-105, AC0058, acalabrutinib, zanubrutinib, spebrutinib, poseltinib, evobrutinib, M7583, or tirabrutinib. In some embodiments, the first BTK inhibitor is a non-covalent inhibitor, e.g., CG'806, ARQ 531, BIIB068, vecabrutinib, AS871, CB1763, CB988, GDC-0853, RN486, or dasatinib. In some embodiments, the methods further comprise (after (b)) (c) determining whether a cancer cell in a sample obtained from the subject has the BTK inhibitor resistance mutation C481S, C481F, C481T, C481G, C481R, T474I, T474M, or T474S; and (d) administering the compound of Formula I, or a pharmaceutically acceptable salt, amorphous, or polymorph form thereof, a spray-dried dispersion thereof, or a pharmaceutical composition thereof, selected from the group consisting of the compound of Formula I, or a pharmaceutically acceptable salt, amorphous, or polymorph form thereof, a spray-dried dispersion thereof, or a pharmaceutical composition thereof, as a monotherapy or in conjunction with another anticancer agent to the subject if the subject has a cancer cell that has at least one BTK inhibitor resistance mutation; or (e) administering additional doses of the first BTK inhibitor of step (b) to the subject if the subject has a cancer cell that does not have a BTK inhibitor resistance mutation.

In some embodiments, the compound of Formula I is a polymorph form. In some embodiments, the compound is polymorph Form A of the compound of Formula I. In some embodiments, the spray dried dispersion comprises the compound of Formula I and an HPMCAS polymer is as described herein. In some embodiments, the HPMCAS polymer is HPMCAS-MG.

As another example, provided herein are methods for treating a BTK-associated cancer in a subject in need of such treatment, the method comprising (a) detecting a dysregulation of a BTK gene, a BTK kinase, or the expression or activity or level of any of the same in a sample from the subject; and (b) administering to the subject a therapeutically effective amount of the compound of Formula I, or a pharmaceutically acceptable salt, amorphous, or polymorph form thereof, a spray-dried dispersion thereof, or a pharmaceutical composition thereof. In some embodiments, the methods further comprise (after (b)) (c) determining whether a cancer cell in a sample obtained from the subject has at least one BTK inhibitor resistance mutation; and (d) administering a second BTK inhibitor, wherein the second BTK inhibitor is selected from the group consisting of ibrutinib, PRN1008, PRN473, ABBV-105, AC0058, acalabrutinib, zanubrutinib, spebrutinib, poseltinib, evobrutinib, tirabrutinib, CG'806, ARQ 531, BIIB068, vecabrutinib, AS871, CB1763, CB988, GDC-0853, RN486, GNE-504, GNE-309, BTK Max, dasatinib, CT-1530, CGI-1746, CGI-560, LFM A13, TP-0158, dtrmwxhs-12, CNX-774, and LOU064, as a monotherapy or in conjunction with another anticancer agent to the subject if the subject has a cancer cell that has at least one BTK inhibitor resistance mutation; or (e) administering additional doses of the compound of Formula I, or a pharmaceutically acceptable salt, amorphous, or polymorph form thereof, a spray-dried dispersion thereof, or a pharmaceutical composition thereof, of step (b) to the subject if the subject has a cancer cell that does not have a BTK inhibitor resistance mutation. In some embodiments, provided herein are methods for treating a BTK-associated cancer in a subject in need of such treatment, the method comprising (a) detecting a dysregulation of a BTK gene, a BTK kinase, or the expression or activity or level of any of the same in a sample from the subject; and (b) administering to the subject a therapeutically effective amount of the compound of Formula I, or a pharmaceutically acceptable salt, amorphous, or polymorph form thereof, a spray-dried dispersion thereof, or a pharmaceutical composition thereof. In some embodiments, the methods further comprise (after (b)) (c) determining whether a cancer cell in a sample obtained from the subject has at least one BTK inhibitor resistance mutation; and (d) administering a second BTK inhibitor, wherein the second BTK inhibitor is selected from the group consisting of: ibrutinib, PRN1008, PRN473, ABBV-105, AC0058, acalabrutinib, zanubrutinib, spebrutinib, poseltinib, evobrutinib, tirabrutinib, CG'806, ARQ 531, BIIB068, vecabrutinib, AS871, CB1763, CB988, GDC-0853, RN486, GNE-504, GNE-309, BTK Max, dasatinib, CT-1530, CGI-1746, CGI-560, LFM A13, TP-0158, dtrmwxhs-12, CNX-774, and LOU064, as a monotherapy or in conjunction with another anticancer agent to the subject if the subject has a cancer cell that has at least one BTK inhibitor resistance mutation; or (e) administering additional doses of the compound of Formula I, or a pharmaceutically acceptable salt, amorphous, or polymorph form thereof, a spray-dried dispersion thereof, or a pharmaceutical composition thereof, of step (b) to the subject if the subject has a cancer cell that does not have a BTK inhibitor resistance mutation.

In some embodiments, provided herein are methods for treating a BTK-associated cancer in a subject in need of such treatment, the method comprising (a) detecting one or more BCR signaling pathway protein mutations of Table 4 in a sample from the subject; and (b) administering to the subject a therapeutically effective amount of the compound of Formula I, or a pharmaceutically acceptable salt, amorphous, or polymorph form thereof, a spray-dried dispersion thereof, or a pharmaceutical composition thereof. In some embodiments, the methods further comprise (after (b)) (c) determining whether a cancer cell in a sample obtained from the subject has at least one BTK inhibitor resistance mutation of Table 2; and (d) administering a second BTK inhibitor, wherein the second BTK inhibitor is selected from the group consisting of: ibrutinib, PRN1008, PRN473, ABBV-105, AC0058, acalabrutinib, zanubrutinib, spebrutinib, poseltinib, evobrutinib, tirabrutinib, CG'806, ARQ 531, BIIB068, vecabrutinib, AS871, CB1763, CB988, GDC-0853, RN486, GNE-504, GNE-309, BTK Max, dasatinib, CT-1530, CGI-1746, CGI-560, LFM A13, TP-0158, dtrmwxhs-12, CNX-774, and LOU064, as a monotherapy or in conjunction with another anticancer agent to the subject if the subject has a cancer cell that has at least one BTK inhibitor resistance mutation; or (e) administering additional doses of the compound of Formula I, or a pharmaceutically acceptable salt, amorphous, or polymorph form thereof, a spray-dried dispersion thereof, or a pharmaceutical composition thereof, of step (b) to the subject if the subject has a cancer cell that does not have a BTK inhibitor resistance mutation. In some embodiments, provided herein are methods for treating a BTK-associated cancer in a subject in need of such treatment, the method comprising (a) detecting MYD88$^{L265P}$ in a sample from the subject; and (b) administering to the subject a therapeutically effective amount of the compound of Formula I, or a pharmaceutically acceptable salt, amorphous, or polymorph form thereof, a spray-dried dispersion thereof, or a pharmaceutical composition thereof. In some embodiments, the methods further comprise (after (b)) (c) determining whether a cancer cell in a sample obtained from the subject has the BTK inhibitor resistance mutation C481S, C481F, C481T, C481G, C481R, T474I, T474M, or T474S; and (d) administering a second BTK inhibitor, wherein the second BTK inhibitor is selected from the group consisting of ibrutinib, PRN1008, PRN473, ABBV-105, AC0058, acalabrutinib, zanubrutinib, spebrutinib, poseltinib, evobrutinib, tirabrutinib, CG'806, ARQ 531, BIIB068, vecabrutinib, AS871, CB1763, CB988, GDC-0853, RN486, GNE-504, GNE-309, BTK Max, dasatinib, CT-1530, CGI-1746, CGI-560, LFM A13, TP-0158, dtrmwxhs-12, CNX-774, and LOU064, as a monotherapy or in conjunction with another anticancer agent to the subject if the subject has a cancer cell that has at least one BTK inhibitor resistance mutation; or (e) administering additional doses of the compound of Formula I, or a pharmaceutically acceptable salt, amorphous, or polymorph form thereof, a spray-dried dispersion thereof, or a pharmaceutical composition thereof, of step (b) to the subject if the subject has a cancer cell that does not have a BTK inhibitor resistance mutation.

In some embodiments, provided herein are methods for treating a BTK-associated cancer in a subject in need of such treatment, the method comprising (a) detecting one or more point mutations/insertions/deletions of Tables 1 and 4 in a sample from the subject; and (b) administering to the subject a therapeutically effective amount of the compound of Formula I, or a pharmaceutically acceptable salt, amorphous, or polymorph form thereof, a spray-dried dispersion thereof, or a pharmaceutical composition thereof. In some embodiments, the methods further comprise (after (b)) (c) determining whether a cancer cell in a sample obtained from the subject has at least one BTK inhibitor resistance mutation of Table 2; and (d) administering a second BTK inhibitor, wherein the second BTK inhibitor is selected from the group consisting of: ibrutinib, PRN1008, PRN473, ABBV-105, AC0058, acalabrutinib, zanubrutinib, spebrutinib, poseltinib, evobrutinib, tirabrutinib, CG'806, ARQ 531, BIIB068, vecabrutinib, AS871, CB1763, CB988, GDC-0853, RN486, GNE-504, GNE-309, BTK Max, dasatinib, CT-1530, CGI-1746, CGI-560, LFM A13, TP-0158, dtrmwxhs-12, CNX-774, and LOU064, as a monotherapy or in conjunction with another anticancer agent to the subject if the subject has a cancer cell that has at least one BTK inhibitor resistance mutation; or (e) administering additional doses of the compound of Formula I, or a pharmaceutically acceptable salt, amorphous, or polymorph form thereof, a spray-dried dispersion thereof, or a pharmaceutical composition thereof, of step (b) to the subject if the subject has a cancer cell that does not have a BTK inhibitor resistance mutation.

As another example, provided herein are methods for treating a BTK-associated cancer in a subject in need of such treatment, the method comprising (a) detecting a dysregulation of a BTK gene, a BTK kinase, or the expression or activity or level of any of the same in a sample from the subject; and (b) administering to the subject a therapeutically effective amount of the compound of Formula I, or a pharmaceutically acceptable salt, amorphous, or polymorph form thereof, a spray-dried dispersion thereof, or a pharmaceutical composition thereof. In some embodiments, the methods further comprise (after (b)) (c) determining whether a cancer cell in a sample obtained from the subject has at least one BTK inhibitor resistance mutation; and (d) administering a second therapeutic agent, wherein the second therapeutic agent is selected from the group consisting of ibrutinib and acalabrutinib, as a monotherapy or in conjunction with the compound of Formula I, or a pharmaceutically acceptable salt, amorphous, or polymorph form thereof, a spray-dried dispersion thereof, or a pharmaceutical composition thereof, to the subject if the subject has a cancer cell that has at least one BTK inhibitor resistance mutation; or (e) administering additional doses of the compound of Formula I, or a pharmaceutically acceptable salt, amorphous, or polymorph form thereof, a spray-dried dispersion thereof, or a pharmaceutical composition thereof, of step (b) to the subject if the subject has a cancer cell that does not have a BTK inhibitor resistance mutation. In some embodiments, provided herein are methods for treating a BTK-associated cancer in a subject in need of such treatment, the method comprising (a) detecting one or more BTK mutations selected from the group consisting of: one or more BTK kinase protein point mutations/insertions of Table 1, BTK fusions of Table 1a, p65BTK, BTK-C, or one or more BCR signaling pathway genetic mutations of Table 4 in a sample from the subject; and (b) administering to the subject a therapeutically effective amount of the compound of Formula I, or a pharmaceutically acceptable salt, amorphous, or polymorph form thereof, a spray-dried dispersion thereof, or a pharmaceutical composition thereof. In some embodiments, the methods further comprise (after (b)) (c) determining whether a cancer cell in a sample obtained from the subject has at least one BTK inhibitor resistance mutation of Table 2; and (d) administering a second therapeutic agent, wherein the second therapeutic agent is selected from the group consisting of ibrutinib and acalabrutinib, as a monotherapy or in conjunction with the compound of Formula I, or a pharmaceutically acceptable salt, amorphous, or polymorph form thereof, a spray-dried dispersion thereof, or a pharmaceutical composition thereof, to the subject if the subject has a cancer cell that has at least one BTK inhibitor resistance mutation; or (e) administering additional doses of the compound of Formula I, or a pharmaceutically acceptable salt, amorphous, or polymorph form thereof, a spray-dried dispersion thereof, or a pharmaceutical composition thereof, of step (b) to the subject if the subject has a cancer cell that does not have a BTK inhibitor resistance mutation. In some embodiments, provided herein are methods for treating a BTK-associated cancer in a subject in need of such treatment, the method comprising (a) detecting one or more BCR signaling pathway protein mutations of Table 4 in a sample from the subject; and (b) administering to the subject a therapeutically effective amount of the compound of Formula I, or a pharmaceutically acceptable salt, amorphous, or polymorph form thereof, a spray-dried dispersion thereof, or a pharmaceutical composition thereof. In some embodiments, the methods further comprise (after (b)) (c) determining whether a cancer cell in a sample obtained from the subject has at least one BTK inhibitor resistance mutation of Table 2; and (d) administering a second therapeutic agent, wherein the second therapeutic agent is selected from the group consisting of ibrutinib and acalabrutinib, as a monotherapy or in conjunction with the compound of Formula I, or a pharmaceutically acceptable salt, amorphous, or polymorph form thereof, a spray-dried dispersion thereof, or a pharmaceutical composition thereof, to the subject if the subject has a cancer cell that has at least one BTK inhibitor resistance mutation; or (e) administering additional doses of the compound of Formula I, or a pharmaceutically acceptable salt, amorphous, or polymorph form thereof, a spray-dried dispersion thereof, or a pharmaceutical composition thereof, of step (b) to the subject if the subject has a cancer cell that does not have a BTK inhibitor resistance mutation In some embodiments of the above, the BTK-associated cancer is a B-cell malignancy.

In some embodiments, the presence of one or more BTK inhibitor resistance mutations in a tumor causes the tumor to be more resistant to treatment with a first BTK inhibitor. Methods useful when a BTK inhibitor resistance mutation causes the tumor to be more resistant to treatment with a first BTK inhibitor are described below. For example, provided herein are methods of treating a subject having a cancer that include: identifying a subject having a cancer cell that has one or more BTK inhibitor resistance mutations; and administering to the identified subject the compound of Formula I, or a pharmaceutically acceptable salt, amorphous, or polymorph form thereof, a spray-dried dispersion thereof, or a pharmaceutical composition thereof. In some embodiments, the compound of Formula I, or a pharmaceutically acceptable salt, amorphous, or polymorph form thereof, a spray-dried dispersion thereof, or a pharmaceutical composition thereof, is administered in combination with the first BTK inhibitor. Also provided are methods of treating a subject identified as having a cancer cell that has one or more BTK inhibitor resistance mutations that include administering to the subject the compound of Formula I, or a pharmaceutically acceptable salt, amorphous, or polymorph form thereof, a spray-dried dispersion thereof, or a pharmaceutical composition thereof. In some embodiments, the compound of Formula I, or a pharmaceutically acceptable salt, amorphous, or polymorph form thereof, a spray-dried dispersion thereof, or a pharmaceutical composition thereof, is administered in combination with the first BTK inhibitor. In some embodiments, the one or more BTK inhibitor resistance mutations confer increased resistance to a cancer cell or tumor to treatment with the first BTK inhibitor. In some embodiments, the one or more BTK inhibitor resistance mutations include one or more BTK inhibitor resistance mutations listed in Table 2. For example, the one or more BTK inhibitor resistance mutations can include a substitution at amino acid position 481, e.g., C481S, C481F, C481T, C481G, and C481R, or a substitution at amino acid position 474, e.g., T474I, T474M, or T474S. As another example, the one or more BTK inhibitor resistance mutations can include a substitution at amino acid position 244, 257, 334, 495, 664, 665, 707, 708, 742, 845, 848, 993, 1140, or 1141 of PLCγ2. In some embodiments, the compound of Formula I, or a pharmaceutically acceptable salt, amorphous, or polymorph form thereof, a spray-dried dispersion thereof, or a pharmaceutical composition thereof, is administered in combination with an additional therapeutic agent that inhibits a protein upstream of BTK in the BCR signaling pathway. In some embodiments, the compound of Formula I, or a pharmaceutically acceptable salt, amorphous, or polymorph form thereof, a spray-dried dispersion thereof, or a pharmaceutical composition thereof, is administered in combination with an additional therapeutic agent that inhibits a protein downstream of BTK in the BCR signaling pathway. In some embodiments, the compound of Formula I, or a pharmaceutically acceptable salt, amorphous, or polymorph form thereof, a spray-dried dispersion thereof, or a pharmaceutical composition thereof, is administered in combination with an additional therapeutic agent that inhibits a protein downstream of BTK in the BCR signaling pathway such as a PLCγ2 inhibitor wherein the one or more resistance mutations include a substitution in PLCγ2 (e.g., at amino acid position 244, 257, 334, 495, 664, 665, 707, 708, 742, 845, 848, 993, 1140, or 1141).

In some embodiments, provided herein are methods for treating a BTK-associated cancer in a subject in need of such treatment, the method comprising (a) detecting one or more BCR signaling pathway protein mutations of Table 4 in a sample from the subject; and (b) administering to the subject a therapeutically effective amount of a first BTK inhibitor, wherein the first BTK inhibitor is selected from the group consisting of: ibrutinib, PRN1008, PRN473, ABBV-105, AC0058, acalabrutinib, zanubrutinib, spebrutinib, poseltinib, evobrutinib, tirabrutinib, CG'806, ARQ 531, BIIB068, vecabrutinib, AS871, CB1763, CB988, GDC-0853, RN486, GNE-504, GNE-309, BTK Max, dasatinib, CT-1530, CGI-1746, CGI-560, LFM A13, TP-0158, dtrmwxhs-12, CNX-774, and LOU064; or a pharmaceutically acceptable salt or solvate thereof. In some embodiments, the methods further comprise (after (b)) (c) determining whether a cancer cell in a sample obtained from the subject has at least one BTK inhibitor resistance mutation of Table 2; and (d) administering the compound of Formula I, or a pharmaceutically acceptable salt, amorphous, or polymorph form thereof, a spray-dried dispersion thereof, or a pharmaceutical composition thereof, as a monotherapy or in conjunction with another anticancer agent to the subject if the subject has a cancer cell that has at least one BTK inhibitor resistance mutation; or (e) administering additional doses of the first BTK inhibitor of step (b) to the subject if the subject has a cancer cell that does not have a BTK inhibitor resistance mutation.

In some embodiments, provided herein are methods for treating a BTK-associated cancer in a subject in need of such treatment, the method comprising (a) detecting a dysregulation of a BTK gene, a BTK kinase, or the expression or activity or level of any of the same in a sample from the subject; and (b) administering to the subject a therapeutically effective amount of a first BTK inhibitor, wherein the first BTK inhibitor is selected from the group consisting of: ibrutinib, PRN1008, PRN473, ABBV-105, AC0058, acalabrutinib, zanubrutinib, spebrutinib, poseltinib, evobrutinib, tirabrutinib, CG'806, ARQ 531, BIIB068, vecabrutinib, AS871, CB1763, CB988, GDC-0853, RN486, GNE-504, GNE-309, BTK Max, dasatinib, CT-1530, CGI-1746, CGI-560, LFM A13, TP-0158, dtrmwxhs-12, CNX-774, and LOU064; or a pharmaceutically acceptable salt or solvate thereof. In some embodiments, the methods further comprise (after (b)) (c) determining whether a cancer cell in a sample obtained from the subject has at least one BTK inhibitor resistance mutation; and (d) administering the compound of Formula I, or a pharmaceutically acceptable salt, amorphous, or polymorph form thereof, a spray-dried dispersion thereof, or a pharmaceutical composition thereof, as a monotherapy or in conjunction with another anticancer agent to the subject if the subject has a cancer cell that has at least one BTK inhibitor resistance mutation; or (e) administering additional doses of the first BTK inhibitor of step (b) to the subject if the subject has a cancer cell that does not have a BTK inhibitor resistance mutation.

In some embodiments, provided herein are methods for treating a BTK-associated cancer in a subject in need of such treatment, the method comprising (a) detecting a dysregulation of a BTK gene, a BTK kinase, or the expression or activity or level of any of the same in a sample from the subject; and (b) administering to the subject a therapeutically effective amount of a first BTK inhibitor, wherein the first BTK inhibitor is selected from the group consisting of: ibrutinib, PRN1008, PRN473, ABBV-105, AC0058, acalabrutinib, zanubrutinib, spebrutinib, poseltinib, evobrutinib, tirabrutinib, CG'806, ARQ 531, BIIB068, vecabrutinib, AS871, CB1763, CB988, GDC-0853, RN486, GNE-504, GNE-309, BTK Max, dasatinib, CT-1530, CGI-1746, CGI-560, LFM A13, TP-0158, dtrmwxhs-12, CNX-774, and LOU064; or a pharmaceutically acceptable salt or solvate thereof. In some embodiments, the methods further comprise (after (b)) (c) determining whether a cancer cell in a sample obtained from the subject has at least one BTK inhibitor resistance mutation; and (d) administering the compound of Formula I, or a pharmaceutically acceptable salt, amorphous, or polymorph form thereof, a spray-dried dispersion thereof, or a pharmaceutical composition thereof, as a monotherapy or in conjunction with another anticancer agent to the subject if the subject has a cancer cell that has at least one BTK inhibitor resistance mutation; or (e) administering additional doses of the first BTK inhibitor of step (b) to the subject if the subject has a cancer cell that does not have a BTK inhibitor resistance mutation.

In some embodiments, provided herein are methods for treating a BTK-associated cancer in a subject in need of such treatment, the method comprising (a) detecting one or more BTK mutations selected from the group consisting of: one or more BTK kinase protein point mutations/insertions of Table 1, BTK fusions of Table 1a, p65BTK, BTK-C, or one or more BCR signaling pathway genetic mutations of Table 4 in a sample from the subject; and (b) administering to the subject a therapeutically effective amount of a first BTK inhibitor, wherein the first BTK inhibitor is selected from the group consisting of: ibrutinib, PRN1008, PRN473, ABBV-105, AC0058, acalabrutinib, zanubrutinib, spebrutinib, poseltinib, evobrutinib, tirabrutinib, CG'806, ARQ 531, BIIB068, vecabrutinib, AS871, CB1763, CB988, GDC-0853, RN486, GNE-504, GNE-309, BTK Max, dasatinib, CT-1530, CGI-1746, CGI-560, LFM A13, TP-0158, dtrmwxhs-12, CNX-774, and LOU064; or a pharmaceutically acceptable salt or solvate thereof. In some embodiments, the methods further comprise (after (b)) (c) determining whether a cancer cell in a sample obtained from the subject has at least one BTK inhibitor resistance mutation of Table 2; and (d) administering the compound of Formula I, or a pharmaceutically acceptable salt, amorphous, or polymorph form thereof, a spray-dried dispersion thereof, or a pharmaceutical composition thereof, as a monotherapy or in conjunction with another anticancer agent to the subject if the subject has a cancer cell that has at least one BTK inhibitor resistance mutation; or (e) administering additional doses of the first BTK inhibitor of step (b) to the subject if the subject has a cancer cell that does not have a BTK inhibitor resistance mutation.

In some embodiments provided herein, circulating tumor DNA can be used to monitor the responsiveness of a subject to a particular therapy (e.g., a first BTK inhibitor, a second BTK inhibitor, or the compound of Formula I, or a pharmaceutically acceptable salt, amorphous, or polymorph form thereof, a spray-dried dispersion thereof, or a pharmaceutical composition thereof). For example, prior to starting treatment with a therapy as described herein (e.g., a first BTK inhibitor, a second BTK inhibitor, or the compound of Formula I, or a pharmaceutically acceptable salt, amorphous, or polymorph form thereof, a spray-dried dispersion thereof, or a pharmaceutical composition thereof), a biological sample can be obtained from the subject and the level of circulating tumor DNA determined in the biological sample. This sample can be considered a base-line sample. The subject can then be administered one or more doses of a therapy as described herein (e.g., a first BTK inhibitor, a second BTK inhibitor, or the compound of Formula I, or a pharmaceutically acceptable salt, amorphous, or polymorph form thereof, a spray-dried dispersion thereof, or a pharmaceutical composition thereof) and the levels of circulating tumor DNA can be monitored (e.g., after the first dose, second dose, third dose, etc. or after one week, two weeks, three weeks, four weeks, etc.). If the level of circulating tumor DNA is lower than the baseline sample (e.g., a 1% to about a 99% reduction, a 1% to about a 95% reduction, a 1% to about a 90% reduction, a 1% to about a 85% reduction, a 1% to about a 80% reduction, a 1% to about a 75% reduction, a 1% reduction to about a 70% reduction, a 1% reduction to about a 65% reduction, a 1% reduction to about a 60% reduction, a 1% reduction to about a 55% reduction, a 1% reduction to about a 50% reduction, a 1% reduction to about a 45% reduction, a 1% reduction to about a 40% reduction, a 1% reduction to about a 35% reduction, a 1% reduction to about a 30% reduction, a 1% reduction to about a 25% reduction, a 1% reduction to about a 20% reduction, a 1% reduction to about a 15% reduction, a 1% reduction to about a 10% reduction, a 1% to about a 5% reduction, about a 5% to about a 99% reduction, about a 10% to about a 99% reduction, about a 15% to about a 99% reduction, about a 20% to about a 99% reduction, about a 25% to about a 99% reduction, about a 30% to about a 99% reduction, about a 35% to about a 99% reduction, about a 40% to about a 99% reduction, about a 45% to about a 99% reduction, about a 50% to about a 99% reduction, about a 55% to about a 99% reduction, about a 60% to about a 99% reduction, about a 65% to about a 99% reduction, about a 70% to about a 99% reduction, about a 75% to about a 95% reduction, about a 80% to about a 99% reduction, about a 90% reduction to about a 99% reduction, about a 95% to about a 99% reduction, about a 5% to about a 10% reduction, about a 5% to about a 25% reduction, about a 10% to about a 30% reduction, about a 20% to about a 40% reduction, about a 25% to about a 50% reduction, about a 35% to about a 55% reduction, about a 40% to about a 60% reduction, about a 50% reduction to about a 75% reduction, about a 60% reduction to about 80% reduction, or about a 65% to about a 85% reduction etc.), this is indicative of responsiveness to the therapy. In some embodiments, the level of circulating tumor DNA in a biological sample obtained from the subject (n) is compared to the sample taken just previous (n−1). If the level of circulating tumor DNA in the n sample is lower than the n−1 sample (e.g., a 1% to about a 99% reduction, a 1% to about a 95% reduction, a 1% to about a 90% reduction, a 1% to about a 85% reduction, a 1% to about a 80% reduction, a 1% to about a 75% reduction, a 1% reduction to about a 70% reduction, a 1% reduction to about a 65% reduction, a 1% reduction to about a 60% reduction, a 1% reduction to about a 55% reduction, a 1% reduction to about a 50% reduction, a 1% reduction to about a 45% reduction, a 1% reduction to about a 40% reduction, a 1% reduction to about a 35% reduction, a 1% reduction to about a 30% reduction, a 1% reduction to about a 25% reduction, a 1% reduction to about a 20% reduction, a 1% reduction to about a 15% reduction, a 1% reduction to about a 10% reduction, a 1% to about a 5% reduction, about a 5% to about a 99% reduction, about a 10% to about a 99% reduction, about a 15% to about a 99% reduction, about a 20% to about a 99% reduction, about a 25% to about a 99% reduction, about a 30% to about a 99% reduction, about a 35% to about a 99% reduction, about a 40% to about a 99% reduction, about a 45% to about a 99% reduction, about a 50% to about a 99% reduction, about a 55% to about a 99% reduction, about a 60% to about a 99% reduction, about a 65% to about a 99% reduction, about a 70% to about a 99% reduction, about a 75% to about a 95% reduction, about a 80% to about a 99% reduction, about a 90% reduction to about a 99% reduction, about a 95% to about a 99% reduction, about a 5% to about a 10% reduction, about a 5% to about a 25% reduction, about a 10% to about a 30% reduction, about a 20% to about a 40% reduction, about a 25% to about a 50% reduction, about a 35% to about a 55% reduction, about a 40% to about a 60% reduction, about a 50% reduction to about a 75% reduction, about a 60% reduction to about 80% reduction, or about a 65% to about a 85% reduction, etc.), this is indicative of responsiveness to the therapy. In the case of responsiveness to therapy, the subject can to be administered one or more doses of the therapy and the circulating tumor DNA can be continued to be monitored.

If the level of circulating tumor DNA in the sample is higher than the baseline (e.g., a 1% to about a 99% increase, a 1% to about a 95% increase, a 1% to about a 90% increase, a 1% to about a 85% increase, a 1% to about a 80% increase, a 1% to about a 75% increase, a 1% increase to about a 70% increase, a 1% increase to about a 65% increase, a 1% increase to about a 60% increase, a 1% increase to about a 55% increase, a 1% increase to about a 50% increase, a 1% increase to about a 45% increase, a 1% increase to about a 40% increase, a 1% increase to about a 35% increase, a 1% increase to about a 30% increase, a 1% increase to about a 25% increase, a 1% increase to about a 20% increase, a 1% increase to about a 15% increase, a 1% increase to about a 10% increase, a 1% to about a 5% increase, about a 5% to about a 99% increase, about a 10% to about a 99% increase, about a 15% to about a 99% increase, about a 20% to about a 99% increase, about a 25% to about a 99% increase, about a 30% to about a 99% increase, about a 35% to about a 99% increase, about a 40% to about a 99% increase, about a 45% to about a 99% increase, about a 50% to about a 99% increase, about a 55% to about a 99% increase, about a 60% to about a 99% increase, about a 65% to about a 99% increase, about a 70% to about a 99% increase, about a 75% to about a 95% increase, about a 80% to about a 99% increase, about a 90% increase to about a 99% increase, about a 95% to about a 99% increase, about a 5% to about a 10% increase, about a 5% to about a 25% increase, about a 10% to about a 30% increase, about a 20% to about a 40% increase, about a 25% to about a 50% increase, about a 35% to about a 55% increase, about a 40% to about a 60% increase, about a 50% increase to about a 75% increase, about a 60% increase to about 80% increase, or about a 65% to about a 85% increase, etc.), this can be indicative of resistance to the therapy. If the level of circulating tumor DNA in the n sample is higher than the n−1 sample (e.g., a 1% to about a 99% increase, a 1% to about a 95% increase, a 1% to about a 90% increase, a 1% to about a 85% increase, a 1% to about a 80% increase, a 1% to about a 75% increase, a 1% increase to about a 70% increase, a 1% increase to about a 65% increase, a 1% increase to about a 60% increase, a 1% increase to about a 55% increase, a 1% increase to about a 50% increase, a 1% increase to about a 45% increase, a 1% increase to about a 40% increase, a 1% increase to about a 35% increase, a 1% increase to about a 30% increase, a 1% increase to about a 25% increase, a 1% increase to about a 20% increase, a 1% increase to about a 15% increase, a 1% increase to about a 10% increase, a 1% to about a 5% increase, about a 5% to about a 99% increase, about a 10% to about a 99% increase, about a 15% to about a 99% increase, about a 20% to about a 99% increase, about a 25% to about a 99% increase, about a 30% to about a 99% increase, about a 35% to about a 99% increase, about a 40% to about a 99% increase, about a 45% to about a 99% increase, about a 50% to about a 99% increase, about a 55% to about a 99% increase, about a 60% to about a 99% increase, about a 65% to about a 99% increase, about a 70% to about a 99% increase, about a 75% to about a 95% increase, about a 80% to about a 99% increase, about a 90% increase to about a 99% increase, about a 95% to about a 99% increase, about a 5% to about a 10% increase, about a 5% to about a 25% increase, about a 10% to about a 30% increase, about a 20% to about a 40% increase, about a 25% to about a 50% increase, about a 35% to about a 55% increase, about a 40% to about a 60% increase, about a 50% increase to about a 75% increase, about a 60% increase to about 80% increase, or about a 65% to about a 85% increase etc.), this can be indicative of resistance to the therapy. When resistance to therapy is suspected, the subject can undergo one or more of imaging, biopsy, surgery, or other diagnostic tests. In some embodiments, when resistance to the therapy is suspected, the subject can be administered (either as a monotherapy or in combination with the previous therapy) a compound capable of treating a BTK inhibitor resistance (e.g., the compound of Formula I, or a pharmaceutically acceptable salt, amorphous, or polymorph form thereof, a spray-dried dispersion thereof, or a pharmaceutical composition thereof, as provided herein). See, for example, Cancer Discov; 7(12); 1368-70 (2017); and Cancer Discov; 7(12); 1394-403 (2017).

Also provided herein are methods of treating a BTK-associated cancer in a subject that include (a) administering one or more (e.g., two or more, three or more, four or more, five or more, or ten or more) doses of a first BTK kinase inhibitor to a subject identified or diagnosed as having a BTK-associated cancer (e.g., any of the types of BTK-associated cancers described herein)(e.g., identified or diagnosed as having a BTK-associated cancer using any of the exemplary methods described herein or known in the art); (b) after step (a), determining a level of circulating tumor DNA in a biological sample (e.g., a biological sample comprising blood, serum, or plasma) obtained from the subject; (c) administering a therapeutically effective amount of a second BTK inhibitor or the compound of Formula I, or a pharmaceutically acceptable salt, amorphous, or polymorph form thereof, a spray-dried dispersion thereof, or a pharmaceutical composition thereof, as a monotherapy or in conjunction with another anticancer agent to a subject identified as having about the same or an elevated level of circulating tumor DNA as compared to a reference level of circulating tumor DNA (e.g., any of the reference levels of circulating tumor DNA described herein). In some examples of these methods, the reference level of circulating tumor DNA is a level of circulating tumor DNA in a biological sample obtained from the subject prior to step (a). Some embodiments of these methods further include determining the level of circulating tumor DNA in the biological sample obtained from the subject prior to step (a). In some examples of these methods, the reference level of circulating tumor DNA is a threshold level of circulating tumor DNA (e.g., an average level of circulating tumor DNA in a population of subjects having a similar BTK-associated cancer and having a similar stage of the BTK-associated cancer, but receiving a non-effective treatment or a placebo, or not yet receiving therapeutic treatment, or a level of circulating tumor DNA in a subject having a similar BTK-associated cancer and having a similar stage of the BTK-associated cancer, but receiving a non-effective treatment or a placebo, or not yet receiving therapeutic treatment). In some examples of these methods, the first BTK inhibitor is selected from the group of: ibrutinib, PRN1008, PRN473, ABBV-105, AC0058, acalabrutinib, zanubrutinib, spebrutinib, poseltinib, evobrutinib, tirabrutinib, CG'806, ARQ 531, BIIB068, vecabrutinib, AS871, CB1763, CB988, GDC-0853, RN486, GNE-504, GNE-309, BTK Max, dasatinib, CT-1530, CGI-1746, CGI-560, LFM A13, TP-0158, dtrmwxhs-12, CNX-774, and LOU064. In other examples of these methods, the first BTK inhibitor is a covalent inhibitor or a non-covalent inhibitor. In some embodiments, the covalent inhibitor is selected from the group consisting of: ibrutinib, PRN1008, PRN473, ABBV-105, AC0058, acalabrutinib, zanubrutinib, spebrutinib, poseltinib, evobrutinib, M7583, and tirabrutinib. In some embodiments, the first BTK inhibitor is selected from the group consisting of: CG'806, ARQ 531, BIIB068, vecabrutinib, AS871, CB1763, CB988, GDC-0853, RN486, and dasatinib, Also provided herein are methods of treating a BTK-associated cancer in a subject that include administering a therapeutically effective amount of the compound of Formula I, or a pharmaceutically acceptable salt, amorphous, or polymorph form thereof, a spray-dried dispersion thereof, or a pharmaceutical composition thereof, to a subject (i) identified or diagnosed as having a BTK-associated cancer (e.g., any of the types of BTK-associated cancers described herein) (e.g., identified or diagnosed as having a BTK-associated cancer using any of the exemplary methods described herein or known in the art), (ii) previously administered one or more (e.g., two or more, three or more, four or more, five or more, or ten or more) doses of a second BTK kinase inhibitor, and (ii) after the prior administration of the one or more doses of the second BTK kinase inhibitor, identified as having about the same or an elevated level of circulating tumor DNA as compared to a reference level of circulating tumor DNA (e.g., any of the reference levels of circulating tumor DNA described herein or known in the art). In some embodiments of these methods, the reference level of circulating tumor DNA is a level of circulating tumor DNA in a biological sample (e.g., a biological sample comprising blood, plasma, or serum) obtained from the subject prior to the administration of the one or more doses of the second BTK kinase inhibitor. Some embodiments of these methods further include determining the level of circulating tumor DNA in the biological sample obtained from the subject prior to administration of the one or more doses of the second BTK kinase inhibitor. In some examples of these methods, the reference level of circulating tumor DNA is a threshold level of circulating tumor DNA (e.g., an average level of circulating tumor DNA in a population of subjects having a similar BTK-associated cancer and having a similar stage of the BTK-associated cancer, but receiving a non-effective treatment or a placebo, or not yet receiving therapeutic treatment, or a level of circulating tumor DNA in a subject having a similar BTK-associated cancer and having a similar stage of the BTK-associated cancer, but receiving a non-effective treatment or a placebo, or not yet receiving therapeutic treatment). In some embodiments of these methods, the second BTK kinase inhibitor is selected from the group consisting of: ibrutinib, PRN1008, PRN473, ABBV-105, AC0058, acalabrutinib, zanubrutinib, spebrutinib, poseltinib, evobrutinib, tirabrutinib, CG'806, ARQ 531, BIIB068, vecabrutinib, AS871, CB1763, CB988, GDC-0853, RN486, GNE-504, GNE-309, BTK Max, dasatinib, CT-1530, CGI-1746, CGI-560, LFM A13, TP-0158, dtrmwxhs-12, CNX-774, and LOU064. In other embodiments of these methods, the second BTK inhibitor is a covalent inhibitor or a non-covalent inhibitor. In some embodiments, the covalent inhibitor is selected from the group consisting of: ibrutinib, PRN1008, PRN473, ABBV-105, AC0058, acalabrutinib, zanubrutinib, spebrutinib, poseltinib, evobrutinib, M7583, and tirabrutinib. In some embodiments, the second BTK inhibitor is selected from the group consisting of: CG'806, ARQ 531, BIIB068, vecabrutinib, AS871, CB1763, CB988, GDC-0853, RN486, and dasatinib, Also provided herein are methods of treating a BTK-associated cancer in a subject that include: (a) administering one or more doses of the compound of Formula I, or a pharmaceutically acceptable salt, amorphous, or polymorph form thereof, a spray-dried dispersion thereof, or a pharmaceutical composition thereof, as a monotherapy to a subject identified or diagnosed as having a BTK-associated cancer (e.g., any of the types of BTK-associated cancer described herein) (e.g., a subject identified or diagnosed as having a BTK-associated cancer using any of the methods described herein or known in the art); (b) after step (a), determining a level of circulating tumor DNA in a biological sample (e.g., a biological sample comprising blood, serum, or plasma) obtained from the subject; (c) administering a therapeutically effective amount of the compound of Formula I, or a pharmaceutically acceptable salt, amorphous, or polymorph form thereof, a spray-dried dispersion thereof, or a pharmaceutical composition thereof, and an additional therapeutic agent or treatment (e.g., any of the additional therapeutic agents or treatments of a BTK-associated cancer described herein or known in the art) to a subject identified as having about the same or an elevated level of circulating tumor DNA as compared to a reference level of circulating tumor DNA (e.g., any of the exemplary reference levels of circulating tumor DNA described herein or known in the art). In some embodiments of these methods, the additional therapeutic agent is a second BTK kinase inhibitor (e.g., a covalent BTK inhibitor or a non-covalent BTK inhibitor, or a BTK kinase inhibitor selected from the group of: ibrutinib, PRN1008, PRN473, ABBV-105, AC0058, acalabrutinib, zanubrutinib, spebrutinib, poseltinib, evobrutinib, tirabrutinib, CG'806, ARQ 531, BIIB068, vecabrutinib, AS871, CB1763, CB988, GDC-0853, RN486, GNE-504, GNE-309, BTK Max, dasatinib, CT-1530, CGI-1746, CGI-560, LFM A13, TP-0158, dtrmwxhs-12, CNX-774, and LOU064). In some examples of any of these methods, the additional therapeutic agent or treatment comprises one or more of: radiation therapy, a chemotherapeutic agent (e.g., any of the exemplary chemotherapeutic agents described herein or known in the art), a checkpoint inhibitor (e.g., any of the exemplary checkpoint inhibitors described herein or known in the art), surgery (e.g., at least partial resection of the tumor) and one or more other kinase or protein inhibitors (e.g., any of the exemplary kinase or protein inhibitors described herein or known in the art). In some examples of these methods, the reference level of circulating tumor DNA is a level of circulating tumor DNA in a biological sample (e.g., a biological sample comprising blood, serum, or plasma) obtained from the subject prior to step (a). In some examples of these methods, the reference level of circulating tumor DNA is a threshold level of circulating tumor DNA (e.g., an average level of circulating tumor DNA in a population of subjects having a similar BTK-associated cancer and having a similar stage of the BTK-associated cancer, but receiving a non-effective treatment or a placebo, or not yet receiving therapeutic treatment, or a level of circulating tumor DNA in a subject having a similar BTK-associated cancer and having a similar stage of the BTK-associated cancer, but receiving a non-effective treatment or a placebo, or not yet receiving therapeutic treatment).

Also provided herein are methods of treating a BTK-associated cancer in a subject that include: administering a therapeutically effective amount of the compound of Formula I, or a pharmaceutically acceptable salt, amorphous, or polymorph form thereof, a spray-dried dispersion thereof, or a pharmaceutical composition thereof, and an additional therapeutic agent or treatment to a subject (i) identified or diagnosed as having a BTK-associated cancer (e.g., any of the types of BTK-associated cancer described herein) (e.g., a subject identified or diagnosed as having a BTK-associated cancer using any of the methods described herein or known in the art), (ii) previously administered one or more doses of the compound of Formula I, or a pharmaceutically acceptable salt, amorphous, or polymorph form thereof, a spray-dried dispersion thereof, or a pharmaceutical composition thereof, as a monotherapy, and (ii) after administration of the one or more (e.g., two or more, three or more, four or more, five or more, or ten or more) doses of the compound of Formula I, or a pharmaceutically acceptable salt, amorphous, or polymorph form thereof, a spray-dried dispersion thereof, or a pharmaceutical composition thereof, as a monotherapy, identified as having about the same or an elevated level of circulating tumor DNA as compared to a reference level of circulating tumor DNA (e.g., any of the exemplary reference levels of circulating tumor DNA described herein). In some embodiments of these methods, the reference level of circulating tumor DNA is a level of circulating tumor DNA in a biological sample obtained from the subject prior to administration of the one or more (e.g., two or more, three or more, four or more, five or more, or ten or more) doses of the compound of Formula I, or a pharmaceutically acceptable salt, amorphous, or polymorph form thereof, a spray-dried dispersion thereof, or a pharmaceutical composition thereof, as a monotherapy. Some embodiments of these methods further include determining the level of circulating tumor DNA in the biological sample obtained from the subject prior to administration of the one or more doses of the compound of Formula I, or a pharmaceutically acceptable salt, amorphous, or polymorph form thereof, a spray-dried dispersion thereof, or a pharmaceutical composition thereof, as a monotherapy. In some examples of these methods, the reference level of circulating tumor DNA is a threshold level of circulating tumor DNA (e.g., an average level of circulating tumor DNA in a population of subjects having a similar BTK-associated cancer and having a similar stage of the BTK-associated cancer, but receiving a non-effective treatment or a placebo, or not yet receiving therapeutic treatment, or a level of circulating tumor DNA in a subject having a similar BTK-associated cancer and having a similar stage of the BTK-associated cancer, but receiving a non-effective treatment or a placebo, or not yet receiving therapeutic treatment). In some embodiments of this method, the additional therapeutic agent is a second BTK kinase inhibitor (e.g., a covalent BTK inhibitor or a non-covalent BTK inhibitor, or a second BTK kinase inhibitor selected from the group of ibrutinib, PRN1008, PRN473, ABBV-105, AC0058, acalabrutinib, zanubrutinib, spebrutinib, poseltinib, evobrutinib, tirabrutinib, CG'806, ARQ 531, BIIB068, vecabrutinib, AS871, CB1763, CB988, GDC-0853, RN486, GNE-504, GNE-309, BTK Max, dasatinib, CT-1530, CGI-1746, CGI-560, LFM A13, TP-0158, dtrmwxhs-12, CNX-774, and LOU064). In some embodiments of these methods, the additional therapeutic agent or treatment includes one or more of radiation therapy, a chemotherapeutic agent (e.g., any of the exemplary chemotherapeutic agents described herein or known in the art), a checkpoint inhibitor (e.g., any of the exemplary checkpoint inhibitors described herein or known in the art), surgery (e.g., at least partial resection of the tumor), and one or more other kinase or protein inhibitors (e.g., any of the kinase or protein inhibitors described herein or known in the art).

Also provided herein are methods of selecting a treatment for a subject that include: selecting a therapeutically effective amount of the compound of Formula I, or a pharmaceutically acceptable salt, amorphous, or polymorph form thereof, a spray-dried dispersion thereof, or a pharmaceutical composition thereof, for a subject (i) identified or diagnosed as having a BTK-associated cancer (e.g., any of the BTK-associated cancers described herein) (e.g., a subject identified or diagnosed as having a BTK-associated cancer using any of the methods described herein or known in the art), (ii) previously administered one or more (e.g., two or more, three or more, four or more, five or more, or ten or more) doses of a second BTK kinase inhibitor (e.g., any of the BTK kinase inhibitors described herein or known in the art), and (ii) after administration of the one or more doses of the second BTK kinase inhibitor, identified as having about the same or an elevated level of circulating tumor DNA as compared to a reference level of circulating tumor DNA. In some embodiments of any of these methods, the reference level of circulating tumor DNA is a level of circulating tumor DNA in a biological sample (e.g., a biological sample comprising blood, serum, or plasma) obtained from the subject prior to administration of the one or more doses of the second BTK kinase inhibitor. Some embodiments of these methods further include determining the level of circulating tumor DNA in the biological sample obtained from the subject prior to administration of the one or more doses of the second BTK kinase inhibitor. In some examples of these methods, the reference level of circulating tumor DNA is a threshold level of circulating tumor DNA (e.g., an average level of circulating tumor DNA in a population of subjects having a similar BTK-associated cancer and having a similar stage of the BTK-associated cancer, but receiving a non-effective treatment or a placebo, or not yet receiving therapeutic treatment, or a level of circulating tumor DNA in a subject having a similar BTK-associated cancer and having a similar stage of the BTK-associated cancer, but receiving a non-effective treatment or a placebo, or not yet receiving therapeutic treatment). In some embodiments of any these methods, the second BTK kinase inhibitor is selected from the group of: ibrutinib, PRN1008, PRN473, ABBV-105, AC0058, acalabrutinib, zanubrutinib, spebrutinib, poseltinib, evobrutinib, tirabrutinib, CG'806, ARQ 531, BIIB068, vecabrutinib, AS871, CB1763, CB988, GDC-0853, RN486, GNE-504, GNE-309, BTK Max, dasatinib, CT-1530, CGI-1746, CGI-560, LFM A13, TP-0158, dtrmwxhs-12, CNX-774, and LOU064. In some embodiments of these methods, the second BTK inhibitor is a covalent inhibitor or a non-covalent inhibitor. In some embodiments, the covalent inhibitor is selected from the group consisting of: ibrutinib, PRN1008, PRN473, ABBV-105, AC0058, acalabrutinib, zanubrutinib, spebrutinib, poseltinib, evobrutinib, M7583, and tirabrutinib. In some embodiments, the second BTK inhibitor is selected from the group consisting of: CG'806, ARQ 531, BIIB068, vecabrutinib, AS871, CB1763, CB988, GDC-0853, RN486, and dasatinib, Also provided herein are methods of selecting a treatment for a subject that include selecting a therapeutically effective amount of the compound of Formula I, or a pharmaceutically acceptable salt, amorphous, or polymorph form thereof, a spray-dried dispersion thereof, or a pharmaceutical composition thereof, and an additional therapeutic agent or treatment for a subject (i) identified or diagnosed as having a BTK-associated cancer (e.g., any of the BTK-associated cancers described herein or known in the art) (e.g., a subject diagnosed or identified as having a BTK-associated cancer using any of the methods described herein or known in the art), (ii) previously administered one or more doses (e.g., two or more, three or more, four or more, five or more, or ten or more) of the compound of Formula I, or a pharmaceutically acceptable salt, amorphous, or polymorph form thereof, a spray-dried dispersion thereof, or a pharmaceutical composition thereof, as a monotherapy, and (ii) after administration of the one or more doses of the compound of Formula I, or a pharmaceutically acceptable salt, amorphous, or polymorph form thereof, a spray-dried dispersion thereof, or a pharmaceutical composition thereof, identified as having about the same or an elevated level of circulating tumor DNA as compared to a reference level of circulating tumor DNA. In some embodiments of these methods, the reference level of circulating tumor DNA is a level of circulating tumor DNA in a biological sample (e.g., a biological sample comprising blood, serum, or plasma) obtained from the subject prior to administration of the one or more doses of the compound of Formula I, or a pharmaceutically acceptable salt, amorphous, or polymorph form thereof, a spray-dried dispersion thereof, or a pharmaceutical composition thereof, as a monotherapy. Some embodiments further include determining the level of circulating tumor DNA in the biological sample obtained from the subject prior to administration of the one or more doses of the compound of Formula I, or a pharmaceutically acceptable salt, amorphous, or polymorph form thereof, a spray-dried dispersion thereof, or a pharmaceutical composition thereof, as a monotherapy. In some examples of these methods, the reference level of circulating tumor DNA is a threshold level of circulating tumor DNA (e.g., an average level of circulating tumor DNA in a population of subjects having a similar BTK-associated cancer and having a similar stage of the BTK-associated cancer, but receiving a non-effective treatment or a placebo, or not yet receiving therapeutic treatment, or a level of circulating tumor DNA in a subject having a similar BTK-associated cancer and having a similar stage of the BTK-associated cancer, but receiving a non-effective treatment or a placebo, or not yet receiving therapeutic treatment). In some embodiments of any of these methods, the additional therapeutic agent is a second BTK kinase inhibitor (e.g., a second BTK kinase inhibitor selected from the group of: ibrutinib, PRN1008, PRN473, ABBV-105, AC0058, acalabrutinib, zanubrutinib, spebrutinib, poseltinib, evobrutinib, tirabrutinib, CG'806, ARQ 531, BIIB068, vecabrutinib, AS871, CB1763, CB988, GDC-0853, RN486, GNE-504, GNE-309, BTK Max, dasatinib, CT-1530, CGI-1746, CGI-560, LFM A13, TP-0158, dtrmwxhs-12, CNX-774, and LOU064). In some embodiments of these methods, the second BTK inhibitor is a covalent inhibitor or a non-covalent inhibitor. In some embodiments, the covalent inhibitor is selected from the group consisting of: ibrutinib, PRN1008, PRN473, ABBV-105, AC0058, acalabrutinib, zanubrutinib, spebrutinib, poseltinib, evobrutinib, M7583, and tirabrutinib. In some embodiments, the second BTK inhibitor is selected from the group consisting of: CG'806, ARQ 531, BIIB068, vecabrutinib, AS871, CB1763, CB988, GDC-0853, RN486, and dasatinib, In some embodiments of any of the methods described herein, the additional therapeutic agent or treatment includes one or more of radiation therapy, a chemotherapeutic agent (e.g., any of the examples of a chemotherapeutic agent described herein or known in the art), a checkpoint inhibitor (e.g., any of the checkpoint inhibitors described herein or known in the art), surgery (e.g., at least partial resection of the tumor), and one or more other kinase or protein inhibitors (e.g., any of the other kinase or other protein inhibitors described herein or known in the art).

Also provided herein are methods of determining the efficacy of a treatment in a subject that include: (a) determining a first level of circulating tumor DNA in a biological sample (e.g., a biological sample including blood, serum, or plasma) obtained from a subject identified or diagnosed as having a BTK-associated cancer at a first time point; (b) administering a treatment including one or more doses of the compound of Formula I, or a pharmaceutically acceptable salt, amorphous, or polymorph form thereof, a spray-dried dispersion thereof, or a pharmaceutical composition thereof, to the subject, after the first time point and before a second time point; (c) determining a second level of circulating tumor DNA in a biological sample (e.g., a biological sample comprising blood, serum, or plasma) obtained from the subject at the second time point; and (d) identifying that the treatment is effective in a subject determined to have a decreased second level of circulating tumor DNA as compared to the first level of circulating tumor DNA; or identifying the treatment is not effective in a subject determined to have about the same or an elevated second level of circulating tumor DNA as compared to the first level of circulating tumor DNA. In some embodiments of these methods, the first time point and the second time point are about 1 week to about 1 year apart (e.g., about 1 week to about 10 months, about 1 week to about 8 months, about 1 week to about 6 months, about 1 week to about 4 months, about 1 week to about 3 months, about 1 week to about 2 months, about 1 week to about 1 month, or about 1 week to about 2 weeks).

Also provided herein are methods of determining whether a subject has developed resistance to a treatment that include: (a) determining a first level of circulating tumor DNA in a biological sample (e.g., a biological sample comprising blood, serum, or plasma) obtained from a subject identified or diagnosed as having a BTK-associated cancer at a first time point; (b) administering a treatment including one or more (e.g., two or more, three or more, four or more, five or more, or ten or more) doses of the compound of Formula I, or a pharmaceutically acceptable salt, amorphous, or polymorph form thereof, a spray-dried dispersion thereof, or a pharmaceutical composition thereof, to the subject, after the first time point and before a second time point; (c) determining a second level of circulating tumor DNA in a biological sample obtained from the subject at the second time point; and (d) determining that a subject having a decreased second level of circulating tumor DNA as compared to the first level of circulating tumor DNA has not developed resistance to the treatment; or determining that a subject having about the same or an elevated second level of circulating tumor DNA as compared to the first level of circulating tumor DNA has developed resistance to the treatment. In some embodiments of these methods, the first time point and the second time point are about 1 week to about 1 year apart (e.g., about 1 week to about 10 months, about 1 week to about 8 months, about 1 week to about 6 months, about 1 week to about 4 months, about 1 week to about 3 months, about 1 week to about 2 months, about 1 week to about 1 month, or about 1 week to about 2 weeks).

Exemplary methods for detecting circulating tumor DNA are described in Moati et al., *Clin. Res. Hepatol. Gastroenterol.* Apr. 4, 2018; Oussalah et al., *EBioMedicine* Mar. 28, 2018; Moon et al., *Adv. Drug Deliv. Rev.* Apr. 4, 2018; Solassaol et al., *Clin. Chem. Lab. Med.* Apr. 7, 2018; Arriola et al., *Clin. Transl. Oncol.* Apr. 5, 2018; Song et al., *J. Circ. Biomark.* Mar. 25, 2018; Aslibekyan et al., *JAMA Cardiol.* Apr. 4, 2018; Isbell et al., *J. Thorac. Cardiovasc. Surg.* Mar. 13, 2018; Boeckx et al., *Clin. Colorectal Cancer* Feb. 22, 2018; Anunobi et al., *J. Surg. Res.* Mar. 28, 2018; Tan et al., *Medicine* 97(13):e0197, 2018; Reithdorf et al., *Transl. Androl. Urol.* 6(6):1090-1110, 2017; Volckmar et al., *Genes Chromosomes Cancer* 57(3):123-139, 2018; and Lu et al., *Chronic Dis. Transl. Med.* 2(4):223-230, 2016. Additional methods for detecting circulating tumor DNA are known in the art.

Also, provided herein are methods for treating a BTK-associated cancer in a subject in need of such treatment, the method comprising (a) detecting a dysregulation of a BTK gene, a BTK kinase, or the expression or activity or level of any of the same in a sample from the subject; and (b) administering to the subject a therapeutically effective amount of the compound of Formula I, or a pharmaceutically acceptable salt, amorphous, or polymorph form thereof, a spray-dried dispersion thereof, or a pharmaceutical composition thereof. In some embodiments, the methods further comprise (after (b)) (c) determining whether a cancer cell in a sample obtained from the subject has at least one BTK inhibitor resistance mutation; and (d) administering additional doses of the compound of Formula I, or a pharmaceutically acceptable salt, amorphous, or polymorph form thereof, a spray-dried dispersion thereof, or a pharmaceutical composition thereof, of step (b) to the subject as a monotherapy or in conjunction with another anticancer agent (e.g., a second BTK inhibitor, a second compound of Formula I, or a pharmaceutically acceptable salt, amorphous, or polymorph form thereof, a spray-dried dispersion thereof, or a pharmaceutical composition thereof, or immunotherapy) or anticancer therapy (e.g., surgery or radiation) if the subject has a cancer cell that has at least one BTK inhibitor resistance mutation. In some embodiments, provided herein are methods for treating a BTK-associated cancer in a subject in need of such treatment, the method comprising (a) detecting a dysregulation of a BTK gene, a BTK kinase, or the expression or activity or level of any of the same in a sample from the subject; and (b) administering to the subject a therapeutically effective amount of the compound of Formula I, or a pharmaceutically acceptable salt, amorphous, or polymorph form thereof, a spray-dried dispersion thereof, or a pharmaceutical composition thereof. In some embodiments, the methods further comprise (after (b)) (c) determining whether a cancer cell in a sample obtained from the subject has at least one BTK inhibitor resistance mutation; and (d) administering additional doses of the compound of Formula I, or a pharmaceutically acceptable salt, amorphous, or polymorph form thereof, a spray-dried dispersion thereof, or a pharmaceutical composition thereof, of step (b) to the subject as a monotherapy or in conjunction with another anticancer agent (e.g., a second BTK inhibitor, a second compound of Formula I, or a pharmaceutically acceptable salt, amorphous, or polymorph form thereof, a spray-dried dispersion thereof, or a pharmaceutical composition thereof, or immunotherapy) or anticancer therapy (e.g., surgery or radiation) if the subject has a cancer cell that has at least one BTK inhibitor resistance mutation. In some embodiments, provided herein are methods for treating a BTK-associated cancer in a subject in need of such treatment, the method comprising (a) detecting one or more BTK mutations selected from the group consisting of: one or more BTK kinase protein point mutations/insertions of Table 1, BTK fusions of Table 1a, p65BTK, BTK-C, or one or more BCR signaling pathway genetic mutations of Table 4 in a sample from the subject; and (b) administering to the subject a therapeutically effective amount of the compound of Formula I, or a pharmaceutically acceptable salt, amorphous, or polymorph form thereof, a spray-dried dispersion thereof, or a pharmaceutical composition thereof, selected from the group consisting of the compound of Formula I, or a pharmaceutically acceptable salt, amorphous, or polymorph form thereof, a spray-dried dispersion thereof, or a pharmaceutical composition thereof. In some embodiments, the methods further comprise (after (b)) (c) determining whether a cancer cell in a sample obtained from the subject has at least one BTK inhibitor resistance mutation of Table 2; and (d) administering additional doses of the compound of Formula I, or a pharmaceutically acceptable salt, amorphous, or polymorph form thereof, a spray-dried dispersion thereof, or a pharmaceutical composition thereof, of step (b) to the subject as a monotherapy or in conjunction with another anticancer agent (e.g., a second BTK inhibitor, a second compound of Formula I, or a pharmaceutically acceptable salt, amorphous, or polymorph form thereof, a spray-dried dispersion thereof, or a pharmaceutical composition thereof, or immunotherapy) or anticancer therapy (e.g., surgery or radiation) if the subject has a cancer cell that has at least one BTK inhibitor resistance mutation. In some embodiments, a second BTK inhibitor selected from the group consisting of: ibrutinib, PRN1008, PRN473, ABBV-105, AC0058, acalabrutinib, zanubrutinib, spebrutinib, poseltinib, evobrutinib, tirabrutinib, CG'806, ARQ 531, BIIB068, vecabrutinib, AS871, CB1763, CB988, GDC- 0853, RN486, GNE-504, GNE-309, BTK Max, dasatinib, CT-1530, CGI-1746, CGI-560, LFM A13, TP-0158, dtrmwxhs-12, CNX-774, and LOU064 is administered in step (d). In some embodiments, provided herein are methods for treating a BTK-associated cancer in a subject in need of such treatment, the method comprising (a) detecting MYD88$^{L265P}$ in a sample from the subject; and (b) administering to the subject a therapeutically effective amount of a compound of Formula I-IV, or a pharmaceutically acceptable salt, amorphous, or polymorph form thereof. In some embodiments, the methods further comprise (after (b)) (c) determining whether a cancer cell in a sample obtained from the subject has the BTK inhibitor resistance mutation C481S, C481F, C481T, C481G, C481R, T474I, T474M, or T474S; and (d) administering additional doses of the compound of Formula I, or a pharmaceutically acceptable salt, amorphous, or polymorph form thereof, a spray-dried dispersion thereof, or a pharmaceutical composition thereof, of step (b) to the subject as a monotherapy or in conjunction with another anticancer agent (e.g., a second BTK inhibitor, a second compound of Formula I, or a pharmaceutically acceptable salt, amorphous, or polymorph form thereof, a spray-dried dispersion thereof, or a pharmaceutical composition thereof, or immunotherapy) or anticancer therapy (e.g., surgery or radiation) if the subject has a cancer cell that has at least one BTK inhibitor resistance mutation. In some embodiments, a second BTK inhibitor selected from the group consisting of: ibrutinib, PRN1008, PRN473, ABBV-105, AC0058, acalabrutinib, zanubrutinib, spebrutinib, poseltinib, evobrutinib, tirabrutinib, CG'806, ARQ 531, BIIB068, vecabrutinib, AS871, CB1763, CB988, GDC-0853, RN486, GNE-504, GNE-309, BTK Max, dasatinib, CT-1530, CGI-1746, CGI-560, LFM A13, TP-0158, dtrmwxhs-12, CNX-774, and LOU064 is administered in step (d).

Also, provided herein are methods for treating a BTK-associated cancer in a subject in need of such treatment, the method comprising (a) detecting a dysregulation of a BTK gene, a BTK kinase, or the expression or activity or level of any of the same in a sample from the subject; and (b) administering to the subject a therapeutically effective amount of the compound of Formula I, or a pharmaceutically acceptable salt, amorphous, or polymorph form thereof, a spray-dried dispersion thereof, or a pharmaceutical composition thereof. In some embodiments, the methods further comprise (after (b)) (c) detecting at least one BTK inhibitor resistance mutation in a cancer cell in a sample obtained from the subject; and (d) administering additional doses of the compound of Formula I, or a pharmaceutically acceptable salt, amorphous, or polymorph form thereof, a spray-dried dispersion thereof, or a pharmaceutical composition thereof, of step (b) to the subject as a monotherapy or in conjunction with another anticancer agent (e.g., a second BTK inhibitor, a second compound of Formula I, or a pharmaceutically acceptable salt, amorphous, or polymorph form thereof, a spray-dried dispersion thereof, or a pharmaceutical composition thereof, or immunotherapy) or anticancer therapy (e.g., surgery or radiation). In some embodiments, provided herein are methods for treating a BTK-associated cancer in a subject in need of such treatment, the method comprising (a) detecting a dysregulation of a BTK gene, a BTK kinase, or the expression or activity or level of any of the same in a sample from the subject; and (b) administering to the subject a therapeutically effective amount of the compound of Formula I, or a pharmaceutically acceptable salt, amorphous, or polymorph form thereof, a spray-dried dispersion thereof, or a pharmaceutical composition thereof. In some embodiments, the methods further comprise (after (b)) (c) detecting at least one BTK inhibitor resistance mutation in a cancer cell in a sample obtained from the subject; and (d) administering additional doses of the compound of Formula I, or a pharmaceutically acceptable salt, amorphous, or polymorph form thereof, a spray-dried dispersion thereof, or a pharmaceutical composition thereof, of step (b) to the subject as a monotherapy or in conjunction with another anticancer agent (e.g., a second BTK inhibitor, a second compound of Formula I, or a pharmaceutically acceptable salt, amorphous, or polymorph form thereof, a spray-dried dispersion thereof, or a pharmaceutical composition thereof, or immunotherapy) or anticancer therapy (e.g., surgery or radiation). In some embodiments, provided herein are methods for treating a BTK-associated cancer in a subject in need of such treatment, the method comprising (a) detecting one or more BTK mutations selected from the group consisting of: one or more BTK kinase protein point mutations/insertions of Table 1, BTK fusions of Table 1a, p65BTK, BTK-C, or one or more BCR signaling pathway genetic mutations of Table 4 in a sample from the subject; and (b) administering to the subject a therapeutically effective amount of the compound of Formula I, or a pharmaceutically acceptable salt, amorphous, or polymorph form thereof, a spray-dried dispersion thereof, or a pharmaceutical composition thereof, selected from the group consisting of the compound of Formula I, or a pharmaceutically acceptable salt, amorphous, or polymorph form thereof, a spray-dried dispersion thereof, or a pharmaceutical composition thereof. In some embodiments, the methods further comprise (after (b)) (c) detecting at least one BTK inhibitor resistance mutation of Table 2 in a cancer cell in a sample obtained from the subject; and (d) administering additional doses of the compound of Formula I, or a pharmaceutically acceptable salt, amorphous, or polymorph form thereof, a spray-dried dispersion thereof, or a pharmaceutical composition thereof, of step (b) to the subject as a monotherapy or in conjunction with another anticancer agent (e.g., a second BTK inhibitor, a second compound of Formula I, or a pharmaceutically acceptable salt, amorphous, or polymorph form thereof, a spray-dried dispersion thereof, or a pharmaceutical composition thereof, or immunotherapy) or anticancer therapy (e.g., surgery or radiation). In some embodiments, a second BTK inhibitor selected from the group consisting of: ibrutinib, PRN1008, PRN473, ABBV-105, AC0058, acalabrutinib, zanubrutinib, spebrutinib, poseltinib, evobrutinib, tirabrutinib, CG'806, ARQ 531, BIIB068, vecabrutinib, AS871, CB1763, CB988, GDC-0853, RN486, GNE-504, GNE-309, BTK Max, dasatinib, CT-1530, CGI-1746, CGI-560, LFM A13, TP-0158, dtrmwxhs-12, CNX-774, LOU064, and combinations thereof is administered in step (d). In some embodiments, the methods further comprise (after (b)) (c) detecting the BTK inhibitor resistance mutation C481S, C481F, C481T, C481G, C481R, T474I, T474M, or T474S in a cancer cell in a sample obtained from the subject; and (d) administering additional doses of the compound of Formula I, or a pharmaceutically acceptable salt, amorphous, or polymorph form thereof, a spray-dried dispersion thereof, or a pharmaceutical composition thereof, of step (b) to the subject as a monotherapy or in conjunction with another anticancer agent (e.g., a second BTK inhibitor, a second compound of Formula I, or a pharmaceutically acceptable salt, amorphous, or polymorph form thereof, a spray-dried dispersion thereof, or a pharmaceutical composition thereof, or immunotherapy) or anticancer therapy (e.g., surgery or radiation). In some embodiments, a second BTK inhibitor selected from the group consisting of ibrutinib, PRN1008, PRN473, ABBV-105, AC0058, acalabrutinib, zanubrutinib, spebrutinib, poseltinib, evobrutinib, tirabrutinib, CG'806, ARQ 531, BIIB068, vecabrutinib, AS871, CB1763, CB988, GDC-0853, RN486, GNE-504, GNE-309, BTK Max, dasatinib, CT-1530, CGI-1746, CGI-560, LFM A13, TP-0158, dtrmwxhs-12, CNX-774, and LOU064 is administered in step (d).

Also provided are methods of selecting a treatment for a subject having a cancer that include: identifying a subject having a cancer cell that has one or more BTK inhibitor resistance mutations; and selecting a treatment that includes administration of the compound of Formula I, or a pharmaceutically acceptable salt, amorphous, or polymorph form thereof, a spray-dried dispersion thereof, or a pharmaceutical composition thereof. In some embodiments, the one or more BTK inhibitor resistance mutations confer increased resistance to a cancer cell or tumor to treatment with a first BTK inhibitor. In some embodiments, the compound of Formula I, or a pharmaceutically acceptable salt, amorphous, or polymorph form thereof, a spray-dried dispersion thereof, or a pharmaceutical composition thereof, is administered in combination with the first BTK inhibitor. Also provided are methods of selecting a treatment for a subject having a cancer that include: selecting a treatment that includes administration of the compound of Formula I, or a pharmaceutically acceptable salt, amorphous, or polymorph form thereof, a spray-dried dispersion thereof, or a pharmaceutical composition thereof, for a subject identified as having a cancer cell that has one or more BTK inhibitor resistance mutations. Also provided are methods of selecting a subject having a cancer for a treatment that does not include a first BTK inhibitor as a monotherapy that include: identifying a subject having a cancer cell that has one or more BTK inhibitor resistance mutations; and selecting the identified subject for a treatment that includes the compound of Formula I, or a pharmaceutically acceptable salt, amorphous, or polymorph form thereof, a spray-dried dispersion thereof, or a pharmaceutical composition thereof. Also provided are methods of selecting a subject having a cancer for a treatment that does not include a first BTK inhibitor as a monotherapy that include: selecting a subject identified as having a cancer cell that has one or more BTK inhibitor resistance mutations for a treatment that includes administration of the compound of Formula I, or a pharmaceutically acceptable salt, amorphous, or polymorph form thereof, a spray-dried dispersion thereof, or a pharmaceutical composition thereof. In some embodiments, the one or more BTK inhibitor resistance mutations include one or more BTK inhibitor resistance mutations listed in Table 2. In some embodiments, the one or more BTK inhibitor resistance mutations can include a substitution at amino acid position 481, e.g., C481S, C481F, C481T, C481G, and C481R, or a substitution amino acid position 474, e.g., T474I, T474M, and T474S. As another example, the one or more BTK inhibitor resistance mutations can include a substitution at amino acid position 244, 257, 334, 495, 664, 665, 707, 708, 742, 845, 848, 993, 1140, or 1141 of PLCγ2. In some embodiments, the compound of Formula I, or a pharmaceutically acceptable salt, amorphous, or polymorph form thereof, a spray-dried dispersion thereof, or a pharmaceutical composition thereof, is administered in combination with an additional therapeutic agent that inhibits a protein upstream of BTK in the BCR signaling pathway. In some embodiments, the compound of Formula I, or a pharmaceutically acceptable salt, amorphous, or polymorph form thereof, a spray-dried dispersion thereof, or a pharmaceutical composition thereof, is administered in combination with an additional therapeutic agent that inhibits a protein downstream of BTK in the BCR signaling pathway. In some embodiments, the compound of Formula I, or a pharmaceutically acceptable salt, amorphous, or polymorph form thereof, a spray-dried dispersion thereof, or a pharmaceutical composition thereof, is administered in combination with an additional therapeutic agent that inhibits a protein downstream of BTK in the BCR signaling pathway such as a PLCγ2 inhibitor wherein the one or more resistance mutations include a substitution in PLCγ2 (e.g., at amino acid position 244, 257, 334, 495, 664, 665, 707, 708, 742, 845, 848, 993, 1140, or 1141).

Also provided are methods of determining the likelihood that a subject having a cancer (e.g., a BTK-associated cancer) will have a positive response to treatment with a first BTK inhibitor as a monotherapy that include: determining whether a cancer cell in a sample obtained from the subject has one or more BTK inhibitor resistance mutations; and determining that a subject having a cancer cell that has one or more BTK inhibitor resistance mutations has a decreased likelihood of having a positive response (i.e. an increased likelihood of having a negative response) to treatment with a first BTK inhibitor as a monotherapy. Also provided are methods of determining the likelihood that a subject having a cancer (e.g., a BTK-associated cancer) will have a positive response to treatment with a first BTK inhibitor as a monotherapy that include: determining whether a cancer cell in a sample obtained from the subject has one or more BTK inhibitor resistance mutations; and determining that a subject not having a cancer cell that has one or more BTK inhibitor resistance mutations has an increased likelihood of having a positive response to treatment with a first BTK inhibitor as a monotherapy as compared to a subject having a cancer cell that has one or more BTK inhibitor resistance mutations. Also provided are methods of predicting the efficacy of treatment with a first BTK inhibitor as a monotherapy in a subject having cancer that include: determining whether a cancer cell in a sample obtained from the subject has one or more BTK inhibitor resistance mutations; and determining that treatment with a first BTK inhibitor as a monotherapy is less likely to be effective in a subject having a cancer cell in a sample obtained from the subject that has one or more BTK inhibitor resistance mutations. Also provided are methods of predicting the efficacy of treatment with a first BTK inhibitor as a monotherapy in a subject having cancer that include: determining that treatment with a first BTK inhibitor as a monotherapy is less likely to be effective in a subject having a cancer cell in a sample obtained from the subject that has one or more BTK inhibitor resistance mutations. In some embodiments, the one or more BTK inhibitor resistance mutations confer increased resistance to a cancer cell or tumor to treatment with the first BTK inhibitor. In some embodiments, the one or more BTK inhibitor resistance mutations include one or more BTK inhibitor resistance mutations listed in Table 2. For example, the one or more BTK inhibitor resistance mutations can include a substitution at amino acid position 804, e.g., V804M, V804L, or V804E, or a substitution at amino acid position 810, e.g., G810S, G810R, G810C, G810A, G810V, and G810D. As another example, the one or more BTK inhibitor resistance mutations can include a substitution at amino acid position 244, 257, 334, 495, 664, 665, 707, 708, 742, 845, 848, 993, 1140, or 1141 of PLCγ2.

Also provided are methods of treating a subject having a cancer that include: (a) administering one or more doses of a first BTK inhibitor to the subject for a period of time; (b)

after (a), determining whether a cancer cell in a sample obtained from the subject has at least one BTK inhibitor resistance mutation; and (c) administering the compound of Formula I, or a pharmaceutically acceptable salt, amorphous, or polymorph form thereof, a spray-dried dispersion thereof, or a pharmaceutical composition thereof, as a monotherapy or in conjunction with another anticancer agent to the subject if the subject has a cancer cell that has at least one BTK inhibitor resistance mutation; or (d) administering additional doses of the first BTK inhibitor of step (a) to the subject if the subject has a cancer cell that does not have a BTK inhibitor resistance mutation. In some embodiments, where the subject is administered additional doses of the first BTK inhibitor of step (a), the subject can also be administered another anticancer agent (e.g., a second BTK inhibitor or the compound of Formula I, or a pharmaceutically acceptable salt, amorphous, or polymorph form thereof, a spray-dried dispersion thereof, or a pharmaceutical composition thereof, or immunotherapy). In some embodiments, the additional anticancer agent is any anticancer agent known in the art. For example, the additional anticancer agent is another BTK inhibitor (e.g., a second BTK inhibitor). In some embodiments, the additional anticancer agent is an immunotherapy. In some embodiments of step (c), another BTK inhibitor can be the first BTK inhibitor administered in step (a). In some embodiments, the one or more BTK inhibitor resistance mutations confer increased resistance to a cancer cell or tumor to treatment with the first BTK inhibitor. In some embodiments, the one or more BTK inhibitor resistance mutations include one or more BTK inhibitor resistance mutations listed in Table 2. For example, the one or more BTK inhibitor resistance mutations can include a substitution at amino acid position 804, e.g., V804M, V804L, or V804E, or a substitution at amino acid position 810, e.g., G810S, G810R, G810C, G810A, G810V, and G810D. As another example, the one or more BTK inhibitor resistance mutations can include a substitution at amino acid position 244, 257, 334, 495, 664, 665, 707, 708, 742, 845, 848, 993, 1140, or 1141 of PLCγ2. In some embodiments, the additional anticancer agent inhibits a protein upstream of BTK in the BCR signaling pathway. In some embodiments, the additional anticancer agent inhibits a protein downstream of BTK in the BCR signaling pathway. In some embodiments, the additional anticancer agent is a PLCγ2 inhibitor wherein the one or more resistance mutations includes a substitution in PLCγ2 (e.g., at amino acid position 244, 257, 334, 495, 664, 665, 707, 708, 742, 845, 848, 993, 1140, or 1141).

Also provided are methods of treating a subject having a cancer that include: (a) administering one or more doses of a first BTK inhibitor to the subject for a period of time; (b) after (a), determining whether a cancer cell in a sample obtained from the subject has at least one BTK inhibitor resistance mutation; and (c) administering a second BTK inhibitor as a monotherapy or in conjunction with another anticancer agent to the subject if the subject has a cancer cell that has at least one BTK inhibitor resistance mutation; or (d) administering additional doses of the first BTK inhibitor step (a) to the subject if the subject has a cancer cell that does not have a BTK inhibitor resistance mutation. In some embodiments, where the subject is administered additional doses of the first BTK inhibitor of step (a), the subject can also be administered another anticancer agent. In some embodiments, the one or more BTK inhibitor resistance mutations confer increased resistance to a cancer cell or tumor to treatment with the first BTK inhibitor. In some embodiments, the one or more BTK inhibitor resistance mutations include one or more BTK inhibitor resistance mutations listed in Table 2. For example, the one or more BTK inhibitor resistance mutations can include a substitution at amino acid position 804, e.g., V804M, V804L, or V804E, or a substitution at amino acid position 810, e.g., G810S, G810R, G810C, G810A, G810V, and G810D. As another example, the one or more BTK inhibitor resistance mutations can include a substitution at amino acid position 244, 257, 334, 495, 664, 665, 707, 708, 742, 845, 848, 993, 1140, or 1141 of PLCγ2. In some embodiments, the additional anticancer agent is any anticancer agent known in the art. For example, the additional anticancer agent is another BTK inhibitor (e.g., the compound of Formula I, or a pharmaceutically acceptable salt, amorphous, or polymorph form thereof, a spray-dried dispersion thereof, or a pharmaceutical composition thereof). In some embodiments, the additional anticancer agent is an immunotherapy. In some embodiments, the additional anticancer agent inhibits a protein upstream of BTK in the BCR signaling pathway. In some embodiments, the additional anticancer agent inhibits a protein downstream of BTK in the BCR signaling pathway. In some embodiments, the additional anticancer agent is a PLCγ2 inhibitor wherein the one or more resistance mutations includes a substitution in PLCγ2 (e.g., at amino acid position 244, 257, 334, 495, 664, 665, 707, 708, 742, 845, 848, 993, 1140, or 1141).

Also provided are methods of treating a subject having a cancer (e.g., a BTK-associated cancer) that include: (a) determining whether a cancer cell in a sample obtained from a subject having a cancer and previously administered one or more doses of a first BTK inhibitor, has one or more BTK inhibitor resistance mutations; and (b) administering the compound of Formula I, or a pharmaceutically acceptable salt, amorphous, or polymorph form thereof, a spray-dried dispersion thereof, or a pharmaceutical composition thereof, as a monotherapy or in conjunction with another anticancer agent to the subject if the subject has a cancer cell that has at least one BTK inhibitor resistance mutation; or (c) administering additional doses of the first BTK inhibitor previously administered to the subject if the subject has cancer cell that does not have a BTK inhibitor resistance mutation. In some embodiments, where the subject is administered additional doses of the first BTK inhibitor previously administered to the subject, the subject can also be administered another anticancer agent (e.g., the compound of Formula I, or a pharmaceutically acceptable salt, amorphous, or polymorph form thereof, a spray-dried dispersion thereof, or a pharmaceutical composition thereof, or immunotherapy). In some embodiments, the one or more BTK inhibitor resistance mutations confer increased resistance to a cancer cell or tumor to treatment with the first BTK inhibitor. In some embodiments, the one or more BTK inhibitor resistance mutations include one or more BTK inhibitor resistance mutations listed in Table 2. For example, the one or more BTK inhibitor resistance mutations can include a substitution at amino acid position 804, e.g., V804M, V804L, or V804E, or a substitution at amino acid position 810, e.g., G810S, G810R, G810C, G810A, G810V, and G810D. As another example, the one or more BTK inhibitor resistance mutations can include a substitution at amino acid position 244, 257, 334, 495, 664, 665, 707, 708, 742, 845, 848, 993, 1140, or 1141 of PLCγ2. In some embodiments, the additional anticancer agent is any anticancer agent known in the art. For example, the additional anticancer agent is another BTK inhibitor (e.g., a second BTK inhibitor). In some embodiments, the additional anticancer agent is an immunotherapy. In some embodiments of step (b), another anticancer agent can be the first BTK inhibitor administered in step (a). In some embodiments, the additional anticancer agent inhibits a protein upstream of BTK in the BCR signaling pathway. In some embodiments, the additional anticancer agent inhibits a protein downstream of BTK in the BCR signaling pathway. In some embodiments, the additional anticancer agent is a PLCγ2 inhibitor wherein the one or more resistance mutations includes a substitution in PLCγ2 (e.g., at amino acid position 244, 257, 334, 495, 664, 665, 707, 708, 742, 845, 848, 993, 1140, or 1141).

Also provided are methods of treating a subject having a cancer that include: (a) determining whether a cancer cell in a sample obtained from a subject having a cancer and previously administered one or more doses of a first BTK inhibitor has one or more BTK inhibitor resistance mutations; and (b) administering a second BTK inhibitor as a monotherapy or in conjunction with another anticancer agent to the subject if the subject has a cancer cell that has at least one BTK inhibitor resistance mutation; or (c) administering additional doses of the first BTK inhibitor previously administered to the subject if the subject has a cancer cell that does not have a BTK inhibitor resistance mutation. In some embodiments, where the subject is administered additional doses of the first BTK inhibitor previously administered to the subject, the subject can also be administered another anticancer agent. In some embodiments, the one or more BTK inhibitor resistance mutations confer increased resistance to a cancer cell or tumor to treatment with the first BTK inhibitor. In some embodiments, the one or more BTK inhibitor resistance mutations include one or more BTK inhibitor resistance mutations listed in Table 2. For example, the one or more BTK inhibitor resistance mutations can include a substitution at amino acid position 804, e.g., V804M, V804L, or V804E, or a substitution at amino acid position 810, e.g., G810S, G810R, G810C, G810A, G810V, and G810D. As another example, the one or more BTK inhibitor resistance mutations can include a substitution at amino acid position 244, 257, 334, 495, 664, 665, 707, 708, 742, 845, 848, 993, 1140, or 1141 of PLCγ2. In some embodiments, the additional anticancer agent is any anticancer agent known in the art. For example, the additional anticancer agent is another BTK inhibitor (e.g., the compound of Formula I, or a pharmaceutically acceptable salt, amorphous, or polymorph form thereof, a spray-dried dispersion thereof, or a pharmaceutical composition thereof). In some embodiments, the additional anticancer agent is an immunotherapy. In some embodiments of (b), another anticancer agent can be the first BTK inhibitor administered in step (a). In some embodiments, the additional anticancer agent inhibits a protein upstream of BTK in the BCR signaling pathway. In some embodiments, the additional anticancer agent inhibits a protein downstream of BTK in the BCR signaling pathway. In some embodiments, the additional anticancer agent is a PLCγ2 inhibitor wherein the one or more resistance mutations includes a substitution in PLCγ2 (e.g., at amino acid position 244, 257, 334, 495, 664, 665, 707, 708, 742, 845, 848, 993, 1140, or 1141).

In some embodiments, a BTK-associated cancer as described herein can occur in a subject along with a dysregulation of another gene, another protein, or the expression or activity or level of any of the same.

For example, a BTK-associated cancer that exhibits a dysregulation of a BTK gene, a BTK protein, or the expression or activity or level of any of the same, can occur in a subject along with one or more of: a dysregulation of a BCR signaling pathway gene, a BCR signaling pathway protein, or expression or activity or level of any of the same (e.g., an amplification in a BCR signaling gene) or a dysregulation of a MYC gene, a MYC protein, or the expression or activity or level of any of the same (e.g., an amplification in a MYC gene).

In some embodiments, the methods described herein can further comprise detecting a dysregulation of a MYC gene, a MYC protein, or the expression or activity or level of any of the same (e.g., an amplification in a MYC gene). In some embodiments, the methods can further comprise administering an inhibitor of MYC.

Exemplary inhibitors of MYC include: 10058-F4, 10074-G5, and KSI-3716.

In some embodiments, the BTK-associated cancer that exhibits a dysregulation of a MYC gene, a MYC protein, or the expression or activity or level of any of the same (e.g., an amplification in a MYC gene) is esophageal cancer (see, e.g., Chong et al., *Gut*. pii: gutjnl-2017-314408, 2017).

Also provided are methods of selecting a treatment for a subject having a cancer that include (a) administering one or more doses of a first BTK inhibitor to the subject for a period of time; (b) after (a), determining whether a cancer cell in a sample obtained from the subject has at least one BTK inhibitor resistance mutation; and (c) selecting the compound of Formula I, or a pharmaceutically acceptable salt, amorphous, or polymorph form thereof, a spray-dried dispersion thereof, or a pharmaceutical composition thereof, as a monotherapy or in conjunction with another anticancer agent for the subject if the subject has a cancer cell that has one or more BTK inhibitor resistance mutations; or (d) selecting additional doses of the first BTK inhibitor of step (a) for the subject if the subject has a cancer cell that does not have a BTK inhibitor resistance mutation. In some embodiments, when additional doses of the first BTK inhibitor of step (a) are selected for the subject, the method can further include selecting doses of another anticancer agent for the subject. In some embodiments, the one or more BTK inhibitor resistance mutations confer increased resistance to a cancer cell or tumor to treatment with the first BTK inhibitor. In some embodiments, the one or more BTK inhibitor resistance mutations include one or more BTK inhibitor resistance mutations listed in Table 2. For example, the one or more BTK inhibitor resistance mutations can include a substitution at amino acid position 481, e.g., C481S, C481F, C481T, C481G, or C481R, or a substitution at amino acid position 474, e.g., T474I, T474M, or T474S. As another example, the one or more BTK inhibitor resistance mutations can include a substitution at amino acid position 244, 257, 334, 495, 664, 665, 707, 708, 742, 845, 848, 993, 1140, or 1141 of PLCγ2. In some embodiments, the additional anticancer agent is any anticancer agent known in the art. For example, the additional anticancer agent is another BTK inhibitor (e.g., a second BTK inhibitor). In some embodiments, the additional anticancer agent is an immunotherapy. In some embodiments of step (c), another BTK inhibitor can be the first BTK inhibitor administered in step (a). In some embodiments, the additional anticancer agent inhibits a protein upstream of BTK in the BCR signaling pathway. In some embodiments, the additional anticancer agent inhibits a protein downstream of BTK in the BCR signaling pathway. In some embodiments, the additional anticancer agent is a PLCγ2 inhibitor wherein the one or more resistance mutations includes a substitution in PLCγ2 (e.g., at amino acid position 244, 257, 334, 495, 664, 665, 707, 708, 742, 845, 848, 993, 1140, or 1141).

Also provided are methods of selecting a treatment for a subject having a cancer that include (a) administering one or more doses of a first BTK inhibitor to the subject for a period of time; (b) after (a), determining whether a cancer cell in a sample obtained from the subject has at least one BTK inhibitor resistance mutation; and (c) selecting a second BTK inhibitor as a monotherapy or in conjunction with another anticancer agent if the subject has a cancer cell that has one or more BTK inhibitor resistance mutations; or (d) selecting additional doses of the first BTK inhibitor of step (a) for the subject if the subject has a cancer cell that does not have a BTK inhibitor resistance mutation. In some embodiments, when additional doses of the first BTK inhibitor of step (a) are selected for the subject, the method can further include selecting doses of another anticancer agent for the subject. In some embodiments, the one or more BTK inhibitor resistance mutations confer increased resistance to a cancer cell or tumor to treatment with the first BTK inhibitor. In some embodiments, the one or more BTK inhibitor resistance mutations include one or more BTK inhibitor resistance mutations listed in Table 2. For example, the one or more BTK inhibitor resistance mutations can include a substitution at amino acid position 481, e.g., C481S, C481F, C481T, C481G, C481R, or a substitution at amino acid position 474, e.g., T474I, T474M, or T474S. As another example, the one or more BTK inhibitor resistance mutations can include a substitution at amino acid position 244, 257, 334, 495, 664, 665, 707, 708, 742, 845, 848, 993, 1140, or 1141 ofPLCγ2. In some embodiments, the additional anticancer agent is any anticancer agent known in the art. For example, the additional anticancer agent is another BTK inhibitor (e.g., the compound of Formula I, or a pharmaceutically acceptable salt, amorphous, or polymorph form thereof, a spray-dried dispersion thereof, or a pharmaceutical composition thereof). In some embodiments, the additional anticancer agent is an immunotherapy. In some embodiments, another BTK inhibitor can be the first BTK inhibitor administered in step (a). In some embodiments, the additional anticancer agent inhibits a protein upstream of BTK in the BCR signaling pathway. In some embodiments, the additional anticancer agent inhibits a protein downstream of BTK in the BCR signaling pathway. In some embodiments, the additional anticancer agent is a PLCγ2 inhibitor wherein the one or more resistance mutations includes a substitution in PLCγ2 (e.g., at amino acid position 244, 257, 334, 495, 664, 665, 707, 708, 742, 845, 848, 993, 1140, or 1141).

Also provided are methods of selecting a treatment for a subject having a cancer that include (a) determining whether a cancer cell in a sample obtained from a subject having a cancer and previously administered one or more doses of a first BTK inhibitor has one or more BTK inhibitor resistance mutations; (b) selecting the compound of Formula I, or a pharmaceutically acceptable salt, amorphous, or polymorph form thereof, a spray-dried dispersion thereof, or a pharmaceutical composition thereof, as a monotherapy or in conjunction with another anticancer agent for the subject if the subject has a cancer cell that has at least one BTK inhibitor resistance mutation; or (c) selecting additional doses of the first BTK inhibitor previously administered to the subject if the subject has a cancer cell that does not have a BTK inhibitor resistance mutation. In some embodiments, when additional doses of the first BTK inhibitor previously administered to the subject are selected for the subject, the method can further include selecting doses of another anticancer agent (e.g., the compound of Formula I, or a pharmaceutically acceptable salt, amorphous, or polymorph form thereof, a spray-dried dispersion thereof, or a pharmaceutical composition thereof, or immunotherapy) for the subject. In some embodiments, the one or more BTK inhibitor resistance mutations confer increased resistance to a cancer cell or tumor to treatment with the first BTK inhibitor. In some embodiments, the one or more BTK inhibitor resistance mutations include one or more BTK inhibitor resistance mutations listed in Table 2. For example, the one or more BTK inhibitor resistance mutations can include a substitution at amino acid position 481, e.g., C481S, C481F, C481T, C481G, C481R, or a substitution at amino acid position 474, e.g., T474I, T474M, or T474S. As another example, the one or more BTK inhibitor resistance mutations can include a substitution at amino acid position 244, 257, 334, 495, 664, 665, 707, 708, 742, 845, 848, 993, 1140, or 1141 of PLCγ2. In some embodiments, the additional anticancer agent is any anticancer agent known in the art. For example, the additional anticancer agent is another BTK inhibitor (e.g., a second BTK inhibitor). In some embodiments, the additional anticancer agent is an immunotherapy. In some embodiments of step (c), another BTK inhibitor can be the first BTK inhibitor administered in step (a). In some embodiments, the additional anticancer agent inhibits a protein upstream of BTK in the BCR signaling pathway. In some embodiments, the additional anticancer agent inhibits a protein downstream of BTK in the BCR signaling pathway. In some embodiments, the additional anticancer agent is a PLCγ2 inhibitor wherein the one or more resistance mutations includes a substitution in PLCγ2 (e.g., at amino acid position 244, 257, 334, 495, 664, 665, 707, 708, 742, 845, 848, 993, 1140, or 1141).

Also provided are methods of selecting a treatment for a subject having a cancer that include (a) determining whether a cancer cell in a sample obtained from a subject having a cancer and previously administered one or more doses of a first BTK inhibitor has one or more BTK inhibitor resistance mutations; (b) selecting a second BTK inhibitor as a monotherapy or in conjunction with another anticancer agent for the subject if the subject has a cancer cell that has at least one BTK inhibitor resistance mutation; or (c) selecting additional doses of the first BTK inhibitor previously administered to the subject if the subject has a cancer cell that does not have a BTK inhibitor resistance mutation. In some embodiments, when additional doses of the first BTK inhibitor previously administered to the subject are selected for the subject, the method can further include selecting doses of another anticancer agent (e.g., the compound of Formula I, or a pharmaceutically acceptable salt, amorphous, or polymorph form thereof, a spray-dried dispersion thereof, or a pharmaceutical composition thereof, or an immunotherapy) for the subject. In some embodiments, the one or more BTK inhibitor resistance mutations confer increased resistance to a cancer cell or tumor to treatment with the first BTK inhibitor. In some embodiments, the one or more BTK inhibitor resistance mutations include one or more BTK inhibitor resistance mutations listed in Table 2. For example, the one or more BTK inhibitor resistance mutations can include a substitution at amino acid position 481, e.g., C481S, C481F, C481T, C481G, C481R, or a substitution at amino acid position 474, e.g., T474I, T474M, or T474S. As another example, the one or more BTK inhibitor resistance mutations can include a substitution at amino acid position 244, 257, 334, 495, 664, 665, 707, 708, 742, 845, 848, 993, 1140, or 1141 of PLCγ2. In some embodiments, the additional anticancer agent is any anticancer agent known in the art. For example, the additional anticancer agent is another BTK inhibitor (e.g., the compound of Formula I, or a pharmaceutically acceptable salt, amorphous, or polymorph form thereof, a spray-dried dispersion thereof, or a pharmaceutical composition thereof). In some embodiments, the additional anticancer agent is an immunotherapy. In some embodiments, another BTK can be the first BTK inhibitor administered in step (a). In some embodiments, the additional anticancer agent inhibits a protein upstream of BTK in the BCR signaling pathway. In some embodiments, the additional anticancer agent inhibits a protein downstream of BTK in the BCR signaling pathway. In some embodiments, the additional anticancer agent is a PLCγ2 inhibitor wherein the one or more resistance mutations includes a substitution in PLCγ2 (e.g., at amino acid position 244, 257, 334, 495, 664, 665, 707, 708, 742, 845, 848, 993, 1140, or 1141).

Also provided are methods of determining a subject's risk for developing a cancer that has some resistance to a first BTK inhibitor that include: determining whether a cell in a sample obtained from the subject has one or more BTK inhibitor resistance mutations; and identifying a subject having a cell that has one or more BTK inhibitor resistance mutations, as having an increased likelihood of developing a cancer that has some resistance to the first BTK inhibitor. Also provided are methods of determining a subject's risk for developing a cancer that has some resistance to a first BTK inhibitor that include: identifying a subject having a cell that has one or more BTK inhibitor resistance mutations, as having an increased likelihood of developing a cancer that has some resistance to the first BTK inhibitor. Also provided are methods of determining the presence of a cancer that has some resistance to a first BTK inhibitor that include: determining whether a cancer cell in a sample obtained from the subject has one or more BTK inhibitor resistance mutations; and determining that the subject having a cancer cell that has one or more BTK inhibitor resistance mutations has a cancer that has some resistance to the first BTK inhibitor. Also provided are methods of determining the presence of a cancer that has some resistance to a first BTK inhibitor in a subject that include: determining that a subject having a cancer cell that has one or more BTK inhibitor resistance mutations, has a cancer that has some resistance to the first BTK inhibitor. In some embodiments, the one or more BTK inhibitor resistance mutations confer increased resistance to a cancer cell or tumor to treatment with the first BTK inhibitor. In some embodiments, the one or more BTK inhibitor resistance mutations include one or more BTK inhibitor resistance mutations listed in Table 2. For example, the one or more BTK inhibitor resistance mutations can include a substitution at amino acid position 481, e.g., C481S, C481F, C481T, C481G, C481R, or a substitution at amino acid position 474, e.g., T474I, T474M, or T474S. As another example, the one or more BTK inhibitor resistance mutations can include a substitution at amino acid position 244, 257, 334, 495, 664, 665, 707, 708, 742, 845, 848, 993, 1140, or 1141 of PLCγ2.

In some embodiments of any of the methods described herein, a BTK inhibitor resistance mutation that confers increased resistance to a cancer cell or tumor to treatment with a first BTK inhibitor can be any of the BTK inhibitor resistance mutations listed in Table 3 or 4 (e.g., a substitution at amino acid position 481, e.g., C481S, C481F, C481T, C481G, C481R, or a substitution at amino acid position 474, e.g., T474I, T474M, or T474S). As another example, the one or more BTK inhibitor resistance mutations can include a substitution at amino acid position 244, 257, 334, 495, 664, 665, 707, 708, 742, 845, 848, 993, 1140, or 1141 of PLCγ2.

In some embodiments, the presence of one or more BTK inhibitor resistance mutations in a tumor causes the tumor to be more resistant to treatment with the compound of Formula I, or a pharmaceutically acceptable salt, amorphous, or polymorph form thereof, a spray-dried dispersion thereof, or a pharmaceutical composition thereof. Methods useful when a BTK inhibitor resistance mutation causes the tumor to be more resistant to treatment with the compound of Formula I, or a pharmaceutically acceptable salt, amorphous, or polymorph form thereof, a spray-dried dispersion thereof, or a pharmaceutical composition thereof, are described below. For example, provided herein are methods of treating a subject having a cancer that include: identifying a subject having a cancer cell that has one or more BTK inhibitor resistance mutations; and administering to the identified subject a treatment that does not include the compound of Formula I, or a pharmaceutically acceptable salt, amorphous, or polymorph form thereof, a spray-dried dispersion thereof, or a pharmaceutical composition thereof, as a monotherapy (e.g., a second BTK kinase inhibitor). Also provided are methods of treating a subject identified as having a cancer cell that has one or more BTK inhibitor resistance mutations that include administering to the subject a treatment that does not include the compound of Formula I, or a pharmaceutically acceptable salt, amorphous, or polymorph form thereof, a spray-dried dispersion thereof, or a pharmaceutical composition thereof, as a monotherapy (e.g., a second BTK kinase inhibitor). In some embodiments, the one or more BTK inhibitor resistance mutations confer increased resistance to a cancer cell or tumor to treatment with the compound of Formula I, or a pharmaceutically acceptable salt, amorphous, or polymorph form thereof, a spray-dried dispersion thereof, or a pharmaceutical composition thereof.

Also provided are methods of selecting a treatment for a subject having a cancer that include: identifying a subject having a cancer cell that has one or more BTK inhibitor resistance mutations; and selecting a treatment that does not include the compound of Formula I, or a pharmaceutically acceptable salt, amorphous, or polymorph form thereof, a spray-dried dispersion thereof, or a pharmaceutical composition thereof, as a monotherapy for the identified subject (e.g., a second BTK kinase inhibitor). Also provided are methods of selecting a treatment for a subject having a cancer that include: selecting a treatment that does not include the compound of Formula I, or a pharmaceutically acceptable salt, amorphous, or polymorph form thereof, a spray-dried dispersion thereof, or a pharmaceutical composition thereof, as a monotherapy (e.g., a second BTK kinase inhibitor) for a subject identified as having a cancer cell that has one or more BTK inhibitor resistance mutations. Also provided are methods of selecting a subject having a cancer for a treatment that does not include the compound of Formula I, or a pharmaceutically acceptable salt, amorphous, or polymorph form thereof, a spray-dried dispersion thereof, or a pharmaceutical composition thereof, as a monotherapy (e.g., a second BTK kinase inhibitor) that include: identifying a subject having a cancer cell that has one or more BTK inhibitor resistance mutations; and selecting the identified subject for a treatment that does not include the compound of Formula I, or a pharmaceutically acceptable salt, amorphous, or polymorph form thereof, a spray-dried dispersion thereof, or a pharmaceutical composition thereof, as a monotherapy (e.g., a second BTK kinase inhibitor). Also provided are methods of selecting a subject having a cancer for a treatment that does not include the compound of Formula I, or a pharmaceutically acceptable salt, amorphous, or polymorph form thereof, a spray-dried dispersion thereof, or a pharmaceutical composition thereof, as a monotherapy (e.g., a second BTK kinase inhibitor) that include: selecting a subject identified as having a cancer cell that has one or more BTK inhibitor resistance mutations for a treatment that does not include the compound of Formula I, or a pharmaceutically acceptable salt, amorphous, or polymorph form thereof, a spray-dried dispersion thereof, or a pharmaceutical composition thereof, as a monotherapy. In some embodiments, the one or more BTK inhibitor resistance mutations confer increased resistance to a cancer cell or tumor to treatment with the compound of Formula I, or a pharmaceutically acceptable salt, amorphous, or polymorph form thereof, a spray-dried dispersion thereof, or a pharmaceutical composition thereof.

Also provided are methods of determining the likelihood that a subject having a cancer will have a positive response to treatment with the compound of Formula I, or a pharmaceutically acceptable salt, amorphous, or polymorph form thereof, a spray-dried dispersion thereof, or a pharmaceutical composition thereof, as a monotherapy that include: determining whether a cancer cell in a sample obtained from the subject has one or more BTK inhibitor resistance mutations; and determining that the subject having the cancer cell that has one or more BTK inhibitor resistance mutations has a decreased likelihood of having a positive response to treatment with the compound of Formula I, or a pharmaceutically acceptable salt, amorphous, or polymorph form thereof, a spray-dried dispersion thereof, or a pharmaceutical composition thereof, as a monotherapy. Also provided are methods of determining the likelihood that a subject having cancer will have a positive response to treatment with the compound of Formula I, or a pharmaceutically acceptable salt, amorphous, or polymorph form thereof, a spray-dried dispersion thereof, or a pharmaceutical composition thereof, as a monotherapy that include: determining that a subject having a cancer cell that has one or more BTK inhibitor resistance mutations has a decreased likelihood of having a positive response to treatment with the compound of Formula I, or a pharmaceutically acceptable salt, amorphous, or polymorph form thereof, a spray-dried dispersion thereof, or a pharmaceutical composition thereof, as a monotherapy. Also provided are methods of predicting the efficacy of treatment with the compound of Formula I, or a pharmaceutically acceptable salt, amorphous, or polymorph form thereof, a spray-dried dispersion thereof, or a pharmaceutical composition thereof, as a monotherapy in a subject having cancer that include: determining whether a cancer cell in a sample obtained from the subject has one or more BTK inhibitor resistance mutations; and determining that treatment with the compound of Formula I, or a pharmaceutically acceptable salt, amorphous, or polymorph form thereof, a spray-dried dispersion thereof, or a pharmaceutical composition thereof, as a monotherapy is less likely to be effective in a subject having a cancer cell in a sample obtained from the subject that has one or more BTK inhibitor resistance mutations. Also provided are methods of predicting the efficacy of treatment with the compound of Formula I, or a pharmaceutically acceptable salt, amorphous, or polymorph form thereof, a spray-dried dispersion thereof, or a pharmaceutical composition thereof, as a monotherapy in a subject having cancer that include: determining that treatment with the compound of Formula I, or a pharmaceutically acceptable salt, amorphous, or polymorph form thereof, a spray-dried dispersion thereof, or a pharmaceutical composition thereof, as a monotherapy is less likely to be effective in a subject having a cancer cell in a sample obtained from the subject that has one or more BTK inhibitor resistance mutations. In some embodiments, the one or more BTK inhibitor resistance mutations confer increased resistance to a cancer cell or tumor to treatment with the compound of Formula I, or a pharmaceutically acceptable salt, amorphous, or polymorph form thereof, a spray-dried dispersion thereof, or a pharmaceutical composition thereof.

Also provided are methods of treating a subject having a cancer that include: (a) administering one or more doses of the compound of Formula I, or a pharmaceutically acceptable salt, amorphous, or polymorph form thereof, a spray-dried dispersion thereof, or a pharmaceutical composition thereof, for a period of time; (b) after (a), determining whether a cancer cell in a sample obtained from the subject has one or more BTK inhibitor resistance mutations; and (c) administering a second BTK inhibitor or a second compound of Formula I, or a pharmaceutically acceptable salt, amorphous, or polymorph form thereof, a spray-dried dispersion thereof, or a pharmaceutical composition thereof, as a monotherapy or in conjunction with another anticancer agent to a subject having a cancer cell that has one or more BTK inhibitor resistance mutations; or (d) administering additional doses of the compound of Formula I, or a pharmaceutically acceptable salt, amorphous, or polymorph form thereof, a spray-dried dispersion thereof, or a pharmaceutical composition thereof, of step (a) to a subject having a cancer cell that does not have a BTK inhibitor resistance mutation. In some embodiments, where the subject is administered additional doses of the compound of Formula I, or a pharmaceutically acceptable salt, amorphous, or polymorph form thereof, a spray-dried dispersion thereof, or a pharmaceutical composition thereof, of step (a), the subject can also be administered another anticancer agent or a second compound of Formula I, or a pharmaceutically acceptable salt, amorphous, or polymorph form thereof, a spray-dried dispersion thereof, or a pharmaceutical composition thereof. In some embodiments, the one or more BTK inhibitor resistance mutations confer increased resistance to a cancer cell or tumor to treatment with the compound of Formula I, or a pharmaceutically acceptable salt, amorphous, or polymorph form thereof, a spray-dried dispersion thereof, or a pharmaceutical composition thereof. In some embodiments, the additional anticancer agent is any anticancer agent known in the art. For example, the additional anticancer agent is another BTK inhibitor (e.g., a second BTK inhibitor). In some embodiments, the additional anticancer agent is an immunotherapy. In some embodiments, another BTK can be the compound of Formula I, or a pharmaceutically acceptable salt, amorphous, or polymorph form thereof, a spray-dried dispersion thereof, or a pharmaceutical composition thereof, administered in step (a).

Also provided are methods of treating a subject having a cancer that include: (a) determining whether a cancer cell in a sample obtained from a subject having a cancer and previously administered one or more doses of the compound of Formula I, or a pharmaceutically acceptable salt, amorphous, or polymorph form thereof, a spray-dried dispersion thereof, or a pharmaceutical composition thereof, has one or more BTK inhibitor resistance mutations; (b) administering a second BTK inhibitor or a second compound of Formula I, or a pharmaceutically acceptable salt, amorphous, or polymorph form thereof, a spray-dried dispersion thereof, or a pharmaceutical composition thereof, as a monotherapy or in conjunction with another anticancer agent to a subject having a cancer cell that has one or more BTK inhibitor resistance mutations; or (c) administering additional doses of the compound of Formula I, or a pharmaceutically acceptable salt, amorphous, or polymorph form thereof, a spray-dried dispersion thereof, or a pharmaceutical composition thereof, previously administered to a subject having a cancer cell that does not have a BTK inhibitor resistance mutation. In some embodiments, where the subject is administered additional doses of the compound of Formula I, or a pharmaceutically acceptable salt, amorphous, or polymorph form thereof, a spray-dried dispersion thereof, or a pharmaceutical composition thereof, of step (a), the subject can also be administered another anticancer agent. In some embodiments, the one or more BTK inhibitor resistance mutations confer increased resistance to a cancer cell or tumor to treatment with the compound of Formula I, or a pharmaceutically acceptable salt, amorphous, or polymorph form thereof, a spray-dried dispersion thereof, or a pharmaceutical composition thereof. In some embodiments, the additional anticancer agent is any anticancer agent known in the art. For example, the additional anticancer agent is another BTK inhibitor (e.g., a second BTK inhibitor). In some embodiments, the additional anticancer agent is an immunotherapy. In some embodiments, another BTK can be the compound of Formula I, or a pharmaceutically acceptable salt, amorphous, or polymorph form thereof, a spray-dried dispersion thereof, or a pharmaceutical composition thereof, administered in step (a).

Also provided are methods of selecting a treatment for a subject having a cancer that include: (a) administering one or more doses of the compound of Formula I, or a pharmaceutically acceptable salt, amorphous, or polymorph form thereof, a spray-dried dispersion thereof, or a pharmaceutical composition thereof, to the subject for a period of time; (b) after (a), determining whether a cancer cell in a sample obtained from the subject has one or more BTK inhibitor resistance mutations; and (c) selecting a second BTK inhibitor or a second compound of Formula I, or a pharmaceutically acceptable salt, amorphous, or polymorph form thereof, a spray-dried dispersion thereof, or a pharmaceutical composition thereof, as a monotherapy or in conjunction with another anticancer agent for the subject if the subject has a cancer cell that has a BTK inhibitor resistance mutation; or (d) selecting additional doses of the compound of Formula I, or a pharmaceutically acceptable salt, amorphous, or polymorph form thereof, a spray-dried dispersion thereof, or a pharmaceutical composition thereof, of step (a) for the subject if the subject has a cancer cell that does not have a BTK inhibitor resistance mutation. In some embodiments, where additional doses of the compound of Formula I, or a pharmaceutically acceptable salt, amorphous, or polymorph form thereof, a spray-dried dispersion thereof, or a pharmaceutical composition thereof, of step (a) are selected for the subject, the method can also include further selecting another anticancer agent. In some embodiments, the one or more BTK inhibitor resistance mutations confer increased resistance to a cancer cell or tumor to treatment with the compound of Formula I, or a pharmaceutically acceptable salt, amorphous, or polymorph form thereof, a spray-dried dispersion thereof, or a pharmaceutical composition thereof. In some embodiments, the additional anticancer agent is any anticancer agent known in the art. For example, the additional anticancer agent is another BTK inhibitor (e.g., a second BTK inhibitor). In some embodiments, the additional anticancer agent is an immunotherapy. In some embodiments, another BTK can be the compound of Formula I, or a pharmaceutically acceptable salt, amorphous, or polymorph form thereof, a spray-dried dispersion thereof, or a pharmaceutical composition thereof, administered in step (a).

Also provided are methods of selecting a treatment for a subject having a cancer that include: (a) determining whether a cancer cell in a sample obtained from a subject having a cancer and previously administered one or more doses of the compound of Formula I, or a pharmaceutically acceptable salt, amorphous, or polymorph form thereof, a spray-dried dispersion thereof, or a pharmaceutical composition thereof, has one or more BTK inhibitor resistance mutations; (b) selecting a second BTK inhibitor or a second compound of Formula I, or a pharmaceutically acceptable salt, amorphous, or polymorph form thereof, a spray-dried dispersion thereof, or a pharmaceutical composition thereof, as a monotherapy or in conjunction with another anticancer agent for the subject if the subject has a cancer cell that has a BTK inhibitor resistance mutation; or (c) selecting additional doses of the compound of Formula I, or a pharmaceutically acceptable salt, amorphous, or polymorph form thereof, a spray-dried dispersion thereof, or a pharmaceutical composition thereof, previously administered to the subject if the subject has a cancer cell that does not have a BTK inhibitor resistance mutation. In some embodiments, where additional doses of the compound of Formula I, or a pharmaceutically acceptable salt, amorphous, or polymorph form thereof, a spray-dried dispersion thereof, or a pharmaceutical composition thereof, of step (a) are selected for the subject, the method can also include further selecting another anticancer agent. In some embodiments, the one or more BTK inhibitor resistance mutations confer increased resistance to a cancer cell or tumor to treatment with the compound of Formula I, or a pharmaceutically acceptable salt, amorphous, or polymorph form thereof, a spray-dried dispersion thereof, or a pharmaceutical composition thereof. In some embodiments, the additional anticancer agent is any anticancer agent known in the art. For example, the additional anticancer agent is another BTK inhibitor (e.g., a second BTK inhibitor). In some embodiments, the additional anticancer agent is an immunotherapy. In some embodiments, another BTK can be the compound of Formula I, or a pharmaceutically acceptable salt, amorphous, or polymorph form thereof, a spray-dried dispersion thereof, or a pharmaceutical composition thereof, administered in step (a).

Also provided are methods of determining a subject's risk for developing a cancer that has some resistance to the compound of Formula I, or a pharmaceutically acceptable salt, amorphous, or polymorph form thereof, a spray-dried dispersion thereof, or a pharmaceutical composition thereof, that include: determining whether a cell in a sample obtained from the subject has one or more BTK inhibitor resistance mutations; and identifying the subject if the subject has a cell that has one or more BTK inhibitor resistance mutations as having an increased likelihood of developing a cancer that has some resistance to the compound of Formula I, or a pharmaceutically acceptable salt, amorphous, or polymorph form thereof, a spray-dried dispersion thereof, or a pharmaceutical composition thereof. Also provided are methods of determining a subject's risk for developing a cancer that has some resistance to the compound of Formula I, or a pharmaceutically acceptable salt, amorphous, or polymorph form thereof, a spray-dried dispersion thereof, or a pharmaceutical composition thereof, that include: identifying a subject having a cell that has one or more BTK inhibitor resistance mutations as having an increased likelihood of developing a cancer that has some resistance to the compound of Formula I, or a pharmaceutically acceptable salt, amorphous, or polymorph form thereof, a spray-dried dispersion thereof, or a pharmaceutical composition thereof. Also provided are methods of determining the presence of a cancer that has some resistance to the compound of Formula I, or a pharmaceutically acceptable salt, amorphous, or polymorph form thereof, a spray-dried dispersion thereof, or a pharmaceutical composition thereof, that includes: determining whether a cancer cell in a sample obtained from the subject has one or more BTK inhibitor resistance mutations; and determining that the subject having the cancer cell that has one or more BTK inhibitor resistance mutations has a cancer that has some resistance to the compound of Formula I, or a pharmaceutically acceptable salt, amorphous, or polymorph form thereof, a spray-dried dispersion thereof, or a pharmaceutical composition thereof. Also provided are methods of determining the presence of a cancer that has some resistance to the compound of Formula I, or a pharmaceutically acceptable salt, amorphous, or polymorph form thereof, a spray-dried dispersion thereof, or a pharmaceutical composition thereof, in a subject that include: determining that a subject having a cancer cell that has one or more BTK inhibitor resistance mutations has a cancer that has some resistance to the compound of Formula I, or a pharmaceutically acceptable salt, amorphous, or polymorph form thereof, a spray-dried dispersion thereof, or a pharmaceutical composition thereof. In some embodiments, the one or more BTK inhibitor resistance mutations confer increased resistance to a cancer cell or tumor to treatment with the compound of Formula I, or a pharmaceutically acceptable salt, amorphous, or polymorph form thereof, a spray-dried dispersion thereof, or a pharmaceutical composition thereof.

In some embodiments of any of the methods described herein, a BTK inhibitor resistance mutation that confers increased resistance to a cancer cell or tumor to treatment with the compound of Formula I, or a pharmaceutically acceptable salt, amorphous, or polymorph form thereof, a spray-dried dispersion thereof, or a pharmaceutical composition thereof, can be any of the BTK inhibitor resistance mutations listed in Table 2. Methods of determining the level of resistance of a cancer cell or a tumor to a BTK inhibitor (e.g., any of the BTK inhibitors described herein or known in the art) can be determined using methods known in the art. For example, the level of resistance of a cancer cell to a BTK inhibitor can be assessed by determining the $IC_{50}$ of a BTK inhibitor (e.g., any of the BTK inhibitors described herein or known in the art) on the viability of a cancer cell. In other examples, the level of resistance of a cancer cell to a BTK inhibitor can be assessed by determining the growth rate of the cancer cell in the presence of a BTK inhibitor (e.g., any of the BTK inhibitors described herein). In other examples, the level of resistance of a tumor to a BTK inhibitor can be assessed by determining the mass or size of one or more tumors in a subject over time during treatment with a BTK inhibitor (e.g., any of the BTK inhibitors described herein). In other examples, the level of resistance of a cancer cell or a tumor to a BTK inhibitor can be indirectly assessed by determining the activity of a BTK kinase including one or more of the BTK inhibitor resistance mutations (i.e., the same BTK kinase expressed in a cancer cell or a tumor in a subject). The level of resistance of a cancer cell or tumor having one or more BTK inhibitor resistance mutations to a BTK inhibitor is relative to the level of resistance in a cancer cell or tumor that does not have a BTK inhibitor resistance mutation (e.g., a cancer cell or tumor that does not have the same BTK inhibitor resistance mutations, a cancer cell or a tumor that does not have any BTK inhibitor resistance mutations, or a cancer cell or a tumor that expresses a wildtype BTK protein). For example, the determined level of resistance of a cancer cell or a tumor having one or more BTK inhibitor resistance mutations can be greater than about 1%, greater than about 2%, greater than about 3%, greater than about 4%, greater than about 5%, greater than about 6%, greater than about 7%, greater than about 8%, greater than about 9%, greater than about 10%, greater than about 11%, greater than about 12%, greater than about 13%, greater than about 14%, greater than about 15%, greater than about 20%, greater than about 25%, greater than about 30%, greater than about 35%, greater than about 40%, greater than about 45%, greater than about 50%, greater than about 60%, greater than about 70%, greater than about 80%, greater than about 90%, greater than about 100%, greater than about 110%, greater than about 120%, greater than about 130%, greater than about 140%, greater than about 150%, greater than about 160%, greater than about 170%, greater than about 180%, greater than about 190%, greater than about 200%, greater than about 210%, greater than about 220%, greater than about 230%, greater than about 240%, greater than about 250%, greater than about 260%, greater than about 270%, greater than about 280%, greater than about 290%, or greater than about 300% of the level of resistance in a cancer cell or tumor that does not have a BTK inhibitor resistance mutation (e.g., a cancer cell or tumor that does not have the same BTK inhibitor resistance mutations, a cancer cell or a tumor that does not have any BTK inhibitor resistance mutations, or a cancer cell or a tumor that expresses a wildtype BTK protein).

Also provided herein are methods of treating a subject having a cancer (e.g., any of the cancers described herein) in which (i) the cancer in the subject has relapsed during therapy with a first BTK inhibitor; and/or (ii) the cancer in the subject is not responding to therapy with a first BTK inhibitor; and/or (iii) the subject is intolerant to a first BTK inhibitor that include administering to the subject a treatment that does not include the first BTK inhibitor (e.g., a first BTK inhibitor such as ibrutinib or acalabrutinib) as a monotherapy (e.g., any treatments that do not include a first BTK inhibitor as a monotherapy described herein). For example, the subject can be administered a second BTK inhibitor as a monotherapy or in combination with another anticancer agent or treatment (e.g., the first BTK inhibitor).

Also provided herein are methods of treating a subject that include administering a therapeutically effective amount of a treatment that does not include a first BTK inhibitor as a monotherapy, to a subject having a clinical record that indicates that (i) the cancer in the subject has relapsed during therapy with the first BTK inhibitor; and/or (ii) the cancer in the subject is not responding to therapy with the first BTK inhibitor; and/or (iii) the subject is intolerant to the first BTK inhibitor. For example, the subject can be administered a second BTK inhibitor as a monotherapy or in combination with another anticancer agent or treatment (e.g., the first BTK inhibitor).

Also provided herein are methods of treating a subject having a cancer (e.g., any of the cancers described herein or known in the art) that include: identifying a subject in which (i) the cancer in the subject has relapsed during therapy with a first BTK inhibitor; and/or (ii) the cancer in the subject is not responding to therapy with a first BTK inhibitor; and/or (iii) the subject is intolerant to a first BTK inhibitor; and administering to the identified subject a treatment that includes the compound of Formula I, or a pharmaceutically acceptable salt, amorphous, or polymorph form thereof, a spray-dried dispersion thereof, or a pharmaceutical composition thereof.

Also provided herein are methods of treating a subject having a cancer (e.g., any of the cancers described herein or known in the art) that include: identifying a subject in which (i) the cancer in the subject has relapsed during therapy with a first BTK inhibitor; and/or (ii) the cancer in the subject is not responding to therapy with a first BTK inhibitor; and/or (iii) the subject is intolerant to a first BTK inhibitor; and administering to the identified subject a treatment that includes the compound of Formula I, or a pharmaceutically acceptable salt, amorphous, or polymorph form thereof, a spray-dried dispersion thereof, or a pharmaceutical composition thereof, and another anticancer agent (e.g., any one or more of the anticancer agents described herein) or anticancer therapy (e.g., any one or more of the anticancer therapies provided herein).

Also provided herein are methods of treating a subject identified as having a cancer wherein (i) the cancer in the subject has relapsed during therapy with a first BTK inhibitor; and/or (ii) the cancer in the subject is not responding to therapy with a first BTK inhibitor; and/or (iii) the subject is intolerant to a first BTK inhibitor, that include administering to the subject a treatment that includes the compound of Formula I, or a pharmaceutically acceptable salt, amorphous, or polymorph form thereof, a spray-dried dispersion thereof, or a pharmaceutical composition thereof.

Also provided herein are methods of treating a subject identified as having a cancer and wherein (i) the cancer in the subject has relapsed during therapy with a first BTK inhibitor; and/or (ii) the cancer in the subject is not responding to therapy with a first BTK inhibitor; and/or (iii) the subject is intolerant to a first BTK inhibitor, that include administering to the subject a treatment that includes the compound of Formula I, or a pharmaceutically acceptable salt, amorphous, or polymorph form thereof, a spray-dried dispersion thereof, or a pharmaceutical composition thereof, and another anticancer agent (e.g., any one or more of the another anticancer agents described herein) or anticancer therapies (e.g., any one or more of the anticancer therapies described herein).

Also provided herein are methods of treating a subject having a cancer that include administering a therapeutically effective amount of a treatment that includes the compound of Formula I, or a pharmaceutically acceptable salt, amorphous, or polymorph form thereof, a spray-dried dispersion thereof, or a pharmaceutical composition thereof, to a subject having a clinical record that indicates that (i) the cancer in the subject has relapsed during therapy with a first BTK inhibitor; and/or (ii) the cancer in the subject is not responding to therapy with a first BTK inhibitor; and/or (iii) the subject is intolerant to a first BTK inhibitor.

Also provided herein are methods of treating a subject that include administering a therapeutically effective amount of a treatment that includes the compound of Formula I, or a pharmaceutically acceptable salt, amorphous, or polymorph form thereof, a spray-dried dispersion thereof, or a pharmaceutical composition thereof, and another anticancer agent (e.g., any one or more of the anticancer agents described herein) or anticancer therapy (e.g., any one or more of the anticancer therapies described herein), to a subject having a clinical record that indicates that (i) the cancer in the subject has relapsed during therapy with a first BTK inhibitor; and/or (ii) the cancer in the subject is not responding to therapy with a first BTK inhibitor; and/or (iii) the subject is intolerant to a first BTK inhibitor.

Also provided herein are methods of treating a subject having a cancer that include (a) administering one or more doses of a first BTK inhibitor to the subject for a period of time; (b) after (a), determining whether (i) the cancer in the subject has relapsed during therapy with the first BTK inhibitor; and/or (ii) the cancer in the subject is not responding to therapy with the first BTK inhibitor; and/or (iii) the subject is intolerant to the first BTK inhibitor; and (c) administering a second BTK inhibitor or a treatment that does not include the BTK inhibitor of step (a) as a monotherapy to a subject in which (i) the cancer in the subject has relapsed during therapy with the first BTK inhibitor; and/or (ii) the cancer in the subject is not responding to therapy with the first BTK inhibitor; and/or (iii) the subject is intolerant to the first BTK inhibitor; or (d) administering additional doses of the first BTK inhibitor to a subject in which (i) the cancer in the subject has not relapsed during therapy with the first BTK inhibitor; and/or (ii) the cancer in the subject is responding to therapy with the first BTK inhibitor; and/or (iii) the subject is not intolerant to the first BTK inhibitor. In some embodiments, the second BTK inhibitor is the compound of Formula I, or a pharmaceutically acceptable salt, amorphous, or polymorph form thereof, a spray-dried dispersion thereof, or a pharmaceutical composition thereof. In some embodiments, the second BTK inhibitor is a pharmaceutical composition comprising a compounding agent as disclosed herein and the compound of Formula I, or a pharmaceutically acceptable salt, amorphous, or polymorph form thereof, a spray-dried dispersion thereof, or a pharmaceutical composition thereof. In some embodiments, the cancer is a BTK-associated cancer.

Also provided herein are methods of treating a subject having a cancer that include: (a) determining whether (i) the cancer in the subject has relapsed during therapy with a first BTK inhibitor; and/or (ii) the cancer in the subject is not responding to therapy with a first BTK inhibitor; and/or (iii) the subject is intolerant to a first BTK inhibitor; and (b) administering a second BTK inhibitor or a treatment that does not include the first BTK inhibitor of step (a) as a monotherapy to a subject in which (i) the cancer in the subject has relapsed during therapy with the first BTK inhibitor; and/or (ii) the cancer in the subject is not responding to therapy with the first BTK inhibitor; and/or (iii) the subject is intolerant to the first BTK inhibitor; or (c) administering additional doses of the first BTK inhibitor to a subject in which (i) the cancer in the subject has not relapsed during therapy with the first BTK inhibitor; and/or (ii) the cancer in the subject is responding to therapy with the first BTK inhibitor; and/or (iii) the subject is not intolerant to the first BTK inhibitor. In some embodiments, the second BTK inhibitor is the compound of Formula I, or a pharmaceutically acceptable salt, amorphous, or polymorph form thereof, a spray-dried dispersion thereof, or a pharmaceutical composition thereof.

In some embodiments, the cancer is a BTK-associated cancer. In some embodiments, the BTK associated cancer exhibits at least one of a point mutation/insertion/deletion and/or fusion as described in Tables 1, 1a, and 4. In some embodiments, the BTK-associated cancer does not exhibit a BTK resistance mutation, e.g., any of the mutations described in Tables 2 and 3.

Also provided herein are methods of treating a subject having a cancer that include (a) detecting a dysregulation of a BTK gene, a BTK kinase, or the expression or activity or level of any of the same; (b) administering one or more doses of a first BTK inhibitor to the subject for a period of time; (c) after (a) and (b), determining whether (i) the cancer in the subject has relapsed during therapy with the first BTK inhibitor; and/or (ii) the cancer in the subject is not responding to therapy with the first BTK inhibitor; and/or (iii) the subject is intolerant to the first BTK inhibitor; and (d) administering a second BTK inhibitor or a treatment that does not include the BTK inhibitor of step (b) as a monotherapy to a subject in which (i) the cancer in the subject has relapsed during therapy with the first BTK inhibitor; and/or (ii) the cancer in the subject is not responding to therapy with the first BTK inhibitor; and/or (iii) the subject is intolerant to the first BTK inhibitor; or (e) administering additional doses of the first BTK inhibitor to a subject in which (i) the cancer in the subject has not relapsed during therapy with the first BTK inhibitor; and/or (ii) the cancer in the subject is responding to therapy with the first BTK inhibitor; and/or (iii) the subject is not intolerant to the first BTK inhibitor. In some embodiments, the second BTK inhibitor is the compound of Formula I, or a pharmaceutically acceptable salt, amorphous, or polymorph form thereof, a spray-dried dispersion thereof, or a pharmaceutical composition thereof.

In some embodiments, step (a) is performed before step (b).

In some embodiments, step (b) is performed before step (a).

In some embodiments, detecting a dysregulation of a BTK gene, a BTK kinase, or the expression or activity or level of any of the same includes next generation sequencing, immunohistochemistry, fluorescence microscopy, break apart FISH analysis, and PCR-based amplification (e.g., RT-PCR and quantitative real-time RT-PCR).

Also provided herein are methods of treating a subject having a cancer, that include: (a) detecting a dysregulation of a BTK gene, a BTK kinase, or the expression or activity or level of any of the same; (b) administering one or more doses of a first BTK inhibitor to the subject for a period of time; (c) after (a) and (b), determining whether (i) the cancer in the subject has relapsed during therapy with the first BTK inhibitor; and/or (ii) the cancer in the subject is not responding to therapy with the first BTK inhibitor; and/or (iii) the subject is intolerant to the first BTK inhibitor; and (d) administering a treatment including one or more doses of a second BTK inhibitor to a subject in which (i) the cancer in the subject has relapsed during therapy with the first BTK inhibitor; and/or (ii) the cancer in the subject is not responding to therapy with the first BTK inhibitor; and/or (iii) the subject is intolerant to the first BTK inhibitor; or (e) administering additional doses of the first BTK inhibitor to a subject in which (i) the cancer has not relapsed during therapy with the first BTK inhibitor; and/or (ii) the cancer in the subject is responding to therapy with the first BTK inhibitor; and/or (iii) the subject is not intolerant to the first BTK inhibitor. In some embodiments, the second BTK inhibitor is the compound of Formula I, or a pharmaceutically acceptable salt, amorphous, or polymorph form thereof, a spray-dried dispersion thereof, or a pharmaceutical composition thereof.

Also provided herein are methods of treating a subject having a cancer, that include: (a) detecting a dysregulation of a BTK gene, a BTK kinase, or the expression or activity or level of any of the same; (b) administering one or more doses of a first BTK inhibitor to the subject for a period of time; (c) after (a) and (b), determining whether (i) the cancer in the subject has relapsed during therapy with the first BTK inhibitor; and/or (ii) the cancer in the subject is not responding to therapy with the first BTK inhibitor; and/or (iii) the subject is intolerant to the first BTK inhibitor; and; and (d) administering a treatment including the compound of Formula I, or a pharmaceutically acceptable salt, amorphous, or polymorph form thereof, a spray-dried dispersion thereof, or a pharmaceutical composition thereof, to a subject in which (i) the cancer in the subject has relapsed during therapy with the first BTK inhibitor; and/or (ii) the cancer in the subject is not responding to therapy with the first BTK inhibitor; and/or (iii) the subject is intolerant to the first BTK inhibitor; or (e) administering additional doses of the first BTK inhibitor to a subject in which (i) the cancer in the subject has not relapsed during therapy with the first BTK inhibitor; and/or (ii) the cancer in the subject is responding to therapy with the first BTK inhibitor; and/or (iii) the subject is not intolerant to the first BTK inhibitor.

Also provided herein are methods of treating a subject having a cancer that include: (a) detecting a dysregulation of a BTK gene, a BTK kinase, or the expression or activity or level of any of the same; (b) administering one or more doses of a first BTK inhibitor to the subject for a period of time; (c) after (a) and (b), determining whether (i) the cancer in the subject has relapsed during therapy with the first BTK inhibitor; and/or (ii) the cancer in the subject is not responding to therapy with the first BTK inhibitor; and/or (iii) the subject is intolerant to the first BTK inhibitor; and; and (d) administering a treatment including the compound of Formula I, or a pharmaceutically acceptable salt, amorphous, or polymorph form thereof, a spray-dried dispersion thereof, or a pharmaceutical composition thereof, and another anticancer agent or anticancer therapy to a subject in which (i) the cancer in the subject has relapsed during therapy with the first BTK inhibitor; and/or (ii) the cancer in the subject is not responding to therapy with the first BTK inhibitor; and/or (iii) the subject is intolerant to the first BTK inhibitor; or (e) administering additional doses of the first BTK inhibitor to a subject in which (i) the cancer in the subject has not relapsed during therapy with the first BTK inhibitor; and/or (ii) the cancer in the subject is responding to therapy with the first BTK inhibitor; and/or (iii) the subject is not intolerant to the first BTK inhibitor.

In some embodiments, step (a) is performed before step (b).

In some embodiments, step (b) is performed before step (a).

In some embodiments, detecting a dysregulation of a BTK gene, a BTK kinase, or the expression or activity or level of any of the same includes next generation sequencing, immunohistochemistry, fluorescence microscopy, break apart FISH analysis, and PCR-based amplification (e.g., RT-PCR and quantitative real-time RT-PCR).

Also provided herein are methods of treating a subject having a cancer that include: (a) determining whether (i) the cancer in the subject has relapsed during therapy with a first BTK inhibitor; and/or (ii) the cancer in the subject is not responding to therapy with a first BTK inhibitor; and/or (iii) the subject is intolerant to a first BTK inhibitor; (b) administering a treatment that includes one or more doses of a second BTK inhibitor to a subject in which (i) the cancer in the subject has relapsed during therapy with the first BTK inhibitor; and/or (ii) the cancer in the subject is not responding to therapy with the first BTK inhibitor; and/or (iii) the subject is intolerant to the first BTK inhibitor; or (c) administering additional doses of the first BTK inhibitor to a subject in which (i) the cancer has not relapsed during therapy with the first BTK inhibitor; and/or (ii) the cancer in the subject is responding to therapy with the first BTK inhibitor; and/or (iii) the subject is not intolerant to the first BTK inhibitor. In some embodiments, the second BTK inhibitor is the compound of Formula I, or a pharmaceutically acceptable salt, amorphous, or polymorph form thereof, a spray-dried dispersion thereof, or a pharmaceutical composition thereof.

Also provided herein are methods of treating a subject having a cancer that include: (a) determining whether (i) the cancer in the subject has relapsed during therapy with a first BTK inhibitor; and/or (ii) the cancer in the subject is not responding to therapy with a first BTK inhibitor; and/or (iii) the subject is intolerant to a first BTK inhibitor; (b) administering a treatment that includes the compound of Formula I, or a pharmaceutically acceptable salt, amorphous, or polymorph form thereof, a spray-dried dispersion thereof, or a pharmaceutical composition thereof, to a subject in which (i) the cancer in the subject has relapsed during therapy with the first BTK inhibitor; and/or (ii) the cancer in the subject is not responding to therapy with the first BTK inhibitor; and/or (iii) the subject is intolerant to the first BTK inhibitor; or (c) administering additional doses of the first BTK inhibitor to a subject in which (i) the cancer has not relapsed during therapy with the first BTK inhibitor; and/or (ii) the cancer in the subject is responding to therapy with the first BTK inhibitor; and/or (iii) the subject is not intolerant to the first BTK inhibitor.

Also provided herein are methods of treating a subject having a cancer, that include: (a) determining whether (i) the cancer in the subject has relapsed during therapy with a first BTK inhibitor; and/or (ii) the cancer in the subject is not responding to therapy with a first BTK inhibitor; and/or (iii) the subject is intolerant to a first BTK inhibitor; (b) administering a treatment that includes the compound of Formula I, or a pharmaceutically acceptable salt, amorphous, or polymorph form thereof, a spray-dried dispersion thereof, or a pharmaceutical composition thereof, and another anticancer agent or anticancer therapy to a subject in which (i) the cancer in the subject has relapsed during therapy with the first BTK inhibitor; and/or (ii) the cancer in the subject is not responding to therapy with the first BTK inhibitor; and/or (iii) the subject is intolerant to the first BTK inhibitor; or (c) administering additional doses of the first BTK inhibitor to a subject in which (i) the cancer has not relapsed during therapy with the first BTK inhibitor; and/or (ii) the cancer in the subject is responding to therapy with the first BTK inhibitor; and/or (iii) the subject is not intolerant to the first BTK inhibitor.

In some embodiments, the cancer is a BTK-associated cancer. In some embodiments, the BTK associated cancer exhibits at least one of a point mutation/insertion/deletion as described in Tables 1, 1a, or 4. In some embodiments, the BTK-associated cancer does not exhibit a BTK resistance mutation, e.g., any of the mutations described in Tables 2 and 3.

In some embodiments, the first BTK inhibitor is selected from the group consisting of: ibrutinib, PRN1008, PRN473, ABBV-105, AC0058, acalabrutinib, zanubrutinib, spebrutinib, poseltinib, evobrutinib, tirabrutinib, CG'806, ARQ 531, BIIB068, vecabrutinib, AS871, CB1763, CB988, GDC-0853, RN486, GNE-504, GNE-309, BTK Max, dasatinib, CT-1530, CGI-1746, CGI-560, LFM A13, TP-0158, dtrmwxhs-12, CNX-774, and LOU064. In some embodiments, the first BTK inhibitor is a covalent inhibitor, e.g., ibrutinib, PRN1008, PRN473, ABBV-105, AC0058, acalabrutinib, zanubrutinib, spebrutinib, poseltinib, evobrutinib, M7583, or tirabrutinib. In some embodiments, the first BTK inhibitor is a non-covalent inhibitor, e.g., CG'806, ARQ 531, BIIB068, vecabrutinib, AS871, CB1763, CB988, GDC-0853, RN486, or dasatinib.

In some embodiments, relapse is one or more of detecting an increase in the number of cancer cells in the subject, an increase in the size of one or more tumors in the subject, an increase in tumor burden, an increase in the rate or extent of metastasis, worsening symptoms, in whole or in part, associated with the cancer, an increase in the extent of disease, and an acceleration of disease progression after a period of improvement. In some embodiments, relapse is progression of the cancer after a period of improvement. In some embodiments, a period of improvement is one or more of a decrease in the number of cancer cells in the subject, a decrease in the size of one or more tumors in the subject, a decrease in tumor burden, a decrease in the rate or extent of metastasis, improving symptoms, in whole or in part, associated with the cancer, a decrease in the extent of disease, and a slowing of disease progression.

In some embodiments, a cancer that is not responding to therapy with a first BTK inhibitor is a cancer that is progressing. In some embodiments, progression of a cancer is one or more of an increase in the number of cancer cells in the subject, an increase in the size of one or more tumors in the subject, an increase in tumor burden, an increase in the rate or extent of metastasis, worsening symptoms, in whole or in part, associated with the cancer, an increase in the extent of disease, and an acceleration of disease progression.

In some embodiments, a bone marrow biopsy, e.g., a bone marrow core biopsy or a bone marrow aspirate specimen, can be used to detect the progression or relapse of a cancer e.g., a hematological cancer. In some embodiments, a bone marrow biopsy can be used to detect one or more of the percentage of blast cells, dysplasia (e.g., abnormal cells), percentage of lymphocytes, percentage of plasma cells, fibrosis, cellularity, distribution pattern of hematopoietic elements, morphology of lymphoid elements, and enumeration of lymphoid elements and plasma cells (see e.g., Sever, et al., Arch Pathol Lab Med. 2016 September; 140(9): 932-49, which is incorporated by reference herein in its entirety). Bone marrow biopsies can be performed at multiple times during a course of diagnosis, a course of monitoring, and/or a course of therapy to determine one or more clinically relevant parameters including, without limitation, progression of the disease and efficacy of a therapy, relapse of the disease, or development of resistance mutations after administering a therapy to the subject. For example, a first bone marrow biopsy can be performed at a first time point and a second bone marrow biopsy can be performed at a second time point during a course of diagnosis, a course of monitoring, and/or a course of therapy. In some embodiments, the first time point can be a time point prior to diagnosing a subject with a disease (e.g., when the subject is healthy), and the second time point can be a time point after subject has developed the disease (e.g., the second time point can be used to diagnose the subject with the disease). In some embodiments, the first time point can be a time point prior to diagnosing a subject with a disease (e.g., when the subject is healthy), after which the subject is monitored, and the second time point can be a time point after monitoring the subject. In some embodiments, the first time point can be a time point after diagnosing a subject with a disease, after which a therapy is administered to the subject, and the second time point can be a time point after the therapy is administered; in such cases, the second time point can be used to assess the efficacy of the therapy.

In some embodiments, progression includes one or more of detecting an increase in the percentage of blast cells, an increase in the myeloid to erythroid ratio, an increase in dysplasia (e.g., white blood cell dysplasia), an increase in the percentage of bone marrow plasma cells, and an increase in the percentage of bone marrow lymphocytes. For example, progression includes detecting one or more of an increase in the percentage of blast cells, an increase in the myeloid to erythroid ratio, an increase in dysplasia (e.g., white blood cell dysplasia), an increase in the percentage of bone marrow plasma cells, and an increase in the percentage of bone marrow lymphocytes at a second time point compared to a first time point.

In some embodiments, relapse can include detecting one or more of an increase in the percentage of blast cells, an increase in the myeloid to erythroid ratio, an increase in dysplasia (e.g., white blood cell dysplasia), an increase in the percentage of bone marrow plasma cells, and an increase in the percentage of bone marrow lymphocytes after a period of improvement. In some embodiments, a period of improvement can include detecting one or more of a decrease in the percentage of blast cells, a decrease in the myeloid to erythroid ratio, a decrease in dysplasia (e.g., white blood cell dysplasia), a decrease in the percentage of bone marrow plasma cells, and a decrease in the percentage of bone marrow lymphocytes.

In some embodiments, a complete blood count can be used to detect the progression or relapse of a cancer, e.g., a hematological cancer. In some embodiments, a complete blood count can be used to detect one or more of the percentage of leukocytes (e.g., polymorphonuclear leukocytes), a decrease in the number of platelets, and a decrease in hemoglobin in peripheral blood. Complete blood counts can be performed at multiple times during a course of diagnosis, a course of monitoring, and/or a course of therapy to determine one or more clinically relevant parameters including, without limitation, progression of the disease and efficacy of a therapy, relapse of the disease, or development of resistance mutations after administering a therapy to the subject. For example, a first complete blood count can be performed at a first time point and a second complete blood count can be performed at a second time point during a course of diagnosis, a course of monitoring, and/or a course of therapy. In some embodiments, the first time point can be a time point prior to diagnosing a subject with a disease (e.g., when the subject is healthy), and the second time point can be a time point after subject has developed the disease (e.g., the second time point can be used to diagnose the subject with the disease). In some embodiments, the first time point can be a time point prior to diagnosing a subject with a disease (e.g., when the subject is healthy), after which the subject is monitored, and the second time point can be a time point after monitoring the subject. In some embodiments, the first time point can be a time point after diagnosing a subject with a disease, after which a therapy is administered to the subject, and the second time point can be a time point after the therapy is administered; in such cases, the second time point can be used to assess the efficacy of the therapy.

In some embodiments, progression can include detecting one or more of an increase in the percentage of leukocytes (e.g., polymorphonuclear leukocytes), a decrease in the number of platelets, and a decrease in hemoglobin in peripheral blood. For example, progression can include detecting one or more of an increase in the percentage of leukocytes (e.g., polymorphonuclear leukocytes), a decrease in the number of platelets, and a decrease in hemoglobin in peripheral blood at a second time point compared to a first time point.

In some embodiments, relapse can include detecting one or more of an increase in the percentage of leukocytes (e.g., polymorphonuclear leukocytes), a decrease in the number of platelets, and a decrease in hemoglobin in peripheral blood after a period of improvement. In some embodiments, a period of improvement can include detecting one or more of a decrease in the percentage of leukocytes (e.g., polymorphonuclear leukocytes), an increase in the number of platelets, and an increase in hemoglobin in peripheral blood.

In some embodiments, the tumor burden can be assessed using PERCIST. In some embodiments, the tumor burden is assessed using RECIST version 1.1.

In some embodiments, the cancer is a lymphoma and the treatment of the lymphoma is assessed by one or more of the methods as described in one or more of Cheson et al. J Clin Oncol. 2007, 25:579-86; Cheson et al., Blood. 2016, 128: 2489-2496; and Cheson et al., Clin Oncol. 2014, 32(27): 3059-3068, each of which are incorporated by reference herein in their entireties.

In some embodiments, the cancer is a leukemia, e.g., CLL, and the treatment of the leukemia is assessed by one or more of the methods as described in Hallek et al., Blood. 2008, 111(12):5446-56, which is incorporated by reference herein in its entirety.

In some embodiments, the cancer is a myeloma and the treatment of the myeloma is assessed by one or more of the methods as described in Fujino et al., J Clin Exp Hematop. 2018, 58(2):61-67, which is incorporated by reference herein in its entirety.

In some embodiments, liquid biopsies can be used to detect the progression of a cancer. In some embodiments, the biological sample to be used in a liquid biopsy can include, blood, plasma, urine, cerebrospinal fluid, saliva, sputum, broncho-alveolar lavage, bile, lymphatic fluid, cyst fluid, stool, ascites, and combinations thereof. In some embodiments, a liquid biopsy can be used to detect circulating tumor cells (CTCs). In some embodiments, a liquid biopsy can be used to detect cell-free DNA. In some embodiments, cell-free DNA detected using a liquid biopsy is circulating tumor DNA (ctDNA) that is derived from tumor cells. Analysis of ctDNA (e.g., using sensitive detection techniques such as, without limitation, next-generation sequencing (NGS), traditional PCR, digital PCR, or microarray analysis) can be used to identify progression of the cancer.

Liquid biopsies can be performed at multiple times during a course of diagnosis, a course of monitoring, and/or a course of therapy to determine one or more clinically relevant parameters including, without limitation, progression of the disease, efficacy of a therapy, or development of resistance mutations after administering a therapy to the subject. For example, a first liquid biopsy can be performed at a first time point and a second liquid biopsy can be performed at a second time point during a course of diagnosis, a course of monitoring, and/or a course of therapy. In some embodiments, the first time point can be a time point prior to diagnosing a subject with a disease (e.g., when the subject is healthy), and the second time point can be a time point after subject has developed the disease (e.g., the second time point can be used to diagnose the subject with the disease). In some embodiments, the first time point can be a time point prior to diagnosing a subject with a disease (e.g., when the subject is healthy), after which the subject is monitored, and the second time point can be a time point after monitoring the subject. In some embodiments, the first time point can be a time point after diagnosing a subject with a disease, after which a therapy is administered to the subject, and the second time point can be a time point after the therapy is administered; in such cases, the second time point can be used to assess the efficacy of the therapy (e.g., if the genetic mutation(s) detected at the first time point are reduced in abundance or are undetectable) or to determine the presence of a resistance mutation that has arisen as a result of the therapy.

In some embodiments provided herein, circulating tumor DNA can be used to monitor the responsiveness of a patient to a particular therapy (e.g., a first BTK inhibitor or a second BTK inhibitor such as the compound of Formula I, or a pharmaceutically acceptable salt, amorphous, or polymorph form thereof, a spray-dried dispersion thereof, or a pharmaceutical composition thereof). For example, prior to starting a therapy as described herein (e.g., a first BTK inhibitor or a second BTK inhibitor such as the compound of Formula I, or a pharmaceutically acceptable salt, amorphous, or polymorph form thereof, a spray-dried dispersion thereof, or a pharmaceutical composition thereof), a biological sample can be obtained from the subject and the level of circulating tumor DNA determined in the biological sample. This sample can be considered a base-line sample. The subject can then be administered one or more doses of a therapy as described herein (e e.g., a first BTK inhibitor or a second BTK inhibitor such as the compound of Formula I, or a pharmaceutically acceptable salt, amorphous, or polymorph form thereof, a spray-dried dispersion thereof, or a pharmaceutical composition thereof) and the levels of circulating tumor DNA can be monitored (e.g., after the first dose, second dose, third dose, etc. or after one week, two weeks, three weeks, four weeks, etc.). If the level of circulating tumor DNA is lower than the baseline sample (e.g., a 1% to about a 99% reduction, a 1% to about a 95% reduction, a 1% to about a 90% reduction, a 1% to about a 85% reduction, a 1% to about a 80% reduction, a 1% to about a 75% reduction, a 1% reduction to about a 70% reduction, a 1% reduction to about a 65% reduction, a 1% reduction to about a 60% reduction, a 1% reduction to about a 55% reduction, a 1% reduction to about a 50% reduction, a 1% reduction to about a 45% reduction, a 1% reduction to about a 40% reduction, a 1% reduction to about a 35% reduction, a 1% reduction to about a 30% reduction, a 1% reduction to about a 25% reduction, a 1% reduction to about a 20% reduction, a 1% reduction to about a 15% reduction, a 1% reduction to about a 10% reduction, a 1% to about a 5% reduction, about a 5% to about a 99% reduction, about a 10% to about a 99% reduction, about a 15% to about a 99% reduction, about a 20% to about a 99% reduction, about a 25% to about a 99% reduction, about a 30% to about a 99% reduction, about a 35% to about a 99% reduction, about a 40% to about a 99% reduction, about a 45% to about a 99% reduction, about a 50% to about a 99% reduction, about a 55% to about a 99% reduction, about a 60% to about a 99% reduction, about a 65% to about a 99% reduction, about a 70% to about a 99% reduction, about a 75% to about a 95% reduction, about a 80% to about a 99% reduction, about a 90% reduction to about a 99% reduction, about a 95% to about a 99% reduction, about a 5% to about a 10% reduction, about a 5% to about a 25% reduction, about a 10% to about a 30% reduction, about a 20% to about a 40% reduction, about a 25% to about a 50% reduction, about a 35% to about a 55% reduction, about a 40% to about a 60% reduction, about a 50% reduction to about a 75% reduction, about a 60% reduction to about 80% reduction, or about a 65% to about a 85% reduction etc.), this is indicative of responsiveness to the therapy. In some embodiments, the level of circulating tumor DNA in a biological sample obtained from the patient (n) is compared to the sample taken just previous (n−1). If the level of circulating tumor DNA in the n sample is lower than the n−1 sample (e.g., a 1% to about a 99% reduction, a 1% to about a 95% reduction, a 1% to about a 90% reduction, a 1% to about a 85% reduction, a 1% to about a 80% reduction, a 1% to about a 75% reduction, a 1% reduction to about a 70% reduction, a 1% reduction to about a 65% reduction, a 1% reduction to about a 60% reduction, a 1% reduction to about a 55% reduction, a 1% reduction to about a 50% reduction, a 1% reduction to about a 45% reduction, a 1% reduction to about a 40% reduction, a 1% reduction to about a 35% reduction, a 1% reduction to about a 30% reduction, a 1% reduction to about a 25% reduction, a 1% reduction to about a 20% reduction, a 1% reduction to about a 15% reduction, a 1% reduction to about a 10% reduction, a 1% to about a 5% reduction, about a 5% to about a 99% reduction, about a 10% to about a 99% reduction, about a 15% to about a 99% reduction, about a 20% to about a 99% reduction, about a 25% to about a 99% reduction, about a 30% to about a 99% reduction, about a 35% to about a 99% reduction, about a 40% to about a 99% reduction, about a 45% to about a 99% reduction, about a 50% to about a 99% reduction, about a 55% to about a 99% reduction, about a 60% to about a 99% reduction, about a 65% to about a 99% reduction, about a 70% to about a 99% reduction, about a 75% to about a 95% reduction, about a 80% to about a 99% reduction, about a 90% reduction to about a 99% reduction, about a 95% to about a 99% reduction, about a 5% to about a 10% reduction, about a 5% to about a 25% reduction, about a 10% to about a 30% reduction, about a 20% to about a 40% reduction, about a 25% to about a 50% reduction, about a 35% to about a 55% reduction, about a 40% to about a 60% reduction, about a 50% reduction to about a 75% reduction, about a 60% reduction to about 80% reduction, or about a 65% to about a 85% reduction, etc.), this is indicative of responsiveness to the therapy. In the case of responsiveness to therapy, the subject can to be administered one or more doses of the therapy and the circulating tumor DNA can be continued to be monitored.

If the level of circulating tumor DNA in the sample is higher than the baseline (e.g., a 1% to about a 99% increase, a 1% to about a 95% increase, a 1% to about a 90% increase, a 1% to about a 85% increase, a 1% to about a 80% increase, a 1% to about a 75% increase, a 1% increase to about a 70% increase, a 1% increase to about a 65% increase, a 1% increase to about a 60% increase, a 1% increase to about a 55% increase, a 1% increase to about a 50% increase, a 1% increase to about a 45% increase, a 1% increase to about a 40% increase, a 1% increase to about a 35% increase, a 1% increase to about a 30% increase, a 1% increase to about a 25% increase, a 1% increase to about a 20% increase, a 1% increase to about a 15% increase, a 1% increase to about a 10% increase, a 1% to about a 5% increase, about a 5% to about a 99% increase, about a 10% to about a 99% increase, about a 15% to about a 99% increase, about a 20% to about a 99% increase, about a 25% to about a 99% increase, about a 30% to about a 99% increase, about a 35% to about a 99% increase, about a 40% to about a 99% increase, about a 45% to about a 99% increase, about a 50% to about a 99% increase, about a 55% to about a 99% increase, about a 60% to about a 99% increase, about a 65% to about a 99% increase, about a 70% to about a 99% increase, about a 75% to about a 95% increase, about a 80% to about a 99% increase, about a 90% increase to about a 99% increase, about a 95% to about a 99% increase, about a 5% to about a 10% increase, about a 5% to about a 25% increase, about a 10% to about a 30% increase, about a 20% to about a 40% increase, about a 25% to about a 50% increase, about a 35% to about a 55% increase, about a 40% to about a 60% increase, about a 50% increase to about a 75% increase, about a 60% increase to about 80% increase, or about a 65% to about a 85% increase, etc.), this can be indicative of progression of the cancer. If the level of circulating tumor DNA in the n sample is higher than the n−1 sample (e.g., a 1% to about a 99% increase, a 1% to about a 95% increase, a 1% to about a 90% increase, a 1% to about a 85% increase, a 1% to about a 80% increase, a 1% to about a 75% increase, a 1% increase to about a 70% increase, a 1% increase to about a 65% increase, a 1% increase to about a 60% increase, a 1% increase to about a 55% increase, a 1% increase to about a 50% increase, a 1% increase to about a 45% increase, a 1% increase to about a 40% increase, a 1% increase to about a 35% increase, a 1% increase to about a 30% increase, a 1% increase to about a 25% increase, a 1% increase to about a 20% increase, a 1% increase to about a 15% increase, a 1% increase to about a 10% increase, a 1% to about a 5% increase, about a 5% to about a 99% increase, about a 10% to about a 99% increase, about a 15% to about a 99% increase, about a 20% to about a 99% increase, about a 25% to about a 99% increase, about a 30% to about a 99% increase, about a 35% to about a 99% increase, about a 40% to about a 99% increase, about a 45% to about a 99% increase, about a 50% to about a 99% increase, about a 55% to about a 99% increase, about a 60% to about a 99% increase, about a 65% to about a 99% increase, about a 70% to about a 99% increase, about a 75% to about a 95% increase, about a 80% to about a 99% increase, about a 90% increase to about a 99% increase, about a 95% to about a 99% increase, about a 5% to about a 10% increase, about a 5% to about a 25% increase, about a 10% to about a 30% increase, about a 20% to about a 40% increase, about a 25% to about a 50% increase, about a 35% to about a 55% increase, about a 40% to about a 60% increase, about a 50% increase to about a 75% increase, about a 60% increase to about 80% increase, or about a 65% to about a 85% increase etc.), this can be indicative of progression of the cancer. When progression of the cancer during therapy with a first BTK inhibitor is suspected, the subject can undergo one or more of imaging, biopsy, surgery, or other diagnostic tests. In some embodiments, when progression of the cancer during therapy with a first BTK inhibitor is suspected, the subject can be administered (either as a monotherapy or in combination with the previous therapy) a second BTK inhibitor, e.g., the compound of Formula I, or a pharmaceutically acceptable salt, amorphous, or polymorph form thereof, a spray-dried dispersion thereof, or a pharmaceutical composition thereof.

If after a period of improvement, e.g., a period of responsiveness to the therapy as described above, the level of circulating tumor DNA in the sample is higher than the level obtained during the period of improvement (e.g., a 1% to about a 99% increase, a 1% to about a 95% increase, a 1% to about a 90% increase, a 1% to about a 85% increase, a 1% to about a 80% increase, a 1% to about a 75% increase, a 1% increase to about a 70% increase, a 1% increase to about a 65% increase, a 1% increase to about a 60% increase, a 1% increase to about a 55% increase, a 1% increase to about a 50% increase, a 1% increase to about a 45% increase, a 1% increase to about a 40% increase, a 1% increase to about a 35% increase, a 1% increase to about a 30% increase, a 1% increase to about a 25% increase, a 1% increase to about a 20% increase, a 1% increase to about a 15% increase, a 1% increase to about a 10% increase, a 1% to about a 5% increase, about a 5% to about a 99% increase, about a 10% to about a 99% increase, about a 15% to about a 99% increase, about a 20% to about a 99% increase, about a 25% to about a 99% increase, about a 30% to about a 99% increase, about a 35% to about a 99% increase, about a 40% to about a 99% increase, about a 45% to about a 99% increase, about a 50% to about a 99% increase, about a 55% to about a 99% increase, about a 60% to about a 99% increase, about a 65% to about a 99% increase, about a 70% to about a 99% increase, about a 75% to about a 95% increase, about a 80% to about a 99% increase, about a 90% increase to about a 99% increase, about a 95% to about a 99% increase, about a 5% to about a 10% increase, about a 5% to about a 25% increase, about a 10% to about a 30% increase, about a 20% to about a 40% increase, about a 25% to about a 50% increase, about a 35% to about a 55% increase, about a 40% to about a 60% increase, about a 50% increase to about a 75% increase, about a 60% increase to about 80% increase, or about a 65% to about a 85% increase, etc.), this can be indicative of relapse of the cancer. If the level of circulating tumor DNA in the n sample is higher than the n−1 sample (e.g., a 1% to about a 99% increase, a 1% to about a 95% increase, a 1% to about a 90% increase, a 1% to about a 85% increase, a 1% to about a 80% increase, a 1% to about a 75% increase, a 1% increase to about a 70% increase, a 1% increase to about a 65% increase, a 1% increase to about a 60% increase, a 1% increase to about a 55% increase, a 1% increase to about a 50% increase, a 1% increase to about a 45% increase, a 1% increase to about a 40% increase, a 1% increase to about a 35% increase, a 1% increase to about a 30% increase, a 1% increase to about a 25% increase, a 1% increase to about a 20% increase, a 1% increase to about a 15% increase, a 1% increase to about a 10% increase, a 1% to about a 5% increase, about a 5% to about a 99% increase, about a 10% to about a 99% increase, about a 15% to about a 99% increase, about a 20% to about a 99% increase, about a 25% to about a 99% increase, about a 30% to about a 99% increase, about a 35% to about a 99% increase, about a 40% to about a 99% increase, about a 45% to about a 99% increase, about a 50% to about a 99% increase, about a 55% to about a 99% increase, about a 60% to about a 99% increase, about a 65% to about a 99% increase, about a 70% to about a 99% increase, about a 75% to about a 95% increase, about a 80% to about a 99% increase, about a 90% increase to about a 99% increase, about a 95% to about a 99% increase, about a 5% to about a 10% increase, about a 5% to about a 25% increase, about a 10% to about a 30% increase, about a 20% to about a 40% increase, about a 25% to about a 50% increase, about a 35% to about a 55% increase, about a 40% to about a 60% increase, about a 50% increase to about a 75% increase, about a 60% increase to about 80% increase, or about a 65% to about a 85% increase etc.), this can be indicative of relapse of the cancer. When relapse of the cancer during therapy with a first BTK inhibitor is suspected, the subject can undergo one or more of imaging, biopsy, surgery, or other diagnostic tests. In some embodiments, when relapse of the cancer during therapy with a first BTK inhibitor is suspected, the subject can be administered (either as a monotherapy or in combination with the previous therapy) a second BTK inhibitor, e.g., the compound of Formula I, or a pharmaceutically acceptable salt, amorphous, or polymorph form thereof, a spray-dried dispersion thereof, or a pharmaceutical composition thereof. See, for example, Cancer Discov; 7(12); 1368-70 (2017); and Cancer Discov; 7(12); 1394-403 (2017). In some embodiments, a BTK resistance mutation, e.g., any of the mutations described in Tables 2 and 3, is not detected.

In some embodiments, the subject that is intolerant to a first BTK inhibitor has had one or more of a severe, disabling, or life-threatening adverse event during therapy with the first BTK inhibitor, an unplanned hospitalization during therapy with the first BTK inhibitor, discontinuation of therapy with the first BTK inhibitor, dose reduction of the first BTK inhibitor, functional decline attributed to therapy with the first BTK inhibitor, and a decrease in performance status.

In some embodiments, the performance status is assessed using the Eastern Cooperative Oncology Group (ECOG) Scale of Performance Status.

In some embodiments, the performance status is assessed using the Karnofsky Performance Status.

In some embodiments, the performance status is assess by the Lansky Performance Score.

In some embodiments, wherein (i) the cancer in the subject has relapsed during therapy with a first BTK inhibitor; and/or (ii) the cancer in the subject is not responding to therapy with the first BTK inhibitor; and/or (iii) the subject is intolerant to the first BTK inhibitor, a BTK resistance mutation, e.g., any of the mutations described in Tables 2 and 3, is not detected.

In some embodiments, wherein (i) the cancer in the subject has relapsed during therapy with a first BTK inhibitor; and/or (ii) the cancer in the subject is not responding to therapy with the first BTK inhibitor; and/or (iii) the subject is intolerant to the first BTK inhibitor, a BTK resistance mutation, e.g., any of the mutations described in Tables 2 and 3, is not detected.

Some examples of these methods further include recording in the subject's clinical record (e.g., a computer readable medium) that the subject should be administered a treatment that does not include the first BTK inhibitor in step (a) as a monotherapy or a different BTK inhibitor in the future.

In some of any of the above embodiments, the subject does not have active uncontrolled autoimmune cytopenia. In some embodiments, the subject has not been diagnosed with autoimmune cytopenia. In some embodiments, the subject does not have clinically significant, uncontrolled cardiac, cardiovascular disease or history of myocardial infarction within 6 months of beginning a treatment as described herein. In some embodiments, the subject has not been diagnosed with a cardiac or cardiovascular disease. In some embodiments, the subject has not had a myocardial infarction. In some embodiments, the subject does not have a clinically significant active malabsorption syndrome. In some embodiments, the subject has not been diagnosed with a malabsorption syndrome. In some embodiments, the subject is not being treated with strong cytochrome P450 3A4 (CYP3A4) inhibitors (e.g., ritonavir, indinavir, nelfinavir, saquinavir, clarithromycin, telithromycin, chloramphenicol, ketoconazole, itraconazole, posaconazole, voriconazole, nefazodone, and cobicistat) or inducers (e.g., carbamazepine, dexamethasone, ethosuximide, glucocorticoids, griseofulvin, phenytoin, primidone, progesterone, rifampin, nafcillin, nelfinavir, nevirapine, oxcarbazepine, phenobarbital, phenylbutazone, rofecoxib (mild), st john's wort, sulfadimidine, sulfinpyrazone, and troglitazone) during any of the treatments as described herein. In some embodiments, the subject is not being treated with proton pump inhibitors (e.g., omeprazole, lansoprazole, dexlansoprazole, esomeprazole, pantoprazole, rabeprazole, ilaprazole) within 7 days of starting any of the treatments described herein. In some embodiments, the subject does not have an active second malignancy. In some embodiments, the subject has an active second malignancy, which is in remission, and the life expectancy of the subject is >2 years.

Also provided herein are methods for treating a subject diagnosed with (or identified as having) idiopathic pulmonary fibrosis or an autoimmune or inflammatory disease including arthritis (e.g., rheumatoid arthritis), multiple sclerosis, osteoporosis, irritable bowel syndrome, inflammatory bowel disease, Crohn's disease, chronic urticaria, myasthenia gravis and lupus (e.g., lupus erythematosus) that include administering to the subject a therapeutically effective amount of the compound of Formula I, or a pharmaceutically acceptable salt, amorphous, or polymorph form thereof, a spray-dried dispersion thereof, or a pharmaceutical composition thereof.

Also provided herein are methods for treating a subject identified or diagnosed as having a BTK-associated idiopathic pulmonary fibrosis or an autoimmune or inflammatory disease (e.g., a subject that has been identified or diagnosed as having a BTK-associated idiopathic pulmonary fibrosis or autoimmune or inflammatory disease through the use of a regulatory agency-approved, e.g., FDA-approved, kit for identifying dysregulation of a BTK gene, a BTK kinase, or expression or activity or level of any of the same, in a subject or a biopsy sample from the subject) that include administering to the subject a therapeutically effective amount of the compound of Formula I, or a pharmaceutically acceptable salt, amorphous, or polymorph form thereof, a spray-dried dispersion thereof, or a pharmaceutical composition thereof.

Also provided are methods for treating idiopathic pulmonary fibrosis or an autoimmune or inflammatory disease in a subject in need thereof, the method comprising: (a) determining if the idiopathic pulmonary fibrosis or autoimmune or inflammatory disease in the subject is a BTK-associated idiopathic pulmonary fibrosis or autoimmune or inflammatory disease (e.g., using a regulatory-agency approved, e.g., FDA-approved, kit for identifying dysregulation of a BTK gene, a BTK kinase, or expression or activity or level of any of the same, in a subject or a biopsy sample from the subject, or by performing any of the non-limiting examples of assays described herein); and (b) if the idiopathic pulmonary fibrosis or autoimmune or inflammatory disease is determined to be a BTK-associated IBS, administering to the subject a therapeutically effective amount of the compound of Formula I, or a pharmaceutically acceptable salt, amorphous, or polymorph form thereof, a spray-dried dispersion thereof, or a pharmaceutical composition thereof.

In some embodiments, the compounds of the present invention are useful for treating an idiopathic pulmonary fibrosis or autoimmune or inflammatory disease in combination with one or more additional therapeutic agents or therapies effective in treating the idiopathic pulmonary fibrosis or autoimmune or inflammatory disease that work by the same or a different mechanism of action. The at least one additional therapeutic agent may be administered with the compound of Formula I, or a pharmaceutically acceptable salt, amorphous, or polymorph form thereof, a spray-dried dispersion thereof, or a pharmaceutical composition thereof, as part of the same or separate dosage forms, via the same or different routes of administration, and on the same or different administration schedules according to standard pharmaceutical practice known to one skilled in the art.

Accordingly, also provided herein are methods of treating idiopathic pulmonary fibrosis or an autoimmune or inflammatory disease, comprising administering to a subject in need thereof a pharmaceutical combination for treating the idiopathic pulmonary fibrosis or autoimmune or inflammatory disease which comprises (a) the compound of Formula I, or a pharmaceutically acceptable salt, amorphous, or polymorph form thereof, a spray-dried dispersion thereof, or a pharmaceutical composition thereof, (b) an additional therapeutic agent, and (c) optionally at least one pharmaceutically acceptable carrier for simultaneous, separate or sequential use for the treatment of the idiopathic pulmonary fibrosis or autoimmune or inflammatory disease, wherein the amounts of the compound of Formula I, or a pharmaceutically acceptable salt, amorphous, or polymorph form thereof, a spray-dried dispersion thereof, or a pharmaceutical composition thereof, and the additional therapeutic agent are together effective in treating the idiopathic pulmonary fibrosis or autoimmune or inflammatory disease. In one embodiment, the compound of Formula I, or a pharmaceutically acceptable salt, amorphous, or polymorph form thereof, a spray-dried dispersion thereof, or a pharmaceutical composition thereof, and the additional therapeutic agent are administered simultaneously as separate dosages. In one embodiment, the compound of Formula I, or a pharmaceutically acceptable salt, amorphous, or polymorph form thereof, a spray-dried dispersion thereof, or a pharmaceutical composition thereof, and the additional therapeutic agent are administered as separate dosages sequentially in any order, in jointly therapeutically effective amounts, e.g. in daily or intermittently dosages. In one embodiment, compound of Formula I, or a pharmaceutically acceptable salt, amorphous, or polymorph form thereof, a spray-dried dispersion thereof, or a pharmaceutical composition thereof, and the additional therapeutic agent are administered simultaneously as a combined dosage.

Also provided herein is (i) a pharmaceutical combination for treating idiopathic pulmonary fibrosis or an autoimmune or inflammatory disease in a subject in need thereof, which comprises (a) the compound of Formula I, or a pharmaceutically acceptable salt, amorphous, or polymorph form thereof, a spray-dried dispersion thereof, or a pharmaceutical composition thereof, (b) at least one additional therapeutic agent (e.g., any of the exemplary additional therapeutic agents described herein for treating idiopathic pulmonary fibrosis or an autoimmune or inflammatory disease or known in the art), and (c) optionally at least one pharmaceutically acceptable carrier for simultaneous, separate or sequential use for the treatment of an idiopathic pulmonary fibrosis or an autoimmune or inflammatory disease, wherein the amounts of the compound of Formula I, or a pharmaceutically acceptable salt, amorphous, or polymorph form thereof, a spray-dried dispersion thereof, or a pharmaceutical composition thereof, and of the additional therapeutic agent are together effective in treating the idiopathic pulmonary fibrosis or autoimmune or inflammatory disease; (ii) a pharmaceutical composition comprising such a combination; (iii) the use of such a combination for the preparation of a medicament for the treatment of rheumatoid arthritis or irritable bowel syndrome; and (iv) a commercial package or product comprising such a combination as a combined preparation for simultaneous, separate or sequential use; and to a method of treatment of idiopathic pulmonary fibrosis or autoimmune or inflammatory disease in a subject in need thereof. In one embodiment, the subject is a human.

In one embodiment, the compound of Formula I, or a pharmaceutically acceptable salt, amorphous, or polymorph form thereof, a spray-dried dispersion thereof, or a pharmaceutical composition thereof, and the additional therapeutic agent are formulated as separate unit dosage forms, wherein the separate dosages forms are suitable for either sequential or simultaneous administration. These also apply to cocktail therapies, e.g. the administration of three or more active ingredients.

Also provided is a method for inhibiting BTK kinase activity in a cell, comprising contacting the cell with a compound of Formula I. In one embodiment, the contacting is in vitro. In one embodiment, the contacting is in vivo. In one embodiment, the contacting is in vivo, wherein the method comprises administering an effective amount of the compound of Formula I, or a pharmaceutically acceptable salt, amorphous, or polymorph form thereof, a spray-dried dispersion thereof, or a pharmaceutical composition thereof, or a pharmaceutical dispersion thereof, or a pharmaceutical composition thereof, to a subject having a cell having BTK kinase activity. In some embodiments, the cell is a cancer cell. In one embodiment, the cancer cell is any cancer as described herein. In some embodiments, the cancer cell is a BTK-associated cancer cell. In some embodiments, the cell is a B-cell.

Also provided is a method for inhibiting BTK kinase activity in a mammalian cell, comprising contacting the cell with a compound of Formula I. In one embodiment, the contacting is in vitro. In one embodiment, the contacting is in vivo. In one embodiment, the contacting is in vivo, wherein the method comprises administering an effective amount of the compound of Formula I, or a pharmaceutically acceptable salt, amorphous, or polymorph form thereof, a spray-dried dispersion thereof, or a pharmaceutical composition thereof, to a mammal having a cell having BTK kinase activity. In some embodiments, the mammalian cell is a mammalian cancer cell. In one embodiment, the mammalian cancer cell is any cancer as described herein. In some embodiments, the mammalian cancer cell is a BTK-associated cancer cell. In some embodiments, the mammalian cell is a B-cell.

Also provided herein is a method of inhibiting cell proliferation, in vitro or in vivo, the method comprising contacting a cell with an effective amount of the compound of Formula I, or a pharmaceutically acceptable salt, amorphous, or polymorph form thereof, a spray-dried dispersion thereof, or a pharmaceutical composition thereof, as defined herein 4. Kits Provided herein are pharmaceutical kits useful, for example, in the treatment of BTK-associated diseases or disorders, such as cancer or idiopathic pulmonary fibrosis or autoimmune or inflammatory disorders, which include one or more containers containing a pharmaceutical composition comprising a therapeutically effective amount of the compound provided herein. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

EXAMPLES

The following examples illustrate the invention.

Example 1: BTK Activity Assay

A. BTK Activity Assay for Mutants of BTK

The activity of the compound of Formula I against full-length wild type (WT) and mutant human BTK enzymes is determined by monitoring the incorporation $[^{33}P]\text{-}PO_4$ from $[\gamma\text{-}^{33}P]\text{-}ATP$ into poly-glutamic acid-tyrosine (poly-EY) peptide substrate. The reaction mixtures each contained polyhistidine-tagged BTK enzyme, poly-EY and BTK inhibitor at the appropriate concentrations. The reaction mixtures are incubated for 20 minutes at room temperature after which $[[\gamma\text{-}^{33}P]\text{-}ATP$ (radiochemical concentration 10 µCi/µL) at 10 µM or the ATP $K_m$ concentration for each enzyme is added. After 2 hours of incubation at room temperature, the radiolabeled peptide substrate is captured, and incorporated radioactivity is quantified. The compound of Formula I is tested against BTK WT, BTK C481S, an identified ibrutinib and acalabrutinib resistance mutation in patients, BTK E41K, a preclinical constitutively active BTK mutant, and BTK P190K, a clinically observed lung cancer mutation. At 10 µM ATP, the IC50 values for the compound of Formula I are 0.95 nM and 0.29 nM for BTK and BTK C481S, respectively. At $K_m$ ATP concentration, the compound of Formula I inhibited BTK WT, BTK C481S, BTK E41K, and BTK P190K with IC50 values of 3.15, 1.42, 7.85, and 2.14 nM respectively.

B. Kinase Selectivity Assay

The compound of Formula I is tested for inhibition of 371 kinases using a radiolabeled ATP activity assay (Reaction Biology Wild-Type Kinase Profiler). Each assay is performed at an ATP concentration close to the $K_m$ for each enzyme. At a compound of Formula I concentration of 1.0 µM, which is approximately 320-fold greater than the $IC_{50}$ against the human wild type BTK enzyme and approximately 700-fold greater than the $IC_{50}$ against the BTK C481S mutant enzyme, only eight of 371 kinases other than BTK demonstrated Percent of Control (POC) values less than 50 (equivalent to more than 50% inhibition): BRK, CSK, ERBB4, FYN, MEK1, MEK2, TXK, and YES1 The inhibitory activity of the compound of Formula I on the enzymatic activity of these kinases and TEC is determined using a radiolabeled ATP activity assay conducted with an ATP concentration near the ATP $K_m$ for each enzyme. After co-incubation with a serial dilution of the compound of Formula I, the quantity of $^{33}P$ incorporated into a peptide substrate is measured and the data analyzed using standard curve fitting methods. The results are shown in Table 5.

TABLE 5

Comparison of $IC_{50}$ values

| Enzyme | $IC_{50}$ value (nM) |
|---|---|
| BTK | 3.15 |
| BTK C481S | 1.42 |
| BRK | 54.25 |
| CSK | 552 |
| ERBB4 | 13.25 |
| FYN | 1710 |
| MEK1 | 147 |
| MEK2 | 82.7 |
| TEC | 1234.08 |

TABLE 5-continued

Comparison of $IC_{50}$ values

| Enzyme | $IC_{50}$ value (nM) |
|---|---|
| TXK | 209 |
| YES1 | 157 |

Example 2: Polymorph Screens for the Compound of Formula I

A. Instrumentation and Methods of Analysis

The instruments and methods of analysis used in the polymorph screens described in this Example below are as follows.

X-Ray Powder Diffraction (XRPD)

XRPD analysis is carried out on a Bruker D5000 diffractometer in Bragg-Brentano configuration. Approximately 1 mg of each sample is mounted on a silicon base for analyses. The data are smoothed by use of Fourier algorithms and the background is subtracted from each diffractogram. The following experimental parameters are used.

Source: CuKα
Wavelength: 1.5406 Å
Scan range: 2-40° (2θ)
Step size: 0.01° (2θ)
Time per step: 4.0 s
Source voltage: 40 kV
Source current: 30 mA
Divergence slit width: 2 mm
Antiscatter slit width: 2 mm
Detector slit width: 0.2 mm
Sample rotation: None Nuclear Magnetic Resonance (NMR) Spectroscopy NMR experiments are performed on a Bruker DRX500 spectrometer equipped a 5 mm $^1$H-broadband normal geometry probehead and operative at 500.13 MHz for protons.

Differential Scanning Calorimetry (DSC)

The sample is packed into an aluminum DSC with a punctured lid. The sample pan is then loaded into a Mettler Toledo 823 calorimeter, interfaced with a TA8000 workstation.

B. Initial Characterization

Many crystallization conditions for the compound of Formula I are screened and observed solids are analyzed by XRPD to determine form and crystallinity. The results are shown in Table 6 below.

TABLE 6

Polymorphism Screening

| Sample | Solvent | Conditions | Stirred or Static | Form |
|---|---|---|---|---|
| 1 | Methanol | Evaporation at 25° C. from non-saturated state | Stirred | Amorphous |
| 2 | Acetonitrile | Evaporation at 25° C. | Stirred | Form A |
| 3 | 2-Propanol | Evaporation at 25° C. | Stirred | Form A |
| 4 | Ethanol | Evaporation at 25° C. | Stirred | Form A |
| 5 | Methanol | Rapid solvent removal with boiling | Not Applicable | Form A |
| 6 | Acetone | Rapid solvent removal with boiling | Not Applicable | Amorphous |
| 7 | Methanol | Evaporation at 25° C. | Stirred | Form A + Form B |
| 8 | Methanol | Evaporation at 25° C. | Static | Form A |
| 9 | Acetonitrile | Evaporation at 25° C. | Stirred | Form A |
| 10 | Acetonitrile | Evaporation at 25° C. | Static | Form A |

TABLE 6-continued

Polymorphism Screening

| Sample | Solvent | Conditions | Stirred or Static | Form |
|---|---|---|---|---|
| 11 | 1,4-Dioxane | Evaporation at 25° C. | Stirred | Form C |
| 12 | Ethanol | Evaporation at 25° C. | Stirred | Form A |
| 13 | Ethanol | Evaporation at 25° C. | Static | Form A |
| 14 | Tetrahydrofuran | Evaporation at 25° C. | Stirred | Form A |
| 15 | Tetrahydrofuran | Evaporation at 25° C. | Static | Form A |
| 16 | Methanol | Cooled to −20° C. | Stirred | No crystallization |
| 17 | Methanol | Cooled to −20° C. | Static | No crystallization |
| 18 | Ethanol | Cooled to −20° C. | Stirred | No crystallization |
| 19 | Ethanol | Cooled to −20° C. | Static | No crystallization |
| 20 | Acetone | Cooled to −20° C. | Stirred | No crystallization |
| 21 | Acetone | Cooled to −20° C. | Static | No crystallization |
| 22 | Tetrahydrofuran | Cooled to −20° C. | Stirred | No crystallization |
| 23 | Tetrahydrofuran | Cooled to −20° C. | Static | No crystallization |
| 24 | 1-Butanol | Evaporation at 50° C. | Stirred | Form A |
| 25 | 1-Butanol | Evaporation at 50° C. | Static | Form A |
| 26 | tert-Butyl-Methyl Ether | Not Applicable | Not Applicable | Poor solubility, insufficient sample |
| 27 | 1:1 water:1,4 Dioxane | Evaporation at 25° C. | Stirred | Form A |
| 28 | 1:1 water:1,4 Dioxane | Evaporation at 25° C. | Static | Form A |
| 29 | Methanol | Addition of water anti-solvent at 25° C., with crystallization | Stirred | Form A |
| 30 | Methanol | Addition of water anti-solvent at 25° C., with precipitation | Not Applicable | Amorphous |
| 31 | Methanol | Evaporation at 25° C. | Stirred | Form A (repeat of sample 7) |
| 32 | 1,4-Dioxane | Evaporation at 25° C. | Stirred | Form C (repeat of Sample 11, scaled up) |
| 33 | Methanol | Cooled to −20° C. | Stirred | Form A |
| 34 | Methanol | Cooled to −20° C. | Static | Form A |
| 35 | Ethanol | Cooled to −20° C. | Stirred | No crystallization |
| 36 | Ethanol | Cooled to −20° C. | Static | Form A |
| 37 | Acetonitrile | Cooled to −30° C. | Stirred | Form A |
| 38 | Acetonitrile | Cooled to −30° C. | Static | Form A |
| 39 | Methanol | Evaporation at 25° C. | Stirred | Form A |
| 40 | Methanol | Evaporation at 25° C. | Static | Amorphous |
| 41 | Methanol | Evaporation at 50° C. | Stirred | Form A |
| 42 | Tetrahydrofuran | Evaporation at 25° C. | Stirred | Form A |
| 43 | Tetrahydrofuran | Evaporation at 25° C. | Static | Amorphous |
| 44 | Tetrahydrofuran | Evaporation at 50° C. | Stirred | Form A |
| 45 | Acetone | Evaporation at 25° C. | Stirred | Form A |
| 46 | Acetone | Evaporation at 50° C. | Stirred | Form A |
| 47 | 1,4-Dioxane | Evaporation at 25° C. | Stirred | Form A |
| 48 | 1,4-Dioxane | Evaporation at 25° C. | Static | Form A |
| 49 | 1,4-Dioxane | Evaporation at 50° C. | Stirred | Form A (weak signals) |
| 50 | 1,4-Dioxane | Evaporation at 50° C. | Static | Amorphous |
| 51 | 1-Propanol | Evaporation at 25° C. | Stirred | Form A |
| 52 | 1-Propanol | Evaporation at 25° C. | Static | Form A |
| 53 | 1-Propanol | Evaporation at 50° C. | Stirred | Form A |
| 54 | 1-Propanol | Evaporation at 50° C. | Static | Form A |
| 55 | Acetonitrile | Evaporation at 50° C. | Stirred | Form A |
| 56 | Methanol | Evaporation at 25° C. | Stirred | Form A (repeat of sample 7, scaled up) |
| 57 | Acetonitrile | Evaporation at 50° C. | Static | Form A |
| 58 | Ethanol | Evaporation at 50° C. | Stirred | Form A |
| 59 | Ethanol | Evaporation at 50° C. | Static | Form A |
| 60 | 1-Butanol | Evaporation at 50° C. | Stirred | Form A |
| 61 | 1-Butanol | Evaporation at 50° C. | Static | Form A |
| 62 | 2-Butanone | Evaporation at 50° C. | Stirred | Form A |
| 63 | 2-Butanone | Evaporation at 50° C. | Static | Form A |
| 64 | Ethylacetate | Evaporation at 50° C. | Stirred | Form A |
| 65 | Ethylacetate | Evaporation at 50° C. | Static | Form A |
| 66 | Ethanol | Evaporation at 25° C. | Static | Form A |
| 67 | Methanol | Evaporation at 25° C. | Stirred | Form A (repeat of sample 7, scaled up) |

TABLE 6-continued

Polymorphism Screening

| Sample | Solvent | Conditions | Stirred or Static | Form |
|---|---|---|---|---|
| 68 | 1,4-Dioxane | Evaporation at 25° C. | Stirred | Form C (repeat of Sample 11, scaled up) |
| 69 | Methanol | Evaporation at 25° C. | Stirred | Form A (repeat of sample 7, scaled up) |
| 70 | 1,4-Dioxane | Evaporation at 25° C. | Stirred | Form C (repeat of Sample 11, scaled up) |
| 71 | Methanol:water (3:1) | Evaporation at 25° C. | Stirred | Form A |
| 72 | Methanol | Evaporation at 50° C. | Stirred | Form A |
| 73 | 1,4-Dioxane | Evaporation at 50° C. | Stirred | Form A |
| 74 | Methanol:water (3:1) | Evaporation at 50° C. | Stirred | Form A |

C. Polymorph Form A of the Compound of Formula I

For Sample 67, approximately 10 mg of the compound of Formula I is weighed into a glass vial and dissolved in methanol to afford a saturated solvent. The solvent is then evaporated at 25° C. with stirring. After the compound of Formula I crashed out of the solution, the crystals are collected via filtering. The compound of Formula I is analyzed by XRPD (FIG. 1) and identified as Form A.

D. Polymorph Form B of the Compound of Formula I

Figure 2A:
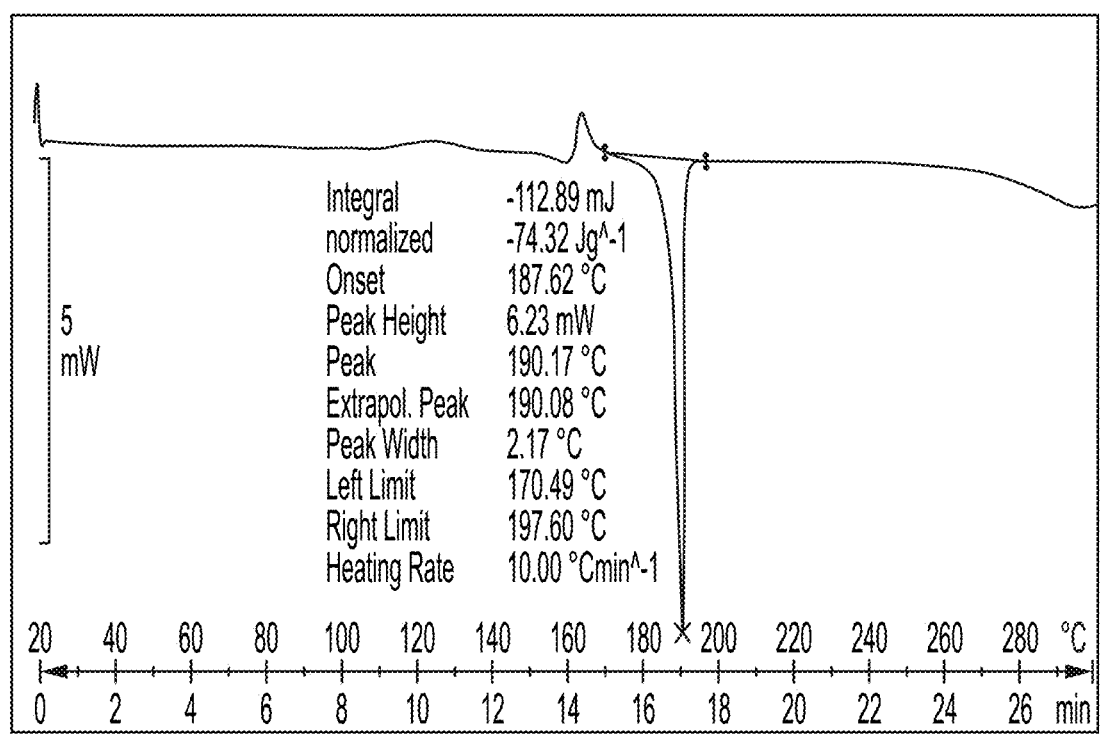
FIGS. 2A-2B are scans of a mixture of Forms A and B of the compound of Formula I.
Figure 2B:
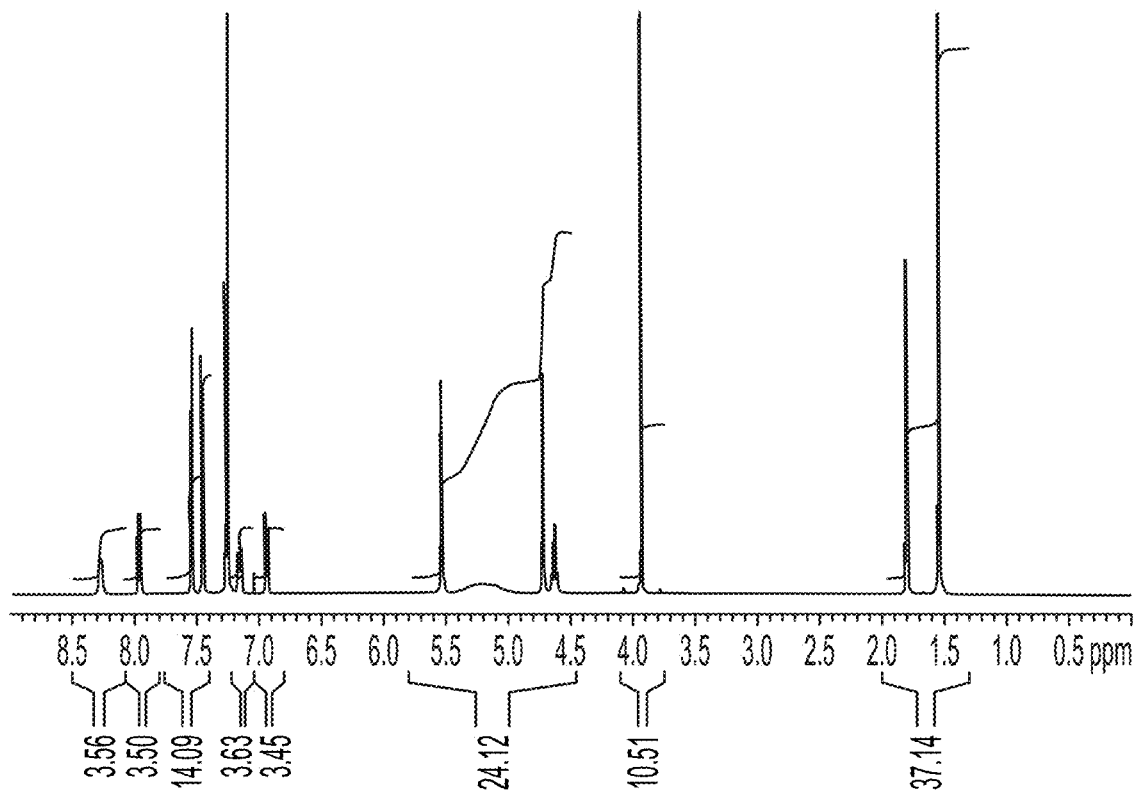

For Sample 7, approximately 10 mg of the compound of Formula I is weighed into a glass vial and dissolved in methanol to afford a saturated solvent. The solvent is then evaporated at 25° C. with stirring, and the crystals are collected. Form B crystallized as a mixture with Form A in methanol. The DSC of the mixture of Forms A and B exhibited a small exotherm having an onset of approximately 120° C. and an onset of a melt at approximately 145° C., likely the melt of Form B (FIG. 2A). Following the melt at approximately 145° C., an exothermic event occurred, which is ascribed to the conversion of the melt to Form A. An endothermic event of onset temperature 180° C. is ascribed to the melt of Form A. A pure sample of Form B is required to determine the DSC curve for Form B. FIG. 2B shows a $^1$H spectrum of the Form A and Form B mixture.

E. Polymorph Form C of the Compound of Formula I

Figure 3A:
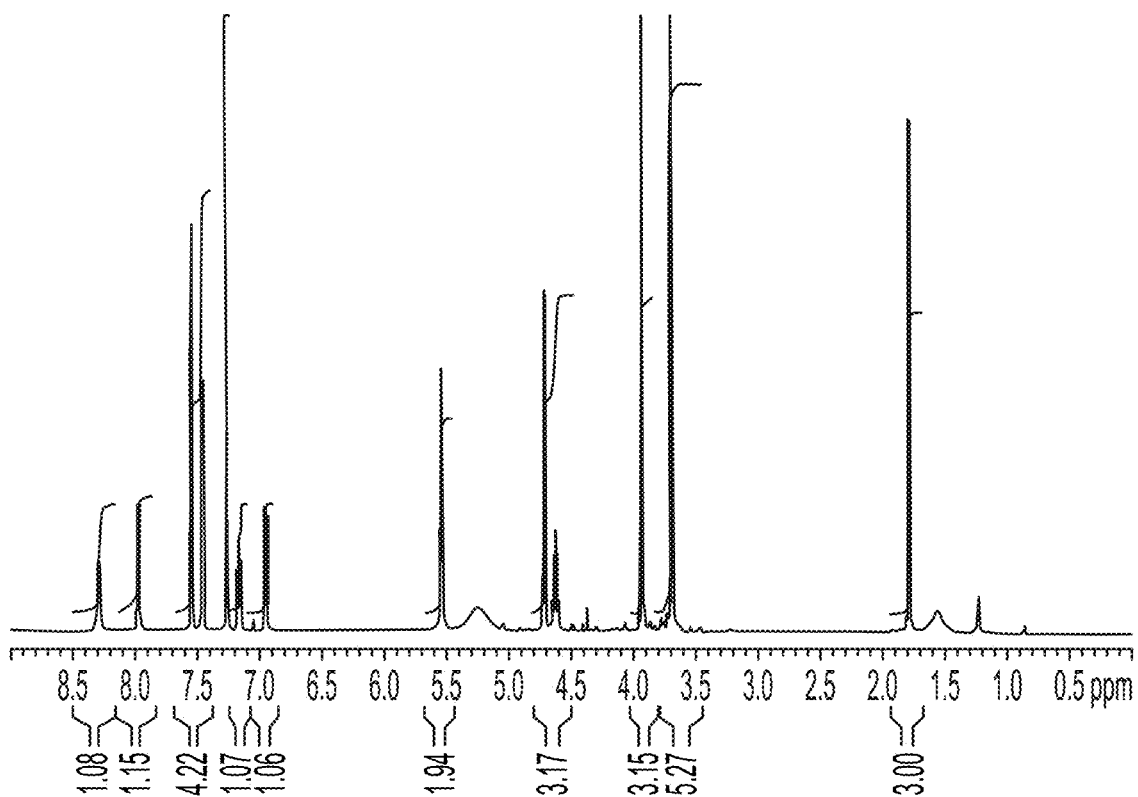
FIGS. 3A-3B. are scans of Form C of the compound of Formula I.
Figure 3B:
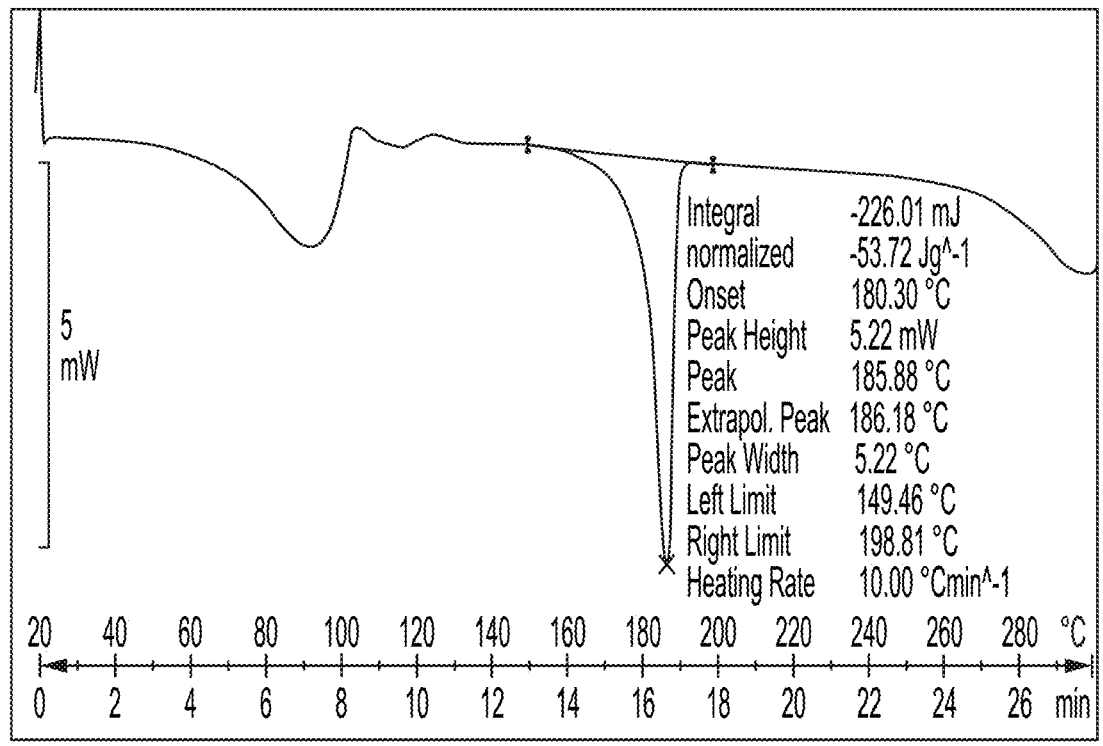

For Sample 32, approximately 10 mg of the compound of Formula I is weighed into a glass vial and dissolved in 1,4-dioxane to afford a saturated solvent. The solvent is then evaporated at 25° C. with stirring, and the crystals collected. Based on the $^1$H NMR spectrum, Form C is a hemi-1,4-dioxane solvate (FIG. 3A). The DSC curve of Form C exhibited an endotherm between 40-110° C., associated with the loss of 1,4-dioxane (FIG. 3B). The endothermic event is followed by a small exothermic event, which is subsequently followed by a melt endotherm, ascribed to melting of Form A. The desolvation may occur to either afford an isomorphous desolvate or a different physical form prior to conversion to polymorphic Form A.

F. Other Methods to Prepare Form A of the Compound of Formula I

About 10 g of the compound of Formula I is suspended in isopropanol (50 mL, 5 mL/g) and heated to dissolution. The warm solution is polish filtered and allowed to cool slowly to room temperature. The resulting solid is collected by filtration and dried to give 8.57 g (86%) of the compound of Formula I as Form A by XRPD.

About 20 g of the compound of Formula I is suspended in isopropanol (50 mL, 5 mL/g) and heated to dissolution. The warm solution is polish filtered and added to a reactor containing water (70 mL, 7 vol). The resulting solid is collected by filtration and dried to give 18.47 g (92%) of the compound of Formula I as Form A by XRPD.

About 15.1 g of the compound of Formula I is suspended in ethanol (76 mL, 5 mL/g) and heated to dissolution (about 70° C.). The warm solution is polish filtered into a jacketed vessel and allowed to cool to −59° C., where the compound of Formula I Form A seeds (15 mg) are charged. The reactor is cooled to 55° C. and heptane (91 mL, 6 mL/g) is added dropwise over 4 hours. The suspension is cooled to 15° C. over 1 hour. The resulting solid is collected by filtration, washed with ethanol:heptane (5:6 ratio, 30 mL, 2 mL/g), and dried to give 10.3 g (68%) of the compound of Formula I as Form A by XRPD.

About 2.5 g of the compound of Formula I is suspended in ethyl acetate (25 mL, 10 mL/g) and heated to dissolution (~75° C.). It is then allowed to cool to ~45° C. and seeded with the compound of Formula I Form A, followed by slow addition of heptane (22.5 mL, 9 mL/g). The suspension is held at 45° C. overnight then allowed to cool to 24° C. The resulting solid is collected by filtration and dried to give 1.6 g (64%) of the compound of Formula I as Form A by XRPD.

Example 3: Larger-Scale Preparation of Form A of the Compound of Formula I

A. Experimental Procedure

To a 1 L cylindrical reactor is charged the compound of Formula I [non-Form A intermediate grade (S)-5-amino-3-(4-((5-fluoro-2-methoxybenzamido)methyl)phenyl)-1-(1,1,1-trifluoropropan-2-yl)-1H-pyrazole-4-carboxamide] (80.0 g, 167 mmol, 1.0 eq). Methanol (600 mL, 7.5 volumes) is added, and the suspension stirred at room temperature until all solids dissolved. The solution is polish filtered, and the filtrate transferred to a clean, dry 5 L cylindrical jacketed reactor. Methanol (40 mL, 0.5 volumes) is used to aid in the transfer of organics to the reactor. The solution is heated to 55±5° C. Water (640 mL, 8 volumes) is charged via addition funnel over the course of 2 hr at a rate of ~5.33 mL/min. A suspension formed. The reactor is cooled to 15±5° C. at a rate of 10° C./hr and stirred at room temperature overnight. The solids are filtered over polypropylene cloth (in a Buchner funnel) and washed with 1:1 water:methanol (2×80 mL, 2×1 volume) and pulled dry on the filter cake for ~10 min. The solids are dried in a vacuum oven at 55° C. until constant mass is achieved to yield 74.0 g of a tan, crystalline/sandy solid of the compound of Formula I that exhibited 100 Area % HPLC purity.

B. Form A of the Compound of Formula I

Figure 4A:
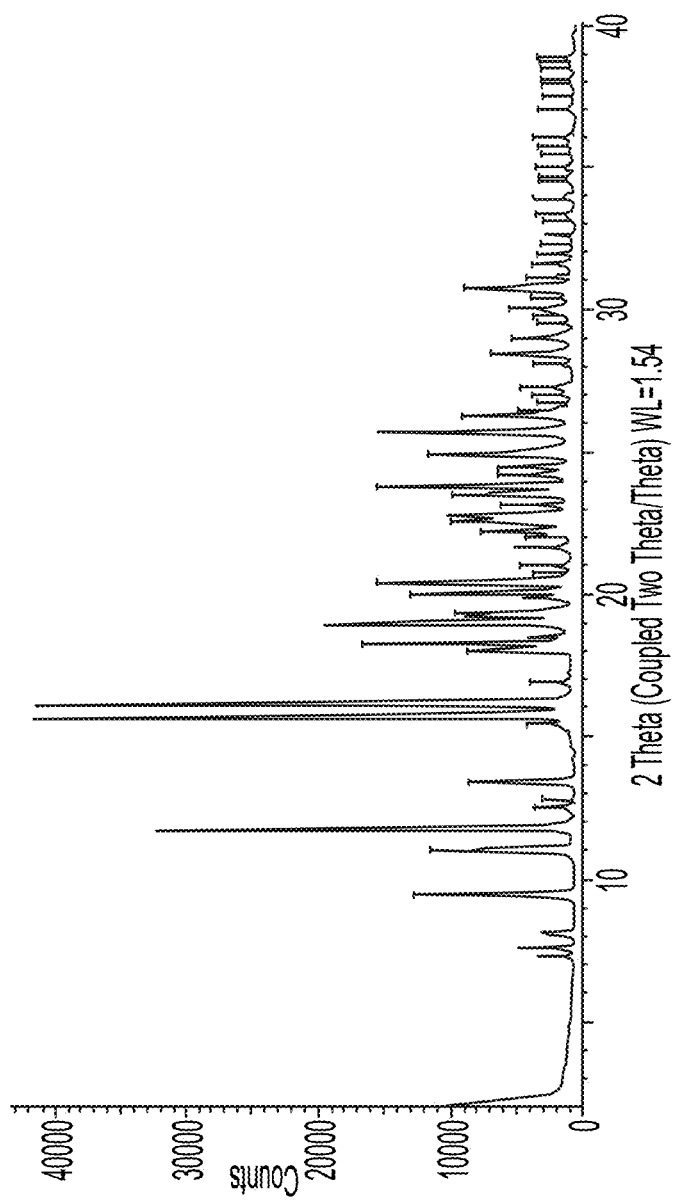
FIGS. 4A-4C are scans of Form A of the compound of Formula I.
Figure 4B:
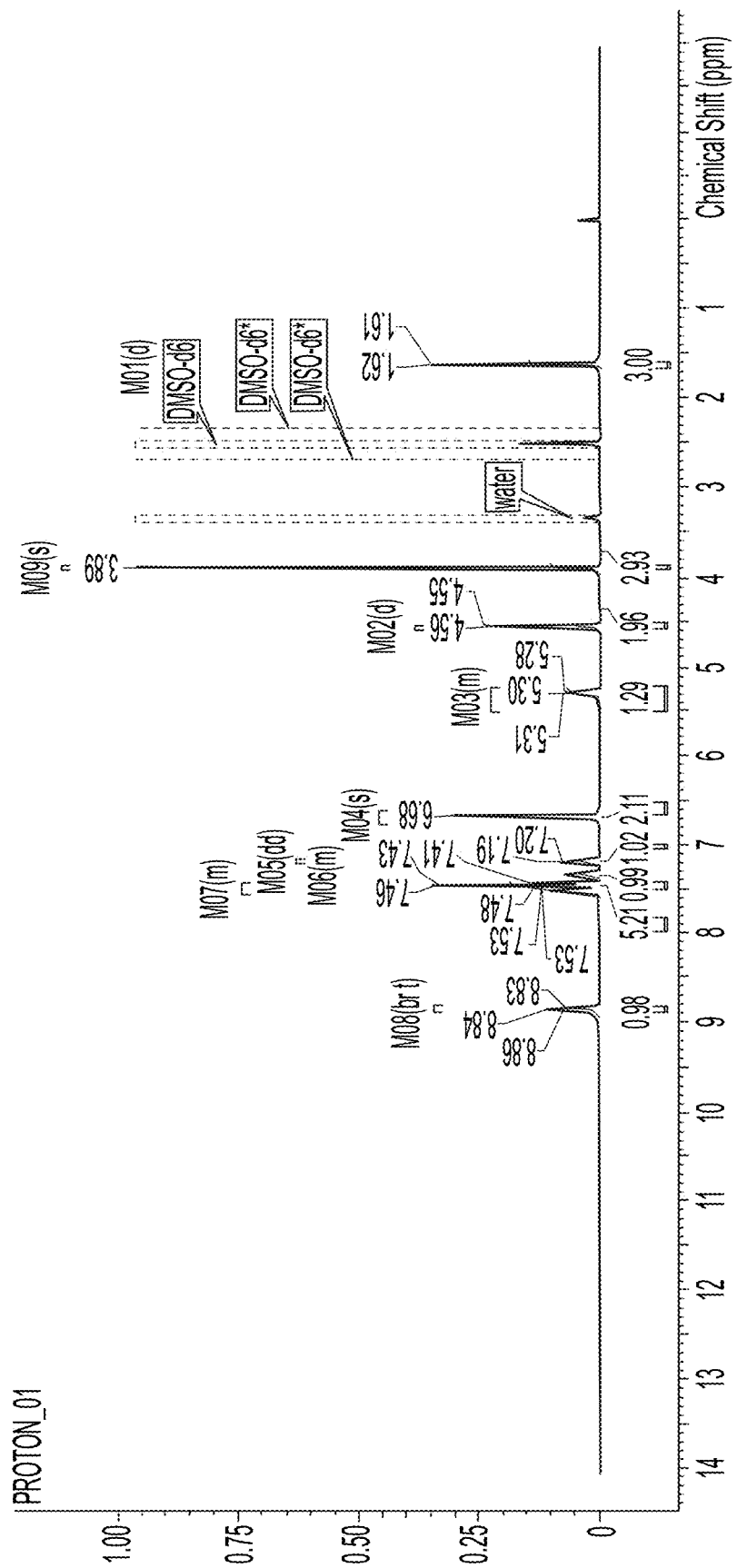
Figure 4C:
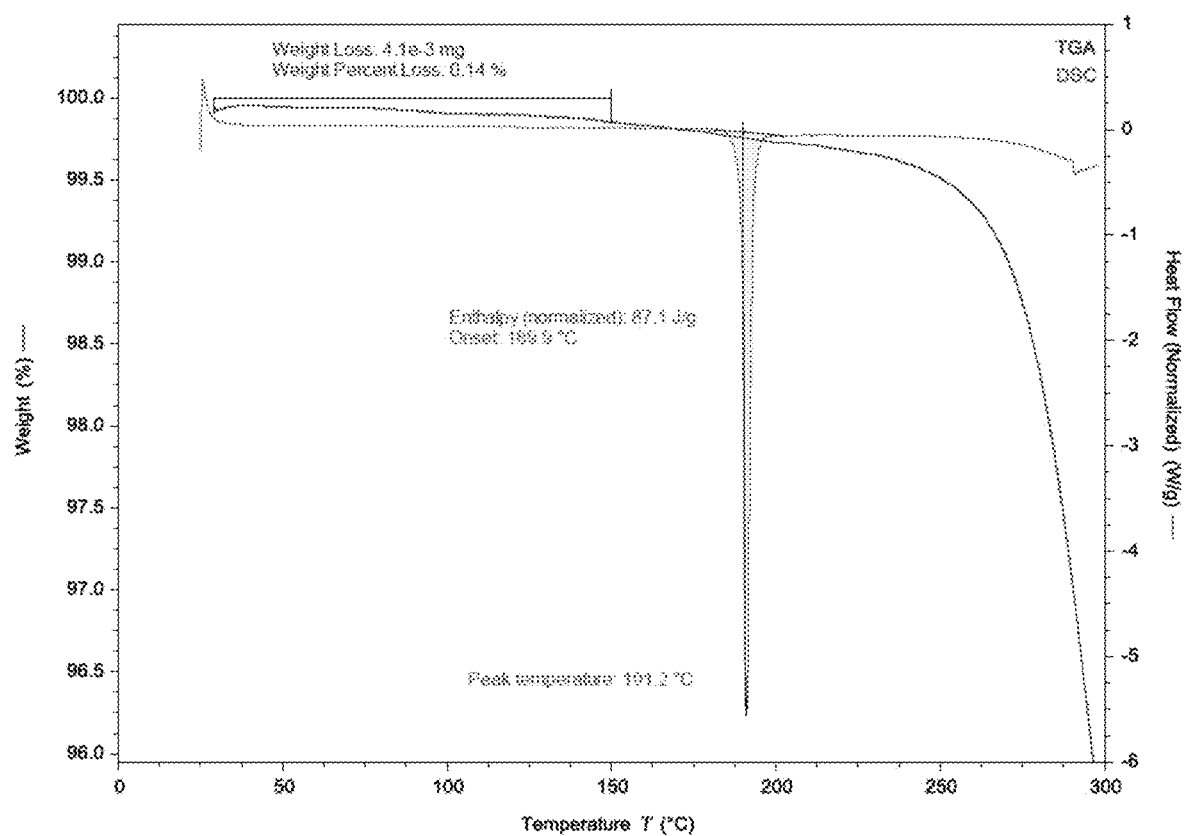

The compound of Formula I, prepared as described in Example 3A, is analyzed by XRPD, $^1$H NMR, and DSC/TGA, and identified as Form A. The X-ray powder diffraction scan of Form A is shown in FIG. 4A. The X-ray powder diffraction peaks of Form A are shown in Table 7. The $^1$H NMR spectrum is shown in FIG. 4B. An endothermic event is observed by DCS at an onset of around 185° C. (FIG. 4C).

TABLE 7

XRPD peaks of Form A of the compound of Formula I

| 2-Theta | d(Å) | Net Intensity | Gross Intensity | H % |
|---|---|---|---|---|
| 7.30 | 12.10 | 569 | 1176 | 1.5 |
| 7.60 | 11.62 | 2089 | 2675 | 5.4 |
| 9.50 | 9.30 | 10102 | 10619 | 25.9 |
| 11.05 | 8.00 | 8776 | 9290 | 22.5 |
| 11.85 | 7.46 | 29569 | 30085 | 75.9 |
| 12.56 | 7.04 | 863 | 1379 | 2.2 |
| 12.80 | 6.91 | 285 | 802 | 0.7 |
| 13.46 | 6.58 | 5918 | 6436 | 15.2 |
| 15.46 | 5.73 | 1560 | 2085 | 4.0 |
| 15.76 | 5.62 | 38951 | 39477 | 100.0 |
| 16.21 | 5.46 | 38698 | 39227 | 99.4 |
| 16.93 | 5.23 | 1097 | 1629 | 2.8 |
| 18.06 | 4.91 | 5979 | 6515 | 15.3 |
| 18.31 | 4.84 | 13762 | 14300 | 35.3 |
| 18.55 | 4.78 | 1349 | 1887 | 3.5 |
| 19.01 | 4.67 | 16646 | 17186 | 42.7 |
| 19.26 | 4.60 | 6157 | 6698 | 15.8 |
| 19.36 | 4.58 | 6825 | 7367 | 17.5 |
| 19.86 | 4.47 | 1744 | 2287 | 4.5 |
| 20.06 | 4.42 | 10380 | 10923 | 26.6 |
| 20.46 | 4.34 | 12770 | 13315 | 32.8 |
| 20.71 | 4.29 | 921 | 1467 | 2.4 |
| 21.01 | 4.23 | 1996 | 2542 | 5.1 |
| 21.66 | 4.10 | 2278 | 2827 | 5.8 |
| 22.04 | 4.03 | 1484 | 2033 | 3.8 |
| 22.21 | 4.00 | 5032 | 5581 | 12.9 |
| 22.61 | 3.93 | 7156 | 7706 | 18.4 |
| 22.76 | 3.90 | 7386 | 7936 | 19.0 |
| 23.16 | 3.84 | 3379 | 3931 | 8.7 |
| 23.51 | 3.78 | 7098 | 7650 | 18.2 |
| 23.81 | 3.73 | 12827 | 13380 | 32.9 |
| 24.21 | 3.67 | 3621 | 4174 | 9.3 |
| 24.46 | 3.64 | 3586 | 4140 | 9.2 |
| 24.91 | 3.57 | 8919 | 9473 | 22.9 |
| 25.71 | 3.46 | 12725 | 13280 | 32.7 |
| 26.27 | 3.39 | 6504 | 7059 | 16.7 |
| 26.46 | 3.37 | 2248 | 2803 | 5.8 |
| 26.74 | 3.33 | 620 | 1176 | 1.6 |
| 27.02 | 3.30 | 1158 | 1714 | 3.0 |
| 27.26 | 3.27 | 2105 | 2661 | 5.4 |
| 28.06 | 3.18 | 839 | 1395 | 2.2 |
| 28.41 | 3.14 | 4360 | 4916 | 11.2 |
| 28.96 | 3.08 | 2596 | 3152 | 6.7 |
| 29.57 | 3.02 | 753 | 1309 | 1.9 |
| 29.81 | 2.99 | 1115 | 1671 | 2.9 |
| 30.01 | 2.98 | 2826 | 3381 | 7.3 |
| 30.39 | 2.94 | 1269 | 1824 | 3.3 |
| 30.76 | 2.90 | 6239 | 6794 | 16.0 |
| 31.12 | 2.87 | 1636 | 2191 | 4.2 |
| 31.61 | 2.83 | 1196 | 1749 | 3.1 |
| 31.94 | 2.80 | 773 | 1326 | 2.0 |
| 32.29 | 2.77 | 481 | 1034 | 1.2 |
| 32.61 | 2.74 | 284 | 836 | 0.7 |
| 33.11 | 2.70 | 311 | 864 | 0.8 |
| 33.32 | 2.69 | 829 | 1382 | 2.1 |
| 33.92 | 2.64 | 989 | 1543 | 2.5 |
| 34.53 | 2.60 | 571 | 1127 | 1.5 |
| 34.66 | 2.59 | 599 | 1155 | 1.5 |
| 35.02 | 2.56 | 884 | 1441 | 2.3 |
| 35.44 | 2.53 | 433 | 990 | 1.1 |
| 35.74 | 2.51 | 685 | 1243 | 1.8 |
| 36.07 | 2.49 | 1106 | 1665 | 2.8 |
| 37.07 | 2.42 | 709 | 1272 | 1.8 |
| 37.52 | 2.40 | 273 | 841 | 0.7 |
| 37.97 | 2.37 | 367 | 939 | 0.9 |
| 38.12 | 2.36 | 470 | 1044 | 1.2 |
| 38.52 | 2.34 | 447 | 1024 | 1.1 |
| 38.77 | 2.32 | 565 | 1144 | 1.4 |
| 38.92 | 2.31 | 772 | 1353 | 2.0 |

Example 4: Preparation of the Spray-Dried Dispersion (SDI/SDD) of the Compound of Formula I A. Solubility Screening The solubility of the compound of Formula I is tested at different pH values in an aqueous solution as shown in Table 8.

TABLE 8

Aqueous solubility of the compound of Formula I at different pH values

| | Actual Media pH | Solubility (μg/mL) | Final Filtrate pH | XRPD |
|---|---|---|---|---|
| (0.1 N HCl) pH 1 | 1.09 | 17 | 1.03 | Form A |
| pH 1.5 | 1.49 | 15 | 1.43 | Form A |
| pH 2 | 2.06 | 15 | 2 | Form A |
| pH 3 | 3.03 | 14 | 3.02 | Form A |
| pH 4 | 4.04 | 14 | 4.04 | Form A |
| pH 6 | 6.04 | 14 | 5.99 | Form A |
| pH 8 | 8.02 | 14 | 7.95 | Form A |
| pH 10 | 9.98 | 14 | 9.88 | Form A |

The solubility of the compound of Formula I is 14-17 μg/mL between pH 1 to pH 10.

The solubility of the compound of Formula I is also tested under conditions that simulate gut fluids (Fasted State Simulated Intestinal Fluid [FaSSIF], Fed State Simulated Intestinal Fluid [FeSSIF], and Fasted State Simulated Gastric Fluid [FaSSGF]) as shown in Table 9.

TABLE 9

Kinetic solubility of the compound of Formula I in FaSSGF, FaSSIF, and FeSSIF media

| Buffer condition | 4 hours, μg/mL | 24 hours, μg/mL | Final pH | XRPD |
|---|---|---|---|---|
| pH 1.6 FaSSGF | 22 | 24 | 1.66 | Form A |
| pH 6.5 FaSSIF | 23 | 20 | 6.5 | Form A |
| pH 6.5 FeSSIF | 44 | 47 | 5.83 | Form A |

The solubility of the compound of Formula I in lipid vehicles is also examined. The compound of Formula I Form A is added into a clear, 20 mL glass vials followed by the corresponding excipients, e.g., MIGLYOL® 812 (saturated coconut and palmkernel oil-derived caprylic and capric fatty acids and glycerin, e.g., C8 and C10 triglycerides), CAPMUL® MCM EP (glyceryl monocaprylocaprate type I (EP)), PECEOL™ (glycerol monooleates (type 40) EP, glyceryl monooleate (type 40) NF), LABRAFIL® M2125CS (linoleoyl polyoxyl-6 glycerides), LAUROGLYCOL™ FCC (propylene glycol monolaurate (type I)), Span® 80 (sorbitane monooleate), PHOSAL® 53 MCT (lecithin in caprylic/capric triglycerides, alcohol, glyceryl stearate, oleic acid, and ascorbyl palmitate), or capmul PG-8 (propylene glycol monocaprylate). The samples are then homogenized with a handheld homogenizer for 10 minutes until the compound of Formula I is visibly dissolved. The samples are mixed overnight at ambient conditions. A set of matching control formulations are also prepared. The excipient screen for the lipid-based formulations showed that the solubility of the compound of Formula I is best in PEG 400, LABRASOL® ALF (e.g., caprylocaproyl polyoxyl-8 glycerides), KOLLIPHOR® EL (e.g., polyoxyl castor oil), Tween 80, and Vitamin E TPGS.

TABLE 10

Summary of solubility screening in lipid vehicles

| Vehicle | Incubation Temp, °C. | HPLC Solubility (mg API per g mixture) | XRPD of Residue |
|---|---|---|---|
| Long chain triglycerides/long chain lipid digestion products | 25 | 0.02 | Form A |
| Medium chain triglycerides/medium chain lipid digestion products | 25 | 0.02 | Form A |
| MIGLYOL® 812 | 25 | 0.62 | Form A |
| Sesame oil | 25 | 0.07 | Form A |
| CAPMUL® MCM EP | 40 | 33.3 | Form A |
| Oleic acid | 25 | 1.2 | Form A |
| Propylene glycol | 25 | 29.4 | Form A |
| PEG-400 (Macrogol 400) | 25 | 168.9 | Form A |
| LABRASOL® ALF | 25 | 104.1 | Form A |
| PECEOL™ | 40 | 6.6 | Form A |
| KOLLIPHOR® EL | 25 | 46.2 | Form A |
| LABRAFIL® M2125CS | 25 | 3.2 | Form A |
| Vitamin E-TPGS NF | 40 | 43.1 | Consistent with Vitamin E TPGS; crystalline compound of Formula I not detected |
| Glycerine | 25 | 0.5 | Form A |
| Polysorbate 80/Tween-80 | 25 | 43.6 | Form A |
| LAUROGLYCOL™ FCC | 25 | 5.1 | Form A |
| SPAN® 80 | 25 | 6.2 | Form A |
| PHOSAL® 53 MCT | 25 | 11.3 | Form A |
| Capmul PG-8 | 25 | 30.3 | Form A |

API refers to active pharmaceutical ingredient.

Of the excipients tested, the compound of Formula I is most soluble in LABRASOL® ALF and PEG-400.

B. Solid Dispersion by Spray-Drying the Compound of Formula I

Solubility screening in organic solvents showed methanol, acetone, dichloromethane, 95:5 tetrahydrofuran:water, and 80:20 dichloromethane:methanol are appropriate solvents for spray-drying. Four spray-dried dispersions (SDD) are prepared comprising the compound of Formula I and HPMCAS-MG (granulated hypromellose acetate with an acetyl content of about 7% to about 11% and succinoyl content of about 10% to about 14%), HPMC E3 (hypromellose with an average content of 29% methoxyl groups and 10% hydroxypropyl groups), KOLLIDON® VA64 (vinylpyrrolidone-vinyl acetate copolymers with an average particle size from about 50 µm to about 250 50 µm) or PVPK30 (polyvinylpyrrolidone polymer with an average molecular weight of 44,000 to 54,000 g/mol). The compositions of the formulations developed is shown in and Table 11 and Table 12.

TABLE 11

Candidate spray-dried dispersion formulations of the compound of Formula I

| Sample | Ingredients | API Content (w/w %) |
|---|---|---|
| 1 | Compound of Formula I in HPMCAS-MG | 20 |
| 2 | Compound of Formula I in HPM CE3 | 20 |
| 3 | Compound of Formula I in KOLLIDON® VA64 | 20 |
| 4 | Compound of Formula I in PVPK30 | 20 |

TABLE 12

Candidate spray solution compositions

| Component | Sample 1 | Sample 2 | Sample 3 | Sample 4 |
|---|---|---|---|---|
| Compound of Formula I (g) | 1.0 | 1.0 | 1.0 | 1.0 |
| Polymer (g) | 4.0 | 4.0 | 4.0 | 4.0 |
| Solvent System—80:20 dicholoromethane:methanol (g) | 95 | 95 | 95 | 95 |

Figure 5:
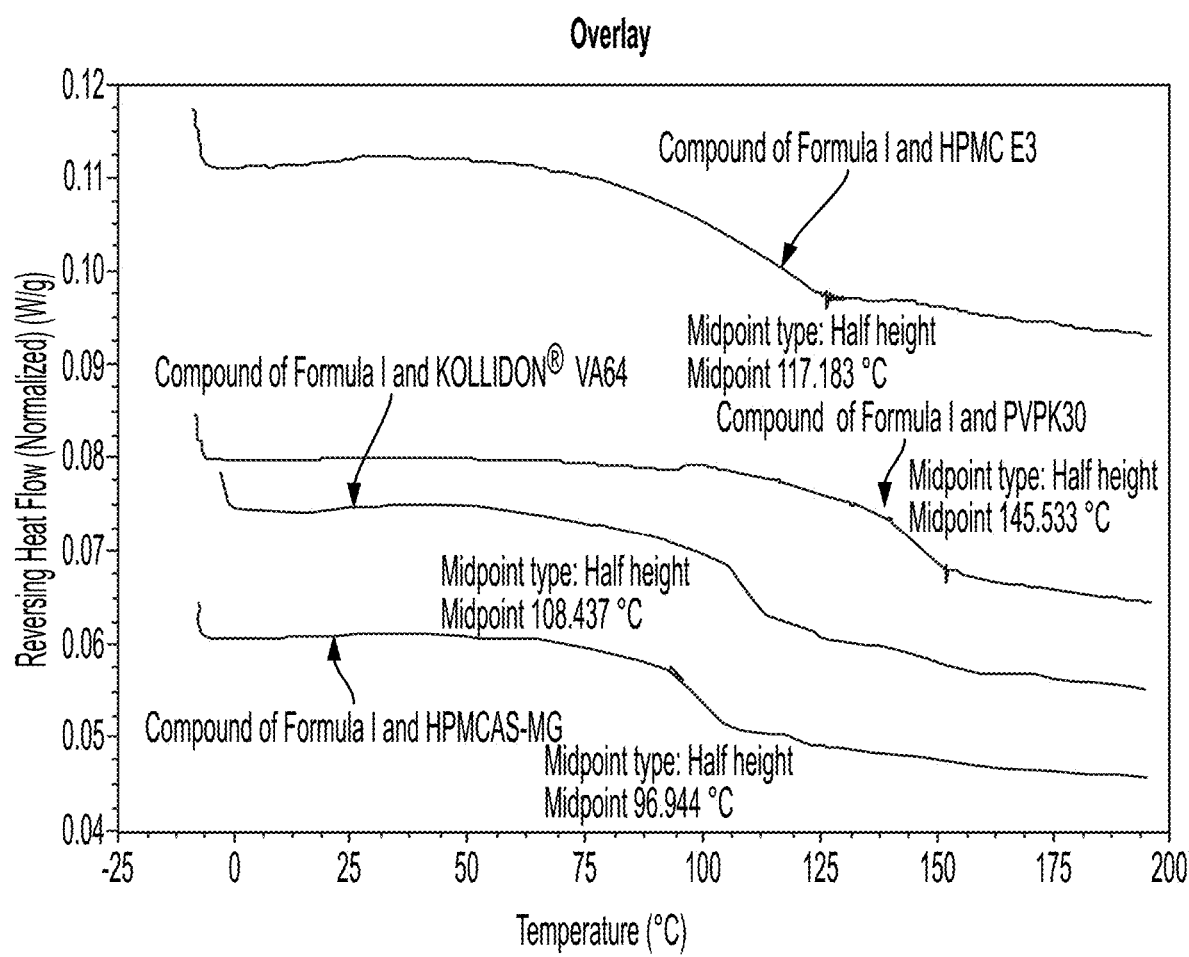
FIG. 5 is a modulated DSC scan of the spray-dried dispersion prototypes of the compound of Formula I.
Figure 6:
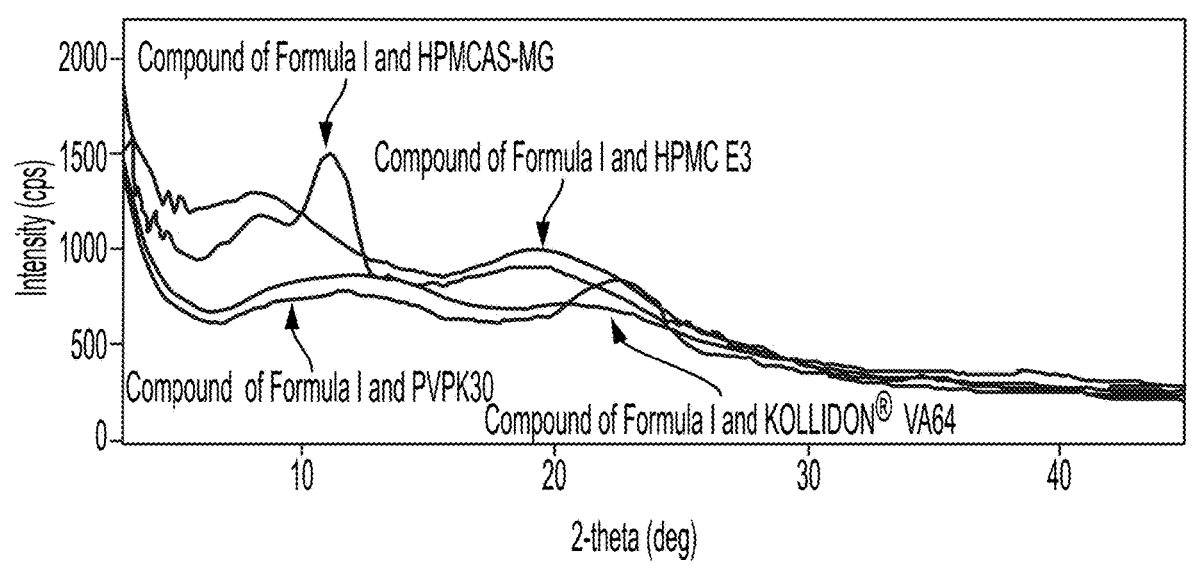
FIG. 6 is an X-ray powder diffraction scan of the spray-dried dispersion prototypes of the compound of Formula I.
Figure 7:
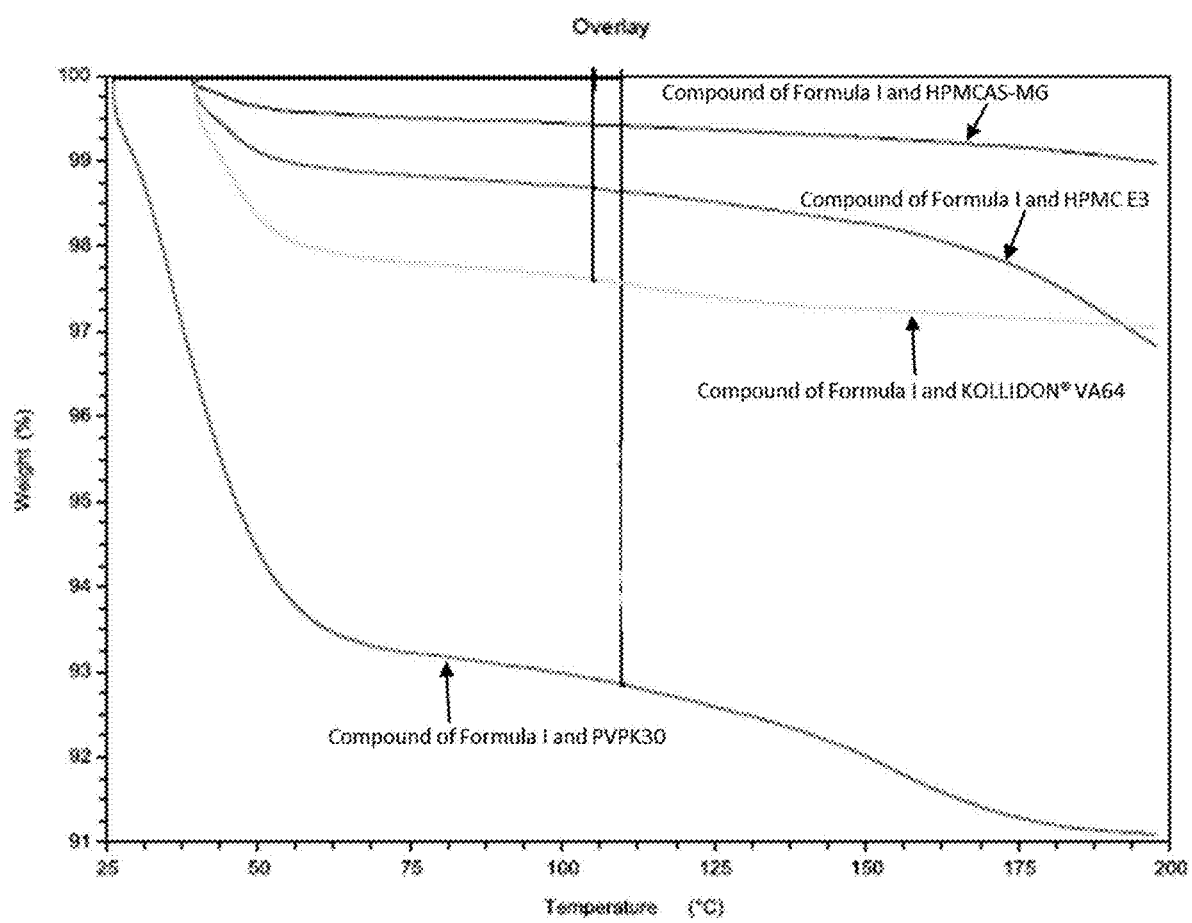
FIG. 7 is a thermogravimetric analysis (TGA) scan of the spray-dried dispersion prototypes of the compound of Formula I.

The prepared spray-dried dispersion prototypes are assessed by mDSC (FIG. 5), by XRPD (FIG. 6) and by TGA (FIG. 7). Key results are summarized in Table 13.

TABLE 13

Post-drying analysis

| Sample | mDSC | XRPD | TGA |
|---|---|---|---|
| 1 | Single Tg = 98.9° C.; no melt endotherm | Amorphous halo | 0.56% |
| 2 | Single Tg = 117.1° C.; no melt endotherm | Amorphous halo | 1.29% |
| 3 | Single Tg = 108.4° C.; no melt endotherm | Amorphous halo | 2.34% |
| 4 | Single Tg = 145.5° C.; no melt endotherm | Amorphous halo | 7.10% |

XRPD and mDSC data both confirmed that the four prototypes are amorphous and free of any detectable levels of crystalline material. All four SDIs are stable at 40° C. for 2 weeks with regard to purity and amorphous form.

C. Spray Solution and Spraying

The spray solution is prepared by adding dichloromethane (14.3 kg) and methanol (3.6 kg) to a 36 L stainless steel mixing vessel. The HPMCAS-MG (984 g) is added to the solvent system while mixing with a top down mixer at a medium vortex until the polymer is completely solubilized. The compound of Formula I (995 g, corrected for 98.8 wt. %) is then added to the solution at a medium vortex and left to mix until completely solubilized (see Table 14). The spray solution is passed through a 140 µm inline filter during spraying. The viscosity of the spray solution is measured as 23.86 cP.

TABLE 14

The compound of Formula I solution preparation weights

| Component | Component Type | Formulation (%) | Total Target Weight (g) |
|---|---|---|---|
| Compound of Formula I | Drug substance | 5.00 | 995 |

TABLE 14-continued

The compound of Formula I solution preparation weights

| Component | Component Type | Formulation (%) | Total Target Weight (g) |
|---|---|---|---|
| HPMCAS-MG | Polymer (Hydroxy propyl methyl cellulose acetate succinate) | 4.95 | 983.6 |
| Dichloromethane | Solvent | 72.04 | 14328 |
| Methanol | Solvent | 18.01 | 3582 |
| Total | | 100.00 | 19888.6 |

A Mobile Minor sprayer dryer is utilized and is setup per Table 15 and warmed up for approximately one hour prior to spraying. A wash solution (80:20 dichloromethane:methanol) is sprayed prior to the active solution to allow the nozzle to equilibrate. The compound of Formula I active solution is sprayed per the settings also in Table 15.

TABLE 15

Mobile Minor Setup/Set Points

| Parameter | Set Point |
|---|---|
| Inline Filter | Swagelok 140 μm Stainless Steel |
| Nozzle | 0.3 mm, 60° Angle |
| Inlet Air Flow | 80 kg/hr |
| Inlet Air Temperature | 90° C. |
| Pump Stroke Length | 4.65 mm |
| Nozzle Pressure | 500 psi |
| Feed Rate (g/min) | 165 g/min |
| Outlet Temp (° C.) | 35 |
| Set Condenser Air Temp (° C.) | −10 |
| Actual Condenser Air Temp (° C.) | −3 |
| Chiller Temp (° C.) | −3 |
| Feed Temp | Ambient |

Approximately 20 kg of solution is sprayed yielding 1840.54 g of 'wet' spray-dried intermediate (SDI). After spraying, the SDI is dried (4 days) in a Shel Vacuum Oven at 40° C. and −25 in Hg vacuum under a nitrogen purge at 10 scfh. Samples are taken before the SDI is put in the oven and after drying to be analyzed for residual solvents via GC analysis to verify the SDI is dry. The GC results after 4 days of drying are within the target limits for both dichloromethane (<600 ppm, actual is 65 ppm) and methanol (<3000 ppm, actual is 9 ppm). The SDI is dried for a total of 86 hours. The dried SDI is analyzed for bulk/tap density and particle size distribution. The SDI is packaged in double low-density polyethylene bags, desiccated, and then sealed in a Mylar bag. 1742.90 g of the compound of Formula I SDI is collected resulting in an 88% yield.

D. Spray Solution and Spraying

The spray solution is prepared by adding methanol (62.0 kg) to the solution preparation vessel. The compound of Formula I (5.9 kg) is added while mixing. The HPMCAS-MG (5.9 kg) is added to the solution preparation vessel while mixing until the polymer and compound of Formula I are completely solubilized. A slightly hazy appearance is acceptable. See Table 16.

TABLE 16

The compound of Formula I solution preparation weights

| Component | Component Type | Formulation (%) | Total Target Weight (kg) |
|---|---|---|---|
| Compound of Formula I | Drug substance | 8.0 | 5.9 |
| HPMCAS-MG | Polymer (Hydroxy propyl methyl cellulose acetate succinate) | 8.0 | 5.9 |
| Methanol | Solvent | 84.0 | 62.0 |
| Total | | 100.00 | 73.8 |

A BLD-200 sprayer dryer is utilized and is setup per Table 17. A wash solution (methanol) is sprayed prior to the active solution to allow the nozzle to equilibrate, and cooling water is run through the spray dryer lid during processing. The compound of Formula I active solution is sprayed per the settings in Table 17.

TABLE 17

BLD-200 and Dryer Set Points

| Parameter | Value |
|---|---|
| Pressure Swirl Nozzle | SK 80-16 |
| Drying Gas Flow | 3300 g/min |
| Drying Gas Inlet Temperature | 125° C. |
| Dryer Outlet Temperature | 45° C. |
| Solution Feed Rate | 225 g/min |
| Nozzle Pressure | 315 psi |
| Calculated Dryer Relative Saturation | 10 wt % |
| Solution feed fdter | ≤250 μm |

After spraying, the SDI is dried (21 hours) in an oven at 40° C./15% relative humidity. The GC results after 19 hours of drying are within the target limits for methanol (<0.3 wt %, actual is below limit of quantitation) and 9.96 kg of the compound of Formula I SDI is collected resulting in an 84% yield.

Example 5: Pharmaceutical Composition Containing a Spray-Dried Dispersion of the Compound of Formula I A. Preparation of an Intragranular Composition Containing the Compound of Formula I The following components are weighed out in the following order and added to an appropriately-sized glass jar: about half of the microcrystalline cellulose, about half of the mannitol or lactose, all of the SDI and disintegrant, the remaining half of the mannitol or lactose, and the remaining half of the microcrystalline cellulose. The components are mixed on a Turbula and then sieved through an 850 μm screen. The components are again mixed on the Turbula. The magnesium stearate is added, and the mixture is mixed on the Turbula. For larger-scale runs, a V-blender is used instead of the Turbula.

B. Granulation of the Intragranular Composition

The intragranular also referred to as the first composition is slugged on a single station tablet press using Natoli 0.7" flat faced tooling at a compression force of 2200 PSI. The slugging procedure is repeated until the first composition is exhausted. A mortar and pestle is used to lightly break up slugs, and the composition is passed through a 1 mm sieve screen and then an 850 μm sieve screen. The granule pieces that are too large to pass through the 1 mm or the 850 μm sieve screens, are broken up further in the mortar and pestle. The process is repeated until all pieces passed through the 850 μm sieve screen.

C. Example of a Pharmaceutical Composition Containing the Compound of Formula I

A pharmaceutical composition can be prepared by combining the intragranular composition, prepared as described above, with extragranulated components including an integrant, a glident and a lubricant as listed in Table 18 to provide the pharmaceutical composition, which can be used to prepare compositions and tablets including various doses of the compound of Formula I as further described in Examples 6-8 below.

TABLE 18

Formula I pharmaceutical composition

| | | Formulation Reference | | | |
|---|---|---|---|---|---|
| | | A* | B | C | D |
| Intragranular Composition | | | | | |
| Function | Intragranular Ingredient | % w/w of Blend | | | |
| Active | 50/50 Loxo-305/HPMCAS-MG | 45.00 | 43.76 | 43.76 | 43.76 |
| Filler | Microcrystalline cellulose (Avicel ® PH-101) | 26.13 | 25.41 | — | — |
| Filler | Microcrystalline cellulose (Avicel ® PH-102) | — | — | 38.11 | 33.50 |
| Filler | Mannitol (Parteck ® M100) | 26.13 | 25.41 | — | — |
| Filler | Mannitol (Mannogem EZ Spray Dried) | — | — | 12.71 | — |
| Filler | Lactose monohydrate (Foremost Fast Flo 316 | — | — | — | 16.74 |
| Disintegrant | Sodium starch glycolate (Explotab ®) | 2.50 | 2.43 | 2.43 | — |
| Disintegrant | Croscarmellose sodium (Ac-Di-Sol) | — | — | — | 5.00 |
| Lubricant | Magnesium stearate | 0.25 | 0.24 | 0.25 | 0.25 |
| Extragranular Composition | | | | | |
| Function | Extragranular Ingredient | % w/w of Blend | | | |
| Disintegrant | Sodium starch glycolate (Explotab ®) | | 2.50 | 2.50 | — |
| Glidant | Silicon dioxide (Syloid 244 FP) | — | — | — | 0.50 |
| Lubricant | Magnesium stearate | | 0.25 | 0.25 | 0.25 |
| | Totals: | 100.0 | 100.0 | 100.0 | 100.0 |

*A is the first composition (intragranular blend).

Example 6: Preparation of 25 mg Compound of Formula I Pharmaceutical Composition The components are weighed out in the following order and added to an appropriately sized container: half of the AVICEL® PH 200; half of the PARTECK® M200; all of the granules of the intragranular composition as prepared in Example 4; the EXPLOTAB®; the PARTECK® M200; and the AVICEL® PH 200. This is mixed on a Turbula at 32 RPM for 5 min and then sieved through an 850 μm screen. The mixture is further mixed on the Turbula at 32 RPM for 5 min. Magnesium stearate is added, and the mixture mixed on the Turbula at 32 RPM for 2 min. For larger-scale runs, a V-blender is used instead of the Turbula.

TABLE 19

25 mg dosage form

| Function | Component | % w/w of Blend | Amount (g) |
|---|---|---|---|
| Granules | Intragranular composition* | 35.00 | 30.0 |
| Filler | Microcrystalline cellulose, 200 um AVICEL ® PH 200 | 31.13 | 26.7 |
| Filler | Mannitol PARTECK ® M200 | 31.13 | 26.7 |
| Disintegrant | Sodium Starch Glycolate EXPLOTAB ® | 2.50 | 2.1 |
| Lubricant | Mg Stearate | 0.25 | 0.2 |
| | Total | 100.00 | 85.7 |

*Contains 8% w/w Loxo-305 and 8% w/w HPMCAS-MG based total weight of the 25 mg dosage form.

Example 7: Preparation of 100 mg Dosage Form

The components are weighed out in the following order and added to an appropriately sized container: about half of the granules of the first composition; all of the Explotab® or or Syloid 244FP®; and the remaining half of the granules of the first composition as prepared in Example 4. This is mixed on the Turbula at 32 RPM for 5 min, and then sieved through an 850 μm screen. It is further mixed on the Turbula at 32 RPM for 5 min. Magnesium stearate is added to the jar, and the mixture is mixed on the Turbula at 32 RPM for 2 min. For larger-scale runs, V-blender is used instead of Turbula

TABLE 20

100 mg compound of Formula I pharmaceutical composition

| | | Formulation Reference | | |
|---|---|---|---|---|
| | | B | C | D |
| Function | Component | % w/w of Blend | | |
| Granules | Intragranular composition | 97.25 | 97.25 | 99.25 |
| Disintegrant | Sodium Starch Glycolate EXPLOTAB ® | 2.50 | 2.50 | |
| Glidant | Silicon Dioxide SYLOID 244 FP | — | — | 0.50 |
| Lubricant | Mg Stearate | 0.25 | 0.25 | 0.25 |
| | Total | 100.00 | 100.00 | 100.00 |

Example 8: Preparing Coated Tablets

The 25 mg compound of Formula I pharmaceutical composition is pressed on a tablet press and sprayed with a 15% Opadry/85% Sterile Water for Injection (SWFI) mixture to make the final coated tablets. The 25 mg tablets are 0.3437" Round (Natoli).

The 100 mg compound of Formula I pharmaceutical composition is pressed on a tablet press and sprayed with a 15% Opadry/85% Sterile Water for Injection (SWFI) mixture to make the final coated tablets. The 100 mg tablets are 0.3750" Round (Natoli).

Figure 8:
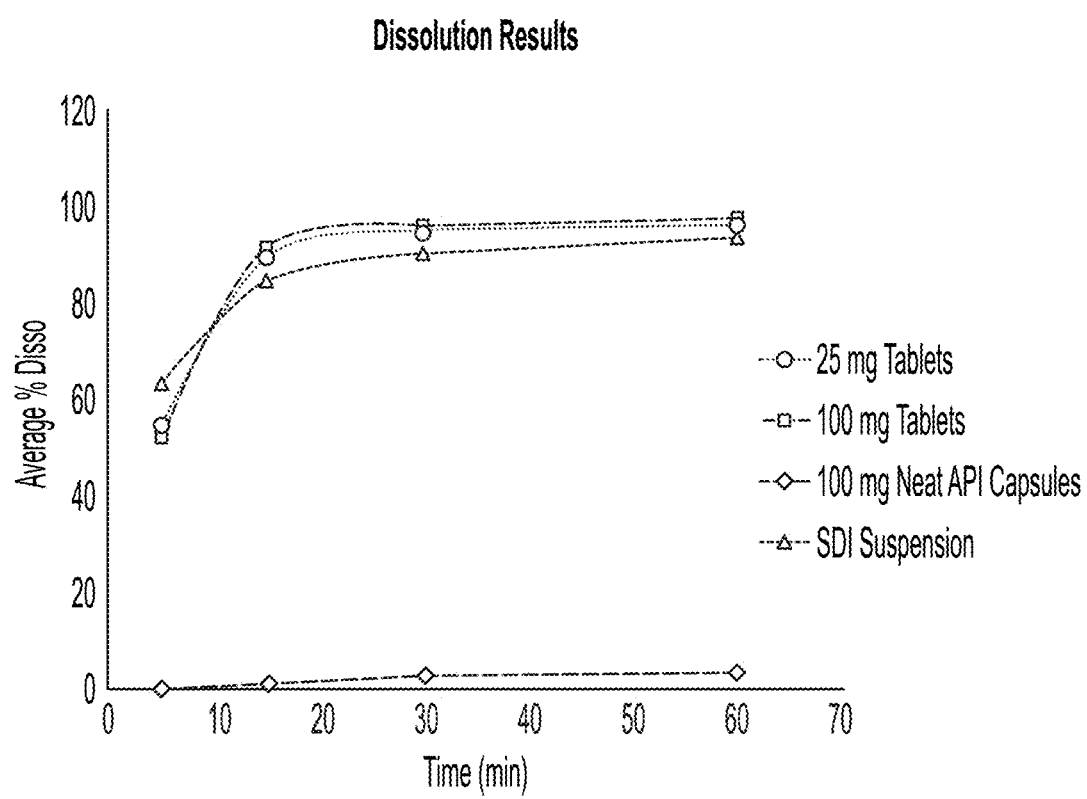
FIG. 8 shows the dissolution of tablets comprising the spray-dried dispersion of the compound of Formula I and an HPMCAS polymer.
Figure 9:
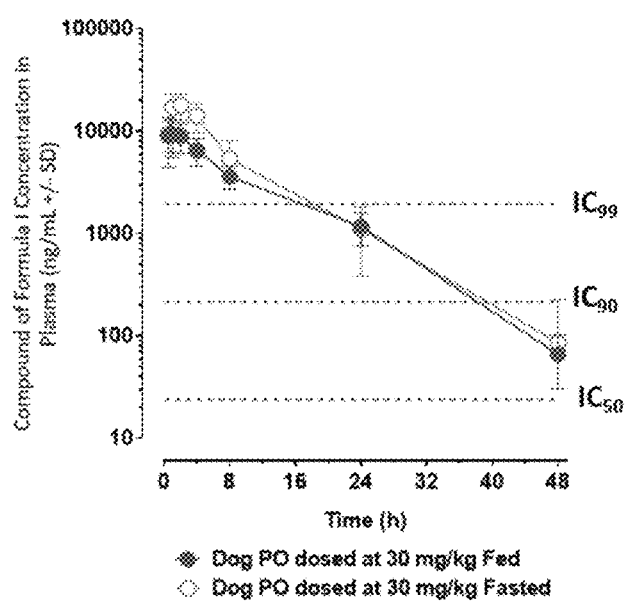
FIG. 9 shows the concentration of the compound of Formula I in the plasma over the time course of an in vivo dog bioavailability and pharmacokinetic study.

The dissolution of the tablets compared to the compound of Formula I spray-dried intermediate, and crystalline compound of Formula I is measured using the conditions in Table 21. The results are shown in FIG. 8.

TABLE 21

Dissolution conditions

| Parameter | Condition |
|---|---|
| Dissolution Media | 0.25% SLS in 50 mM Citric Acid Buffer, pH 4.0 |
| Apparatus | USP Apparatus 2 (Paddles) |
| Vessel Size | 1000 mL |
| Media Volume | 900 mL |
| Time Points | 5, 15, 30, 60 minutes |
| Temperature | 37.0 ± 0.5° C. |
| Paddle Speed | 0-60 min: 75 ± 5 RPM<br>60-90 min: 200 ± 8 RPM |
| Nominal Concentration | 25 mg: 27.7778 µg/mL<br>100 mg: 111.1111 µg/mL |
| Sampling Procedure | At each time point, filter 3 mL through a 13 mm 0.45 µm Nylon filter, discarding the first 2 mL to waste before collecting the remaining 1 mL in an HPLC vial for analysis. |

Example 9: Comparison of In Vivo Pharmacokinetic Parameters and Bioavailability of Spray-Dried Dispersions of the Compound of Formula I A. Comparison Using Different Polymers in the Spray-Dried Dispersion of the Compound of Formula I An in vivo rat bioavailability and pharmacokinetic study is performed to investigate the difference in bioavailability of suspensions of Sample 1, Sample 2, and Sample 3 from Example 4, Table 11.

Each formulation is suspended in 0.5% HPMC and given at a dose of 400 mg/kg to three (3) to five (5) male Sprague Dawley rats. Samples for pharmacokinetic (PK) analysis are collected at 0.5, 1, 2, 4, 8, 24, 48 and 72 hours post-dose. Blood samples are processed to plasma and stored frozen at −70° C. until analysis of the concentrations of the compound of Formula I. The concentration of the compound of Formula I in the plasma is determined by reverse phase HPLC with mass spectrometry detection. The compound of Formula I area under the curve (AUC) is calculated by the trapezoidal method over the time course of the study. ANOVA with Dunett correction for multiple comparisons is used to determine statistical significant of differences from the reference formulation. The values of AUC and the maximum concentration (Cmax) are reported as averages±standard deviation for each group of rats in Table 22.

TABLE 22

The compound of Formula I concentration in plasma of Sprague Dawley rats

| Formulation | Dose (mg/kg) | N | AUC (ng*h/mL) Value | p-value vs reference | Cmax (ng/mL) Value | p-value vs reference |
|---|---|---|---|---|---|---|
| Sample 1 | 400 | 5 | 239369 ± 86083 | 0.0015 | 18260 ± 6342 | 0.0011 |
| Sample 2 | 400 | 3 | 138427 ± 63422 | 0.3938 | 10260 ± 4164 | 0.3748 |
| Sample 3 | 400 | 5 | 136119 ± 81206 | 0.3047 | 13680 ± 6915 | 0.0298 |

B. Comparison Using Different Drug Loads of the Compound of Formula I

An in vivo rat bioavailability and pharmacokinetic study is performed to investigate the increase in bioavailability of suspension of 30%, 40%, or 50% drug load (SDD of either 7:3, 3:2, or 1:1 HPMCAS-MG: compound of Formula I, respectively) at a dose of 400 mg/kg or 50% drug load (SDD of 1:1 HPMCAS-MG: compound of Formula I) at a dose of 100 mg/kg. Each formulation is suspended in 0.5% HPMC and given to five (5) male Sprague Dawley rats. Samples for pharmacokinetic (PK) analysis are collected at 0.5, 1, 2, 4, 8, 24, 48 and 72 hours post-dose. Blood samples are processed to plasma and stored frozen at −70° C. until analysis of the compound of Formula I concentrations. The concentration of the compound of Formula I in the plasma is determined by reverse phase HPLC with mass spectrometry detection. The compound of Formula I area under the curve (AUC) is calculated by the trapezoidal method over the time course of the study. The values of AUC and Cmax are reported as averages±standard deviation for each group of rats in Table 23.

TABLE 23

Compound of Formula I concentration in plasma of Sprague Dawley rats

| Formulation | Dose (mg/kg) | N | AUC(ng*h/mL) | Cmax (ng/mL) |
|---|---|---|---|---|
| 30% Drug Load (SDD—7:3 HPMCAS-MG:compound of Formula I) | 400 | 5 | 127561 ± 44138 | 14180 ± 3284 |
| 40% Drug Load (SDD—3:2 HPMCAS-MG:compound of Formula I) | 400 | 5 | 112534 ± 28799 | 18300 ± 4356 |
| 50% Drug Load (SDD - 1:1 HPMCAS-MG:compound of Formula I) | 400 | 5 | 112778 ± 49956 | 13816 ± 7385 |
| 50% (100 mg/kg) Drug Load (SDD - 1:1 HPMCAS-MG:compound of Formula I) | 100 | 5 | 32346 ± 11341 | 3936 ± 2682 |

C. In Vivo Dog Bioavailability and Pharmacokinetic Study

An in vivo dog bioavailability and pharmacokinetic study is performed to investigate the difference in bioavailability of a reference form (micronized compound of Formula I) and an SDD formulation (1:1 HPMCAS-MG: compound of Formula I) of the compound of Formula I. The reference and SDD forms are suspended in 0.5% HPMC in water and given to seven or eight dogs at a dose of 30 mg/kg. Dogs are fasted overnight prior to dosing (fasted) or fed canned food 45 min prior to dosing (fed). Samples for pharmacokinetic (PK) analysis are collected at 30 min, 1, 2, 4, 8, 24, and 48 hours post-dose. Blood samples are processed to plasma and stored frozen at −70° C. until analysis of the compound of Formula I concentrations. The concentration of the compound of Formula I in the plasma is determined by reverse phase HPLC with mass spectrometry detection. The compound of Formula I area under the curve is calculated by the trapezoidal method over the time course of the study. ANOVA with Dunett correction for multiple comparisons is used to determine statistical significant of differences from the reference formulation. The values of AUC and Cmax are reported as averages±standard deviation for each group of dogs in Table 24.

TABLE 24

Compound of Formula I concentration in plasma of dogs

| Food Condition | Formulation | Dose (mg/kg) | N | AUC(ng*h/mL) Value | p-value | Cmax (ng/mL) Value | p-value |
|---|---|---|---|---|---|---|---|
| Fasted | Reference | 30 | 7 | 11260 ± 6801 | <0.0001 | 597 ± 197 | <0.0001 |
|  | SDD | 30 | 8 | 162384 ± 63966 |  | 18121 ± 5585 |  |
| Fed | Reference | 30 | 8 | 47836 ± 21323 | 0.0089 | 2370 ± 679 | 0.0003 |
|  | SDD | 30 | 8 | 104739 ± 24490 |  | 9998 ± 3864 |  |

Figure 10A:
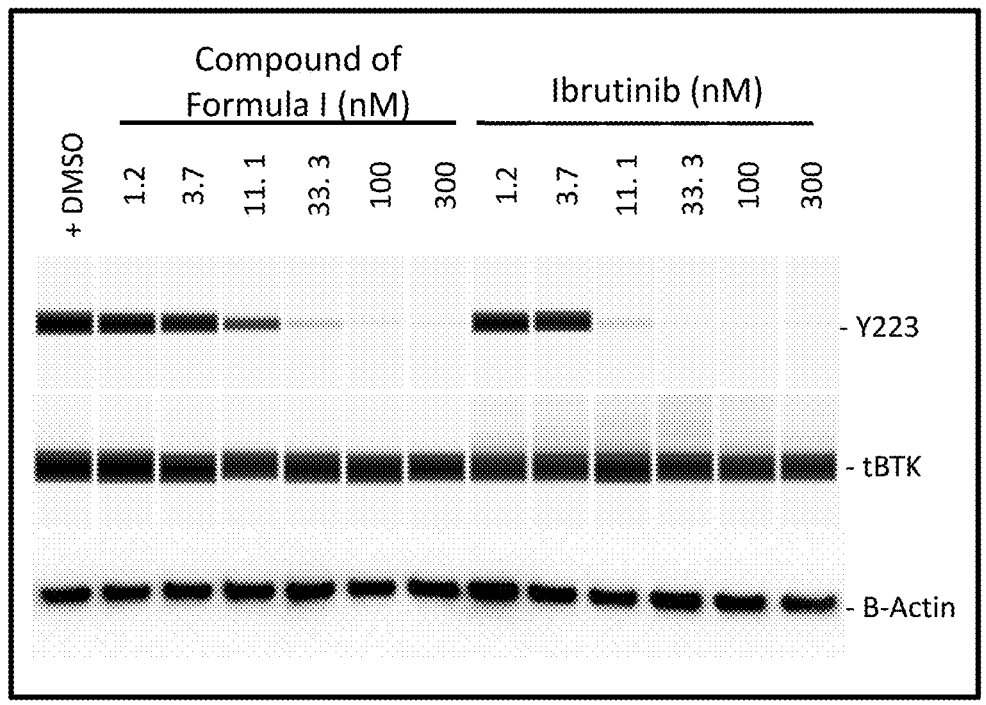
FIGS. 10A-10D show the dose response effects on Y223 autophosphorylation in HEK293 cells stably expressing BTK and BTK C481S.
Figure 10B:
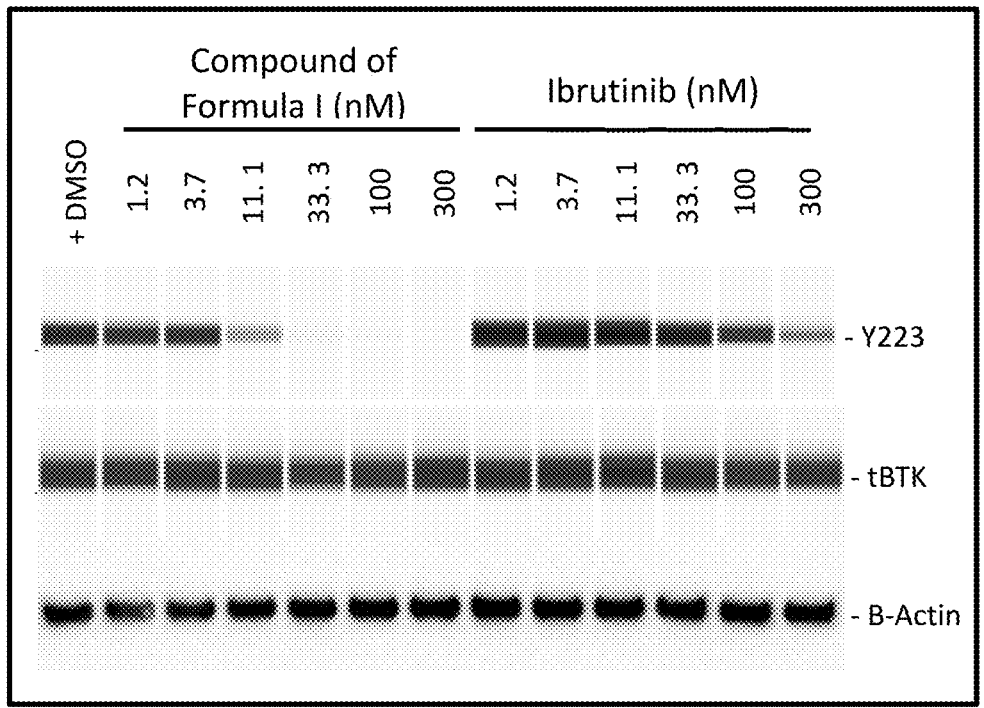
Figure 10C:
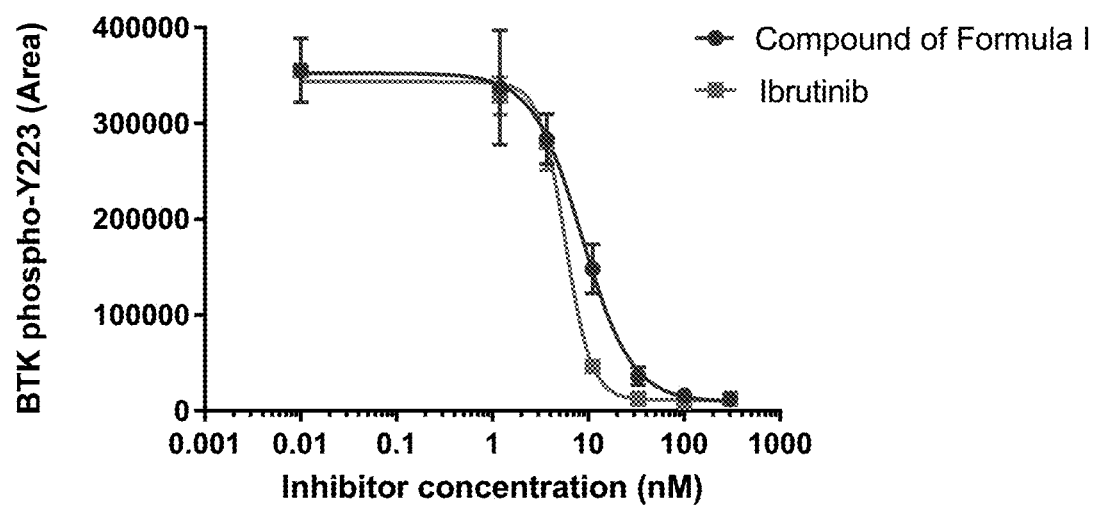
Figure 10D:
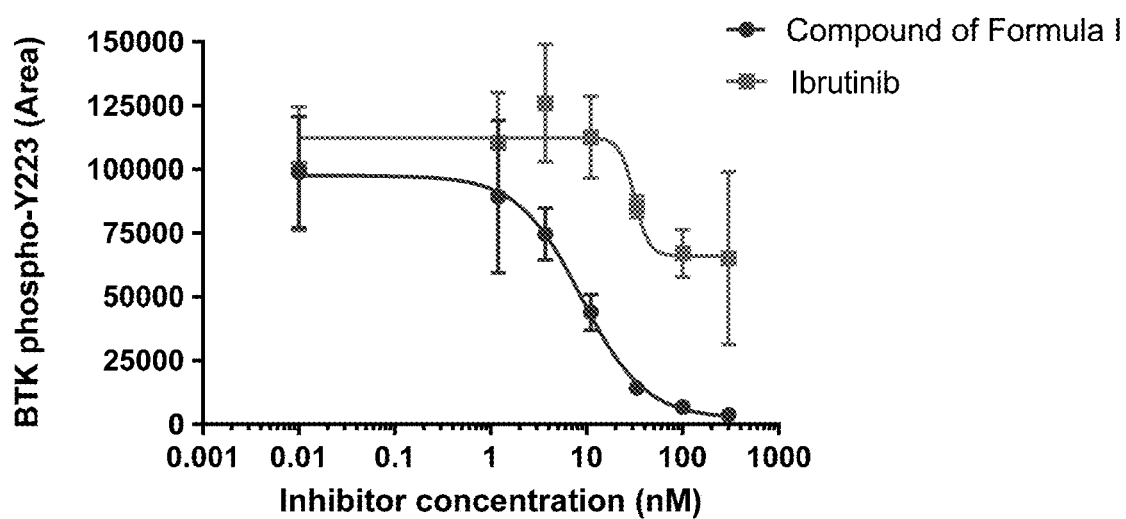

Example 10: The Compound of Formula I and Ibrutinib Dose Response Effects on Y223 Autophosphorylation in HEK293 Cells Stably Expressing BTK and BTK C481S HEK293 cell lines stably expressing BTK wild type and the mutant form C481S are generated using standard transfection methods. For assessment of cellular inhibition potency, cells are grown in DMEM +10% Fetal Bovine Serum (FBS)+1 µg/ml puromycin (complete growth media) at 37° C. in a $CO_2$ incubator. Cells are harvested according to standard protocols using TRYPLE™ (Gibco #12604-013), counted, resuspended in complete growth media, and added to 6 well assay plates at 4×10^5 cell/well in 2 mL. Plates are incubated overnight at 37° C. with 5% $CO_2$. The following day, cells are treated for 2 hr with the compound of Formula I or ibrutinib, prepared as a 6-point dose curve, 1:3 dilution series with final concentrations starting at a maximum concentration of 300 nM and a constant DMSO concentration of 0.5% (v/v). Control wells contained 0.5% (v/v) DMSO alone (no inhibition control). All samples are tested in triplicate. Following compound incubation, the growth medium is discarded, cells are washed with DPBS (1×) (Gibco #14190-144) and lysed in 1 mL of CEL-LYTIC™ M (Sigma #C2978) containing 1× Halt phosphatase and protease inhibitor cocktails (Pierce #78442). Plates are placed on ice for 1 hr with gentle agitation and stored at −80° C. overnight. The next day, cell lysates are placed in 1.5 mL tubes and cleared by centrifugation at 16,000×g for 10 min at 4° C. Supernatants are quantified by BCA (Pierce #23225) and stored at −80° C. Samples are analyzed by Simple Western (Protein Simple) with anti-phospho-BTK (Y223) (Cell Signaling Technologies (CST) #5082) and anti-BTK (CST #8547) (FIGS. 10A and 10B). β-actin is used as a loading control and detected by regular Western blot with an anti-3-actin antibody (CST #4970). Simple Western results are analyzed with Compass software (Protein Simple). BTK Y223 phosphorylation signal is normalized to total BTK, and $IC_{50}$ values are calculated using a 4-parameter fit in GraphPad Prism 7.04 software. FIGS. 10C and 10D show the inhibitor concentration versus the average BTK Y223 phosphorylation signal with the standard deviation for three independent assays. The compound of Formula I inhibited autophosphorylation of BTK Y223 in both wild type and the C481S mutant proteins with $IC_{50}$ values of 8.6±0.3 nM and 8.8±1.8 nM, respectively. Ibrutinib inhibited BTK wild type with an $IC_{50}$ of 5.7±0.5 nM, and its activity on the C481S mutant could not be fit to an $IC_{50}$ curve.

Figure 11A:
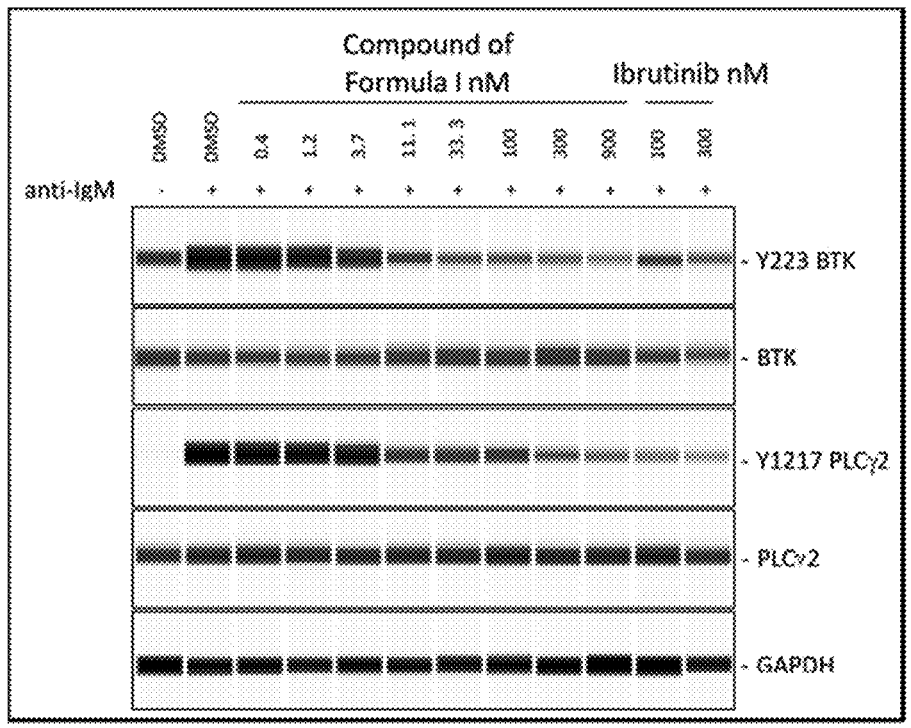
FIG. 11A is a Western blot showing the compound of Formula I dose response on BTK Y223 and PLCγ2 Y1217 phosphorylation in Ramos R A1 cells.
Figure 11B:
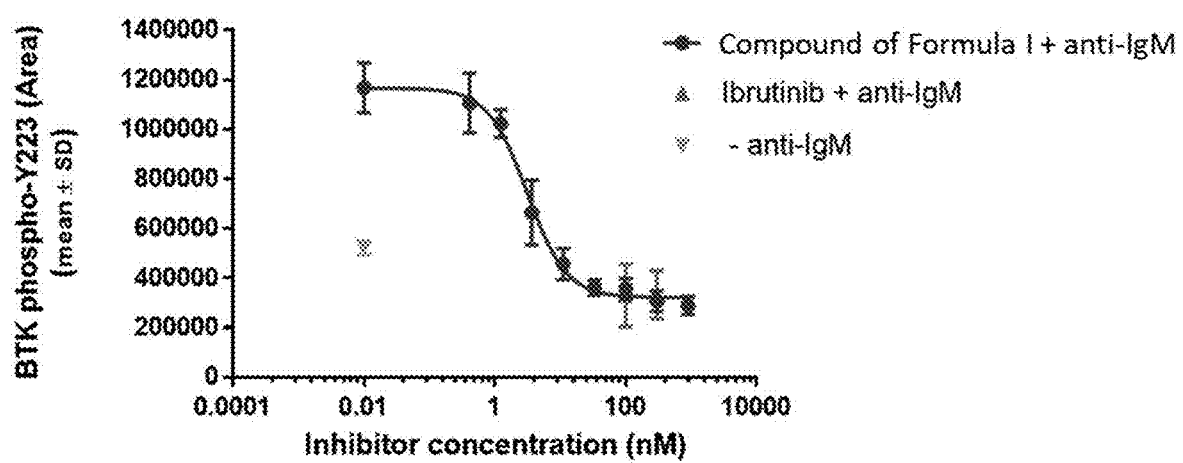
FIGS. 11B and 11C are plots of the Western blot data for BTK Y223 (FIG. 11B) and PLCγ2 Y1217 phosphorylation (FIG. 11C) in Ramos R A1 cells. The compound of Formula I inhibited autophosphorylation of BTK Y223 with an $IC_{50}$ of 3.2±0.6 nM and phosphorylation of PLCγ2 Y1217 with an $IC_{50}$ of 8.2 nM±4.3.
Figure 11C:
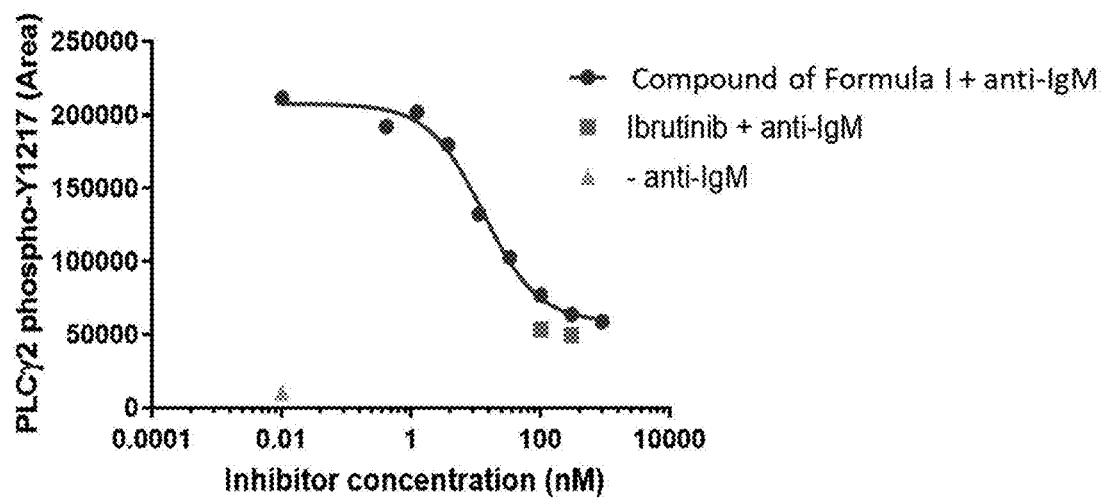

Example 11: Inhibition Activity of the Compound of Formula I Against BTK Y223 Autophosphorylation and PLCγ2 Y1217 Phosphorylation in Ramos RA1 Cells Ramos RA1 cells, obtained from ATCC (CRL-1596), are grown in RPMI 1640+10% fetal bovine serum (FBS) at 37° C. in a CO2 incubator. Cells are harvested and washed with RPMI 1640 without FBS and resuspended at a concentration of 1.2×10^7 cells/mL. Nine hundred µL of cell/well are added to 24 well plates and 100 uL of 10× stocks of inhibitor are added. The 10× compound of Formula I stocks are prepared in 1% DMSO, by doing a 1:3 dilution series with final concentrations in the wells ranging between 900 nM to 0.41 nM. Ibrutinib is tested at 100 and 300 nM, and control wells had 0.01% DMSO final concentration. All samples are tested in triplicate. After 2 hours (starvation and dosing) sodium orthovanadate is added to a final concentration of 200 µM and incubated for 30 more min. Cells are then stimulated with 4 uL of goat F(ab')2 anti-human IgM (Jackson ImmunoResearch #109-006-129) for 5 min at room temperature, spun down, resuspended in 100 uL of CEL-LYTIC™ M (Sigma #C2978) containing 5× Halt phosphatase and protease inhibitor cocktails (Pierce #78442), and stored at −80° C. Lysates are quantified by BCA (Pierce #23225) and analyzed by Simple Western (Protein Simple) with the following antibodies: anti-phospho-BTK (Y223) (Cell Signaling Technologies (CST) #5082), anti-BTK (CST #8547), anti-phospho-PLCγ2 (Y1217) (CST 3871), anti-PLCγ2 (CST 3872), and anti-GAPDH (GAPDH refers to glyceraldehyde 3-phosphate dehydrogenase) (Novus #MAB5718-SP). GAPDH is used as a loading control. FIG. 11A shows a representative Western blot. Results are analyzed with Compass software (Protein Simple), and $IC_{50}$ values are calculated on GraphPad Prism 7.04 software. The BTK Y223 phosphorylation signal is normalized to total BTK and the PLCγ2 Y1217 phosphorylation is normalized to total PLCγ2. FIG. 11B shows the BTK Y223 phosphorylation signal versus the inhibitor concentration, and FIG. 11C shows the PLCγ2 Y1217 phosphorylation signal versus the inhibitor concentration. The compound of Formula I inhibited autophosphorylation of BTK Y223 with an $IC_{50}$ of 3.2±0.6 nM and phosphorylation of PLCγ2 Y1217 with an $IC_{50}$ of 8.2 nM±4.3.

Example 12: Effects of the Compound of Formula I on BTK-Dependent Cell Proliferation in Human TMD8 Diffuse Large B-Cell Lymphoma Cell Line The TMD8 cells are maintained in RPMI 1640 (Gibco Catalog #31870-025) with 10% Fetal Calf Serum (FCS), 1% GLUTAMAX™, Non-Essential Amino-Acids and 1 mM sodium pyruvate. The cells are harvested by centrifugation (5 min, 1200 rpm) prior to reaching a concentration of 3×106 cells/mL. The medium is removed and cell pellet resuspended in fresh medium before counting with a Cellometer (Nexcelom). TMD8 cells are seeded at 5×104 cells/mL in 20 mL of culture medium in a T75 culture flask and held at 37° C. with 5% $CO_2$.

Figure 12A:
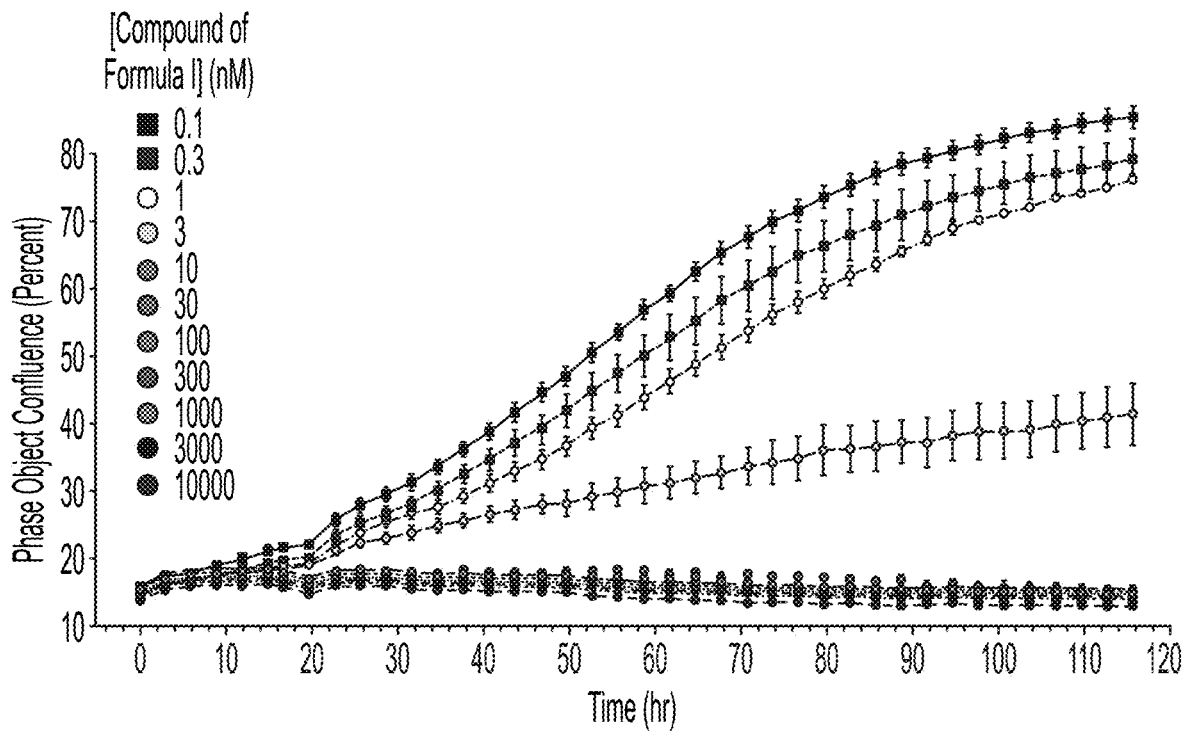
FIG. 12A is a plot showing the dose response inhibition of the compound of Formula I on TMD8 proliferation.
Figure 12B:
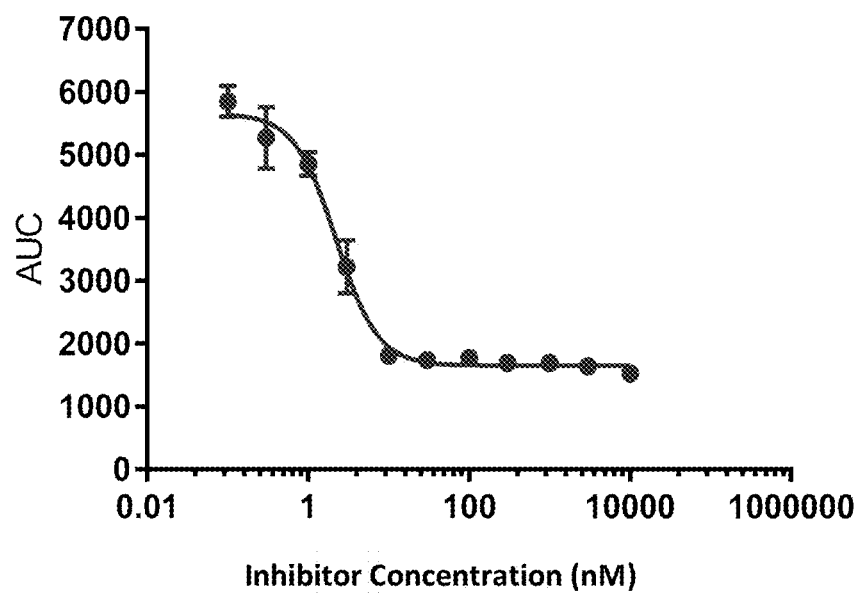
FIG. 12B is a plot showing the area under the curve (AUC) (mean±SD) vs the inhibitor concentration from FIG. 12A. Quantification of the area under the curve (AUC) for each individual curve allowed the determination of an $IC_{50}$ of 2.33 nM for the compound of Formula I on TMD8 proliferation.

The anti-proliferation activity of the compound of Formula I with TMD8 cells is accessed by the addition of increasing concentrations of inhibitor from 0.1 to 1,000 nM. A dose-dependent inhibition is observed by real-time assessment of TMD8 confluence. Individual curves for each compound of Formula I concentration are represented in the FIG. 12A. Quantification of the area under the curve (AUC) for each individual curve allowed the determination of an $IC_{50}$ of 2.33 nM for the compound of Formula I on TMD8 proliferation (FIG. 12B). These data indicate that the compound of Formula I inhibits the proliferation of TMD8 cells in a dose dependent manner.

Example 13: Tumor Growth Inhibition of the Compound of Formula I in Male NOD SCID Mice Implanted with OCI-Ly10 Xenografts A total of 65 male NOD-SCIO mice are used for the study. At the start of the study the animals are aged 6-8 weeks and weighed approximately 21-27 g. Animals are housed in IVC cages (up to 5 per cage) with individual mice identified by tail marking. All animals are allowed free access to a standard certified commercial diet and sanitized water during the study. The holding room is maintained under standard conditions: 20-24° C., 40-70% humidity and a 12 hr light/dark cycle. Animals are randomly assigned to treatment groups. OCI-Ly10 cells are implanted subcutaneously into the flanks of male NOD SCID mice and allowed to grow to a volume of approximately 150-200 mm³. The dosages are prepared by stirring the compound of Formula I or ibrutinib until it is wetted, sonicating for 30 minutes, and stirring overnight at room temperature and between dosing periods. The formulation used is 0.5% hydroxypropyl methylcellulose. The dosing volume is 10 mL/kg. An individual animal's dose is calculated from the bodyweight recorded on the day of dosing. Animals are dosed for 28 days. Bodyweight and health observation of animals is recorded daily for the duration of dosing.

Figure 13A:
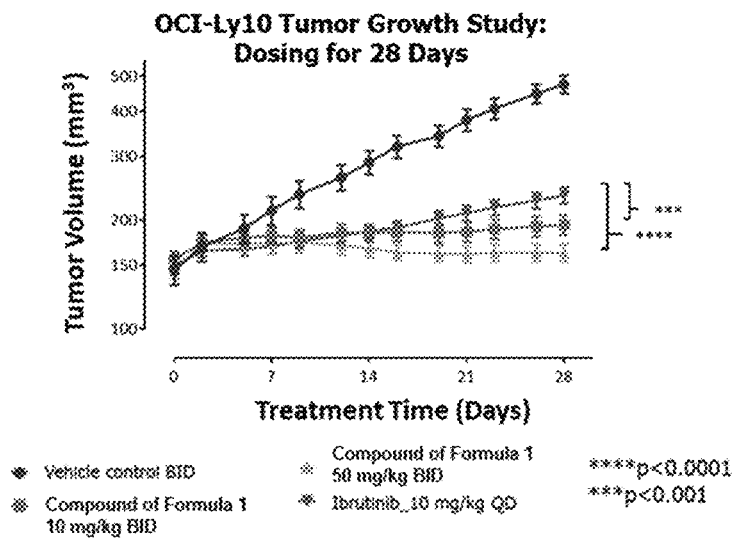
FIGS. 13A-C show the dose-dependent inhibition of tumor growth in an OCI-Ly10 human B-cell lymphoma cell line xenograft tumor mouse model.
Figure 13B:
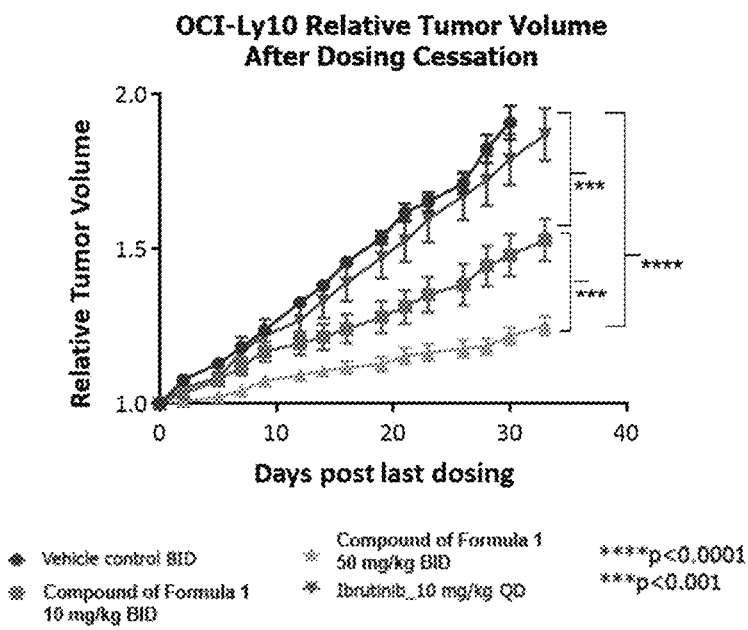
Figure 13C:
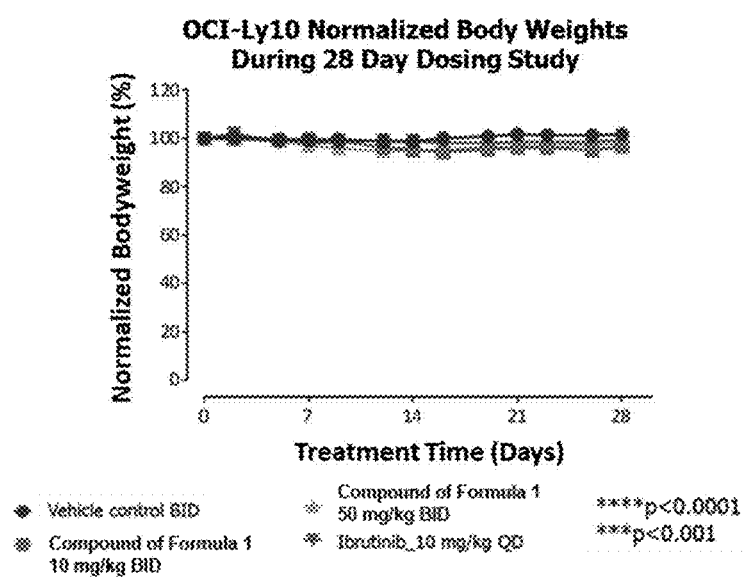

Tumor volume is measured three times per week during the study. The compound of Formula I at both 10 mg/kg and 50 mg/kg BID resulted in inhibition of tumor growth during the dosing period. FIG. 13A shows the tumor growth with the tumor volumes displayed as mean±SEM for mice orally dosed with the indicated vehicle or inhibitor. Inhibition of tumor growth with the compound of Formula I is maintained even after dosing had stopped (FIG. 13B). Treatment with the compound of Formula I at both 10 and 50 mg/kg BID resulted in tumors that are significantly smaller than those from animals treated with ibrutinib (p=0.0008 and <0.0001, respectively, ANOVA with Tukey post-hoc test). FIG. 13C shows the normalized body weight values during the course of treatment displayed as the mean±SEM.

Example 14: Tumor Growth in a Human Xenograft Diffuse Large B Cell Lymphoma Model in SCID Mice Cell Culture The human diffuse large B cell lymphoma TMD8 cells are maintained in suspension in RPMI 1640 with 10% Fetal Calf Serum (FCS) and 1% of Glutamax. The cells are transferred to a 50 mL Falcon tube and centrifuged at 1200 rpm for 5 min. The supernatant is removed and the cell pellet resuspended in PBS before being mixed with Matrigel (1/1, v/v). The cell suspension:Matrigel mixture at a final target cell concentration of 40×106 cells/mL is kept on ice until the s.c. injections (250 μL/mouse) to maintain the Matrigel solution in a liquid state.

Animal Strain

The animals are female BalB/c mice aged 9 weeks-old at the day of injection. The mice are housed in individually ventilated cage racks with HEPA filtered air supply and all materials that contact the immunodeficient animals are steam sterilized. This includes cages, bedding, water and feed. The animal room conditions are set as follows. The temperature is 22±2° C., and the relative humidity is 50±10%. The light/dark cycle is 12 h/12 h, and the air change rate is 12 to 15 cycles/hour of filtered, 100% fresh air. All animals had free access to sterilized water and irradiated controlled food (reference A04CSafe, Augy-France).

Preparation of the Compound of Formula I

The compound of Formula I is formulated in methylcellulose/Tween80/Water (0.6%/0.5%/98.5%; w/w/v). The vehicle for the dosing of control group is methylcellulose/Tween 80/Water (0.6%/0.5%/98.5%; w/w/v), 10 mL/kg. 151.4 mg of the compound of Formula I are weighed and formulated with 50.4 mL of vehicle to obtain a solution at 3 mg/mL of free base. For the 1 mg/mL suspension preparation, 50.1 mg of the compound of Formula I are weighed and solubilized in 50.1 mL of vehicle.

Tumor Cell Injection and Tumor Growth Monitoring

The female SCID mice are anaesthetized by inhalation of ISOFLURANE® (5% mixed with $O_2$/Air, 2 L/min). The area of the injection (lower flank) is shaved. The skin is cleaned and disinfected with chlorhexidine before injection of the TMD8 cells suspension. A volume of 250 μL of the cell suspension (cells in PBS mixed with MATRIGEL®, corresponding to 10×106 cells) is injected by s.c using a 30-gauge needle. After several seconds, the needle is removed and the area of injection is cleaned with chlorhexidine. Mice are then kept in the postoperative chamber at 28° C. until complete recovery.

Figure 14A:
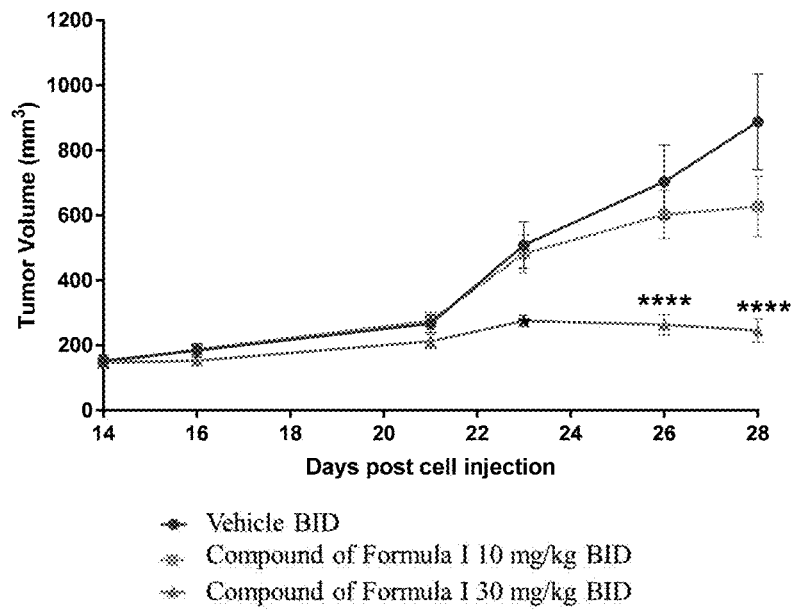
FIG. 14A-C show the dose-dependent inhibition of tumor growth in TMD8 human B-cell lymphoma cell line xenograft tumor mouse model.

Tumor width and length are measured with digital calipers. The tumor volume in mm³ is calculated by the formula: Volume=0.52×(width)²×length/2, width and length measured in mm. When the volume of the tumors reached a mean size of 150 mm³ (14 days post cell injection in this study), the mice are divided in 3 separate experimental groups in order to make homogeneous groups with close mean tumor volume±SEM. Mice weights are checked daily and tumor volumes are checked 2-3 times/week. The summary of the groups of the study for the treatment is described in Table 25. FIG. 14A shows the tumor volume displayed as the mean±SEM versus the days post cell injection for the three groups. The last dosing is performed at day 28 post cell injection, corresponding to a 14 day period of chronic dosing.

TABLE 25

Summary of the groups of the study for the treatment

| Group | Compound | Number of animals | Frequency of Dosing | Final Compound Concentration for Each Dosing |
|---|---|---|---|---|
| 1 | Vehicle | N = 12 | BID | 0 mg/kg |
| 2 | Compound of Formula I | N = 12 | BID | 10 mg/kg |

TABLE 25-continued

Summary of the groups of the study for the treatment

| Group | Compound | Number of animals | Frequency of Dosing | Final Compound Concentration for Each Dosing |
|---|---|---|---|---|
| 3 | Compound of Formula I | N = 12 | BID | 30 mg/kg |

Figure 14B:
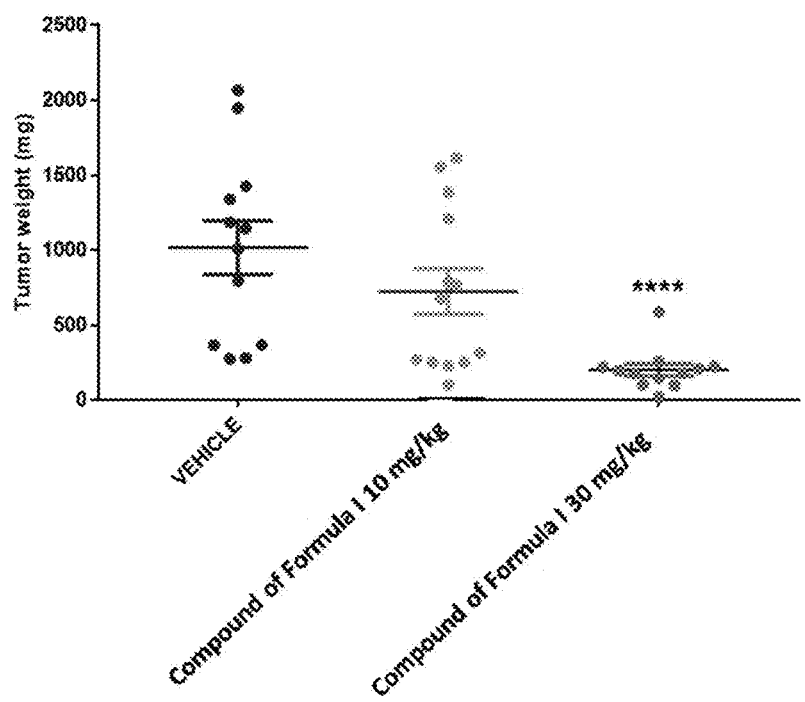
Figure 14C:
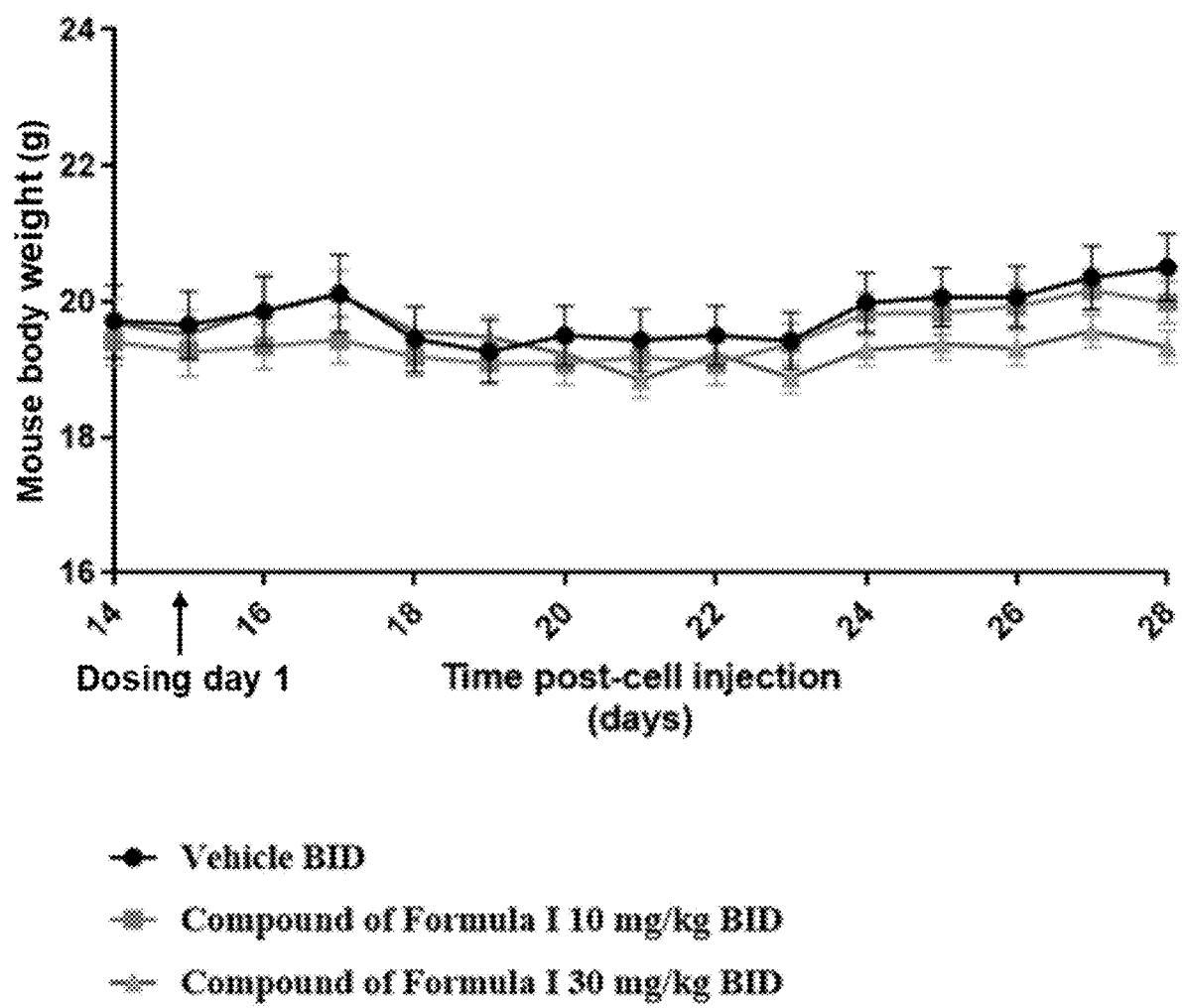

Tumors are collected from each mouse at Day 28 post the cell injection. The mice are anaesthetized by inhalation of isoflurane® (5% mixed with $O_2$/Air, 2 L/min). The tumors are weighed. FIG. 14B shows the tumor weight at the end of the study displayed as the mean±SEM for the three groups. Tumor weight statistical analysis between each group is determined by a 1-way ANOVA and by 2-Way ANOVA with repeated measures for the mice weight and the tumor volume monitoring, followed by a Dunnett's test. Differences are considered significant with a P value <0.05. FIG. 14C shows the mice body weights versus days post cell injection displayed as the mean±SEM for the three groups.

The chronic oral BID administration of the compound of Formula I for 14 days at 10 and 30 mg/kg is well tolerated. At the higher dose, treatment significantly decreased the growth of TMD8 tumor xenografts in SCID mice (TGI of 35% and 87%, respectively, vs the vehicle treated group). The strong inhibitory effect of the tumor growth by the twice-daily treatment of the compound of Formula I at 30 mg/kg is confirmed by the tumor weights at end point.

Example 15: Comparison of Bioavailability and Pharmacokinetics of Crystalline Compound of Formula I in Suspension and a Spray-Dried Dispersion of the Compound of Formula I in Suspension in Dogs A. Pharmacokinetics of the Compound of Formula I Administered as Crystalline Compound of Formula I in Suspension Crystalline compound of Formula I is prepared as a suspension in 0.5% hydroxypropyl methylcellulose (IPMC) at 6 mg/mL for administration of 30 mg/kg; no correction factor is used for dose formulation. Three male and five female beagle dogs are administered a single PO gavage dose of 30 mg/kg compound of Formula I formulated as a suspension in 0.5% HPMC. All animals are administered the suspension of the crystalline compound of Formula I in fed and fasted states, following a 7-day washout period between dosing periods/feeding conditions. For both feeding conditions, access to food is removed at least 12 hours prior to dose administration. In Crossover #1, 6 dogs are fed a mix of canned and dry food approximately 45 minutes prior to dose administration (Group 1), and 2 dogs are administered the compound of Formula I in a fasted state and fed 4 hours after dosing (Group 2). In Crossover #2, the 2 dogs that are administered the compound of Formula I in the fasted state in Crossover #1 are fed a mix of canned and dry food approximately 45 minutes prior to dose administration (Group 3), and 5 of the dogs that are administered the compound of Formula I in the fed state in Crossover #1 are administered the compound of Formula I in a fasted state and fed 4 hours after dosing (Group 4) (Table 26). The same 3 males and 3 females are assigned to Groups 1 and 4 (with the exception of one female, which is assigned to Group 1 but is not included in Group 4), and the same 2 females are assigned to Groups 2 and 3.

TABLE 26

Summary of the study design

| Crossover | Group | Number of Animals | Fed/Fasted | Dose of the compound of Formula I (mg/kg) | Dosing solution concentration (mg/mL) | Dose volume (mL/kg) | Day Administered PO |
|---|---|---|---|---|---|---|---|
| 1 | 1 | 6 | Fed | 30 | 6 | 5 | Day 0 |
|   | 2 | 2 | Fasted | 30 | 6 | 5 | Day 0 |
| 2 | 3 | 12 | Fed | 30 | 6 | 5 | Day 7 |
|   | 4 | 5* | Fasted | 30 | 6 | 5 | Day 7 |

Blood samples are collected via the jugular vein following PO doses at 0 (pre-dose), 0.5, 1, 2, 4, 8 24 and 48 hours into EDTA blood collection tubes. Samples are centrifuged at 3500 rpm for 10 minutes at 4-8° C. and the plasma fraction is stored frozen at −70° C. prior to bioanalytical analysis. Concentrations of the compound of Formula I in dog plasma are determined by LC-MS/MS following protein precipitation with acetonitrile. Non-compartmental pharmacokinetic parameters of the compound of Formula I are calculated by conventional methods using individual plasma concentration profiles over time and Microsoft Excel.

B. Pharmacokinetics of the Compound of Formula I Administered as a Spray-Dried Dispersion of the Compound of Formula I in Suspension The spray-dried intermediate (SDI) of the compound of Formula I (1:1 HPMCAS-MG: compound of Formula I) is prepared as a suspension in 0.5% hydroxypropylmethyl cellulose (HPMC) at 6 mg/mL for administration of 30 mg/kg. Four male and four female beagle dogs are administered a single PO gavage dose of 30 mg/kg the compound of Formula I 50% SDI formulated as a suspension in 0.5% HPMC. All animals are administered the test article in fed and fasted states, following a 7-day washout period between dosing periods/feeding conditions. For both feeding conditions, access to food is removed at least 12 hours prior to dose administration. In Crossover #1, 4 dogs are fed a mix of canned and dry food approximately 45 minutes prior to dose administration (Group 1), and 4 dogs are administered the compound of Formula I in a fasted state and fed 4 hours after dosing (Group 2). In Crossover #2, the 4 dogs that are fasted in Crossover #1 are fed a mix of canned and dry food approximately 45 minutes prior to dose administration (Group 4), and the 4 dogs that are fasted in Crossover #1 are administered the compound of Formula I in a fasted state and fed 4 hours after dosing (Group 3) (Table 27). The same 2 males and 2 females are assigned to Groups 1 and 3, and the same 2 males and 2 females are assigned to Groups 2 and 4.

TABLE 27

Summary of the study design

| Cross-over | Group | Number of Animals | Fed/Fasted | Dose of the compound of Formula I (mg/kg) | Dosing solution concentration (mg/mL) | Dose volume (mL/kg) | Day Administered PO |
|---|---|---|---|---|---|---|---|
| 1 | 1 | 4 | Fed | 30 | 6 | 5 | Day 0 |
|  | 2 | 4 | Fasted | 30 | 6 | 5 | Day 0 |
| 2 | 3 | 4 | Fed | 30 | 6 | 5 | Day 7 |
|  | 4 | 4 | Fasted | 30 | 6 | 5 | Day 7 |

Blood samples are collected via the jugular vein following PO doses at 0 (pre-dose), 0.5, 1, 2, 4, 8 24 and 48 hours into EDTA blood collection tubes. Samples are centrifuged at 3500 rpm for 10 minutes at 4-8° C. and the plasma fraction is stored frozen at −70° C. prior to bioanalytical analysis. Concentrations of the compound of Formula I in dog plasma are determined by LC-MS/MS following protein precipitation with acetonitrile. Non-compartmental pharmacokinetic parameters of the compound of Formula I are calculated by conventional methods using individual plasma concentration profiles over time and Microsoft Excel.

C. Pharmacokinetics of the Compound of Formula I Administered as a Tablet of a Spray-Dried Dispersion of the Compound of Formula I Each animal is administered 3 tablets for administration of 300 mg/dog (approximately 30 mg/kg). The tablets comprised the compound of Formula I 50% SDI. Four male and four female beagle dogs are administered a single PO gavage dose of three 100-mg compound of Formula I tablets. All animals are administered the test article in fed and fasted states, following a 7-day washout period between dosing periods/feeding conditions. For both feeding conditions, access to food is removed at least 12 hours prior to dose administration. In Crossover #1, 4 dogs are fed a mix of canned and dry food approximately 45 minutes prior to dose administration (Group 1), and 4 dogs are administered the compound of Formula I in a fasted state and fed 4 hours after dosing (Group 2). In Crossover #2, the 4 dogs that are dosed under fasted conditions in Crossover #1 are fed a mix of canned and dry food approximately 45 minutes prior to dose administration (Group 4), and the 4 dogs that are dosed under fed conditions in Crossover #1 are administered the compound of Formula I in a fasted state and fed 4 hours after dosing (Group 3) (Table 28). The same 2 males and 2 females are assigned to Groups 1 and 3, and the same 2 males and 2 females are assigned to Groups 2 and 4.

TABLE 28

Summary of the study design

| Cross-over | Group | Number of Animals | Fed/Fasted | Dose of the compound of Formula I (mg/tablet/dog) | Day Administered PO |
|---|---|---|---|---|---|
| 1 | 1 | 4 | Fed | 3 × 100 mg Tablets (300 mg/dog) | Day 0 |
|  | 2 | 4 | Fasted | 3 × 100 mg Tablets (300 mg/dog) | Day 0 |
| 2 | 3 | 4 | Fed | 3 × 100 mg Tablets (300 mg/dog) | Day 7 |
|  | 4 | 4 | Fasted | 3 × 100 mg Tablets (300 mg/dog) | Day 7 |

Blood samples are collected via the jugular vein following PO doses at 0 (pre-dose), 0.5, 1, 2, 4, 8 24 and 48 hours into EDTA blood collection tubes. Samples are centrifuged at 3500 rpm for 10 minutes at 4-8° C. and the plasma fraction is stored frozen at −70° C. prior to bioanalytical analysis. Concentrations of the compound of Formula I in dog plasma are determined by LC-MS/MS following protein precipitation with acetonitrile. Non-compartmental pharmacokinetic parameters of the compound of Formula I are calculated by conventional methods using individual plasma concentration profiles over time and Microsoft Excel.

D. Summary of the Results of Parts a, B, and C

TABLE 29

Summary of the results of Parts A, B, and C

| Study (from Example 15) | Formulation | Feeding State | $C_{max}$ (ng/mL) | $AUC_{0-t}$ (ng*h/mL) | F** (%) |
|---|---|---|---|---|---|
| Part A | Crystalline compound of Formula I | Fasted | 597 ± 197 | 8180 ± 3680 | 5.09 |
|  |  | Fed | 2370 ± 679 | 47800 ± 21300 | 29.7 |
|  |  | Fold Change * | 4.8 ± 2.1 | 7.5 ± 3.3 | — |
| Part B | Compound of Formula I 50% SDI Suspension | Fasted | 18100 ± 5580 | 162000 ± 64000 | 101 |
|  |  | Fed | 10000 ± 3860 | 105000 ± 24500 | 65.3 |
|  |  | Fold Change * | 0.7 ± 0.5 | 0.7 ± 0.3 | — |
| Part C | Compound of Formula I 50% SDI Tablet | Fasted | 12900 ± 3400 | 136000 ± 49300 | 84.6 |
|  |  | Fed | 16500 ± 8020 | 133000 ± 27100 | 82.8 |
|  |  | Fold Change * | 1.4 ± 0.9 | 1.1 ± 0.5 | — |

* Fold change is fed/fasted ratio.
**Bioavailability (F) is based on $AUC_{0-inf}$ of 10700 ng*h/mL in dogs given a 2-mg/kg IV dose of stable-labeled compound of Formula I. Bioavailability is calculated based on $AUC_{0-t}$ after oral dosing.

Figure 15A:
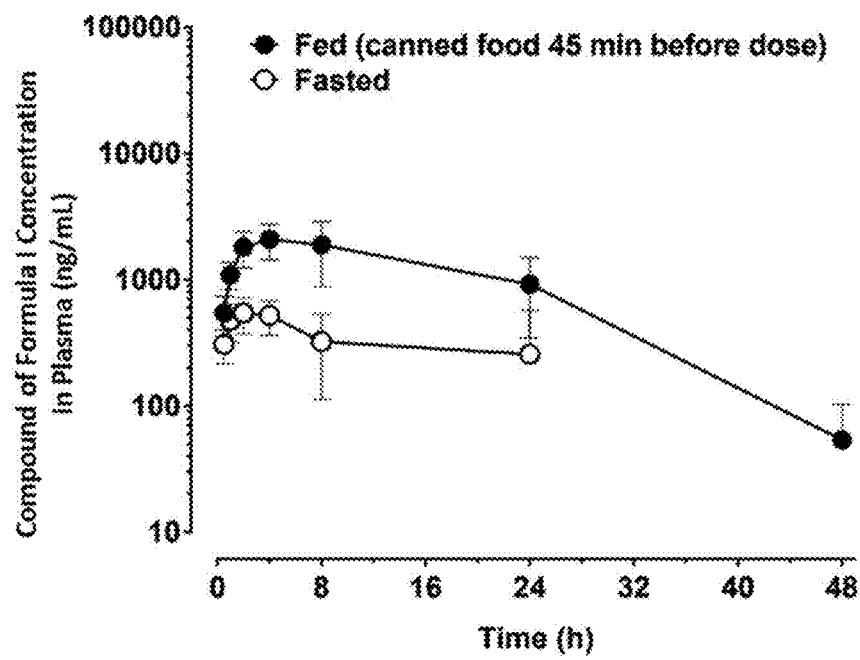
FIGS. 15A-B show the compound of Formula I concentration in plasma over 48 hours in dogs.

FIG. 15A shows the concentration of the compound of Formula I in plasma for fed or fasted dogs for dogs administered crystalline compound of Formula I in suspension in Part A. The mean compound of Formula I exposures (Cmax and AUC0-t) are 5- to 7-fold greater in fed compared to fasted animals.

Figure 15B:
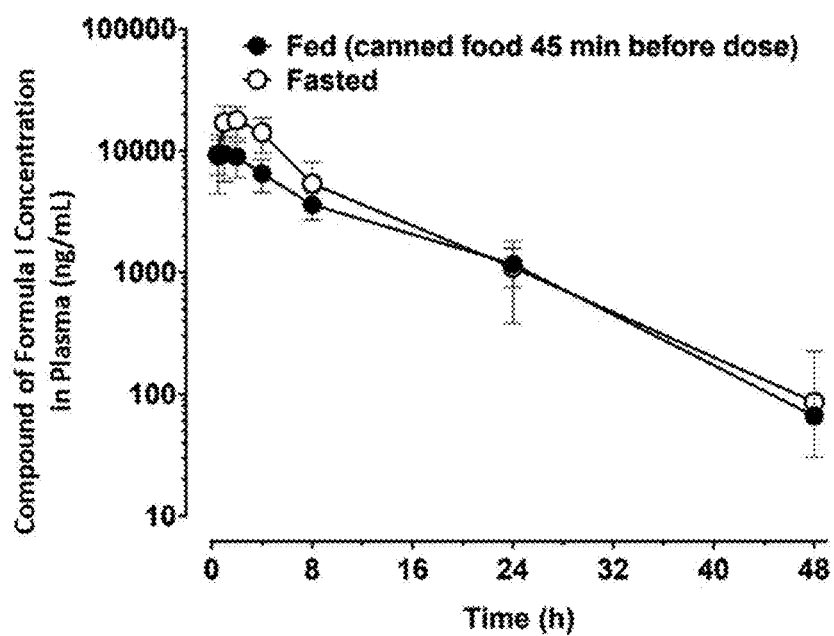

FIG. 15B shows the concentration of the compound of Formula I in plasma for fed or fasted dogs for dogs administered the compound of Formula I 50% SDI in Part B. There are no apparent differences in the compound of Formula I exposures following administration of the compound of Formula I 50% SDI to fed or fasted animals.

Other aspects of the invention are described below.

The present invention provides a spray-dried dispersion comprising the compound of Formula I, or a pharmaceutically acceptable salt, amorphous, or polymorph form thereof, and a hypromellose acetate succinate (HPMCAS) polymer. The one embodiment the ratio of the compound of Formula I, or a pharmaceutically acceptable salt, amorphous, or polymorph form thereof, to the HPMCAS polymer is about 1:4 to about 4:1. In another embodiment the ratio of the compound of Formula I, or a pharmaceutically acceptable salt, amorphous, or polymorph form thereof, to the HPMCAS polymer is about 1:1.

The present invention provides a process of preparing the spray-dried dispersion as described herein, wherein the compound of Formula I, or a pharmaceutically acceptable salt, amorphous, or polymorph form thereof, is dissolved in one or more organic solvents prior to being spray-dried. In one embodiment, the compound of Formula I, or a pharmaceutically acceptable salt, amorphous, or polymorph form thereof, is dissolved in 80:20 dichloromethane:methanol prior to being spray-dried. In embodiment the compound of Formula I, or a pharmaceutically acceptable salt, amorphous, or polymorph form thereof, is Form A of the compound of Formula I.

The present invention provides a pharmaceutical composition comprising a first composition comprising a spray-dried dispersion and one or more pharmaceutical excipients, wherein the spray-dried dispersion comprises a HPMCAS polymer and the compound of Formula I, or a pharmaceutically acceptable salt, amorphous, or polymorph form thereof. The ratio of the compound of Formula I, or a pharmaceutically acceptable salt, amorphous, or polymorph form thereof, to the HPMCAS polymer in the spray-dried dispersion is about 1:4 to about 4:1. Alternatively the ratio of the compound of Formula I, or a pharmaceutically acceptable salt, amorphous, or polymorph form thereof, to the HPMCAS polymer in the spray-dried dispersion is about 1:1. In one embodiment, the spray-dried dispersion is present in an amount of about 20% to about 75% w/w of the first composition. In one embodiment, the spray-dried dispersion is present in an amount of about 30% to about 60% w/w of the first composition. In one embodiment, the spray-dried dispersion is present in an amount of about 40% to about 50% w/w of the first composition. In one embodiment, the spray-dried dispersion is present in an amount of about 45% w/w of the first composition.

In one embodiment, the pharmaceutical excipients are selected from the group consisting of: a filler, a lubricant, and combinations thereof. The filler can be present in an amount of about 25% to about 80% w/w of the first composition. In one embodiment, the filler is present in an amount of about 45% to about 65% w/w of the first composition. In one embodiment, the filler is present in an amount of about 55% w/w of the first composition. In one embodiment, the filler is selected from the group consisting of a saccharide, gelatin, a synthetic polymer, or combinations thereof. In one embodiment, the filler is selected from the group consisting of: sucrose, lactose, microcrystalline cellulose, methyl cellulose, ethyl cellulose, hydroxypropyl cellulose, hydroxypropyl methylcellulose, a starch, xylitol, sorbitol, mannitol, a polyvinylpyrrolidone, a polyethylene glycol, a polyvinyl alcohol, a polymethacrylate, a poloxamer, magnesium stearate, calcium stearate, sodium stearate, stearic acid, a hydrogenated vegetable oil, a mineral oil, sodium lauryl sulfate, magnesium lauryl sulfate, glyceryl palmitostearate, sodium stearyl fumarate, colloidal silicon dioxide, sodium benzoate, sodium oleate, sodium acetate, and combinations thereof.

In one embodiment, the filler is a binder, a disintegrant, or a combination thereof. In one embodiment, the binder is present in an amount of about 30% to about 80% w/w of the first composition. In one embodiment, the binder is present in an amount of about 40% to about 60% w/w of the first composition. In one embodiment, the binder is present in an amount of about 52% w/w of the first composition. In one embodiment, the binder is selected from the group consisting of: microcrystalline cellulose, cellulose ethers, hydroxypropyl cellulose, hydroxypropyl methylcellulose, sodium carboxy methyl cellulose starches, methyl cellulose, ethyl cellulose, mannitol, xylitol, sorbitol, lactose, sucrose, sorbitol, gelatin, polyvinylpyrrolidone, polyethylene glycol, polyvinyl alcohols, polymethacrylates, and combinations thereof. In one embodiment, wherein the binder is microcrystalline cellulose, mannitol, or a combination thereof. In one embodiment, wherein the microcrystalline cellulose is present in an amount of about 5% to about 55% w/w of the first composition. In one embodiment, the microcrystalline cellulose is present in an amount of about 10% to about 40% w/w of the first composition. In one embodiment, the microcrystalline cellulose is present in an amount of about 20% to about 30% w/w of the first composition. In one embodiment, the microcrystalline cellulose is present in an amount of about 26% w/w of the first composition.

In one embodiment, the mannitol is present in an amount of about 5% to about 55% w/w of the first composition. In one embodiment, the mannitol is present in an amount of about 10% to about 40% w/w of the first composition. In one embodiment, wherein the mannitol is present in an amount of about 20% to about 30% w/w of the first composition. In one embodiment, wherein the mannitol is present in an amount of about 26% w/w of the first composition.

In one embodiment, the disintegrant is present in an amount of about 0.5% to about 5% w/w of the first composition. In one embodiment, wherein the disintegrant is present in an amount of about 1.5% to about 3.5% w/w of the first composition. In one embodiment, wherein the disintegrant is present in an amount of about 2.5% w/w of the first composition. In one embodiment, wherein the disintegrant is selected from the group consisting of: sodium starch glycolate, alginic acid, sodium alginate, an ion exchange resin, and combinations thereof. In one embodiment, wherein the disintegrant is sodium starch glycolate.

In one embodiment, the lubricant is present in an amount of about 0.05% to about 2.5% w/w of the first composition. In one embodiment, the lubricant is present in an amount of about 0.1% to about 1% w/w of the first composition. In one embodiment, the lubricant is present in an amount of about 0.25% w/w of the first composition. In one embodiment, the lubricant is selected from the group consisting of: magnesium stearate, calcium stearate, sodium stearate, stearic acid, a hydrogenated vegetable oil, a mineral oil, a polyethylene glycol, sodium lauryl sulfate, magnesium lauryl sulfate, glyceryl palmitostearate, sodium benzoate, sodium stearyl fumarate, colloidal silicon dioxide, sodium benzoate, sodium oleate, sodium acetate, and combinations thereof. In one embodiment, the lubricant is magnesium stearate.

In one embodiment, the spray-dried dispersion is present in an amount of about 20% to about 75% w/w of the first composition, the filler is present in an amount of about 25% to about 80% w/w of the first composition, and the lubricant is present in an amount of about 0.05% to about 2% w/w of the first composition. In one embodiment, the spray-dried dispersion is present in an amount of about 45% w/w of the first composition, the filler is present in an amount of about 55% w/w of the first composition, and the lubricant is present in an amount of about 0.25% w/w of the first composition. In one embodiment, the spray-dried dispersion is present in an amount of about 40% to about 50% w/w of the first composition, the microcrystalline cellulose is present in an amount of about 20% to about 30% w/w of the first composition, the mannitol is present in an amount of about 20% to about 30% w/w of the first composition, the sodium starch glycolate is present in an amount of about 0.5% to about 5% w/w of the first composition, and the magnesium stearate is present in an amount of about 0.05% to about 2% w/w of the first composition. In one embodiment, the spray-dried dispersion and pharmaceutical excipients are blended. In one embodiment, the first composition is granulated. In one embodiment, the first composition is granulated by roller compaction In one embodiment, the first composition is present in an amount of about 15% to about 99% w/w of the total composition. In one embodiment, the one or more pharmaceutical excipients are selected from the group consisting of: a filler, a lubricant, and combinations thereof. In one embodiment, the lubricant is present in an amount of about 0.05% to about 2% w/w of the total composition. In one embodiment, the lubricant is present in an amount of about 0.1% to about 0.8% w/w of the total composition. In one embodiment, the lubricant is present in an amount of about 0.3% w/w of the total composition. In one embodiment, the lubricant is selected from the group consisting of: magnesium stearate, calcium stearate, sodium stearate, stearic acid, a hydrogenated vegetable oil, a mineral oil, polyethylene glycol, sodium lauryl sulfate, magnesium lauryl sulfate, glyceryl palmitostearate, sodium benzoate, sodium stearyl fumarate, colloidal silicon dioxide, sodium oleate, sodium acetate, and combinations thereof. In one embodiment, wherein the lubricant is magnesium stearate. In one embodiment, the filler is present in an amount of about 1% to about 85% w/w of the total composition. In one embodiment, the filler is selected from the group consisting of: sucrose, lactose, microcrystalline cellulose, methyl cellulose, ethyl cellulose, hydroxypropyl cellulose, hydroxypropyl methylcellulose, starch, xylitol, sorbitol, mannitol, a polyvinylpyrrolidone, a polyethylene glycol, a polyvinyl alcohol, a polymethacrylate, a poloxamer, magnesium stearate, calcium stearate, sodium stearate, stearic acid, a hydrogenated vegetable oil, a mineral oil, sodium lauryl sulfate, magnesium lauryl sulfate, glyceryl palmitostearate, sodium stearyl fumarate, colloidal silicon dioxide, sodium benzoate, sodium oleate, sodium acetate, and combinations thereof. In one embodiment, wherein the filler is a binder, a disintegrant, or a combination thereof. In one embodiment, the disintegrant is present in an amount of about 0.5% to about 5% w/w of the total composition. In one embodiment, the disintegrant is present in an amount of about 2.5% w/w of the total composition. In one embodiment, the disintegrant is selected from the group consisting of: sodium starch glycolate, alginic acid, sodium alginate, an ion exchange resin, and combinations thereof. In one embodiment, the disintegrant is sodium starch glycolate. In one embodiment, the first composition is present in an amount of about 90% to about 99% w/w of the total composition. In one embodiment, the first composition is present in an amount of about 97% w/w of the total composition. In one embodiment, the first composition is present in an amount of about 15% to about 60% w/w of the total composition. In one embodiment, the first composition is present in an amount of about 30% to about 40% w/w of the total composition. In one embodiment, the first composition is present in an amount of about 35% w/w of the total composition. In one embodiment, the binder is present in an amount of about 40% to about 85% w/w of the total composition. In one embodiment, the binder is present in an amount of about 55% to about 75% w/w of the total composition. In one embodiment, the binder is selected from the group consisting of: microcrystalline cellulose, a cellulose ether, hydroxypropyl cellulose, hydroxypropyl methylcellulose, sodium carboxy methyl cellulose starch, a cellulose, methyl cellulose, ethyl cellulose, mannitol, xylitol, sorbitol, lactose, sucrose, sorbitol, gelatin, a polyvinylpyrrolidone, a polyethylene glycol, a polyvinyl alcohol, a polymethacrylate, and combinations thereof. In one embodiment, the binder is microcrystalline cellulose, mannitol, or a combination thereof. In one embodiment, the microcrystalline cellulose is present in an amount of about 25% to about 35% w/w of the total composition. In one embodiment, the microcrystalline cellulose is present in an amount of about 31% w/w of the total composition. In one embodiment, the mannitol is present in an amount of about 25% to about 35% w/w of the total composition. In one embodiment, the mannitol is present in an amount of about 31% w/w of the total composition. In one embodiment, the first composition is blended with the pharmaceutical excipients. In one embodiment, the pharmaceutical composition is co-milled. In one embodiment, the pharmaceutical composition is formulated as a tablet. In one embodiment, the compound of Formula I, or a pharmaceutically acceptable salt, amorphous, or polymorph form thereof, is present in an amount of about 10 mg to about 50 mg. In one embodiment, the compound of Formula I, or a pharmaceutically acceptable salt, amorphous, or polymorph form thereof, is present in an amount of about 25 mg to about 220 mg.

The present invention provides a pharmaceutical composition, wherein the pharmaceutical composition comprises: (S)-5-amino-3-(4-((5-fluoro-2-methoxybenzamido)methyl)phenyl)-1-(1,1,1-trifluoropropan-2-yl)-1H-pyrazole-4-carboxamide; a HPMCAS polymer; and one or more pharmaceutical excipients. In one embodiment, the one or more pharmaceutical excipients are selected from the group consisting of: a filler, a lubricant, and a combination thereof. In one embodiment, the filler is selected from the group consisting of: sucrose, lactose, microcrystalline cellulose, methyl cellulose, ethyl cellulose, hydroxypropyl cellulose, hydroxypropyl methylcellulose, starch, xylitol, sorbitol, mannitol, polyvinylpyrrolidone, a polyethylene glycol, a polyvinyl alcohol, a polymethacrylate, magnesium stearate, calcium stearate, sodium stearate, stearic acid, a hydrogenated vegetable oil, a mineral oil, sodium lauryl sulfate, magnesium lauryl sulfate, glyceryl palmitostearate, sodium stearyl fumarate, colloidal silicon dioxide, sodium benzoate, sodium oleate, sodium acetate, and combinations thereof. In one embodiment, the lubricant is selected from the group consisting of: magnesium stearate, calcium stearate, sodium stearate, stearic acid, a hydrogenated vegetable oil, a mineral oil, polyethylene glycol, sodium lauryl sulfate, magnesium lauryl sulfate, glyceryl palmitostearate, sodium stearyl fumarate, colloidal silicon dioxide, sodium benzoate, sodium oleate, sodium acetate, and combinations thereof. In one embodiment, the composition comprises: (S)-5-amino-3-(4-((5-fluoro-2-methoxybenzamido)methyl)phenyl)-1-(1,1,1-trifluoropropan-2-yl)-1H-pyrazole-4-carboxamide; the HPMCAS polymer; microcrystalline cellulose; mannitol; sodium starch glycolate; and magnesium stearate. In one embodiment, the composition comprises: (S)-5-amino-3-(4-((5-fluoro-2-methoxybenzamido)methyl)phenyl)-1-(1,1,1-trifluoropropan-2-yl)-1H-pyrazole-4-carboxamide present in an amount of about 5% to about 30% w/w of the composition; the HPMCAS polymer present in an amount of about 5% to about 30% w/w of the composition; microcrystalline cellulose present in an amount of about 30% to about 60% w/w of the composition; mannitol present in an amount of about 30% to about 60% w/w of the composition; sodium starch glycolate present in an amount of about 0.5% to about 5% w/w of the composition; and magnesium stearate present in an amount of about 0.05% to about 2% w/w of the composition. In one embodiment, the composition comprises: (S)-5-amino-3-(4-((5-fluoro-2-methoxybenzamido)methyl)phenyl)-1-(1,1,1-trifluoropropan-2-yl)-1H-pyrazole-4-carboxamide present in an amount of about 8% w/w of the composition; the HPMCAS polymer present in an amount of about 8% w/w of the composition; microcrystalline cellulose present in an amount of about 40% w/w of the composition; mannitol present in an amount of about 40% w/w of the composition; sodium starch glycolate present in an amount of about 3.5% w/w of the composition; and magnesium stearate present in an amount of about 0.3% w/w of the composition. In one embodiment, the composition comprises: (S)-5-amino-3-(4-((5-fluoro-2-methoxybenzamido)methyl)phenyl)-1-(1,1,1-trifluoropropan-2-yl)-1H-pyrazole-4-carboxamide present in an amount of about 10% to about 30% w/w of the composition; the HPMCAS polymer present in an amount of about 10% to about 30% w/w of the composition; microcrystalline cellulose present in an amount of about 20% to about 30% w/w of the composition; mannitol present in an amount of about 20% to about 30% w/w of the composition; sodium starch glycolate present in an amount of about 2% to about 8% w/w of the composition; and magnesium stearate present in an amount of about 0.05% to about 2% w/w of the composition. In one embodiment, the composition comprises: (S)-5-amino-3-(4-((5-fluoro-2-methoxybenzamido)methyl)phenyl)-1-(1,1,1-trifluoropropan-2-yl)-1H-pyrazole-4-carboxamide present in an amount of about 22% w/w of the composition; the HPMCAS polymer present in an amount of about 22% w/w of the composition; microcrystalline cellulose present in an amount of about 25% w/w the composition; mannitol present in an amount of about 25% w/w the composition; sodium starch glycolate present in an amount of about 5% w/w of the composition; and magnesium stearate present in an amount of about 0.5% w/w of the composition. In one embodiment, the pharmaceutical composition is formulated as a tablet. In one embodiment, the tablet is coated.

The present invention provides a method for preparing the pharmaceutical composition as described herein, comprising: mixing (S)-5-amino-3-(4-((5-fluoro-2-methoxybenzamido)methyl)phenyl)-1-(1,1,1-trifluoropropan-2-yl)-1H-pyrazole-4-carboxamide, the HPMCAS polymer, and an organic solvent to form a mixture; spray-drying the mixture to form a spray-dried dispersion; and granulating the spray-dried dispersion to form a first composition. In one embodiment, the organic solvent is a mixture of dichloromethane and methanol. In one embodiment, the organic solvent is 80:20 dichloromethane:methanol. In one embodiment, the spray-dried dispersion is blended with one or more pharmaceutical excipients prior to being granulated. In one embodiment, the spray-dried dispersion is dried in an oven prior to being granulated. In one embodiment, the spray-dried dispersion is blended with one or more pharmaceutical excipients prior to being granulated. In one embodiment, the spray-dried dispersion is granulated by roller compaction. In one embodiment, the first composition is blended with one or more pharmaceutical excipients. In one embodiment, the first composition is co-milled. In one embodiment, the first composition is pressed into a tablet. In one embodiment, the tablet is coated. In one embodiment, the coating comprises a polymer, a plasticizer, a pigment, or combinations thereof. In one embodiment, the ratio of (S)-5-amino-3-(4-((5-fluoro-2-methoxybenzamido)methyl)phenyl)-1-(1,1,1-trifluoropropan-2-yl)-1H-pyrazole-4-carboxamide to the HPMCAS polymer in the spray-dried dispersion is about 1:4 to about 4:1. In one embodiment, the ratio of (S)-5-amino-3-(4-((5-fluoro-2-methoxybenzamido)methyl)phenyl)-1-(1,1,1-trifluoropropan-2-yl)-1H-pyrazole-4-carboxamide to the HPMCAS polymer in the spray-dried dispersion is about 1:1.

The present invention provides a crystalline form of a compound of Formula I having the formula

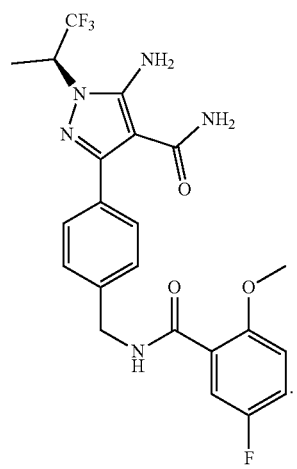

I

In one embodiment, the crystalline form is Form A, characterized by having an X-ray powder diffraction (XRPD) pattern comprising peaks at °2θ values of 15.8±0.2, 16.2±0.2, and 11.9±0.2.

In one embodiment, the crystalline form is Form A, characterized by having an X-ray powder diffraction (XRPD) pattern comprising peaks at °2θ values of 15.8±0.2, 16.2±0.2, 11.9±0.2, 19.0±0.2, and 18.3±0.2. In one embodiment, the crystalline form is Form A, characterized by having an X-ray powder diffraction (XRPD) pattern comprising peaks at ° 2θ values of 15.8±0.2, 16.2±0.2, 11.9±0.2, 19.0±0.2, 18.3±0.2, 23.8±0.2, and 20.5±0.2. In one embodiment, the crystalline form is Form A, characterized by having an X-ray powder diffraction (XRPD) pattern comprising peaks at °2θ values of 15.8±0.2, 16.2±0.2, 11.9±0.2, 19.0±0.2, 18.3±0.2, 23.8±0.2, 20.5±0.2, 25.7±0.2, 20.1±0.2, and 9.5±0.2. In one embodiment, the crystalline form is Form A, characterized by having an X-ray powder diffraction (XRPD) pattern comprising peaks at °2θ values of 15.8±0.2, 16.2±0.2, 11.9±0.2, 19.0±0.2, 18.3±0.2, 23.8±0.2, 20.5±0.2, 25.7±0.2, 20.1±0.2, 9.5±0.2, 25.0±0.2, and 11.1±0.2. In one embodiment, the crystalline form is Form A and has an XRPD pattern substantially as shown in FIG. 4A. In one embodiment, the crystalline form is Form A and has a differential scanning calorimetry (DSC) curve comprising an endotherm with an onset of about 185° C. In one embodiment, the crystalline form is Form A and has a DSC thermogram substantially as shown in FIG. 4C.

The present invention provides a solid oral pharmaceutical composition comprising a pharmaceutical excipient and a crystalline form. In one embodiment, the pharmaceutical composition made by mixing a crystalline form and a pharmaceutical excipient.

The present invention provides a process for making a solid oral pharmaceutical composition comprising mixing a crystalline form as described herein and a pharmaceutical excipient. In one embodiment, the liquid pharmaceutical composition is made by mixing a crystalline form as described herein and a pharmaceutical excipient. In one embodiment, the process comprises mixing a crystalline form and a pharmaceutical excipient.

The present invention provides a method for treating cancer in a subject in need thereof, the method comprising administering a spray-dried dispersion, a pharmaceutical composition or a therapeutically effective amount of a compound of Formula I. In one embodiment, the cancer is a BTK-associated cancer. In one embodiment, the method comprises: (a) detecting a dysregulation of a BTK gene, a BTK kinase, or expression or activity or level of any of the same; and (b) administering to the subject a spray-dried dispersion as described herein, a pharmaceutical composition as described herein, or a therapeutically effective amount of the compound as described herein. In one embodiment, the method comprises administering to a subject identified or diagnosed as having a BTK-associated cancer a spray-dried dispersion, a pharmaceutical composition, or a therapeutically effective amount of the compound of Formula I, to the subject. In one embodiment, the method comprises detecting a dysregulation of a BTK gene, a BTK kinase, or expression or activity or level of any of the same; and administering to a subject determined to have a BTK-associated cancer a spray-dried dispersion, a pharmaceutical composition, or a therapeutically effective amount of the compound of Formula I. In one embodiment, the method comprises administering a spray-dried dispersion a pharmaceutical composition or a therapeutically effective amount of the compound of Formula I, to a subject having a clinical record that indicates that the subject has a dysregulation of a BTK gene, a BTK kinase, or expression or activity or level of any of the same.

In one embodiment, the method comprises inhibiting metastasis of a cancer in a subject in need thereof, the method comprising administering to the subject a spray-dried dispersion, a pharmaceutical composition, or a therapeutically effective amount of a compound of Formula I. In one embodiment, the cancer is a BTK-associated cancer.

The present invention provides a method of selecting a treatment for a subject comprising selecting a treatment comprising administration of a spray-dried dispersion, a pharmaceutical composition, or a therapeutically effective amount of the compound of Formula to a subject identified or diagnosed as having a BTK-associated cancer. In one embodiment, the method comprises detecting a dysregulation of a BTK gene, a BTK kinase, or expression or activity or level of any of the same in the subject; and selecting a treatment for the subject including administration of a spray-dried dispersion, a pharmaceutical composition, or a therapeutically effective amount of Formula I.

In one embodiment, the method comprises selecting a subject for treatment the method comprising: identifying a subject having a BTK-associated cancer; and selecting the subject for treatment including administration of a spray-dried dispersion, a pharmaceutical composition, or a therapeutically effective amount of the compound of Formula I. In one embodiment, the method comprises selecting a subject having cancer for treatment the method comprising: detecting a dysregulation of a BTK gene, a BTK kinase, or expression or activity or level of any of the same in the subject; and selecting the subject for treatment including administration of a spray-dried dispersion, a pharmaceutical composition, or a therapeutically effective amount of Formula I. In one embodiment, the method comprises the step of determining if the cancer in the subject is a BTK-associated cancer includes performing an assay to detect dysregulation in a BTK gene, a BTK kinase protein, or expression or activity or level of any of the same in a sample from the subject. In one embodiment, the method comprises obtaining a sample from the subject. The sample can be a biopsy sample. In one embodiment, the assay is selected from the group consisting of sequencing, immunohistochemistry, immunoblots, enzyme-linked immunosorbent assay, and fluorescence in situ hybridization (FISH). In one embodiment, the FISH is break apart FISH analysis. In one embodiment, the sequencing is pyrosequencing or next generation sequencing.

In one embodiment, the dysregulation in a BTK gene, a BTK kinase protein, or expression or activity or level of any of the same is the result of a dysregulation in BCR signaling pathway gene, a BCR signaling pathway protein, or expression or activity or level of any one of the same. In one embodiment, the BCR signaling pathway gene or BCR signaling pathway protein is selected from the group consisting of: cyclin-D1, CARD11, CD79B, CD79A, MYD88, and combinations thereof. In one embodiment, the dysregulation in the BCR signaling pathway gene, a BCR signaling pathway protein, or expression or activity or level of any one of the same is the result of one or more genetic alterations. In one embodiment, the one or more genetic alterations are selected from the group consisting of: chromosomal translocation t(11;14)(q13;q32), deletions of the chromosomal region 17p13, deletions of the chromosomal region 11q23, deletions of the chromosomal region 13q14, and trisomy of chromosome 12. In one embodiment, the one or more genetic alterations is one or more point mutations in a gene encoding a BCR signaling pathway protein. In one embodiment, the one or more point mutations in a gene encoding a BCR signaling pathway protein results in the translation of BCR signaling pathway protein having one or more amino acid substitutions, wherein the BCR signaling pathway protein is selected from the group consisting of: CARD11, CD79B, CD79A, MYD88, and combinations thereof. In one embodiment, the one or more point mutations in a gene encoding a BCR signaling pathway protein results in the translation of BCR signaling pathway protein having one or more amino acid substitutions at one or more of the following amino acid positions: $MYD88^{L265}$. In one embodiment, the amino acid substitution is $MYD88^{L265P}$. In one embodiment, the dysregulation in a BTK gene, a BTK kinase protein, or expression or activity or level of any of the same is one or more point mutations in the BTK gene. In one embodiment, the one or more point mutations in a BTK gene results in the translation of a BTK protein having one or more amino acid substitutions at one or more of the following amino acid positions: 117, 316, 474, 481, 528, 560, 562, and 601. In one embodiment, the one or more point mutations in a BTK gene results in the translation of a BTK protein having one or more of the following amino acid substitutions: T117P, T316A, T474I, T474M, T474S, C481S, C481F, C481T, C481G, C481R, L528W, P560L, R562W, R562G, and F601L.

The present invention provides a method for treating cancer in a subject in need thereof, the method comprises:

(a) detecting a dysregulation of a BCR signaling pathway gene, a BCR signaling pathway protein, or expression or activity or level of any of the same; and (b) administering to the subject a spray-dried dispersion, a pharmaceutical composition, or a therapeutically effective amount of the compound of Formula I. In one embodiment, the subject has a dysregulation of a BCR signaling pathway gene, a BCR signaling pathway protein, or expression or activity or level of any of the same. In one embodiment, the step of determining if the cancer in the subject is a BTK-associated cancer includes performing an assay to detect a dysregulation of a BCR signaling pathway gene, a BCR signaling pathway protein, or expression or activity or level of any of the same in a sample from the subject and further comprising obtaining a sample from the subject. In one embodiment, the sample is a biopsy sample. In one embodiment, the assay is selected from the group consisting of sequencing, immunohistochemistry, enzyme-linked immunosorbent assay, and fluorescence in situ hybridization (FISH). In one embodiment, the FISH is break apart FISH analysis. In one embodiment, the sequencing is pyrosequencing or next generation sequencing. In one embodiment, the BCR signaling pathway gene or BCR signaling pathway protein is selected from the group consisting of: cyclin-D1, CARD11, CD79B, CD79A, MYD88, and combinations thereof. In one embodiment, the dysregulation in the BCR signaling pathway gene, a BCR signaling pathway protein, or expression or activity or level of any one of the same is the result of one or more genetic alterations. In one embodiment, the one or more genetic alterations are selected from the group consisting of: chromosomal translocation t(11;14)(q13;q32), deletions of the chromosomal region 17p13, deletions of the chromosomal region 11q23, deletions of the chromosomal region 13q14, and trisomy of chromosome 12. In one embodiment, the one or more genetic alterations is one or more point mutations in a gene encoding a BCR signaling pathway protein. In one embodiment, the one or more point mutations in a gene encoding a BCR signaling pathway protein results in the translation of BCR signaling pathway protein having one or more amino acid substitutions, wherein the BCR signaling pathway protein is selected from the group consisting of: CARD11, CD79B, CD79A, MYD88, and combinations thereof. In one embodiment, the one or more point mutations in a gene encoding a BCR signaling pathway protein results in the translation of BCR signaling pathway protein having one or more amino acid substitutions at one or more of the following amino acid positions: $MYD88^{L265}$. In one embodiment, the amino acid substitution is $MYD88^{L265P}$.

In one embodiment, the BTK-associated cancer is selected from the group consisting of: Hodgkin lymphoma, diffuse large B cell lymphoma (DLBCL) (e.g., activated B cell-like DLBCL (ABC-DLBCL)), follicular lymphoma, mantle cell lymphoma, marginal zone lymphoma (e.g., extranodal marginal zone B cell lymphoma, splenic marginal zone lymphoma), Burkitt lymphoma, Waldenstrom's macroglobulinemia (lymphoplasmacytic lymphoma (LPL)), primary central nervous system lymphoma, small lymphocytic lymphoma, chronic lymphocytic leukemia (CLL), acute lymphocytic leukemia (ALL), B-cell prolymphocytic leukemia, precursor B-lymphoblastic leukemia, hairy cell leukemia, acute myeloid leukemia (AML), chronic myeloid leukemia, multiple myeloma, plasma cell myeloma, plasmacytoma, bone cancer, bone metastasis, breast cancer, gastro-esophageal cancer, pancreatic cancer, ovarian cancer, prostate cancer, lung cancer, colon cancer, uterine cancer, hepatocellular cancer, head and neck cancer, or glioma.

In one embodiment, the BTK-associated cancer is a hematological cancer. In one embodiment, the hematological cancer is selected from the group consisting of: leukemias, lymphomas (non-Hodgkin's lymphoma), Hodgkin's disease, and myeloma. In one embodiment, the hematological cancer is selected from the group consisting of: acute lymphocytic leukemia (ALL), acute myeloid leukemia (AML), acute promyelocytic leukemia (APL), chronic lymphocytic leukemia (CLL), chronic myeloid leukemia (CML), chronic myelomonocytic leukemia (CMML), chronic neutrophilic leukemia (CNL), acute undifferentiated leukemia (AUL), anaplastic large-cell lymphoma (ALCL), prolymphocytic leukemia (PML), juvenile myelomonocytic leukemia (JMML), adult T-cell ALL, AML with trilineage myelodysplasia (AML/TMDS), mixed lineage leukemia (MLL), myelodysplastic syndromes (MDSs), myeloproliferative disorders (MPD), diffuse large B cell lymphoma (DLBCL) (e.g., activated B cell-like DLBCL (ABC-DLBCL)), follicular lymphoma, mantle cell lymphoma, marginal zone lymphoma (e.g., extranodal marginal zone B cell lymphoma, splenic marginal zone lymphoma), Burkitt lymphoma, Waldenstrom's macroglobulinemia (lymphoplasmacytic lymphoma (LPL)), primary central nervous system lymphoma, small lymphocytic lymphoma, precursor B-lymphoblastic leukemia, hairy cell leukemia, chronic myeloid leukemia, anaplastic large cell lymphoma, MALT lymphoma, plasma cell myeloma, plasmacytoma, and multiple myeloma (MM).

In one embodiment, the BTK-associated cancer is a B-cell malignancy. In one embodiment, the B-cell malignancy is selected from the group consisting of: a Hodgkin lymphoma, diffuse large B cell lymphoma (DLBCL) (e.g., activated B cell-like DLBCL (ABC-DLBCL)), follicular lymphoma, mantle cell lymphoma, marginal zone lymphoma (e.g., extranodal marginal zone B cell lymphoma, splenic marginal zone lymphoma), Burkitt lymphoma, Waldenstrom's macroglobulinemia (lymphoplasmacytic lymphoma (LPL)), primary central nervous system lymphoma, small lymphocytic lymphoma, chronic lymphocytic leukemia, acute lymphoblastic leukemia (ALL), B-cell prolymphocytic leukemia, precursor B-lymphoblastic leukemia, or hairy cell leukemia.

In one embodiment, the BTK-associated cancer is selected from the group consisting of: mantle cell lymphoma, chronic lymphocytic leukemia, small lymphocytic lymphoma, Waldenstrom's macroglobulinemia, and marginal zone lymphoma. In one embodiment, the BTK-associated cancer is a solid tumor. In one embodiment, the solid tumor is selected from the group consisting of: bone cancer, bone metastasis, breast cancer, gastro-esophageal cancer, pancreatic cancer, ovarian cancer, prostate cancer, lung cancer, colon cancer, uterine cancer, hepatocellular cancer, head and neck cancer, and glioma.

The present invention further comprises administering an additional therapy or therapeutic agent to the subject. In one embodiment, the additional therapy or therapeutic agent is selected from radiotherapy, cytotoxic chemotherapeutics, kinase-targeted therapeutics, apoptosis modulators, signal transduction inhibitors, immune-targeted therapies, transcriptional regulation inhibitors, and angiogenesis-targeted therapies. In one embodiment, the additional therapeutic agent is selected from one or more kinase-targeted therapeutics. In one embodiment, the kinase-targeted therapeutic targets a kinase from a kinase family selected from: JAK, Src, IRAK, and combinations thereof. In one embodiment, the additional therapeutic inhibits a protein selected from the group consisting of antiapoptotic proteins, heat shock proteins, nuclear export proteins, kinases, histone deacetylases, E3 ubiquitin ligases, histone-lysine N-methyltransferases, and combinations thereof. In one embodiment, the additional therapeutic inhibits a protein selected from the group consisting of PI3K, JAK-2, IRAK1, IRAK4, BMX, TAK1, Src family, HDAC6, MDM2, BCL-2, EZH2, EHMT2, PIM, JAK3, mTOR, ROR-1, Syk, PKC, Hsp90, XPO1, and combinations thereof. In one embodiment, the additional therapeutic agent(s) is/are administered simultaneously as separate dosages. In one embodiment, the additional therapeutic agent(s) is/are administered as separate dosages sequentially in any order.

The present invention provides a method of treating a subject having a cancer, wherein the method comprises: (a) administering one or more doses of a first BTK inhibitor to the subject for a period of time; (b) after (a), determining whether a cancer cell in a sample obtained from the subject has at least one BTK inhibitor resistance mutation that confers increased resistance to a cancer cell or tumor to treatment with the first BTK inhibitor of step (a); and (c) administering the pharmaceutical composition as a monotherapy or in conjunction with another anticancer agent to the subject if the subject has a cancer cell that has at least one BTK inhibitor resistance mutation that confers increased resistance to a cancer cell or tumor to treatment with the first BTK inhibitor of step (a); or (d) administering additional doses of the first BTK inhibitor of step (a) to the subject if the subject has a cancer cell that does not have a BTK inhibitor resistance mutation that confers increased resistance to a cancer cell or tumor to treatment with the first BTK inhibitor of step (a). In one embodiment, the anticancer agent in step (c) is a second BTK inhibitor, an immunotherapy, or a combination thereof. In one embodiment, the anticancer agent in step (c) is the first BTK inhibitor administered in step (a). In one embodiment, the anticancer agent in step (c) is selected from one or more kinase-targeted therapeutics. T In one embodiment, the kinase-targeted therapeutic targets a kinase from a kinase family selected from: JAK, Src, IRAK, and combinations thereof. In one embodiment, the anticancer agent in step (c) is a protein inhibitor that inhibits a protein selected from the group consisting of: antiapoptotic proteins, heat shock proteins, nuclear export proteins, kinases, histone deacetylases, E3 ubiquitin ligases, histone-lysine N-methyltransferases, and combinations thereof. In one embodiment, the protein inhibitor inhibits a protein selected from the group consisting of: PI3K, JAK-2, IRAK1, IRAK4, BMX, TAK1, Src family, HDAC6, MDM2, BCL-2, EZH2, EHMT2, PIM, JAK3, mTOR, ROR-1, Syk, PKC, Hsp90, XPO1, and combinations thereof. In one embodiment, the subject is administered additional doses of the first BTK inhibitor of step (a), and the method further comprises (e) administering another anticancer agent to the subject. In one embodiment, the anticancer agent of step (e) is a second BTK inhibitor, an immunotherapy, or a combination thereof. In one embodiment, the anticancer agent of step (e) is the spray-dried dispersion or the pharmaceutical composition.

The present invention provides a method of treating a subject having a cancer, wherein the method comprises: (a) administering one or more doses of a first BTK inhibitor, to the subject for a period of time; (b) after (a), determining whether a cancer cell in a sample obtained from the subject has at least one BTK inhibitor resistance mutation that confers increased resistance to a cancer cell or tumor to treatment with the first BTK inhibitor of step (a); (c) administering a second BTK inhibitor as a monotherapy or in conjunction with another anticancer agent to the subject if the subject has a cancer cell that has at least one BTK inhibitor resistance mutation that confers increased resistance to a cancer cell or tumor to treatment with the first BTK inhibitor of step (a); or (d) administering additional doses of the first BTK inhibitor of step (a) to the subject if the subject has a cancer cell that does not have a BTK inhibitor resistance mutation that confers increased resistance to a cancer cell or tumor to treatment with the first BTK inhibitor of step (a); wherein the mutation is a substitution at amino acid position 481, e.g., C481S, C481F, C481T, C481G, and C481R. In one embodiment, the anticancer agent of step (c) is the first BTK inhibitor administered in step (a). In one embodiment, the subject is administered additional doses of the first BTK inhibitor of step (a), and the method further comprises (e) administering another anticancer agent. In one embodiment, the anticancer agent of step (e) is a second BTK inhibitor, an immunotherapy, or a combination thereof. In one embodiment, the anticancer agent of step (e) is a pharmaceutical composition as described herein or a pharmaceutically acceptable salt thereof.

The present invention provides a method of treating a subject having a cancer, wherein the method comprises: (a) administering one or more doses of a first BTK inhibitor, to the subject for a period of time; (b) after (a), determining whether a cancer cell in a sample obtained from the subject has at least one BTK inhibitor resistance mutation that confers increased resistance to a cancer cell or tumor to treatment with the first BTK inhibitor of step (a); (c) administering a spray-dried dispersion as described herein or a pharmaceutical composition as described herein as a monotherapy or in conjunction with another anticancer agent to the subject if the subject has a cancer cell that has at least one BTK inhibitor resistance mutation that confers increased resistance to a cancer cell or tumor to treatment with the first BTK inhibitor of step (a); or (d) administering additional doses of the first BTK inhibitor of step (a) to the subject if the subject has a cancer cell that does not have a BTK inhibitor resistance mutation that confers increased resistance to a cancer cell or tumor to treatment with the first BTK inhibitor of step (a); wherein the mutation is a substitution at one or more amino acid positions 244, 257, 334, 495, 664, 665, 707, 708, 742, 845, 848, 993, 1140, or 1141 of PLCγ2. In one embodiment, the anticancer agent of step (c) is selected from one or more kinase-targeted therapeutics. In one embodiment, the kinase-targeted therapeutic targets a kinase from a kinase family selected from: JAK, Src, IRAK, and combinations thereof. In one embodiment, the anticancer agent in step (c) is a protein inhibitor that inhibits a protein selected from the group consisting of antiapoptotic proteins, heat shock proteins, nuclear export proteins, kinases, histone deacetylases, E3 ubiquitin ligases, histone-lysine N-methyltransferases, and combinations thereof. In one embodiment, the protein inhibitor inhibits a protein selected from the group consisting of: PI3K, JAK-2, IRAK1, IRAK4, BMX, TAK1, Src family, HDAC6, MDM2, BCL-2, EZH2, EHMT2, PIM, JAK3, mTOR, ROR-1, Syk, PKC, Hsp90, XPO1, and combinations thereof.

The present invention provides a method of treating a subject having a cancer, wherein the method comprises: (a) determining whether a cancer cell in a sample obtained from a subject having a cancer and previously administered one or more doses of a first BTK inhibitor has one or more BTK inhibitor resistance mutations that confer increased resistance to a cancer cell or tumor to treatment with the first BTK inhibitor that was previously administered to the subject; and (b) administering a spray-dried dispersion as described herein or a pharmaceutical composition as described herein, as a monotherapy or in conjunction with another anticancer agent to the subject if the subject has a cancer cell that has at least one BTK inhibitor resistance mutation that confers increased resistance to a cancer cell or tumor to treatment with the first BTK inhibitor that was previously administered to the subject; or (c) administering additional doses of the first BTK inhibitor to the subject if the subject has cancer cell that does not have a BTK inhibitor resistance mutation that confers increased resistance to a cancer cell or tumor to treatment with the first BTK inhibitor previously administered to the subject. In one embodiment, the anticancer agent of step (b) is a second BTK inhibitor, an immunotherapy, or a combination thereof. In one embodiment, the anticancer agent of step (b) is the first BTK inhibitor previously administered to the subject. In one embodiment, the anticancer agent in step (b) is selected from one or more kinase-targeted therapeutics. In one embodiment, the kinase-targeted therapeutic targets a kinase from a kinase family selected from: JAK, Src, IRAK, and combinations thereof. In one embodiment, the anticancer agent in step (b) is a protein inhibitor that inhibits a protein selected from the group consisting of: antiapoptotic proteins, heat shock proteins, nuclear export proteins, kinases, histone deacetylases, E3 ubiquitin ligases, histone-lysine N-methyltransferases, and combinations thereof. In one embodiment, the protein inhibitor inhibits a protein selected from the group consisting of: PI3K, JAK-2, IRAK1, IRAK4, BMX, TAK1, Src family, HDAC6, MDM2, BCL-2, EZH2, EHMT2, PIM, JAK3, mTOR, ROR-1, Syk, PKC, Hsp90, XPO1, and combinations thereof. In one embodiment, the subject is administered additional doses of the first BTK inhibitor previously administered to the subject, and the method further comprises (d) administering another anticancer agent to the subject. In one embodiment, the anticancer agent of step (d) is a second BTK inhibitor, an immunotherapy, a protein inhibitor, or a combination thereof. In one embodiment, the anticancer agent of step (d) is a spray-dried dispersion or the pharmaceutical composition.

The present invention provides a method of treating a subject having a cancer, wherein the method comprises: (a) determining whether a cancer cell in a sample obtained from a subject having a cancer and previously administered one or more doses of a first BTK inhibitor has one or more BTK inhibitor resistance mutations that confer increased resistance to a cancer cell or tumor to treatment with the first BTK inhibitor previously administered to the subject; and (b) administering a second BTK inhibitor to the subject as a monotherapy or in conjunction with another anticancer agent to the subject if the subject has a cancer cell that has at least one BTK inhibitor resistance mutation that confers increased resistance to a cancer cell or tumor to treatment with the first BTK inhibitor that was previously administered to the subject; or (c) administering additional doses of the first BTK inhibitor that was previously administered to the subject if the subject has cancer cell that does not have a BTK inhibitor resistance mutation that confers increased resistance to a cancer cell or tumor to treatment with the first BTK inhibitor that was previously administered to the subject. In one embodiment, the anticancer agent of step (b) is the first BTK inhibitor previously administered to the subject. In one embodiment, the subject is administered additional doses of the first BTK inhibitor previously administered to the subject, and the method further comprises (d) administering another anticancer agent to the subject.

The present invention provides a method of treating a subject having a cancer, wherein the method comprises: (a) administering one or more doses of a spray-dried dispersion or the pharmaceutical composition for a period of time; (b) after (a), determining whether a cancer cell in a sample obtained from the subject has one or more BTK inhibitor resistance mutations that confer increased resistance to a cancer cell or tumor to treatment with the spray-dried dispersion or the pharmaceutical composition of step (a); and (c) administering a second BTK inhibitor as a monotherapy or in conjunction with another anticancer agent to a subject having a cancer cell that has one or more BTK inhibitor resistance mutations that confer increased resistance to a cancer cell or tumor to treatment with the spray-dried dispersion or the pharmaceutical composition of step (a); or (d) administering additional doses of the spray-dried dispersion the pharmaceutical composition to a subject having a cancer cell that does not have a BTK inhibitor resistance mutation that confers increased resistance to a cancer cell or tumor to treatment with the spray-dried dispersion of step (a). In one embodiment, the anticancer agent of step (c) is a first BTK inhibitor, an immunotherapy, or a combination thereof. In one embodiment, the anticancer agent of step (c) is the spray-dried dispersion or the pharmaceutical composition administered in step (a). In one embodiment, the subject is administered additional doses of the spray-dried dispersion or the pharmaceutical composition of step (a), and the method further comprises (e) administering another anticancer agent to the subject. In one embodiment, the anticancer agent of step (e) is a second BTK inhibitor, an immunotherapy, or a combination thereof.

The present invention provides a method of treating a subject having a cancer, wherein the method comprises: (a) determining whether a cancer cell in a sample obtained from a subject having a cancer and previously administered one or more doses of the spray-dried dispersion or the a pharmaceutical composition has one or more BTK inhibitor resistance mutations that confer increased resistance to a cancer cell or tumor to treatment with the spray-dried dispersion or the pharmaceutical composition that was previously administered to the subject; (b) administering a second BTK inhibitor as a monotherapy or in conjunction with another anticancer agent to a subject having a cancer cell that has one or more BTK inhibitor resistance mutations that confer increased resistance to a cancer cell or tumor to treatment with the spray-dried dispersion or the pharmaceutical composition that was previously administered to the subject; or (c) administering additional doses of the spray-dried dispersion or the pharmaceutical composition previously administered to a subject having a cancer cell that does not have a BTK inhibitor resistance mutation that confers increased resistance to a cancer cell or tumor to treatment with the spray-dried dispersion or the pharmaceutical composition that was previously administered to the subject. In one embodiment, the anticancer agent of step (b) is a second BTK inhibitor, an immunotherapy, or a combination thereof. In one embodiment, the anticancer agent of step (b) is the spray-dried dispersion or the pharmaceutical composition that was previously administered to the subject. In one embodiment, the subject is administered additional doses of the spray-dried dispersion or the pharmaceutical composition that was previously administered to the subject, and the method further comprises (d) administering another anticancer agent to the subject. In one embodiment, the anticancer agent of step (d) is a second BTK inhibitor, an immunotherapy, or a combination thereof.

The present invention provides a method of treating a BTK-associated cancer in a subject, the method comprising: (a) administering one or more doses of a spray-dried dispersion or the pharmaceutical composition, as a monotherapy to a subject identified or diagnosed as having a BTK-associated cancer; (b) after step (a), determining a level of circulating tumor DNA in a biological sample obtained from the subject; (c) administering a spray-dried dispersion or the pharmaceutical composition and an additional therapeutic agent or treatment to a subject identified as having about the same or an elevated level of circulating tumor DNA as compared to a reference level of circulating tumor DNA, wherein the additional therapeutic agent is a second BTK kinase inhibitor. In one embodiment, the additional therapeutic agent or treatment comprises one or more of: radiation therapy, a chemotherapeutic agent, a checkpoint inhibitor, surgery, and one or more second kinase inhibitors. In one embodiment, the reference level of circulating tumor DNA is a level of circulating tumor DNA in a biological sample obtained from the subject prior to step (a).

The present invention provides a method of treating a BTK-associated cancer in a subject, the method comprising: administering a therapeutically effective amount of the spray-dried dispersion or the pharmaceutical composition, and an additional therapeutic agent or treatment to a subject (i) identified or diagnosed as having a BTK-associated cancer, (ii) previously administered one or more doses of the spray-dried dispersion or the pharmaceutical composition, as a monotherapy, and (ii) after administration of the one or more doses of the spray-dried dispersion or the pharmaceutical composition, as a monotherapy, identified as having about the same or an elevated level of circulating tumor DNA as compared to a reference level of circulating tumor DNA. In one embodiment, the reference level of circulating tumor DNA is a level of circulating tumor DNA in a biological sample obtained from the subject prior to administration of the one or more doses of the spray-dried dispersion or the pharmaceutical composition, as a monotherapy. In one embodiment, the additional therapeutic agent is a second BTK kinase inhibitor. In one embodiment, the additional therapeutic agent or treatment comprises one or more of radiation therapy, a chemotherapeutic agent, a checkpoint inhibitor, surgery, and one or more second protein inhibitors.

The present invention provides a method of selecting a treatment for a subject, the method comprising: selecting a therapeutically effective amount of the spray-dried dispersion or the pharmaceutical composition, for a subject (i) identified or diagnosed as having a BTK-associated cancer, (ii) previously administered one or more doses of a second BTK kinase inhibitor, and (ii) after administration of the one or more doses of the second BTK kinase inhibitor, identified as having about the same or an elevated level of circulating tumor DNA as compared to a reference level of circulating tumor DNA. In one embodiment, the reference level of circulating tumor DNA is a level of circulating tumor DNA in a biological sample obtained from the subject prior to administration of the one or more doses of the second BTK kinase inhibitor.

The present invention provides a method of selecting a treatment for a subject, the method comprising: selecting a therapeutically effective amount of the spray-dried dispersion or the pharmaceutical composition, and an additional therapeutic treatment for a subject (i) identified or diagnosed as having a BTK-associated cancer, (ii) previously administered one or more doses of the spray-dried dispersion or the pharmaceutical composition3, as a monotherapy, and (ii) after administration of the one or more doses of the spray-dried dispersion or the pharmaceutical composition, identified as having about the same or an elevated level of circulating tumor DNA as compared to a reference level of circulating tumor DNA. In one embodiment, the reference level of circulating tumor DNA is a level of circulating tumor DNA in a biological sample obtained from the subject prior to administration of the one or more doses of the spray-dried dispersion as described herein or the pharmaceutical composition as described herein, as a monotherapy. In one embodiment, the additional therapeutic treatment is a second BTK kinase inhibitor. In one embodiment, the additional therapeutic treatment comprises one or more of radiation therapy, a chemotherapeutic agent, a checkpoint inhibitor, and one or more second protein inhibitors.

The present invention provides a method of determining efficacy of a treatment in a subject, the method comprises: (a) determining a first level of circulating tumor DNA in a biological sample obtained from a subject identified or diagnosed as having a BTK-associated cancer at a first time point; (b) administering a treatment comprising one or more doses of a spray-dried dispersion as described herein or a pharmaceutical composition as described herein, to the subject, after the first time point and before a second time point; (c) determining a second level of circulating tumor DNA in a biological sample obtained from the subject at the second time point; and (d) identifying that the treatment is effective in a subject determined to have a decreased second level of circulating tumor DNA as compared to the first level of circulating tumor DNA; or identifying the treatment is not effective in a subject determined to have about the same or an elevated second level of circulating tumor DNA as compared to the first level of circulating tumor DNA. In one embodiment, the first time point and the second time point are about 1 week to about 1 year apart.

The present invention provides a method of determining whether a subject has developed resistance to a treatment, the method comprises: (a) determining a first level of circulating tumor DNA in a biological sample obtained from a subject identified or diagnosed as having a BTK-associated cancer at a first time point; (b) administering a treatment comprising one or more doses of the spray-dried dispersion or the pharmaceutical composition, to the subject, after the first time point and before a second time point; (c) determining a second level of circulating tumor DNA in a biological sample obtained from the subject at the second time point; and (d) determining that a subject having a decreased second level of circulating tumor DNA as compared to the first level of circulating tumor DNA has not developed resistance to the treatment; or determining that a subject having about the same or an elevated second level of circulating tumor DNA as compared to the first level of circulating tumor DNA has developed resistance to the treatment. In one embodiment, the first time point and the second time point are about 1 week to about 1 year apart.

The present invention provides the use of the spray-dried dispersion or the pharmaceutical composition for the manufacture of a medicament for treating a BTK-associated cancer in a subject. In one embodiment, the BTK-associated cancer is a cancer having a dysregulation in a BTK gene, a BTK kinase protein, or expression or activity or level of any of the same. T In one embodiment, the dysregulation in a BTK gene, a BTK kinase protein, or expression or activity or level of any of the same is the result of a dysregulation in BCR signaling pathway gene, a BCR signaling pathway protein, or expression or activity or level of any one of the same. In one embodiment, the BCR signaling pathway gene or BCR signaling pathway protein is selected from the group consisting of: cyclin-D1, CARD11, CD79B, CD79A, MYD88, and combinations thereof. In one embodiment, the dysregulation in the BCR signaling pathway gene, a BCR signaling pathway protein, or expression or activity or level of any one of the same is the result of one or more genetic alterations. In one embodiment, the one or more genetic alterations are selected from the group consisting of: chromosomal translocation t(11;14)(q13;q32), deletions of the chromosomal region 17p13, deletions of the chromosomal region 11q23, deletions of the chromosomal region 13q14, and trisomy of chromosome 12. In one embodiment, the one or more genetic alterations is one or more point mutations in a gene encoding a BCR signaling pathway protein. In one embodiment, the one or more point mutations in a gene encoding a BCR signaling pathway protein results in the translation of BCR signaling pathway protein having one or more amino acid substitutions, wherein the BCR signaling pathway protein is selected from the group consisting of: CARD11, CD79B, CD79A, MYD88, and combinations thereof. In one embodiment, the one or more point mutations in a gene encoding a BCR signaling pathway protein results in the translation of BCR signaling pathway protein having one or more amino acid substitutions at one or more of the following amino acid positions: MYD88$^{L265}$. In one embodiment, the amino acid substitution is MYD88$^{L265P}$. In one embodiment, the dysregulation in a BTK gene, a BTK kinase protein, or expression or activity or level of any of the same is one or more point mutations in the BTK gene. In one embodiment, the one or more point mutations in a BTK gene results in the translation of a BTK protein having one or more amino acid substitutions at one or more of the following amino acid positions: 117, 316, 474, 481, 528, 560, 562, and 601. In one embodiment, the one or more point mutations in a BTK gene results in the translation of a BTK protein having one or more of the following amino acid substitutions: T117P, T316A, T474I, T474M, T474S, C481S, C481F, C481T, C481G, C481R, L528W, P560L, R562W, R562G, and F601L.

In one embodiment, the BTK-associated cancer is selected from the group consisting of: Hodgkin lymphoma, diffuse large B cell lymphoma (DLBCL) (e.g., activated B cell-like DLBCL (ABC-DLBCL)), follicular lymphoma, mantle cell lymphoma, marginal zone lymphoma (e.g., extranodal marginal zone B cell lymphoma, splenic marginal zone lymphoma), Burkitt lymphoma, Waldenstrom's macroglobulinemia (lymphoplasmacytic lymphoma (LPL)), primary central nervous system lymphoma, small lymphocytic lymphoma, chronic lymphocytic leukemia (CLL), acute lymphocytic leukemia (ALL), B-cell prolymphocytic leukemia, precursor B-lymphoblastic leukemia, hairy cell leukemia, acute myeloid leukemia (AML), chronic myeloid leukemia, multiple myeloma, plasma cell myeloma, plasmacytoma, bone cancer, bone metastasis, breast cancer, gastro-esophageal cancer, pancreatic cancer, ovarian cancer, prostate cancer, lung cancer, colon cancer, uterine cancer, hepatocellular cancer, head and neck cancer, or glioma.

In one embodiment, the BTK-associated cancer is a hematological cancer. In one embodiment, the hematological cancer is selected from the group consisting of: leukemias, lymphomas (non-Hodgkin's lymphoma), Hodgkin's disease, and myeloma. In one embodiment, the hematological cancer is selected from the group consisting of: acute lymphocytic leukemia (ALL), acute myeloid leukemia (AML), acute promyelocytic leukemia (APL), chronic lymphocytic leukemia (CLL), chronic myeloid leukemia (CML), chronic myelomonocytic leukemia (CMML), chronic neutrophilic leukemia (CNL), acute undifferentiated leukemia (AUL), anaplastic large-cell lymphoma (ALCL), prolymphocytic leukemia (PML), juvenile myelomonocytic leukemia (JMML), adult T-cell ALL, AML with trilineage myelodysplasia (AML/TMDS), mixed lineage leukemia (MLL), myelodysplastic syndromes (MDSs), myeloproliferative disorders (MPD), diffuse large B cell lymphoma (DLBCL) (e.g., activated B cell-like DLBCL (ABC-DLBCL)), follicular lymphoma, mantle cell lymphoma, marginal zone lymphoma (e.g., extranodal marginal zone B cell lymphoma, splenic marginal zone lymphoma), Burkitt lymphoma, Waldenstrom's macroglobulinemia (lymphoplasmacytic lymphoma (LPL)), primary central nervous system lymphoma, small lymphocytic lymphoma, precursor B-lymphoblastic leukemia, hairy cell leukemia, chronic myeloid leukemia, anaplastic large cell lymphoma, MALT lymphoma, plasma cell myeloma, plasmacytoma, and multiple myeloma (MM).

In one embodiment, the BTK-associated cancer is a B-cell malignancy. In one embodiment, the cancer is B-cell malignancy is selected from the group consisting of: a Hodgkin lymphoma, diffuse large B cell lymphoma (DLBCL) (e.g., activated B cell-like DLBCL (ABC-DLBCL)), follicular lymphoma, mantle cell lymphoma, marginal zone lymphoma (e.g., extranodal marginal zone B cell lymphoma, splenic marginal zone lymphoma), Burkitt lymphoma, Waldenstrom's macroglobulinemia(lymphoplasmacytic lymphoma (LPL)), primary central nervous system lymphoma, small lymphocytic lymphoma, chronic lymphocytic leukemia, acute lymphoblastic leukemia (ALL), B-cell prolymphocytic leukemia, precursor B-lymphoblastic leukemia, or hairy cell leukemia.

In one embodiment, the BTK-associated cancer is selected from the group consisting of: mantle cell lymphoma, chronic lymphocytic leukemia, small lymphocytic lymphoma, Waldenstrom's macroglobulinemia, and marginal zone lymphoma.

In one embodiment, the BTK-associated cancer is a solid tumor. In one embodiment, the solid tumor is selected from the group consisting of: bone cancer, bone metastasis, breast cancer, gastro-esophageal cancer, pancreatic cancer, ovarian cancer, prostate cancer, lung cancer, colon cancer, uterine cancer, hepatocellular cancer, head and neck cancer, and glioma.

In one embodiment, the medicament is formulated for oral administration.

The present invention provides a spray-dried dispersion as described herein or a pharmaceutical composition as described herein for use in treating a subject identified or diagnosed as having a BTK-associated cancer. In one embodiment, the BTK-associated cancer is a cancer having a dysregulation in a BTK gene, a BTK kinase protein, or expression or activity or level of any of the same. In one embodiment, the dysregulation in a BTK gene, a BTK kinase protein, or expression or activity or level of any of the same is one or more point mutations in the BTK gene. In one embodiment, the one or more point mutations in a BTK gene results in the translation of a BTK protein having one or more amino acid substitutions at one or more of the following amino acid positions: 117, 316, 474, 481, 528, 560, 562, and 601. In one embodiment, the one or more point mutations in a BTK gene results in the translation of a BTK protein having one or more of the following amino acid substitutions: T117P, T316A, T474I, T474M, T474S, C481S, C481F, C481T, C481G, C481R, L528W, P560L, R562W, R562G, and F601L.

In one embodiment, the dysregulation in a BTK gene, a BTK kinase protein, or expression or activity or level of any of the same is a dysregulation in BCR signaling pathway gene, a BCR signaling pathway protein, or expression or activity or level of any one of the same.

In one embodiment, the BCR signaling pathway gene or BCR signaling pathway protein is selected from the group consisting of: cyclin-D1, CARD11, CD79B, CD79A, MYD88, and combinations thereof. In one embodiment, the dysregulation in the BCR signaling pathway gene, a BCR signaling pathway protein, or expression or activity or level of any one of the same is the result of one or more genetic alterations.

In one embodiment, the one or more genetic alterations are selected from the group consisting of: chromosomal translocation t(11;14)(q13;q32), deletions of the chromosomal region 17p13, deletions of the chromosomal region 11q23, deletions of the chromosomal region 13q14, and trisomy of chromosome 12. In one embodiment, the one or more genetic alterations is one or more point mutations in a gene encoding a BCR signaling pathway protein.

In one embodiment, the one or more point mutations in a gene encoding a BCR signaling pathway protein results in the translation of BCR signaling pathway protein having one or more amino acid substitutions, wherein the BCR signaling pathway protein is selected from the group consisting of: CARD11, CD79B, CD79A, MYD88, and combinations thereof. In one embodiment, the one or more point mutations in a gene encoding a BCR signaling pathway protein results in the translation of BCR signaling pathway protein having one or more amino acid substitutions at one or more of the following amino acid positions: $MYD88^{L265}$.

In one embodiment, the amino acid substitution is $MYD88^{L265P}$.

In one embodiment, the BTK-associated cancer is selected from the group consisting of: Hodgkin lymphoma, diffuse large B cell lymphoma (DLBCL) (e.g., activated B cell-like DLBCL (ABC-DLBCL)), follicular lymphoma, mantle cell lymphoma, marginal zone lymphoma (e.g., extranodal marginal zone B cell lymphoma, splenic marginal zone lymphoma), Burkitt lymphoma, Waldenstrom's macroglobulinemia (lymphoplasmacytic lymphoma (LPL)), primary central nervous system lymphoma, small lymphocytic lymphoma, chronic lymphocytic leukemia (CLL), acute lymphocytic leukemia (ALL), B-cell prolymphocytic leukemia, precursor B-lymphoblastic leukemia, hairy cell leukemia, acute myeloid leukemia (AML), chronic myeloid leukemia, multiple myeloma, plasma cell myeloma, plasmacytoma, bone cancer, bone metastasis, breast cancer, gastro-esophageal cancer, pancreatic cancer, ovarian cancer, prostate cancer, lung cancer, colon cancer, uterine cancer, hepatocellular cancer, head and neck cancer, or glioma.

In one embodiment, the BTK-associated cancer is a hematological cancer. In one embodiment, the hematological cancer is selected from the group consisting of leukemias, lymphomas (non-Hodgkin's lymphoma), Hodgkin's disease, and myeloma. In one embodiment, the hematological cancer is selected from the group consisting of acute lymphocytic leukemia (ALL), acute myeloid leukemia (AML), acute promyelocytic leukemia (APL), chronic lymphocytic leukemia (CLL), chronic myeloid leukemia (CML), chronic myelomonocytic leukemia (CMML), chronic neutrophilic leukemia (CNL), acute undifferentiated leukemia (AUL), anaplastic large-cell lymphoma (ALCL), prolymphocytic leukemia (PML), juvenile myelomonocytic leukemia (JMML), adult T-cell ALL, AML with trilineage myelodysplasia (AML/TMDS), mixed lineage leukemia (MLL), myelodysplastic syndromes (MDSs), myeloproliferative disorders (MPD), diffuse large B cell lymphoma (DLBCL) (e.g., activated B cell-like DLBCL (ABC-DLBCL)), follicular lymphoma, mantle cell lymphoma, marginal zone lymphoma (e.g., extranodal marginal zone B cell lymphoma, splenic marginal zone lymphoma), Burkitt lymphoma, Waldenstrom's macroglobulinemia (lymphoplasmacytic lymphoma (LPL)), primary central nervous system lymphoma, small lymphocytic lymphoma, precursor B-lymphoblastic leukemia, hairy cell leukemia, chronic myeloid leukemia, anaplastic large cell lymphoma, MALT lymphoma, plasma cell myeloma, plasmacytoma, and multiple myeloma (MM).

In one embodiment, the BTK-associated cancer is a B-cell malignancy. In one embodiment, the cancer is B-cell malignancy is selected from the group consisting of: a Hodgkin lymphoma, diffuse large B cell lymphoma (DLBCL) (e.g., activated B cell-like DLBCL (ABC-DLBCL)), follicular lymphoma, mantle cell lymphoma, marginal zone lymphoma (e.g., extranodal marginal zone B cell lymphoma, splenic marginal zone lymphoma), Burkitt lymphoma, Waldenstrom's macroglobulinemia(lymphoplasmacytic lymphoma (LPL)), primary central nervous system lymphoma, small lymphocytic lymphoma, chronic lymphocytic leukemia, acute lymphoblastic leukemia (ALL), B-cell prolymphocytic leukemia, precursor B-lymphoblastic leukemia, or hairy cell leukemia.

In one embodiment, the BTK-associated cancer is selected from the group consisting of: mantle cell lymphoma, chronic lymphocytic leukemia, small lymphocytic lymphoma, Waldenstrom's macroglobulinemia, and marginal zone lymphoma.

In one embodiment, the BTK-associated cancer is a solid tumor. In one embodiment, the solid tumor is selected from the group consisting of: bone cancer, bone metastasis, breast cancer, gastro-esophageal cancer, pancreatic cancer, ovarian cancer, prostate cancer, lung cancer, colon cancer, uterine cancer, hepatocellular cancer, head and neck cancer, or glioma.

The present invention provides a method for inhibiting BTK kinase activity in a mammalian cell, the method comprising contacting the mammalian cell with a spray-dried dispersion as described herein or the pharmaceutical composition as described herein. In one embodiment, the contacting occurs in vivo. In one embodiment, the contacting occurs in vitro.

In one embodiment, the mammalian cell is a mammalian cancer cell. In one embodiment, the mammalian cancer cell is a mammalian BTK-associated cancer cell. In one embodiment, the cell has dysregulation of a BTK gene, a BTK kinase protein, or expression or activity or level of any of the same. In one embodiment, the dysregulation in a BTK gene, a BTK kinase protein, or expression or activity or level of any of the same is one or more point mutations in the BTK gene. In one embodiment, the one or more point mutations in a BTK gene results in the translation of a BTK protein having one or more amino acid substitutions at one or more of the following amino acid positions: 117, 316, 474, 481, 495, 528, 560, 562, and 601. In one embodiment, the one or more point mutations in a BTK gene results in the translation of a BTK protein having one or more of the following amino acid substitutions: T117P, T316A, T474I, T474M, T474S, C481S, C481F, C481T, C481G, C481R, L528W, P560L, R562W, R562G, and F601L.

In one embodiment, the dysregulation in a BTK gene, a BTK kinase protein, or expression or activity or level of any of the same is the result of a dysregulation of a BCR signaling pathway gene, a BCR signaling pathway protein, or expression or activity or level of any one of the same. In one embodiment, the BCR signaling pathway gene or BCR signaling pathway protein is selected from the group consisting of: cyclin-D1, CARD11, CD79B, CD79A, MYD88, and combinations thereof. In one embodiment, the dysregulation in the BCR signaling pathway gene, a BCR signaling pathway protein, or expression or activity or level of any one of the same is the result of one or more genetic alterations.

In one embodiment, the one or more genetic alterations are selected from the group consisting of: chromosomal translocation t(11;14)(q13;q32), deletions of the chromosomal region 17p13, deletions of the chromosomal region 11q23, deletions of the chromosomal region 13q14, and trisomy of chromosome 12.

In one embodiment, the one or more genetic alterations is one or more point mutations in a gene encoding a BCR signaling pathway protein. In one embodiment, the one or more point mutations in a gene encoding a BCR signaling pathway protein results in the translation of BCR signaling pathway protein having one or more amino acid substitutions, wherein the BCR signaling pathway protein is selected from the group consisting of: CARD11, CD79B, CD79A, MYD88, and combinations thereof. In one embodiment, the one or more point mutations in a gene encoding a BCR signaling pathway protein results in the translation of BCR signaling pathway protein having one or more amino acid substitutions at one or more of the following amino acid positions: MYD88$^{L265}$. In one embodiment, the amino acid substitution is MYD88$^{L265P}$.

The present invention provides a method of treating an autoimmune or inflammatory disease in a subject, the method comprising administering to a subject identified or diagnosed as having an autoimmune or inflammatory disease a spray-dried dispersion as described herein or a pharmaceutical composition as described herein, or a therapeutically effective amount of the compound according to Formula I to the subject. In one embodiment, the autoimmune or inflammatory disease is selected from the group consisting of: rheumatoid arthritis, multiple sclerosis, osteoporosis, irritable bowel syndrome, inflammatory bowel disease, Crohn's disease, chronic urticaria, myasthenia gravis, and systemic lupus erythematosus.

What is claimed is:

1. A spray-dried dispersion comprising a compound of Formula I:

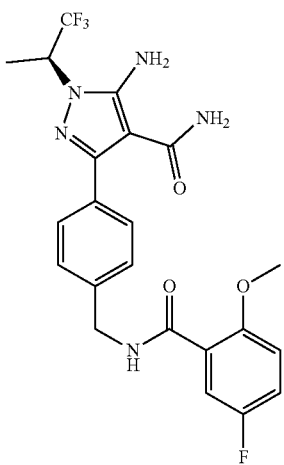

or a pharmaceutically acceptable salt thereof and one or more polymers selected from the group consisting of an HPMCAS polymer, an HPMC polymer, a vinylpyrrolidone-vinyl acetate copolymer, and a polyvinylpyrrolidone (PVP) polymer.

2. The spray-dried dispersion according to claim 1, comprising the compound of Formula I.

3. The spray-dried dispersion according to claim 2, wherein the compound of Formula I is present in amorphous form.

4. The spray-dried dispersion according to claim 3, comprising the compound of Formula I and an HPMCAS polymer.

5. The spray-dried dispersion according to claim 4, wherein the ratio of the compound of Formula I to the HPMCAS polymer is about 1:4 to about 4:1.

6. The spray-dried dispersion according to claim 4, wherein the ratio of the compound of Formula I to the HPMCAS polymer is about 1:1.

7. The spray-dried dispersion according to claim 6, wherein the HPMCAS polymer is one or more of HPMCAS-MG, HPMCAS-LF, HPMCAS-LG, HPMCAS-MF, HPMCAS-HF, or HPMCAS-HG.

8. The spray-dried dispersion according to claim 7, wherein the HPMCAS polymer is HPMCAS-MG.

* * * * *

SEQUENCE LISTING

```
Sequence total quantity: 1
SEQ ID NO: 1           moltype = AA   length = 659
FEATURE                Location/Qualifiers
source                 1..659
                       mol_type = protein
                       organism = Homo sapiens
SEQUENCE: 1
MAAVILESIF LKRSQQKKKT SPLNFKKRLF LLTVHKLSYY EYDFERGRRG SKKGSIDVEK   60
ITCVETVVPE KNPPPERQIP RRGEESSEME QISIIERFPY PFQVVYDEGP LYVFSPTEEL  120
RKRWIHQLKN VIRYNSDLVQ KYHPCFWIDG QYLCCSQTAK NAMGCQILEN RNGSLKPGSS  180
HRKTKKPLPP TPEEDQILKK PLPPEPAAAP VSTSELKKVV ALYDYMPMNA NDLQLRKGDE  240
YFILEESNLP WWRARDKNGQ EGYIPSNYVT EAEDSIEMYE WYSKHMTRSQ AEQLLKQEGK  300
EGGFIVRDSS KAGKYTVSVF AKSTGDPQGV IRHYVVCSTP QSQYYLAEKH LFSTIPELIN  360
YHQHNSAGLI SRLKYPVSQQ NKNAPSTAGL GYGSWEIDPK DLTFLKELGT GQFGVVKYGK  420
WRGQYDVAIK MIKEGSMSED EFIEEAKVMM NLSHEKLVQL YGVCTKQRPI FIITEYMANG  480
CLLNYLREMR HRFQTQQLLE MCKDVCEAME YLESKQFLHR DLAARNCLVN DQGVVKVSDF  540
GLSRYVLDDE YTSSVGSKFP VRWSPPEVLM YSKFSSKSDI WAFGVLMWEI YSLGKMPYER  600
FTNSETAEHI AQGLRLYRPH LASEKVYTIM YSCWHEKADE RPTFKILLSN ILDVMDEES   659
```